(12) United States Patent
Azhakanandam et al.

(10) Patent No.: US 12,173,297 B2
(45) Date of Patent: Dec. 24, 2024

(54) PROMOTERS FOR REGULATION OF GENE EXPRESSION IN PLANTS

(71) Applicant: Syngenta Crop Protection AG, Basel (CH)

(72) Inventors: Kasimalai Azhakanandam, Research Triangle Park, NC (US); Joseph Dallas Clarke, V, Research Triangle Park, NC (US); Ailing Zhou, Research Triangle Park, NC (US); Jared Conville, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 82 days.

(21) Appl. No.: 17/640,963

(22) PCT Filed: Aug. 26, 2020

(86) PCT No.: PCT/US2020/047899
§ 371 (c)(1),
(2) Date: Mar. 7, 2022

(87) PCT Pub. No.: WO2021/045942
PCT Pub. Date: Mar. 11, 2021

(65) Prior Publication Data
US 2022/0325293 A1      Oct. 13, 2022

Related U.S. Application Data

(60) Provisional application No. 62/896,735, filed on Sep. 6, 2019.

(51) Int. Cl.
*C12N 15/82* (2006.01)
(52) U.S. Cl.
CPC ..... *C12N 15/8223* (2013.01); *C12N 15/8205* (2013.01); *C12N 15/8286* (2013.01)
(58) Field of Classification Search
None
See application file for complete search history.

(56) References Cited

U.S. PATENT DOCUMENTS

| | | | | |
|---|---|---|---|---|
| 5,955,330 A | * | 9/1999 | Vasil et al. | C12N 15/8216 800/292 |
| 2006/0272049 A1 | * | 11/2006 | Waterhouse et al. | C12N 15/8218 800/279 |
| 2010/0299784 A1 | | 11/2010 | Medrano et al. | |
| 2015/0337323 A1 | | 11/2015 | Lee et al. | |
| 2017/0114366 A1 | | 4/2017 | Egli | |

FOREIGN PATENT DOCUMENTS

| | | |
|---|---|---|
| CN | 103261425 A | 8/2013 |
| WO | 2004076611 A2 | 9/2004 |

OTHER PUBLICATIONS

Manjunath, S. and Sachs, M.M.; *Zea mays* glyceraldehyde-3-phosphate dehydrogenase (gpc2) gene, complete cds; GenBank assession U45858; Jan. 16, 1996.*
Whitt et al., (2002), GenBank: AF544126 (Year: 2002).*
International Search Report cited in Internation Application No. PCT/US2020/047899, mailed Feb. 17, 2021.
GenBank Accession No. AC212194, *Zea mays* culitvar B73 chromosome 6 clone CH201-548C2, Sep. 2013. Retrieved on Jan. 7, 2021, Retrieved from the internet: <URL: https://www.ncbi.nlm.nih.gov/nuccore/AC212494>.
Chen, Wen-Bo et al., Transgenic cotton coexpressing Vip3A and Cry1Ac has a Broad Insecticidal Spectrum Against Lepidopteran Pests, Journal of Invertebrate Pathology, San Diego, CA, US. vol. 149, Aug. 4, 2017, pp. 59-65, XP085195043, ISSN: 0022-2011, DOI: 10.1016/J.JIP.2017.08.001.
Koziel, M. G. et al., Field preformance of Elite Transgenic Maize Plants Expressing an Insecticidal Protein Derived from Bacillus Thuringiensis, Biotechnology. The Inter=national Monthly for Industrial Biology, Nature Publishing Group, US, vol. 11, Feb. 1, 1993, pp. 194-200, XP002029715, ISSN:0733-222X, DOI: 10.1038/NBT0293-194, p. 197, table 83.
Extended European Search Report for EP20859787.2, mailed on Dec. 6, 2023.

* cited by examiner

*Primary Examiner* — Cathy Kingdon Worley
*Assistant Examiner* — Christina L Meadows
(74) *Attorney, Agent, or Firm* — Katherine Seguin

(57) ABSTRACT

The present invention is directed to promoters that have particular utility in driving root-specific expression of heterologous genes that impart increased agronomic, horticultural and/or pesticidal characteristics to a given transgenic plant. The present invention is also drawn to DNA molecules comprising the promoters of the invention and transformed plant tissues containing DNA molecules comprising a promoter of the invention operably linked to a heterologous gene or genes, and seeds thereof.

16 Claims, No Drawings
Specification includes a Sequence Listing.

SEQUENCE LISTING

```
<160> NUMBER OF SEQ ID NOS: 29

<210> SEQ ID NO 1
<211> LENGTH: 2738
<212> TYPE: DNA
<213> ORGANISM: Zea mays

<400> SEQUENCE: 1
gagatatgtg atgtatatgt gatatatgtg atgattatgt gatatatttt ttgtttgttt      60
ggatggaata ataaaaacaa ataaaaaggg tatgttggcc acttttggcg agtgtaacac     120
tcagcaaaga ggtactttgc cgagtgtcac agtcatatca ttcggcaaag aaggcacaca     180
tgggaaccga taaagcttct ttgccgagtg ttgtggcctt agcactcggc aaagaagcaa     240
cttttgccga gagcctccta gtgtactcgg caaggaact gacaaaggag cccactgatg     300
attcctttga tgagtggtag tccggcagac acacggcaaa gataaagtct ttgccgagtg     360
ccacctaata cgcccggcaa aggaactggc aaaggacaca cgatgagttt atttgtcgag     420
```

```
tgctagtaca atagacactc gacaaagagt gagcctttgc agagtgtcac cgtggcactc    480
ggcaaagtcc actctttgtc gagtgtcacc gtgacactca gcgaagtctc cgtcgctgtc    540
atctgtcgcc gtgacgtcga cttttttttg ccgagtaccg agtggttgcc gagtgtccga    600
caaaaaatac tcggttaaag accgttgccg atgtcagttc accaagacct tttttatcaa    660
gtgtcatact tgataaagtc ttccccaagt attttcaaaa ctttgtcgat tacctcacac    720
accaaggggt aggatcgtgt tgaggcggtt tgctgcttgt ttcttgcttt cgccgaacca    780
acggaccatg agcgcataaa ccaatgggcg agcggccgca tatacaggcc tgcgcggcga    840
gcctcacctt gctggatttg aatgccccct cggcatggtc aatgaccatg catctttgtg    900
cagaacatat aaaatgcaca aattaattaa ttaataaaaa tacatgaaag agtacataat    960
ttgtttgtgg attattaatt atatttataa atatattata gtatattata ttttatcttt   1020
atctaactac aaaaataatt atagattgtt aactttttt tgcattactg gtaagatttt   1080
gtcgatttta taattttgtc taacatgttt tattatcaat ctaaaattgc aaattatatg   1140
ttaacgaact aaatttgtaa taaatatat gtaataaagg tcgtctaaaa gtaagctaaa   1200
attcacgcac ctaaattta tttagtaaag tgtttttct tgacatatga cactagtgtt   1260
ttcaaagctt gtctcttaat ttaggattaa attaataggc ctctctaaat tgctttttat   1320
aagataaata aatcctattc cgtctgctca tcttcaaaga acatttcaat gaaacaaata   1380
tttgggaaaa ccaatggaaa aagaataaaa ataaaaattg aaaaagagaa gtggaggaaa   1440
agtagggttc cattccacgg cctgtcgagt gtcgacccac aaaccacgca accgatatat   1500
tccccagcac ccccagtctc cagccgtcca accgagacac cgcgtgcgaa ccaagcagac   1560
cacaacaaga agaagcgtag tcgtcgccgg aaggaaaggc gcggagcaag atctcgtggc   1620
aggcgtacgt cgacgagcac ctgaagtgcg agatcgaagg acagcatctc agcgccgccg   1680
ccatcgtcgg tcacgacggc agcgtttggg cgcagtccga gagcttcccc gaggtcattc   1740
actcccacct tatctcttcc cgctctactt gcttagttgc tttatccatg ttcagtgctc   1800
ctgcgctgat ttagacccgc gcgactctgg atctgcccca gccgtgcggc ccggccggat   1860
cggagcgagg ggatgtccgg atctcggtcg ctgaggcgag atgcggatct aaggcccctt   1920
ccctcggtga cgtggttgct gctgctgctg ttctccgggc gtttgatgcc aatatagctg   1980
agatcaagct tgatgatctg cgtactgtgg atttgctagt gagggatggc cggatcgggc   2040
tgttggcgtc cgacctgatt tggttgttcg cttgaataga cttacttacc agtggacagt   2100
ggtagtgatc gttcagcagc agtagagcaa tttgttttac atgtaaaatt tgagtggctg   2160
ctagagatgc accaatggcc gagctgcatg tgtttattcc tatatagcga cagttgtgtg   2220
attgatccaa aacgcaaaat tttagttttc atcaaatgat gatttcctga tgccactacc   2280
tgtgtgtgag gcacttatta aatgaaaagt aactttcggt tgggatctgg gaatctgtat   2340
tgtgttccgt ggttggtcac agcttgtggc ctgcattgtt ccataggcca aatggctagg   2400
caaggaaaat aaatcatgta atttggaaaa aaataactgc catagtcagt agtgtacagc   2460
agtacatgct tgtccgggcc ttttatttca ccatcgtgtt gtggtatatg gagtacttgg   2520
attgtgcgat gctttataca tttgtttgtt ctagcagagt ttgagtttat atttctattc   2580
ttatgtaggg cgtcacgagt gtcgtcaatt gttacatcct tacatccttg tgttcacaat   2640
atgatccatc aactctttct tctgcggtct cttatccctg tgttctcatg tccatgtttc   2700
ctgcttcttg ttgcagttaa agccttagga ggtaaacc                           2738
```

<210> SEQ ID NO 2
<211> LENGTH: 2627
<212> TYPE: DNA
<213> ORGANISM: Artificial Sequence
<220> FEATURE:
<223> OTHER INFORMATION: The 5' regulatory sequence from the Zm061393 gene with a T to A mutation to remove a start codon.

<400> SEQUENCE: 2

```
tctgcctttc tgttcttcaa acgatgtctc atgtctgcgc tggacaactt tcttgttgcc      60
gcctgtcgct tgcgctgtgc tgactggacg cagctccgga ggtttggttg tgcttggttt     120
tcgtagagaa ctcgccactt gccgcccgca cgttcttggt gtttcctcct ccccgctgtg     180
ttctgcgcac gggcttttc tgagagaccc atgtttccct tttacttta taaacagtat       240
acatgctatg tttctagaag gagggggaaac ctaatccccc taatccaatg gcggggagga    300
aatagggtgg ggtggggtgg ggggagggaa atatctcgct acttttaat ccggacaagc      360
tcatttgcgt ttgcgtctga atgatgatga ctgcaatgct gatcgcacct cgggtgtcgg     420
atcaccagct tttggctgct ctcaccaaat cagctgcaag aagattagag cacaaaagaa     480
ttacagaaag agagcctttt tcttttcttc cttgtggggt tcctttcatt tcgtgctctc     540
ctttctctgc cagccagtcc gtccttgcgt ccactgcacc tgcacacagg tcaccccgac     600
ccgcactgtt ctagactcca ttagaaaaaa aaggtctga acctttccga aaccagccag      660
ccattggtct ggcaggccag catatgctaa ttggattttt tgccgcatc attgagtgcg      720
ccatcaggat ttggaaatcc tggttttgag taatacagta atttggcatt atccattgcc     780
gaattcccaa gctccgtcag cttgaacgtg gaccccacc atctgcacca gctcggcacc      840
tcacgctcgc agcgctagga gcctaggagc agctgcccgt ctatttattg gtccctctcc     900
cgtcccagag aaaccctccc tccctcctcc attggactgc ttgctccctg ttgaccattg     960
gggtatgctt gctgccttgc tctcctgttc atctccgtgc taaacctctg tcctctgggt    1020
gggttttgc tgggattttg agctaatctg ctggtcccgg tagaaaaaga tcatgtcccc     1080
tgacgtgctc aagcgctcgc cttagccgcg tccttgcccc ccgccatttt tgcggtttc     1140
ggtgtgttcc cgtgactcgc cgggtgcgtc atcgcctgaa tcttgtctgg gctctgctga    1200
catgttcttg gctagttggg tttatagatt cctctgatct aaaccgtgcc tgtgctgcgc    1260
acagaactct cccctgtcct ttcctggggt tttggttacg tggtggtagt aagcttggat    1320
ttgcacatgg ataaagttgt tctaagctcc gtgggttgct tgagatcttg ctgttattgc    1380
gtgccgtgct cactttttt gcaatccgag gaatgaattt gtcgtttact cgttttggtg    1440
gattattagc gcgaaaaaaa aactctttt tttttgttct tttactacga aaagcatctt    1500
cttggatttt gctatcttct tttactacga aaaactcttg agtctaggaa tttgaatttg    1560
tgatgtccat tcttgcagtg cgctgtgctt tattgggaag ccaaatccta ttattttctg    1620
cctctagggt ctgaatggaa tcagtactct tgagacagaa atcaatcca atcaagttga    1680
tttctttctt taaaaatatt atcacagaac taagtgcttg tgcggaatca gtactggctt    1740
ttgtttggtg gaggatcaat acttgctttt gtttggggt ggcaactgtt ttgctataag    1800
attccatgtg ttcctgttga gatgaatcat atatagtata gctgcatact acaaatctgt    1860
ttttcaaatt taggttgctt tggcatgatc tattttttg tcagacagac tttctaagtg    1920
gtagctcttg atttcttgtt cttgtacaac tggtgctgct gaatcttgac cgtatagctc    1980
gaattgcagt attctgaacc atcgagccaa ggctgccaag ctgactcgcc tccacagtct    2040
tcgcgaacgc cttggtgcca ccttctcctc ccatcccaat gaactgatag cactcttttc    2100
```

```
caggtgggct taccaaaatc ataaacttg catttcattc ggtactgaaa gttgttaatt    2160
tgttattctc ttcatgcctg tcttaatagc acacccagat gtaaacacga gattatgcaa    2220
cttcttactt ggtttctttt gttggcacca tcatgcatgc taattgctaa ggatgttacc    2280
tattcatcct tgactcatat tatcatatgt aatgatttta tgatcacgag actattgatt    2340
gtgaagcata gtatagctgt tcttcagttt ttgtaccctt ttgttttttt ccttaagcta    2400
gaactggtac aatttagttg ataagacagt gtagtttgta gtacgtcatt tgacagattg    2460
tttgtcttta gctggtaaag tgccatttaa tatctgtatc cttcagatct aataaaaagg    2520
atatgagatg tccatcacaa gaggggaaaa attacatgat ctgagatgta acatccgttt    2580
ttatttgtga ataccactt ctacaggtat cttcactagg gtaaacc                  2627
```

<210> SEQ ID NO 3
<211> LENGTH: 2695
<212> TYPE: DNA
<213> ORGANISM: Artificial Sequence
<220> FEATURE:
<223> OTHER INFORMATION: TMV enhancer added to the 3' end.

<400> SEQUENCE: 3

```
tctgcctttc tgttcttcaa acgatgtctc atgtctgcgc tggacaactt tcttgttgcc     60
gcctgtcgct tgcgctgtgc tgactggacg cagctccgga ggtttggttg tgcttggttt    120
tcgtagagaa ctcgccactt gccgcccgca cgttcttggt gtttcctcct ccccgctgtg    180
ttctgcgcac gggcttttc tgagagaccc aagtttccct tttactttta taaacagtat    240
acatgctatg tttctagaag gaggggaaac ctaatccccc taatccaatg gcggggagga    300
aatagggtgg ggtggggtgg gggagggaa atatctcgct acttttaat ccggacaagc    360 tcatttgcgt ttgcgtctga atgatgatga ctgcaatgct gatcgcacct cgggtgtcgg    420
atcaccagct tttggctgct ctcaccaaat cagctgcaag aagattagag cacaaaagaa    480
ttacagaaag agagcctttt tcttttcttc cttgtggggt tcctttcatt tcgtgctctc    540 cttttctctgc cagccagtcc gtccttgcgt ccactgcacc tgcacacagg tcaccccgac    600
ccgcactgtt ctagactcca ttagaaaaaa aaaggtctga acctttccga aaccagccag    660
ccattggtct ggcaggccag catatgctaa ttggattttt ttgccgcatc attgagtgcg    720
ccatcaggat ttgaaaatcc tggttttgag taatacagta atttggcatt atccattgcc    780
gaattcccaa gctccgtcag cttgaacgtg gaccctaccc atctgcacca gctcggcacc    840
tcacgctcgc agcgctagga gcctaggagc agctgcccgt ctatttattg gtccctctcc    900
cgtcccagag aaaccctccc tccctcctcc attggactgc ttgctccctg ttgaccattg    960
gggtatgctt gctgccttgc tctcctgttc atctccgtgc taaacctctg tcctctgggt   1020 gggttttttgc tgggattttg agctaatctg ctggtcccgg tagaaaaaga tcatgtcccc   1080
tgacgtgctc aagcgctcgc cttagccgcg tccttgcccc ccgccatttt ttgcggtttc   1140
ggtgtgttcc cgtgactcgc cgggtgcgtc atcgcctgaa tcttgtctgg gctctgctga   1200
catgttcttg gctagttggg tttatagatt cctctgatct aaaccgtgcc tgtgctgcgc   1260
acagaactct cccctgtcct ttcctggggt tttggttacg tggtggtagt aagcttggat   1320
ttgcacatgg ataaagttgt tctaagctcc gtgggttgct tgagatcttg ctgttattgc   1380
gtgccgtgct cactttttt gcaatccgag gaatgaattt gtcgtttact cgttttggtg   1440
gattattagc gcgaaaaaaa aactcttttt tttttgttct tttactacga aaagcatctt   1500
```

```
cttggatttt gctatcttct tttactacga aaaactcttg agtctaggaa tttgaatttg      1560
tgatgtccat tcttgcagtg cgctgtgctt tattgggaag ccaaatccta ttattttctg      1620
cctctagggt ctgaatggaa tcagtactct tgagacagaa atcaatcca atcaagttga       1680 tttcttcct taaaaatatt atcacagaac taagtgcttg tgcggaatca gtactggctt       1740
ttgtttggtg gaggatcaat acttgctttt gtttgggggt ggcaactgtt ttgctataag     1800
attccatgtg ttcctgttga gatgaatcat atatagtata gctgcatact acaaatctgt     1860
ttttcaaatt taggttgctt tggcatgatc tatttttttg tcagacagac tttctaagtg     1920
gtagctcttg atttcttgtt cttgtacaac tggtgctgct gaatcttgac cgtatagctc     1980
gaattgcagt attctgaacc atcgagccaa ggctgccaag ctgactcgcc tccacagtct     2040
tcgcgaacgc cttggtgcca ccttctcctc ccatcccaat gaactgatag cactcttttc     2100
caggtgggct taccaaaatc atataacttg catttcattc ggtactgaaa gttgttaatt     2160
tgttattctc ttcatgcctg tcttaatagc acacccagat gtaaacacga gattatgcaa     2220
cttcttactt ggtttctttt gttggcacca tcatgcatgc taattgctaa ggatgttacc     2280
tattcatcct tgactcatat tatcatatgt aatgatttta tgatcacgag actattgatt     2340
gtgaagcata gtatagctgt tcttcagttt ttgtacccct ttgttttttt ccttaagcta    2400
gaactggtac aatttagttg ataagacagt gtagtttgta gtacgtcatt tgacagattg     2460
tttgtcttta gctggtaaag tgccatttaa tatctgtatc cttcagatct aataaaaagg    2520
atatgagatg tccatcacaa gaggggaaaa attacatgat ctgagatgta acatccgttt     2580
ttatttgtga ataccacttt ctacaggtat cttcactagg gtttgtcgaa caacaacaaa    2640
caacaaacaa caaagtcgaa caacaacaaa caacaaacaa caaagtcgac caaaa          2695
```

<210> SEQ ID NO 4
<211> LENGTH: 2694
<212> TYPE: DNA
<213> ORGANISM: Artificial Sequence
<220> FEATURE:
<223> OTHER INFORMATION: Includes point mutation to eliminate ORFS.

<400> SEQUENCE: 4

```
tctgcctatc tgttcttcaa acgatgtctc atgtctgcgc tggacaactt tcttgttgcc       60
gcctgtcgct tgcgctgtgc tgactggacg cagctccgga ggtttggttg tgcttggttt      120
tcgtagagaa ctcgccactt gccgcccgca cgttcttggt gtttcctcct cccgctgtg       180 ttctgcgcac gggcttttc tgagagaccc aagtttccct tttactttta taaacagtat      240
acatgctatg tttctagaag gaggggaaac ctaatccccc taatccaatg gcggggagga    300
aatagggtgg ggtggggtgg ggggagggaa atatctcgct actttttaat ccggacaagc    360
tcatttgcgt ttgcgtctga atgatgatga ctgcaatgct gatcgcacct cgggtgtcgg     420
atcaccagct tttggctgct ctcaccaaat cagctgcaag aagattagag cacaaaagaa    480
ttacagaaag agagcctttt tcttttcttc cttgtggggt tcctttcatt tcgtgctctc     540
ctttctctgc cagccagtcc gtccttgcgt ccactgcacc tgcacacagg tcaccccgac   600
ccgcactgtt ctagactcca ttagaaaaaa aaaggtctga accttccgga aaccagccag    660
ccattggtct ggcaggccag catatgctaa ttggattttt ttgccgcatc attgagtgcg    720
ccatcaggat ttggaaatcc tggttttgag taatacagta atttggcatt atccattgcc     780
gaattcccaa gctccgtcag cttgaacgtg gaccctaccc atctgcacca gctcggcacc   840
tcacgctcgc agcgctagga gcctaggagc agctgcccgt ctatttattg gtccctctcc    900
```

```
cgtcccagag aaaccctccc tccctcctcc attggactgc ttgctccctg ttgaccattg    960
gggtatgctt gctgccttgc tctcctgttc atctccgtgc taaacctctg tcctctgggt   1020 gggttttgc tgggattttg agctaatctg ctggtcccgg tagaaaaaga tcatgtcccc    1080
tgacgtgctc aagcgctcgc cttagccgcg tccttgcccc ccgccatttt ttgcggtttc   1140
ggtgtgttcc cgtgactcgc cgggtgcgtc atcgcctgaa tcttgtctgg gctctgctga   1200
catgttcttg gctagttggg tttatagatt cctctgatct aaaccgtgcc tgtgctgcgc   1260
acagaactct cccctgtcct ttcctggggt tttggttacg tggtggtagt aagcttggat   1320
ttgcacatgg ataaagttgt tctaagctcc gtgggttgct tgagatcttg ctgttattgc   1380
gtgccgtgct cactttttt gcaatccgag gaatgaattt gtcgtttact cgttttggtg    1440
gattattagc gcgaaaaaaa aactcttttt tttttgttct tttactacga aaagcatctt   1500
cttggatttt gctatcttct tttactacga aaaactcttg agtctaggaa tttgaatttg   1560
tgatgtccat tcttgcagtg cgctgtgctt tattgggaag ccaaatccta ttattttctg   1620
cctctagggt ctgaatggaa tcagtactct tgagacagaa aatcaatcca atcaagttga   1680
tttctttctt taaaaatatt atcacagaac taagtgcttg tgcggaatca gtactggctt   1740
ttgtttggtg gaggatcaat acttgctttt gtttgggggt ggcaactgtt ttgctataag   1800
attccatgtg ttcctgttga gatgaatcat atatagtata gctgcatact acaaatctgt   1860
ttttcaaatt taggttgctt tggcatgatc tatttttttg tcagacagac tttctaagtg   1920
gtagctcttg atttcttgtt cttgtacaac tggtgctgct gaatcttgac cgtatagctc   1980
gaattgcagt attctgaacc atcgagccaa ggctgccaag ctgactcgcc tccacagtct   2040
tcgcgaacgc cttggtgcca ccttctcctc ccatcccaat gaactgatag cactcttttc   2100
caggtgggct taccaaaatc atataacttg catttcattc ggtactgaaa gttgttaatt   2160
tgttattctc ttcatgcctg tcttaatagc acacccagat gtaaacacga gattatgcaa   2220
cttcttactt ggtttctttt gttggcacca tcatgcatgc taattgctaa ggatgttacc   2280
tattcatcct tgactcatat tatcatatgt aatgatttta tgatcacgag actattgatt   2340
gtgaagcata gtatagctgt tcttcagttt ttgtacccctt ttgtttttt ccttaagcta   2400 gaactggtac aatttagttg ataagacagt gtagtttgta gtacgtcatt tgacagattg   2460
tttgtcttta gctggtaaag tgccatttaa tatctgtatc cttcagatct aataaaaagg   2520
atatgagatg tccatcacaa gaggggaaaa attacatgat ctgagatgta acatccgttt   2580
ttatttgtga ataccactt ctacaggtat cttcactagg gttgtcgaa caacaacaaa     2640 caacaaacaa caaagtcgaa caacaacaaa caacaaacaa caaagtcgac caaa          2694
```

<210> SEQ ID NO 5
<211> LENGTH: 2626
<212> TYPE: DNA
<213> ORGANISM: Artificial Sequence
<220> FEATURE:
<223> OTHER INFORMATION: Comprises point mutation to eliminate cross
      component ORF on antisense strand.

<400> SEQUENCE: 5

```
tctgcctttc tgttcttcaa acgatgtcac atgtctgcgc tggacaactt tcttgttgcc     60
gcctgtcgct tgcgctgtgc tgactggacg cagctccgga ggtttggttg tgcttggttt    120
tcgtagagaa ctcgccactt gccgcccgca cgttcttggt gtttcctcct ccccgctgtg    180
ttctgcgcac gggcttttc tgagagaccc atgtttccct tttactttta taaacagtat     240
```

```
acatgctatg tttctagaag gaggggaaac ctaatccccc taatccaatg gcggggagga        300
aatagggtgg ggtggggtgg ggggagggaa atatctcgct acttttaat ccggacaagc         360 tcatttgcgt ttgcgtctga atgatgatga ctgcaatgct gatcgcacct cgggtgtcgg        420
atcaccagct tttggctgct ctcaccaaat cagctgcaag aagattagag cacaaaagaa        480
ttacagaaag agagccttt tcttttcttc cttgtggggt tcctttcatt tcgtgctctc        540
ctttctctgc cagccagtcc gtccttgcgt ccactgcacc tgcacacagg tcaccccgac        600
ccgcactgtt ctagactcca ttagaaaaaa aaggtctga acctttccga aaccagccag         660
ccattggtct ggcaggccag catatgctaa ttggattttt ttgccgcatc attgagtgcg       720
ccatcaggat ttgaaaatcc tggttttgag taatacagta atttggcatt atccattgcc       780
gaattcccaa gctccgtcag cttgaacgtg acccctacc atctgcacca gctcggcacc         840
tcacgctcgc agcgctagga gcctaggagc agctgcccgt ctatttattg gtccctctcc       900
cgtcccagag aaaccctccc tccctcctcc attggactgc ttgctccctg ttgaccattg      960
gggtatgctt gctgccttgc tctcctgttc atctccgtgc taaacctctg tcctctgggt       1020 gggttttgc tgggattttg agctaatctg ctggtcccgg tagaaaaaga tcatgtcccc       1080
tgacgtgctc aagcgctcgc cttagccgcg tccttgcccc ccgccatttt ttgcggtttc     1140
ggtgtgttcc cgtgactcgc cgggtgcgtc atcgcctgaa tcttgtctgg gctctgctga     1200
catgttcttg gctagttggg tttatagatt cctctgatct aaaccgtgcc tgtgctgcgc       1260
acagaactct cccctgtcct ttcctggggt tttggttacg tggtggtagt aagcttggat      1320
ttgcacatgg ataaagttgt tctaagctcc gtgggttgct tgagatcttg ctgttattgc      1380
gtgccgtgct cacttttttt gcaatccgag gaatgaattt gtcgtttact cgttttggtg      1440
gattattagc gcgaaaaaaa aactctttt tttttgttct tttactacga aaagcatctt       1500
cttggatttt gctatcttct tttactacga aaaactcttg agtctaggaa tttgaatttg      1560
tgatgtccat tcttgcagtg cgctgtgctt tattgggaag ccaaatccta ttattttctg     1620
cctctagggt ctgaatggaa tcagtactct tgagacagaa aatcaatcca atcaagttga      1680
tttctttctt taaaaatatt atcacagaac taagtgcttg tgcggaatca gtactggctt       1740
ttgtttggtg gaggatcaat acttgctttt gtttgggggt ggcaactgtt ttgctataag      1800
attccatgtg ttcctgttga gatgaatcat atatagtata gctgcatact acaaatctgt      1860
ttttcaaatt taggttgctt tggcatgatc tatttttttg tcagacagac tttctaagtg      1920
gtagctcttg atttcttgtt cttgtacaac tggtgctgct gaatcttgac cgtatagctc       1980
gaattgcagt attctgaacc atcgagccaa ggctgccaag ctgactcgcc tccacagtct       2040
tcgcgaacgc cttggtgcca ccttctcctc ccatcccaat gaactgatag cactcttttc      2100
caggtgggct taccaaaatc atataacttg catttcattc ggtactgaaa gttgttaatt      2160
tgttattctc ttcatgcctg tcttaatagc acacccagat gtaaacacga gattatgcaa      2220
cttcttactt ggtttctttt gttggcacca tcatgcatgc taattgctaa ggatgttacc      2280
tattcatcct tgactcatat tatcatatgt aatgatttta tgatcacgag actattgatt     2340
gtgaagcata gtatagctgt tcttcagttt ttgtacccctt ttgttttttt ccttaagcta     2400
gaactggtac aatttagttg ataagacagt gtagtttgta gtacgtcatt tgacagattg     2460
tttgtcttta gctggtaaag tgccatttaa tatctgtatc cttcagatct aataaaaagg     2520
atatgagatg tccatcacaa gagggaaaa attacatgat ctgagatgta acatccgttt     2580
```

```
ttatttgtga ataccactt ctacaggtat cttcactagg gtaaac         2626
```

<210> SEQ ID NO 6
<211> LENGTH: 2510
<212> TYPE: DNA
<213> ORGANISM: Zea mays

<400> SEQUENCE: 6

```
atgccttacg atcatctgac atcttaaata tttcaaactg cagtatttca aaaactgtgg     60
ttttgtcaaa aactttgttc ccaaactgag actaaaatgt agtgctagat aataaggcct    120
tacccgttgg aatgacaaaa aagaaacaga aacacctga aaaatagtat tgccttggct     180
ctaaattata aatcgttttg gttttatttta atatctattt tttaagcata ctaaaatcta   240
tgtacctatg aaaaataaaa tatgaactac aatttaagac tgagtacagt gtacagcgat    300
aagttatatg aaccacaatt gttttgaaa ggaaaaaaac taaattgaca agagaaacaa     360
tcaactcttt tagaaacttt gtataccaaa aacgaaata aagaagaaga aaaaaataca    420
cacgatgagt ttattagccc acaaaacatg aaaaaaaatg agagttaaag cctaactcag    480
gcccacaaag aatcacaagc gcccatattc acagccgccg aaaggtttcg gcccccagtt    540
ggatctcaga gcccagtgtg aaataggact gacttgtctc tgatggttac gttacgtagg    600
gattgaaaca acaggcagt gagccgatgt ggcagaccgg agcgcagaag cgacgacgac     660
catgaactga aggcgctggc agtgggccat gcgcccagaa cgctgacgaa ccacgacgac    720
gcggacgttc tacgaggtcg gtggggccgt cggcagcccg ccggagcata ttcgccgtcg    780
acagaggcag agaaggggaa tgtgtgggag catattccac ccgtgggaag cctcggagtc    840
ggagatgtgc agatctgccg gacgcacatg cgcacagctg ccgcaataga aaccagtgtc    900
ttttattttt attttataag aaaaaactag aaaagaaaat ccagtcttct atacaggcct    960
gcacagagag agaggaggga aggtcaaatc gtagaaaaaa aatgcttcct tttattgtta   1020
cgacattggc ctgaatatat actcattgtt tctttcctta acttcaacaa ttattgattt   1080
tgacaatcca ttttttattt tagttcgcca aggttttggt tggagaagaa tttaaaacct   1140
agccaagcag tcgagcacga gagccgccgc cgccgccgcc gccgttggca ggacctgctg   1200
acctctgacg accggacacg gacgttttcc aaagtccaaa ctcggggtag gtaggtcgtg   1260
aggctgctgc gttcgccaag ggaagaagca tctagttgaa gctagaaacg ggcagggggg   1320
aggggccgac gctatcggaa atctgaagcc cagcacggac ggacggacgg gcaggggcgg   1380
cggcacatcc tcgtctgacc gccgcgccgc gtccgacatg cgcaagctgc tgctcttccc   1440
gcgcccccac ggcggccggg ccggcagagc acggacgcg cggggcgggc ctgacgtcgt   1500
tttcacgtgg tccgtcaccg ttgcttgcat agcgtacagg agtatagtcc catttccgaa   1560
accaaaaaaa gtaaacaaaa aaatgccgtc gcattagttg gctggcaagg gaagaccaag   1620
atggttttca aatcaaacat gtaaaaaaat gtttctttct ttttttgaacg aacttaccag   1680
ttcgaattct ttaccggcat tattggttta aattgttccc caagaaagaa agaaaagaaa   1740
agcgggggga aatatgcctt ccttccttct tgcgtcacag accacgcgcg gatacaccgc   1800
acaacagcca ggcagcaagc agagcaccca ccgccggaag cggccgtcgg acagaacgac   1860
acgtggggca cggcacagtc cgggcccgca cgtcatcgaa gacacctgac ctgcccatgc   1920
gtcttctaga gaaaggcgga cggacaggtc acccccgcac ctcattccag gagttgcatt   1980
tcgctttctc cttatttat ttataccaat aaaaaataaa tccgccttttt ctcctcccta   2040
tcgtgtgtct tcctctcgcc ggctttaaaa acgcacacaa gcgctaaaac cctctccacc   2100
```

```
gtccacctca gctcccatat ccgctcccct acctctccag catcctcccg tctccgtcgt    2160
ctcgtctccg ctcctcacct cgccgctagc caagggtaac tcctcgctcc cggccggccc    2220
ccgcgtcggg gttttccatt tactactact cgctgctccc tcctgctccg tgctcagact    2280
cagatccgac caaagcggtt tcgctgacta aattctcctt cgttttttt tcttttctg     2340 gacggattcc tggacgcagg caagatcaag atcggaatca acggtgagtc tgtaccccca    2400
acacaaactc gttcttcctg ctcggttcgt tgggtctgga ctctggagtg atctgagtgg    2460
ggtctctgcg cgcctgcgtg ctcaggtttc tgaaggatcg gcagtaaacc              2510
```

<210> SEQ ID NO 7
<211> LENGTH: 2046
<212> TYPE: DNA
<213> ORGANISM: Zea mays

<400> SEQUENCE: 7

```
aaatgaatta atatattatc taaattcaga cgggaaaaag agagaaggaa tcaggaaggc      60
tgagtgcaat attagttttt cattgagcac aatcttatta tgtttgatga acatcttgaa     120
caaagtatga gtggaaaaca acacttatgt tatatctgca gcacagattg ttagaagtga     180
aggctacctt gagatggtga taggtctctg aacccatctg cattgcttct tcgaagttca     240
tagcaccaac aagaagaatc ataatttcct acaaataaga aatgtttata gttactccaa     300
aactacagtt aaacatattg atatggttga tatacatgaa caactaactg tcttaatatg     360
tttctgttta ggcaaaagat gacacaagtg gacaaagtaa gggaataatg cattcaactt     420
ctcagactct aaaggtttgg atgaatactt gaatgggaag accatttcca gcatgctttc     480
caccattaat gactgtattt gcagggacag gaagagttgt agcgcttttg ccaacaagat     540
ccgctatatg cttgtagagt ggaacctgca cagcaacaag catccaatga tctgagaata     600
agaattatgt gcggtggcat gacacattta ccaaattatg atgatttag cagaagagca      660 gcacctcttt ttcagcagca ccagctttgc aagctgcaat tgacactgcc agcatagtat     720
ttgctccaag ctcagcctgc atttcgcaca atatcatatc tatttccatt tggataaaat     780
ctatttgcca gaaatatggg aacggaatca agatacagaa aaaagttgag gctgtagtgg     840
taagtgggaa cacaagtaca gtgaaaagat agcattattt tccgaacagt caaattaacc     900
gaaataagta gtatcacata ctgaccctaa attgactaca cccaatgtaa agaattgctt     960
gtgcatattg agccatcagt tgtttgtttg tgtaatggat ttgacaatgc agaattcagg    1020
agcaaaaaaa accgcaaagg agagagaggg aaaggatctc cgagtatccc acctgtggcg    1080
cgccttgtca gtccatgat ggcctggtcg atctgcgcct gctgctgcgg atccatccca     1140
acgagtgcct ccgacacctt gtcgttgatc acccgcaccg gtaggcgac cccctggcg      1200 aggaacttcc gcctctcgga ggccccggcc gcgtcggcgg cggcgcccac gagcgcgccc    1260
acgctagccg tagatgctcg gtgcacggcc ttgttggtgt gcaactcgac ctcaacggcc    1320
ggtgcgctac gcccgtcaag gatctggcgc gcccgcaccc tcgtgatcac ggtgggcgcc    1380
tcccgcctca tgtggccgac gatgaaaagc gccgggtcag gggccttggc gcggagcgcc    1440
gtattcaggg cctcctcgct cttgcgcgag agcaggtgct ccccaggta tcctgcact     1500 gacatggctg ccacagcggt ggaattttct tgtcctcacg acttcgccac gtcgtcctca    1560
cctccctggc ttcccacgac tccgccgtat cgaggtgctc ggtgggtcgc cttaatccga    1620
agtccgaact aggaagacga gacagagagg tctgaggaat gggcctcgtt tgatgttgag    1680
```

| | |
|---|---|
| ctgaattatt tttccagcat aagcccaggt cttggtccat gaacaaaatt actagaaacc | 1740 |
| cagcccagta ctacgatcta aaagagggac tgccactgga tagctctctc tagcattctc | 1800 |
| cacgctccaa tacagcggcg tagggtctat ccgggtctat ccgcgaacac gtgagaactc | 1860 |
| tccagaaact gctttctcct ccacttcatc tctctcgctt tccctctata aaagacccc | 1920 |
| ttctaggaat tgagggagac agcaagcagc gatccgaagc tcaatcaatt cactcaaacc | 1980 |
| tcttccccaa atcttcgatt agattctcgt tgacaagaag actataaccg aacctgaccg | 2040 |
| taaacc | 2046 |

<210> SEQ ID NO 8
<211> LENGTH: 2489
<212> TYPE: DNA
<213> ORGANISM: Zea mays

<400> SEQUENCE: 8

| | |
|---|---|
| tagtcaccac accatgatca tcttgtttgt tgtagaatac ccacttgtta cctacaacaa | 60 |
| tttggtttgg acgtggaact aaatgcaaga ccttattcct cgtgaagttg ttgagcacct | 120 |
| cttgcattgc caccacccag tctggatctc taagtgcatc ctctatcatg tatggctcaa | 180 |
| tagaagacac acaagagtaa tgttcacaaa atgagcaac ttgagagcga gtgattaacc | 240 |
| cctttgaat gtcaccaagg atggagttga cggggtgata tcgctgaatt gcttggtgaa | 300 |
| ctcttgagtg aggtggtctt tgatcttgaa tctcttggtc atcctccttt tcttgaacaa | 360 |
| cttcatctcc cccttgattg attcgttctt cttgaggtgg ctcattgtct tgaacttgat | 420 |
| cttcttcttc ttcttgagct ggttcctcat cttaagttgg tggagatgtt tgtatggaat | 480 |
| atgatagttg atcatgtgct tgtgaaggct cttcgggttt ttgtggacac atgtctccaa | 540 |
| tggacatgtt tcttagcgcg atgcatggag cctctttatc atctaaatca tcaagatcaa | 600 |
| cttgctctag ttgagagcct ctagtggaca cacatcttcg ggttaaatgg ttttatggaa | 660 |
| tatttttct tcacagatac aaatagtatc gaatatttca gatatttcat ggttttgtcg | 720 |
| aatacaaata taaaatcgga tagagaaaac taaatttaat tatatccatt tccatccata | 780 |
| ttaaaattga atacggatat agatatccat attagcattt tatttgaata cgaatatata | 840 |
| taatttggat gtctagacat tcgaatccat ctctaattag tgtgggaatg agggacactg | 900 |
| aaaaacaatg acgtgcatgg tgacatcata caatagtaca attctgacga cgatgaagga | 960 |
| atttacgtgc ggatcagcga caccacctgg tttggtggtt cctgtcgccg gaggcgcaag | 1020 |
| aaataaagag ggcacataac tacgtgaaat caagcccaat tagtctgcct tggctcccct | 1080 |
| atgctgtttt aaaagtttta gggttaagtc attagtagac tgttgcgggt ttagaaattt | 1140 |
| ttagagaatt ttgtttacaa cagcccctaa actaaagttt tgggaacaa attttagtag | 1200 |
| tcttttaagt tgctctaaga ctatattttt ttagttgagg aggacagtga caattttgga | 1260 |
| gttgctctaa aaccatgttt tttagtcgag tgggacagtg gcaattactt aactacaatg | 1320 |
| cacaacacca ggaatccagg atgaaaaatt actacaccga gggctagttt gggaacctca | 1380 |
| ttttcccaag agattttcat tttcccaaag aaaattagtt tattttcct tgggaaaata | 1440 |
| gaaatccttt ggaaaattgg agtttccaaa ctagccttga ttttttttcc taagatatgt | 1500 |
| gcagatcttt ctttgagagg acacaaaaaa aatggattgg gattgggctc atcgaaggcc | 1560 |
| gaatattcct atccatcgtt cgtgccggat taggcccaga accagaaaag agctaggccg | 1620 |
| ggctgcagta gcactatcct ctgtttcaca atattatgca cttttgatca ctttatttat | 1680 |
| gtcaaaaata cttgatacat cacgttttat tttcactttc gcctctataa aagtattaag | 1740 |

```
ggatttctag acaattcaaa atgtaatttt ataagactat gtttgtcatt ttataaaaaa      1800
aaatagtttg attattttgg tgaacgtgcc ttggtcaaaa tttgtgggaa cggaggatgc      1860
tatcaaattc gtctgcgcag atgtacgccc agtaacgaag tatcgtcaat cgactgatga      1920
ccccgtcacc gtcagcaaga cagcaactca acattcaaat tcgaccgtaa taacatccac      1980
atacatacac ggagtatcaa tctagactag aggagacggg tgaacgtggt gagcctccgc      2040
ccataatgca accctactag tgctagcttt cggccgcgaa aaaacgtccc cacccccacg      2100
tctcaacttt atagccgccc cctccccacc gccgcggccg ccacgcgcag cagcaacccg      2160
gtagcaggag cgcagccagc aagctcaggc ccccagccct actgccaccg cgccgaacga      2220
caaggccgag ccggcggagc accgtccagc tgaggaggag gaggccgcgg cggccggcga      2280
ggatgaggac accggcgccc aggtcgcgcc catcgtgaag ctggaggagg tcgccgttac      2340
cactggagag gaggacgagg acgcgctcct ggacttgtga ggcatccgcg gccgcttcga      2400 ttccccccc tccccgatcc gatttgccca tgtcttgttg atctgatgtg cggcggctgt      2460
gcaggaaggc gaagctctac cggtaaacc                                        2489

<210> SEQ ID NO 9
<211> LENGTH: 2320
<212> TYPE: DNA
<213> ORGANISM: Zea mays

<400> SEQUENCE: 9
tttgtattgt tgtatgtaat gaataatctt tatatatata tatatatata tatatatata      60
tatatatata tatatatata tatatatgtg tgtgtgtggg ggggtgtggg ggtgtgtgta     120
ttgatgtctc ttggacaaca agattacaca aaacacaatt agaataaaaa aatatcctcg     180
tgtatataaa cttgtccgta taccatatta gaacacataa attttaggca acattttttc     240
catcaacatt cttcaatcat caaccaaaat ttacggatac acaagataag aggggggtatg     300 taaggttgta cgtaatgggc tacatgataa catcaaagat tatgcaagca aatctcaatc     360
caccaggcga tcataaacat catagttcac atgcttcagt tttaaagcca tcgtagttcc     420
cgtgcaaaga caaaaacatt agaattattc aatacaagtt gcacaagata gttcaataaa     480
atttaaacca caatagtatt atccaacaaa gctagttcat accattatag tttctagtaa     540
acaagaatag agaacatata ttaagcaaac agaccacata ggataaggct aaggatgtat     600
ttttgtctat tgttttctgt gacatcgatc tcgtttgcac gagtaaaact aaaacatgag     660
aaaattccga taaaaatag gaatctagaa atacgaacgg aaaacactaa accatttta     720 ttcctgtttc taaatatat catctcgttt ctgttttct ctgtaaatat gaaaacgatc     780
agatcatagt taaaacggaa tacagtaccg gacgaaacaa tatttctctc tcgtttcccc     840
cttatagcat ctccaaaagc tccccagaag tctccctaa atctatttt ttggaaaaac     900 acaaaaacat gtctccaaca gttcctctaa agcgccccca actttttcat agcccttaaa     960
actccctcat ttgtagctac aaatgagggg ttttttgggc tccccagaaa caaactgctg    1020
ctttaagatg tttggttgag gagccaagta gaatggagtc gttcatccc tgattctagg    1080 aacggagccg ttctgttctg tgtttggtaa tctggaacgg agcggctctg tttttgtttt    1140
ggttgcagag tgaacggaac ggagcgtgac tgtgagagcg ggatgagaac ggagcggctc    1200
cgttcggttg atttttgga gcggaatggt tccggattg aggagaatat tccataattg    1260
gagtcattcc gttctagttc ctttataacc aaacagcaac aaaactggga tagaatggtt    1320
```

```
ccgttctact tggctcttca accaaacact aactaaggga cctgttggag aaatgattaa    1380
aatttaccct cacttattat ttagatattc cttaaaacta attttgagaa gtcgttttat    1440
ggagtgctct tggagatgct cttagttcgt agatctgatt gtgtgtatgt atgtaagcat    1500
atgcgtctgt actacgatcc acggtaaaaa agtcacaaac atataataat agcgtcattc    1560
aataaattga taacgtaaag tataaatgaa cttttaactc tgtttgagta aacaactcgt    1620
gcagagactg caatgaaatc tattatttt tctaaaataa ttatacaagt tgaggaaatg    1680
ctatttgttc cactaagcga cgatgtattt tgttttttaa aaaaatcgac gaggtactgc    1740
tcggttatta ttttcacatg caccgcgcgt tgttttggg ccggcccatt tgtattgcga    1800
atttgcggag acgaatatga ccgaatggag tttagaaagc ccagctcact taggattgtc    1860
tattttctca agaaaagaga gaatgggccc aaaggcctaa acaccaaaac ccgatccgct    1920
tatgggatgt catggacatg gagtctggga ccgtccggca gatgagacga cagccgtcgg    1980
atcagaaacc ctagcgcggg aggctctccc tattaatacc cacccctgcac ccgcgggag    2040 gagtcttttcc tagggtttcg tagcttctag ccgccgccgc gtccgcctcg ccaagcgcag    2100
cagccgccgc agcacatcgc tctctcgatc tcagccatag cggaggtgga gcagcaacag    2160
gacacgccga agctcttcaa ccgctggacc ttcgatgatg tccaggtacg cgaacgagtc    2220
ttcgcatctc tgcatgcttc gattctttag ccttgccgct actagcagtg gatggaaccg    2280
acgatgaaat ctgcaggtga acgacatctc gctgtaaacc                         2320

<210> SEQ ID NO 10
<211> LENGTH: 2686
<212> TYPE: DNA
<213> ORGANISM: Artificial Sequence
<220> FEATURE:
<223> OTHER INFORMATION: Includes maize-optimized Kozak sequence.

<400> SEQUENCE: 10
ggatcctgag gtgtggcttg tatgtttcct gaccccctgg tggtgttccc agtttgcaat      60
acatcatttt ctgtagccct tgtacttgct gtgatccctg tttattgttc agggaaaact     120
tagtgcagtg tattagaaat atagaaacct cacatttcga agagcagaat agtgtttgat     180
aacagttttt ttaacgcaac aacgtttgtt agactgtgtc cagcggccag cgggtagtgt     240
aaaataggtg acgcgaaact atatgtgata ttgtttgaca ctatttgcag agtatagttt     300 aaaataggggg gtgtgagtaa tctgctgaag atagccttaa gagttaagat accaaggtat     360
agtttatcat atgcaaaaga aagaaaaaa aaggaaatac aaaccattgt ttttatgttg     420
gttagagcta ggtaattatc tcttgaccag tgtatttcca aacctgttct tctcagtttc     480
tgtgctccgt cgatactgaa cattgttgtt catttctcat ttgttgaacg atggtatttc     540
aggagctaga gaagaggaga gaggagcttg agtctctgtt aactgctgac cggatccgct     600
gcgtttgggg gcggcaggat ctccgaccgg atccgcccgc cgtgcccgcg accggatccg     660
ctgcgtttgg ggggggcag gatctccgac cggatccgcc cgccgtggcc gcaaccggat     720
ccgctgcgtt tggggcggca ggatctccga ccggatccgc ccaccgtggc ggcgaccgga     780
tccgctgcgt ttggggggcgg caaggaagcg ggtggggctt ctagggttca ggtgcgggc     840 gtcggggtag agagtgcctg cggcgattct ggcgggcatg cgcagggtgg ggcaggggtg     900
tggtcgagcg ggccatgcac aaccttccat ccgcgggatt ttgcgggcgt tgctggcgcg     960
acggatttgc aggagttgct ggcgcggagc tttgagggcg cggccgattt ggggactgcg    1020
ggcgttggcg attttgcggg cgttgctggc gcggcagatt ctgcgggcgt tgctggcgcg    1080
```

```
gggactgcgg acgcgacagc tgtgctcgcc tgcggccgcg aggaaggcga cggggactgc   1140
gggcgcgggg agggaaatcg cgggcggagc gcgcgatggc agaacacaca gaactatgga   1200
cgcctacact aaggggtgt ttggtttcta gggactaatg tttagtccct tcattttatt    1260 ccttttagt atataaattg ctaaatatag aaactaaaat aaagttttag tttctatatt    1320
tagcaatttt agaacaaaaa tggaataaaa tgtagggact aaacattagt ccctaaaaac   1380
caaacacccc ttaaatacat aagaagtagt agagattatt attatttgtg tctattgata   1440
tgatcattat gatattatat tttactgttt taatctaaat atagttatta tattcagata   1500 attatttat taaatccaaa aatatttaac ttctaatgta ataaggagag aatactctaa    1560
tatcataata atttcttcta aagtgaccct cggatttgga gatgactgac agggagggct   1620 gtgcacccett ctttctttcc ttttcaattg aagaacttgg gttgtgcttg ctcacacaac   1680
cgaatgaccg atgcacaccg acgcgcacgg agcggaccag cacagcccgg aaactgccct   1740
acgccgacac gttttccggt gcggcccagc agcagcaggg aggaaggttc gctcggtcgc   1800
tgggcctggc tccgcgtgcc gtccctccta taaatgcgag tcctcgccga gtccactggg   1860
caccagaagc tcactcactg ctcgttgccg gctgccccg cggccccggc cagtccatcc     1920
cctcgctcgc tccccaactc cagcaggcag atcagataca tccatccatt cgcgcaccgg   1980
aaggtgagcg ccgtgaacga accatccgcc ctgctagctg cgatctgtag ccttgcgtcg   2040
ctttcgcgcc tagatcgtca cgtcacctat cacgatccgt gcggttctag atctgtggtt   2100
tttccttccc ctggtggtcg aatccttcca tccaccagac caccacggga cctcgtggat   2160
tccttttggt tttcctgtgc cgagagccaa aatcgagggg gggggcttgt ttttttattgg   2220 ctcggtctcc cgctgtctcg tgatctgatt tgctgtagta atcagcagga aaggaagggt   2280
tgaactaaga gcgccgtggc ggtttcgtcg tcgctgaacc cggacgcgcc gctcttcatc   2340
ccggcggcgc tgctgcaggt ggaggacttc tcgccgcagt ggtgggacct catcaccacc   2400
actgcctggt tccgcgacca ctggtcccgc gagcgcgccc acctggacga gatcgccgag   2460
cagatcgacg cggccggcct cctccccgac gacgaggacc tcttctacga cgaccaggtc   2520
gagcagggcc ccgtcgccgc cgcccttaag ataggtactg atgtctctct ctctctctct   2580
ctcttactct cccctcgatt ttagatctgc ctgaaggacg aatcatagtg acctcacgtt   2640
ggtgcgtttt tctccaccag attcggtgct caaggcgctg taaacc                  2686
```

<210> SEQ ID NO 11
<211> LENGTH: 7672
<212> TYPE: DNA
<213> ORGANISM: Artificial Sequence
<220> FEATURE:
<223> OTHER INFORMATION: Includes maize-optimized Kozak sequence.

<400> SEQUENCE: 11

```
tatagaatag ctcactatcc tatttattat agtttaagta tatagccaat attttaaatt      60
tactatttat taaattctag ggaagatagt ctcaattcat aactttatta taatacgttt     120
gaaattttaa atctttagga aattttctta attcacctag atacgattct ggagtgttac     180
aagctgcgaa tatactggtg ccattgagta tacataaatg gatttaggtg gtgctcaata    240
ggtgaaaatg agatactaat cacttaaatt tcaaaatttc tatggtgcca ctgtactcgg    300
ataggtctat ctagggctgg acaaaatgct cgtggctcgc tggctcgctc gtttcgtggt   360
cagctcggct cggctcggat cggctcattt gaatttgtc acgagctgag ctgacattct     420
```

```
agctcggttc gttaacgagc cagctcgcga gctaaacgag ctaccatatt ctagtaaaac    480
gaaattatat tcatatcatt tatagaataa ttgatgaaca tgttatatat atgtgagatg    540
tctatggcct atgaattaaa ctaatgatta atgaactatg cctatgtgtt aatttggtct    600
atgcaaatat aattatgggt taaactgatg aacatgcatg tgaattgtga attaatgagt    660
gatgaattgt gctaatttgg tgttatattg acatggtttg tgaaactatg agtataatta    720
ctattttcta ttgttaaatt agtttgaaat taactaaaaa ataattatta tatacatttt    780
attttttttc tgctctggct cgcgagctaa acgagccagc tcgacctcgt aaacgagccg    840
agccgagctg actctgtggc tcgttacctt aacgagccga gccgagctgg ctcgttagct    900
taacgagcca gctcgaactc ggacgagccg agccgagctg gctcgttatc caccccctagg   960 tctatctagc ttctgatgtt tgcaaacctt agagttggag tgttcagcca gctactcctt   1020
tgctttgctg aataaccata ccaaacacgc ccatattaat acccgctcgg cggtggttct   1080
gcaatcaaac gcaggccgca gtcgcgtgcg gaactagagg tccttcagag aagtgccgtg   1140
ccagtgccac cgccggccgc atcatcgttc cgcccccctg gtacgagcac ttcgcagagc   1200
tgcaacctac atccctttta cataaatcta ttgtctcgta ttgccgttga cgccggaata   1260
gtcttcgcat ccctttttaca taaatccgat gttttctttc tccgattcct ttgaggaatc   1320
atcacgggtc agggcaggtg ttctgccgtt tgccctttc tttatattct ccttagaaga    1380
aatatttagt tggaggctgg acatagccgg aggagctaac taatcgagcg tgtactggc    1440 aaaacaaaag gagcggagca agaaggggga gaaaaaacta gccactgccg gagcgctatt   1500
ggccgtgttg ggcctggaag cttgcatcaa tacttccctc gccccgattt ggttccaaaa   1560
tcatacaagt cccaaagttg tcaagatatt ggaggtatgc aagcgacttg gatctcaaaa   1620
tagaagaaat ttcggatctg agcacaaatc tgagttgaaa aaactgcaac tcaaaatcat   1680
caaaaaaaga agaagaaaga aacgaatata ttcgctcctc ttctcagccg aacccaaagg   1740
aattgaatcc aaaccctggg taggcagaca gtgagatatg gaggagagca ggaggcgaac   1800
aagagaggct gcggccacga atatctcacg aacaagcaca tcatgggtcc acggagcggg   1860
cagggtgacg ggctcccgac ggcgagctac atctcggaag agcaccaggg cagcatgtcg   1920
tgttgggcag gttggccgtc tggcggacgg cggacggtga ctcgtggtca gggtgcacct   1980
gctcgattaa ggcgcctgac tactcatgtc ttggtctctt tgcttgtgtt tgctatatgc   2040
tgctcgtacc tcatgagcat actaagttga ctgctcagtc tgctgagtct gttttttctag   2100 ggtatagtgc tgagcacaag ggatatcatt gttgggatat gattgctcgt tggatgaggg   2160
tctcttggga tgttgtcttt gatgaggctc attcttttta ttcttgtcct tctttcgatg   2220
ctttgtcaac atccttggtt gatcccatct ctttttctata ttttctagat gcccgtgtta   2280
ctattggacc tgcctcacgc ttggtgcgcc cacgatagta gccttagctc cttctgacat   2340
gttcatctct ctttcggtgc cttccttttgt ggtgccttct atagtgtttt ctttggagcc   2400
tgctgcttta gccctgact acgctatgaa cacttgtcta cacccgccgg gtcatcaatt   2460
cttttggtac accatcatcc tctcatgcgt tgccctctta tgatgtgcgc tcttctgcaa   2520
ctcattcatt tcttgcgat ttacctttga ctgatgctcc ctattcatct ctggatccag    2580
cttcctcagt tgactctttg ctggagccac ctcttagacg gagtcatcgt tttcgtcagc   2640
cacctaatgg gtactctcct tcaggtttag tcgctaccgt tctttctgag ctgacttctt   2700
atcatgatgc tattcttcat ctgtaacgac aacatgcgat ttctgaggag attgctactc   2760
ttgagcgcac tagcacgttg gaacttgttc cttgtccatc acgtgtttgt cctatcacca   2820
```

```
gtatgtgggt ctataaggtc aagacccgtt ctgatggttc tcttgatcgc tataaatctc    2880
gtctagttgc ccaaggcttc cagtaggaac atggttgtgg ctatgatgag attttttgcac   2940 ctgttgctca tatgaccact gttcgcactc ttcttgctat ggcctctgtt cgtgcgtggt    3000
ccatctctca tcttgatgtc aagaatacct tccttgatgg taagctactt gagttctata    3060
tgtagccatc gcctaggtat tctatttctg cttgtatggt tgttgtcttt cgccgttccc    3120
cttatggcct caagcaggct ccacattctt ggtttcagct ctttgcttct atgataactg    3180
ttgttggttt ttctaccagt aatcatggtc ctgcactctt tgtgtactac ctcctctcgg    3240
ggtcggactc ttctttatgt tgatgatata attatcactg gagataacct tgagtatgtt    3300
gactttgtta aggcacgtct tagttatcat tttctcatgt ctgatcttgg tcctctgtgt    3360
tactttcttg ggacaaaggt ttcttctttg tctcagggcc tttatctatc tcaagaggag    3420
tacattcaag attttcttca tcgggcttct cttaccgatc actagattgt tgagactccc    3480
aagcagctca atcttcacct tagtgccgat gatggcgagt cttttcccga ccatactcgt    3540
tatcgtcaac atactgtagg aagttttgtt tatctctgtg tcactcgtct tgacatttca    3600
tatgttgtgt gtatcctgag ttagtttgct tcagatccca tccaggtaca ctatagtcac    3660
ttgctttgtg tcctacaata tctttgtgga accatatcta gatgtatgtt cttttccacat   3720 tctagctcgt tgcaactgca atcttgttct gatgctactt gggctagtga ttttttcgat    3780
agttggtctc tttctcaata ttgtgttttt cttggtggtt ctctcattgc tcggaagact    3840
aagtagcagg tagcagtttc tcgtttgagt accgaggctg agttgcgtgc tatggccctt    3900
gtgactgcag aggttacttg gttacgatag ttgcttgagg attttcatgt ttctgtttcc    3960
atgacgactc cttttgtctg acagtacagg tgttatcagt attgctcgtg atgcggtgaa    4020
gcatgaggtc accaagcata ttggagttga tgtttcgtat acacgagctg aagtctagga    4080
tgatgttatc ttgatttggt atgtgccttt agagcttcag ttggctaatt tcttcacgag    4140
ggcacaggct cgcgctgagc ataaattttt cctctcaaaa ctcagtgtta tagatccacc    4200
ttgagtttga gggagtatta gatagatatg ggtttatttg tattttttcca ttttataagg   4260 gtattagata gataggcaac gactgctatg caagtagtca ttctgtgcaa gcgtgcaagc    4320
aaaccatctg atccattata tcgtgatcca accgtgggtc acatttaaca cttaaaccct    4380
tccaccacca actcaataat cttataaaaa aaccccctaa caaacaatgg ttatatctgt    4440
ggttggatcg taatctaata gatcagatgg tttgcttgta cgcttgcaca gaatgactgc    4500
ttgcatagca gttgttgcct agatagatat gggtttattt gtattttttct cttaagggtt   4560 tttgtgtata tttgtactca tgtacctata tatttgtgct agttgacccc ataatgaata    4620
gacctgctat tcataatatt tgcaaaccat gaaaatttga ttattacgaa ctatccaaat    4680
actcgaacac atgggcatta tagctcacaa aaatggaagg ttgagctgct gcttgaagaa    4740
cctcaacatc tttgaacaac aacctcaacg aaacttgtat atgaaccaac ttccaaacaa    4800
tcccttgtgg aaggatagta atgacttcag ggcattgatc acacatatcc gacggtggaa    4860
ctactgtaac aaccctcttt tctgtggaat atagttgaaa ctctacaact tgaccaaaac    4920
caagatgacg acatatggtg gaactaacaa acaagagga ctacactacc tcattagctt     4980
attaagcaca atctcttggc accacaacaa cgaacaacaa aaccatcatt tggatgctct    5040
gtgggcgact aaatgcaaat tctttgcatg gttgatcatc ccaaattggt ggcacttagc    5100
tataggctag cagtgagagg atggccgaac aacatgcatt gtccactatg ttggtgtagc    5160
```

```
catgagacca accaccacat aaatgccaaa cgttcattca ccaaaaaaat ctaggcaaca    5220
atggcttgga tttcttacct gcagctccac caagctaact ggagttcaat taggtcaacg    5280
tatgggtggt ggtcgagtat agcagtcaca aatgatgttc taaagatggg gttgtgttaa    5340
cacatcttgc ttgtagcacg agaacactgg aaggagtgaa accaaagaat ctttcaacac    5400
aaggacctat caacgctatc catgattggg aaattcaagg acgaaactag aatttgggtg    5460
aacacatgca caaggcacct aggagagcct ttcttttgta ctgttaatcc cttttttaaac   5520 tctctctgtc cttaggagtt cgtttcttcc gctctattca atgaagttag gcacaatctt    5580
gtgtgatttc attagaaaaa cacaagtaaa ttgcatggtc agtacttgaa gtattacagg    5640
aatctcgtct gcccccaaac tattaaacct tatatttggc tccctaatgt acttaactga    5700
tctcattctg gtcaaactaa acatggtgat ggcaaggagc cgatatggtc gcccatgtgg    5760
atgtgattta agcaaaaaat ctcatggtcc atagctgtgt caacaagcca acatgccatc    5820
gcttccttat gccgagactg cccatgtcgc tcgcttttac tgtcatcatc atcaaactgc    5880
ctgtcatgtc tacggatgcc atgaccgctg tcacacatga tgtggagatg aacctgtcca    5940
tcaacttcca cgtgctgcca ctatcgctag ctgacaccgt cttggtcatt gctgtgtagg    6000
gctaggctaa gagtcgctga atgatccttt cgctctcctt tacaggaaca tgctgtttac    6060
tttgtgtcgc caaggcgtgc tagagtacct cttctacacc tccagcacca gtagccttat    6120
tgttagcttg cacatcccac ataagcaggc cgatgtgaat gataacttca gggacgtcga    6180
cggcatgtca ctgccaagag tcatttggtg ggaagcgttg tcatgccatc tgtcgtgcca    6240
ttttgtcctc agttcgaccg ccattaccgt gagcacaacc tttgcgcatg ttggccgct    6300 tccatcaccc ttattccgtt tcctcgtgtt ggtcttgccc caaggctatg gttagcagac    6360
cgtgcatatg gccggcaaaa gactattttg cactgtagat tgcactcttt atatagtgaa    6420
gtttaaaata ggagatgaga tgaataaggc tgctggagat agcctaaacc cttgcagctc    6480
gtgcttgcat cggggagcc aaaaggcgtc cacctccacc atcgccgaag cactgagcac      6540
tactctggct tgtgtttcag caccacaccg cagagtgctt agggccacca acctcctctt     6600
gcctctgtgc ccagagcacc atcagctctg ctgcctccct ctgttccttg tgcttgctag    6660
gcaggcaatt ccgagctggg gcccaacttg taacgctgat ttcaccatct tgccactgcc    6720
gggcaccaag tggacacatt tgacttggcc tagtgggttt tctgcataaa tcacatacat    6780
gtggatgcca tatcaggctc tttggtgttg tcgtgtctac tttcgacaag gatgagatca    6840
cttaaacata ttagggagcc aagtatgtaa tttcatagtt tagggaccta cacaaaaatc    6900
gtataatact ttagaacagc cgtgcagttt actcaatcaa cacatacaaa gtcagatctt    6960
aagctctgat acttcaaagg aatggttgag cccagttgac aaacaatctt gcttcattca    7020
ttgaattgtt tataggagtg ctatgtaac tactgggtgg ttttgtttga cctgtcatcc     7080
aaattgtgta gtcaaccata acatacacg tcacacaata cattttggat gtgacagata     7140
ggatttaggc gagagaatgt acaatgtcac tgaaaaatta ccactgtatg gaaggacaa     7200 tctaagtgaa aagagaacca gggcctaatg gtttcaggac ttcaaactcc ggccaaatga    7260
atttacagtg cttaaattaa ctcatgttaa tcatgatagc caaagcatgg gcaaaagaga    7320
aactatgaat aaatcgacaa tgtattctat atagcagtaa tataccatgt cacgagcttt    7380
tacactaatg ggctgtattt ttctgcagtt attttaactg gcaatattct atgtcacagt    7440
aatatttgtt aaatttttc cagaatagca actgaactag aagtctagta tttcttaatt     7500
ggataacaaa aggaattagt gtgcatttgg cttacgaaca atcagtcacc caacattgaa    7560
```

```
tttgaagttc tgtttcctct tgttcagac gacactctcc aaatgaatgc cttatatttt    7620
gtgttgctcc tctttctgc agagtgttca gtaacttctt ccgatgtaaa cc            7672
```

<210> SEQ ID NO 12
<211> LENGTH: 1014
<212> TYPE: DNA
<213> ORGANISM: Zea mays

<400> SEQUENCE: 12

```
aagttcgtca tgttctgttt tggtcatttg ggcaccaaag tttgcgcctc atttggttct     60
gtaatccgtg aggtcgtgca tgtacttggc gtattgcatg cagtgaataa tttagcttgg    120
gtttgtttgt tgggggcagt gttggggacg gatttggatt ggggtttatg cttggcatcg    180
cgtcgtatcg aaactcagct gctgtttcgc tgagtaatgt acatttccct ggtaatggta    240
cttgtggact ctgatgcttt tatgggaacg agtgcatttt actgccgtgc ttggccgtgc    300
tgttgaatta ttcccgtagt gtattaaata ttggatgcac cagattgttt gtcccattta    360
cgcataattt tcccgtcata tgttgaatta tttacgaatt ataaaatatg taatttatat    420 ttattttat gaagtatata aaattttact ttttgttat ataattaaat attttttgtt    480
ttgataaaat ggtatgtttt attttaaata aaaatctata aaaaagatg atatggtggc    540 tggaaggtaa cgataaatta tgtatactaa agtattaacg atagtaaata tagttggacg    600
atagatgatg tgacggggtt tgttcttttg atttaatct ataatgcttg tctatagatt    660
acagccgcat caatttaaat agctgctttt aatctgaagc gaacaaccga taaaaataga    720
cattaggcca tctccaacag ttcgaccgtg caaagtatta ttttgctatt gcactatttg    780
aataatggat tttagaatag ggagtgataa aaagtgagat aaaaagttta ataaaaatag    840
tcttagatcc aacaaatata cgctgccctc ccatcagttg cctggaccca tgccaagaag    900
tgccagccat agtcgtatga aaatgattc taagggcgtt cgcaatggtt gtcttaaata    960
gttagctatt gtgaagctga aactaagaga agaataaaaa tataatttat ttca        1014
```

<210> SEQ ID NO 13
<211> LENGTH: 1216
<212> TYPE: DNA
<213> ORGANISM: Zea mays

<400> SEQUENCE: 13

```
tacggggaaa gaaggagaag aagaagaaga agcccaggcc ggagaaccat cgcctgcatt     60
tcgatctgtt tcaccgcaat tcgcattgtt agtcgtgtat tggagttatg tgtacttggt    120
ttccaagaac tttggttcct tctcgttttt ttttccttgc ttgtttgagc gttttttgggc   180 agcgctggcc tggttcctag tatggtggga attggctgca ccttttgctt cgaataaaaa    240
tgcctgctcg ttcacctgtc ttccagagtg caatgcgatg ttctgttgcc caggtcgtgt    300
ggttctgact gatggcgatg ttgtgttctt ctgttaatcg cctgttttaa cgtggtaggc    360
tgatgcttgt tcttgttgag aaagcttgct gtgccagaca tggctgcttg aatacaagtg    420
aaggaaaaaa aaagccatgc caagtaaagt tgcacaaaat ttcaactgct cagtggacca    480
ctggaccatg ttcttggtta ttgcagttgc agggcttcac atggcgtttg dacagcagtc    540
ttggattgat gcataaagag gtggtggtta atgaggacgc aaggccgttc cctcagagtc    600
agtcacaagg ttgcagaggt cacggttctc ttccctttcc gcttcctgtc acatcggaat    660
tgttgtttac gccatctgcc catcacccac caagtctatg tttctgtact ggatctttca    720
```

```
atggcggaac gcgcttagtt cttcgtcaca gtcgaatcac atgatctaat cgatgtcttt      780
aatctcgctg taaaaagggt gggacggtgg gtgcagggta gggaccaggg aaggcctgcc      840
taaacgtatc cataaacatg cacagcaacc ctaagatatt atactgccta cttcctaaga      900
tatagttatt tctagtctat ttttttttccg tccacatcca aataagtgat aatatataga    960
catacatata tatactatat tcatcataga ttaatgaacg aatgtatact tagtttaaac    1020
ctaattatat tttaggaagg atggagtatg aaacatgaca atacaacaaa aaaaaatcat    1080
gtaattgcat atcgtcaaag ttatctgaag taaccaatcc aggggaaat cccgttagca     1140 aacatacaag agcaccgccc cactacatcc cagaaaataa aacaaaacca gaactcagat    1200 ggataaaataa tactac                                                    1216
```

<210> SEQ ID NO 14
<211> LENGTH: 1216
<212> TYPE: DNA
<213> ORGANISM: Artificial Sequence
<220> FEATURE:
<223> OTHER INFORMATION: Comprises two mutations to remove unintended
      ORFS.

<400> SEQUENCE: 14

```
tacggggaaa gaaggagaag aagaagaaga agcccaggcc ggagaaccat cgcctgcatt       60
tcgatctgtt tcaccgcaat tcgcattgtt agtcgtgtat tggagttatg tgtacttggt     120
ttccaagaac tttggttcct tctcgttttt ttttccttgc ttgtttgagc gttttttgggc    180 agcgctggcc tggttcctag tatggtggga attggctgca ccttttgctt cgaataaaaa     240
tgcctgctcg ttcacctgtc ttccagagtg caatgcgatg ttctgttgcc caggtcgtgt    300
ggttctgact gatggcgatg ttgtgttctt ctgttaatcg cctgttttaa cgtggtaggc    360
tgttgcttgt tcttgttgag aaagcttgct gtgccagaca tggctgcttg aatacaagtg    420
aaggaaaaaa aaagccatgc caagtaaagt tgcacaaaat ttcaactgct cagtggacca    480
ctggaccatg ttcttggtta ttgcagttgc agggcttcac atggcgtttg dacagcagtc    540
ttggattgat ccataaagag gtggtggtta atgaggacgc aaggccgttc cctcagagtc    600
agtcacaagg ttgcagaggt cacggttctc ttcccttttcc gcttcctgtc acatcggaat    660
tgttgtttac gccatctgcc catcacccac caagtctatg tttctgtact ggatctttca    720
atggcggaac gcgcttagtt cttcgtcaca gtcgaatcac atgatctaat cgatgtcttt    780
aatctcgctg taaaaagggt gggacggtgg gtgcagggta gggaccaggg aaggcctgcc    840
taaacgtatc cataaacatg cacagcaacc ctaagatatt atactgccta cttcctaaga    900
tatagttatt tctagtctat ttttttttccg tccacatcca aataagtgat aatatataga   960
catacatata tatactatat tcatcataga ttaatgaacg aatgtatact tagtttaaac  1020
ctaattatat tttaggaagg atggagtatg aaacatgaca atacaacaaa aaaaaatcat  1080
gtaattgcat atcgtcaaag ttatctgaag taaccaatcc aggggaaat cccgttagca    1140 aacatacaag agcaccgccc cactacatcc cagaaaataa aacaaaacca gaactcagat  1200 ggataaaataa tactac                                                  1216
```

<210> SEQ ID NO 15
<211> LENGTH: 1004
<212> TYPE: DNA
<213> ORGANISM: Zea mays

<400> SEQUENCE: 15

```
agagagatat tctgcctcc ctatcgtggg tcgtccccaa tggcctttgg tcgcagacca        60
tctttgctgc ttgtctatgc tgagaataaa tgtgaacggt gccctgacc gctggatcca       120
tgctggtttt ggacacggtt gtcttttgt gtttaactta tctgctaccg tcctgtaacg       180
aattcactaa gttctagttc ttttgtgctt tgttaagaat ataaacaatg aggtttcaat       240
tttggtggcg ccatccggtc tgattgcgta ctagtatcat gcatatctga gctggtcttt       300
ccggagtaac agttttttt tgtttcgtgt caatgattct cagcctgttc atttggtctt       360
aatccatatc ggttactact ataatgttgt cttgtctcta tagattgcag cagtctaaca       420
catgttcttg gtatccttt gggtgtgttt aatgctattt gctctgtgtt gtctttttcg       480
ttaatcggga cagagttttc tctctgtttt gacagtttcg gtggttcttt tttgtgtgtg       540
gtcagcgagt cacgaactgc tggttggcca gcgaaatagc gcagactatt atgggtcttc       600
tgctggtgaa tatggaagga cgaggttaaa ttttctgctt tgatgtgtct gccctctgcc       660
gctgtgctgc atgcatgtgt ttgggagcga agcagcgtgc tgtttgggcg tatggttggc       720
atggtgttaa attattcgc tgattcagct ttgggttatc actggttttg atggtcacgc       780
tgtgtcgtaa gagagatcgt ggcagcaaaa tggagaaaaa ggcagtgaaa caaacttca       840
gggtgtgaa tgtatgggat tcgtatggtt gaggccagga tttgtcaatt ggtcaagttg       900
aaaagtaaag gcgagacaga ttggcgagga ccgaggagag attggggttc agaaacttcg       960
gttacacttt aatcccctcc atctccctcc actcctccct tcta                      1004

<210> SEQ ID NO 16
<211> LENGTH: 1023
<212> TYPE: DNA
<213> ORGANISM: Zea mays

<400> SEQUENCE: 16
acctcggtct gcggtcgtcg tacctgcgtg gtttgaggaa cggcagttcg cctcggtcgt        60
tctgtgaaat aaaattgggt tacaagaatt atggcgtttg tcaatatggt cgtaatgtcg       120
taggatggtg gaatgtggtc acaaactttg cgtatgttgg gtctactggt ggtgtctgaa       180
tctatgtatg gatgtcatga gtttgtctac tagagttcta gttcctgtgg tgttcgtatg       240
atgtatatca tgagttaact ctatctaaaa tttcttcatt atggtatttt taagaaataa       300
attctttatt atggtttttt taaagggact atgtccatcc taacaagagc aacgtccaat       360
aattctctaa aacttaaatt taagaaccga ataaaaaatg agtagttttt aaatactttc       420
tatctaacct tatttactct tctccatatt ttagtagttt tttaaataga cttactaaat       480
ttagttactc tatatttgg taactcgaca gaatacaatc tgtgattaat ttttctcaca       540
tgtggtagct agatacgaca cttttttttt tactttttag cacatgcaca atggagtagt       600
tagattcaac acttatgaca caagtttttt cttcaccgtt ggactattat tgtcgcatat       660
gttgccaccg cgaaccaccg ctcctctata ggttatgtca atcgaccttt cctcttttgt       720
cttcgacatc atccaagact aacaaagtta gattcaaatc aaactagatg tccagactgg       780
caaagttaga tttaaaatca aactactatc tacatataag caactattag ggactaagtt       840
attttctac ttcaatagtt gttgctagca acttgctaaa cataattta gaaaacttt       900
ttagagaact attagagttg ctctaaaagg ttttgtagtc ccatttactg ttttgtgact       960
attattaggt ggagtttggg cagtaaaaag gccaaataga aatgggggtt gagattggga      1020
aaa                                                                   1023
```

```
<210> SEQ ID NO 17
<211> LENGTH: 1028
<212> TYPE: DNA
<213> ORGANISM: Zea mays

<400> SEQUENCE: 17
aggttgaagg caaacaaggg tcaaatggat gccattccat tcatttcgtt tccaaggttc      60
agcttccccg caaattttca ttgtgttttc tccgagatga atgtttgtgt tcggtgaaat     120
cagagtcgtc agtcatctac atagctttc ttggttgata gactgttatt ttaagtcgca     180
tgtttatctg ggatggctgg ggtcagcatg tttgtacaat tatttggagt tgcttttgga     240
atggtcgcgg tttgatgagt tgcctacagc catgagatgc tttttcgctc cacttttatg     300
gttcattcgt tctcaataat atgggatgct atacttgtgt tgatccatta tcttgatgca     360
tcgttgtctg tgcactgcaa caacaatacc catctgaaca ccctatcaa taaaatacca     420
tttttttct ttccatccca ctaatctagg cccactttct cactcttttc ttatccacta     480
tattgtcaat atagaatctg gggagagaga gagagagaga gagattgaga gagagagaga     540
gagagagatt taggctccct cccttcctat attcaaaata ggtatcgcct ttgggtcacc     600
tgttggaatg atttatttta gtatcgtcca tatttaattt aaacaaatgt tgaattttac     660
atgcatattg atttaaagtt tgttagttta tgagcatcac caactaagat ctctaatgcc     720
aaagagcatc tccactagtt ccaaaaaact ctctaaattt aatttaggat gttagtaacc     780
agaaattatg ctccaacagt ttcctaaatg agttccttaa ataccaac ttttaaata     840
tctctattta gtcaaacttg agaaattgtt tcacactccc aatagttgtc atcaatcaca     900
tcgtaaaatc atttgagttc gcacccgtgt acaagtggtg cactttaaat aaattaaatt     960
acgaaaatga taaatttact atcgagttag cataatttaa aaatatataa caacataaga    1020
actgggaa                                                             1028

<210> SEQ ID NO 18
<211> LENGTH: 1002
<212> TYPE: DNA
<213> ORGANISM: Zea mays

<400> SEQUENCE: 18
actgagcttg tatcctggtg cactctgcgc tggaaacttt tatgtcgctg gcagtcgtat      60
cggttcttgt tttaccaatg tttagagttt tttgagacct atatgcggtt ttggttttca     120
gtgcacaatt aaaattactg agtaatgtag ttgattggga acagaaatgt ttggtgcctg     180
gtttaccgaa ctccagttct cttgtcattt ttctttattc tatagtctgt attatgtatg     240
cgtatgagta ttgagatgat tctgcatttg aattgtctgc tttgttgctg tcgctgtatg     300
cgtaccaatg gtaacagggt agttgtggga agtagacacg gccggttcta tgttttcgtg     360
cttccgcggt tcaggctggt taagcctatg gagcgtacgc acgctcctcc cgtctctccg     420
tgtcctgcat gctggcaaca ggagtgcggc ccagcgcacg ccctaatcga cggcggtata     480
tttgtctgtc cctccatttt gtggtgaggc tattcgcaac cgttatcctt aaattttttc     540
tcctatatca ctattcccct attttttcctt atattttttc atcttcagca gcggttctcc     600
taaatactcc ctctataccc actacaacta taaatattat tttccatatc tattcatcat     660
ttattaccac ttttttttcaa ctaaaaaata ctcgcatgca tggatttac ggaaggggg     720
ctgtcacagt atcccttga tctgctgtga gagaaaaggg ggacactagg tagggtgcaa     780
ggtagggagc agcggtgcgg gtggtagcgt ggttactgca gccgctacga cgtgagcagt     840
```

| gttaggggag aggatggaag ggtggtgcgc tgctgcagat aacccgagcg ccaaacactc | 900 |
| atgggtgata attaggtata agaaaagata ttttatggtt aggagagtat agagagaatt | 960 |
| tagtggtaac ttctatggaa gatggaaaaa tagggtgaa at | 1002 |

<210> SEQ ID NO 19
<211> LENGTH: 1001
<212> TYPE: DNA
<213> ORGANISM: Zea mays

<400> SEQUENCE: 19

| gttcgctggg ggaactcatc aggaaggctg ctgcccctct tgcagccttg ctcctggctg | 60 |
| ccgccgctgt cgtggtctgc tcttccaagt cgaagtaacg gtggttcgag ctagtggata | 120 |
| gtgtggctca actgtagaag ttccttttgt atagcaagca agtaaaaaaa aaaatgacc | 180 |
| aaaaatata acaaaatgca gctgtaagtt tactgctgct ctctaagtcg tgttcagtca | 240 |
| tccagtgtgt ctagtctagg gaaaccccat aaaaatggtg aaggtggaat cccatcccag | 300 |
| tgtcataatt aaggatgcac ttcttctgta agcaaatgta tgatgtacaa tggccggccg | 360 |
| gcagtctaaa tgttacaact agctcttctt ggtgaattca ccggtccaca ctgatgtgct | 420 |
| gctatgtatc attactatcc agttagggct tgttcggtta ttcctacgcc atatggattg | 480 |
| gacgggattg gaaaatttta gtagacattt tgacttctat ggatttaaac ccacccaatc | 540 |
| ccctccaatc cacatggatt gagatgaaac cgaacaagcc cttagttgga tggatgatg | 600 |
| atctcacgcg cttgagttta tctagttgct gatatgggag agcccctcaa cacctcaaat | 660 |
| attgtggata agtttaatcc tacactgtca gtcttcagtt ataaggcacg cactcttcga | 720 |
| cgttgggcgc tgtctttgt ttcaaaggtt gaggcaacct caacctcgtt taaaacagag | 780 |
| agcaaagcta atttccaaac tgatgtaagt catgtgtcct taattaccaa agtagcaatg | 840 |
| atgacattgt tatgttgtgt gctaatgagc cattacgtga acatcagttc ctgccttgcc | 900 |
| gcttcgttca gccgggccgg ggtatatttt gagtcactaa aaggacacgt cggatgaatg | 960 |
| gaaaattgcc tcttgtcttt accaagagtg tcgcccgcga g | 1001 |

<210> SEQ ID NO 20
<211> LENGTH: 2037
<212> TYPE: DNA
<213> ORGANISM: Zea mays

<400> SEQUENCE: 20

| cgacgtacaa atctcatctg tgccttgctc tagtttccca aatggaatta actatgcatg | 60 |
| atttgtttgg aaactcttat tgcatccatc cagataatgc atccaccata aggtaatatc | 120 |
| ttgatgacat ctgtgcctga tggtgtacca aatgtctcta tctctgcatt gagccacgag | 180 |
| taggaggata gcctaggggt gccttgactc caaagttgta ttgaaaaaga tggatgaagc | 240 |
| aggcaaatgc tgcctgaatc catgactcag ggcacagatt ttccactcaa aggaagataa | 300 |
| gattgcatta cttcatgatc ttttgaactg cctctgcaag acgggactcg gatagtggat | 360 |
| gcaaagatct aatactggcc tcaggcaacg agttgtttca ctcgaaagtc tagaaatgac | 420 |
| cgggctcaaa ttttgcaccc caaggaaagt gagtttgcat tacttcatga ccttttgaac | 480 |
| tgcctctgca agactggact cagattacgc ttgattggtt gccggcctca ccttcgcctg | 540 |
| gcttgcgcga gcctgcgtct atagaaatgc gccggactca cgtctccgtc gatgcaggca | 600 |
| ttcgactgaa aaaacatttta aactgcaccc atgcgtgcgg gctgagctta tgtcatacaa | 660 |
| gtaaccaatc acaggcttaa gttcagtcaa cgcatgcgct aagcttggat gtggctgacc | 720 |

| gggcaaccaa tcacacagat agtggatgca cggatctaat attggctaat ttggttaaac | 780 |
| ttgtctaacc ttagacgtgg caagtgagtc agcggatcaa atctgctcta aaattgtctg | 840 |
| cctcctagat gtccttggtg ttccaagatt taatcatcac tgcactattt ctttgcgttg | 900 |
| cttcgctgca gcttcgcgtt acttgcattc gcttaatcag gattactttg atcaactagg | 960 |
| tttctaactt ctactacctt cacttgcaca gggtgcccgt cctgctagcc ggtgtgcttg | 1020 |
| ctgtgcgatc gtttggcatg tgcttgttga ggggttgcta ggggattgga gaggattgaa | 1080 |
| gggattaaat ctcctcctat tcaattttga ataggagggg atttaatccc cttcaatccc | 1140 |
| cctcaaacca ctagtaaccg aacgtggcct gaggggggcgg gcgagtcttt atattgaatg | 1200 |
| aaactacata aaatagcatg ccgtctctgt cactggcaat ggacggtggt gcctagcgca | 1260 |
| actcagcgca caactgtgtg tcttgatttt tcttctgttt atcacggcat tagtgccatg | 1320 |
| ccgtttatg ttacagtgtt gtgtgctcgc aagcatccga aaatatgcgt ctgagtttag | 1380 |
| ggttgggtca aacttgtcga atttgggtt ctgttataat atgttgagca tgaataaaga | 1440 |
| tggatgctgg tgactctgtc gccatcgccg tccatcatga gtgtcctgta attcaactta | 1500 |
| tatctatcat gtatgtatgt atgtatgtat gtatgtatgt atatgctgtc tactatgctt | 1560 |
| ctttgtttta actgaaatgt gtgttacagt gttacttctc tggggtccat ttaaaacggc | 1620 |
| atttcgttta cgataggaac cagccattat aatctttaac caataatttc gctaaccaat | 1680 |
| ttcaactatt gcaatgcgaa cttaatatta tcagatttat aaccgaatgc gctatcaaat | 1740 |
| aatcataagg ttgtaatcat aataatataa tataaaataa atgagtgctc gaagtgaaat | 1800 |
| tttagagagc gttataagaa aaattgatgt gatctccaag aataatagcc cctcccggct | 1860 |
| cccggtacaa acatagggct tctttagaat gcaggattgt gagaacatag gaataggaaa | 1920 |
| aatataggaa ttctatagga atgtatatgg aaaacagagg attgaaaaac acagaaaaaa | 1980 |
| tgtgaaagca agtctttgga tgaagcgtag gaaacttata ggaataggaa ttcataa | 2037 |

<210> SEQ ID NO 21
<211> LENGTH: 16119
<212> TYPE: DNA
<213> ORGANISM: Artificial Sequence
<220> FEATURE:
<223> OTHER INFORMATION: Recombinant vector.

<400> SEQUENCE: 21

| attcctgtgg ttggcatgca catacaaatg gacgaacgga taaacctttt cacgcccttt | 60 |
| taaatatccg attattctaa taaacgctct tttctcttag gttacccgc caatatatcc | 120 |
| tgtcaaacac tgatagttta aactgaaggc gggaaacgac aatctgatca tgagcggaga | 180 |
| attaagggag tcacgttatg acccccgccg atgacgcggg acaagccgtt ttacgtttgg | 240 |
| aactgacaga accgcaacgc tgcaggaatt ggccgcagcg gccatttaaa tcaattgggc | 300 |
| gcgccagctg cttgtgggga ccagacaaaa aggaatggt gcagaattgt taggcgcacc | 360 |
| taccaaaagc atctttgcct ttattgcaaa gataaagcag attcctctag tacaagtggg | 420 |
| gaacaaaata acgtggaaaa gagctgtcct gacagcccac tcactaatgc gtatgacgaa | 480 |
| cgcagtgacg accacaaaac tcgagacttt tcaacaaagg gtaatatccg gaaacctcct | 540 |
| cggattccat tgcccagcta tctgtcactt tattgtgaag atagtggaaa aggaaggtgg | 600 |
| ctcctacaaa tgccatcatt gcgataaagg aaaggctatc gttgaagatg cctctgccga | 660 |
| cagtggtccc aaagatggac ccccacccac gaggagcatc gtggaaaaag aagacgttcc | 720 |

```
aaccacgtct tcaaagcaag tggattgatg tgatatctcc actgacgtaa gggatgacga    780
acaatcccac tatccttcgg taccggaccc gagatatgtg atgtatatgt gatatatgtg    840
atgattatgt gatatatttt ttgtttgttt ggatggaata ataaaaacaa ataaaaaggg    900
tatgttggcc acttttggcg agtgtaacac tcagcaaaga ggtactttgc cgagtgtcac    960
agtcatatca ttcggcaaag aaggcacaca tgggaaccga taaagcttct tgccgagtg   1020
ttgtggcctt agcactcggc aaagaagcaa cttttgccga gagcctccta gtgtactcgg   1080
caaaggaact gacaaaggag cccactgatg attcctttga tgagtggtag tccggcagac   1140
acacggcaaa gataaagtct tgccgagtg ccacctaata cgcccggcaa aggaactggc   1200
aaaggacaca cgatgagttt atttgtcgag tgctagtaca atagacactc gacaaagagt   1260
gagcctttgc agagtgtcac cgtggcactc ggcaaagtcc actctttgtc gagtgtcacc   1320
gtgacactca gcgaagtctc cgtcgctgtc atctgtcgcc gtgacgtcga cttttttttg   1380
ccgagtaccg agtggttgcc gagtgtccga caaaaaatac tcggttaaag accgttgccg   1440
atgtcagttc accaagacct tttttatcaa gtgtcatact tgataaagtc ttccccaagt   1500
attttcaaaa ctttgtcgat tacctcacac accaaggggt aggatcgtgt tgaggcggtt   1560
tgctgcttgt ttcttgcttt cgccgaacca acggaccatg agcgcataaa ccaatgggcg   1620
agcggccgca tatacaggcc tgcgcggcga gcctcacctt gctggatttg aatgcccct    1680
cggcatggtc aatgaccatg catctttgtg cagaacatat aaaatgcaca aattaattaa   1740
ttaataaaaa tacatgaaag agtacataat ttgtttgtgg attattaatt atatttataa   1800
atatattata gtatattata ttttatcttt atctaactac aaaaataatt atagattgtt   1860
aactttttt tgcattactg gtaagatttt gtcgatttta aattttgtc taacatgttt    1920
tattatcaat ctaaaattgc aaattatatg ttaacgaact aaatttgtaa taaaatatat   1980
gtaataaagg tcgtctaaaa gtaagctaaa attcacgcac ctaaatttta tttagtaaag   2040
tgttttttct tgacatatga cactagtgtt ttcaaagctt gtctcttaat ttaggattaa   2100
attaataggc ctctctaaat tgcttttat aagataaata aatcctattc cgtctgctca   2160
tcttcaaaga acatttcaat gaaacaaata tttgggaaaa ccaatggaaa aagaataaaa   2220
ataaaaattg aaaagagaa gtggaggaaa agtagggttc cattccacgg cctgtcgagt   2280
gtcgacccac aaaccacgca accgatatat tccccagcac ccccagtctc cagccgtcca   2340
accgagacac cgcgtgcgaa ccaagcagac cacaacaaga agaagcgtag tcgtcgccgg   2400
aaggaaaggc gcggagcaag atctcgtggc aggcgtacgt cgacgagcac ctgaagtgcg   2460
agatcgaagg acagcatctc agcgccgccg ccatcgtcgg tcacgacggc agcgtttggg   2520
cgcagtccga gagcttcccc gaggtcattc actcccacct tatctcttcc cgctctactt   2580
gcttagttgc tttatccatg ttcagtgctc ctgcgctgat ttagacccgc gcgactctgg   2640
atctgcccca gccgtgcggc ccggccggat cggagcgagg ggatgtccgg atctcggtcg   2700
ctgaggcgag atgcggatct aaggcccctt ccctcggtga cgtggttgct gctgctgctg   2760
ttctccgggc gtttgatgcc aatatagctg agatcaagct tgatgatctg cgtactgtgg   2820
atttgctagt gagggatggc cggatcgggc tgttggcgtc cgacctgatt tggttgttcg   2880
cttgaataga cttacttacc agtggacagt ggtagtgatc gttcagcagc agtagagcaa   2940
tttgttttac atgtaaaatt tgagtggctg ctagagatgc accaatggcc gagctgcatg   3000
tgtttattcc tatatagcga cagttgtgtg attgatccaa aacgcaaaat tttagttttc   3060
atcaaatgat gatttcctga tgccactacc tgtgtgtgag gcacttatta aatgaaaagt   3120
```

```
aactttcggt tgggatctgg gaatctgtat tgtgttccgt ggttggtcac agcttgtggc   3180
ctgcattgtt ccataggcca aatggctagg caaggaaaat aaatcatgta atttggaaaa   3240
aaataactgc catagtcagt agtgtacagc agtacatgct tgtccgggcc ttttatttca   3300
ccatcgtgtt gtggtatatg gagtacttgg attgtgcgat gctttataca tttgtttgtt   3360
ctagcagagt ttgagtttat atttctattc ttatgtaggg cgtcacgagt gtcgtcaatt   3420
gttacatcct tacatccttg tgttcacaat atgatccatc aactctttct tctgcggtct   3480
cttatccctg tgttctcatg tccatgtttc ctgcttcttg ttgcagttaa agccttagga   3540
ggtaaaccat ggacaacaac cccaacatca acgagtgcat cccctacaac tgcctgagca   3600
accccgaggt ggaggtgctg gcggcgagc gcatcgagac cggctacacc cccatcgaca   3660
tcagcctgag cctgacccag ttcctgctga gcgagttcgt gcccggcgcc ggcttcgtgc   3720
tgggcctggt ggacatcatc tggggcatct tcggccccag ccagtgggac gccttcctgg   3780
tgcagatcga gcagctgatc aaccagcgca tcgaggagtt cgcccgcaac caggccatca   3840
gccgcctgga gggcctgagc aacctgtacc aaatctacgc cgagagcttc cgcgagtggg   3900
aggccgaccc caccaacccc gccctgcgcg aggagatgcg catccagttc aacgacatga   3960
acagcgccct gaccaccgcc atccccctgt tcgccgtgca gaactaccag gtgcccctgc   4020
tgagcgtgta cgtgcaggcc gccaacctgc acctgagcgt gctgcgcgac gtcagcgtgt   4080
tcggccagcg ctgggcttc gacgccgcca ccatcaacag ccgctacaac gacctgaccc   4140
gcctgatcgg caactacacc gaccacgccg tgcgctggta caacaccggc ctggagcgcg   4200
tgtggggtcc agacagccgc gactggatca ggtacaacca gttccgccgc gagctgaccc   4260
tgaccgtgct ggacatcgtg agcctgttcc ccaactacga cagccgcacc taccccatcc   4320
gcaccgtgag ccagctgacc cgcgagattt acaccaaccc cgtgctggag aacttcgacg   4380
gcagcttccg cggcagcgcc cagggcatcg agggcagcat ccgcagcccc cacctgatgg   4440
acatcctgaa cagcatcacc atctacaccg acgcccaccg cggcgagtac tactggagcg   4500
gccaccagat catggccagc cccgtcggct tcagcggccc cgagttcacc ttccccctgt   4560
acggcactat gggcaacgct gcacctcagc agcgcatcgt ggcacagctg ggccaggag   4620 tgtaccgcac cctgagcagc acctgtacc gtcgacctt caacatcggc atcaacaacc   4680
agcagctgag cgtgctggac ggcaccgagt tcgcctacgg caccagcagc aacctgcccA   4740
gcgccgtgta ccgcaagagc ggcaccgtgg acagcctgga cgagatcccc cctcagaaca   4800
acaacgtgcc acctcgacag ggcttcagcc accgtctgag ccacgtgagc atgttccgca   4860
gtggcttcag caacagcagc gtgagcatca tccgtgcacc tatgttcagc tggattcacc   4920
gcagtgccga gttcaacaac atcatcccca gcagccagat cacccagatc cccctgacca   4980
agagcaccaa cctgggcagc ggcaccagcg tggtgaaggg ccccggcttc accggcggcg   5040
acatcctgcg ccgcaccagc cccggccaga tcagcaccct gcgcgtgaac atcaccgccc   5100
ccctgagcca gcgctaccgc gtccgcatcc gctacgccag caccaccaac ctgcagttcc   5160
acaccagcat cgacggccgc cccatcaacc agggcaactt cagcgccacc atgagcagcg   5220
gcagcaacct gcagagcggc agcttccgca ccgtgggctt caccacccc ttcaacttca   5280 gcaacggcag cagcgtgttc accctgagcg cccacgtgtt caacagcggc aacgaggtgt   5340
acatcgaccg catcgagttc gtgcccgcg aggtgacctt cgaggccgag tacgacctgg   5400
agagggctca gaaggccgtg aacgagctgt tcaccagcag caaccagatc ggcctgaaga   5460
```

```
ccgacgtgac cgactaccac atcgatcagg tgtaggagct caagttcgtc atgttctgtt    5520
ttggtcattt gggcaccaaa gtttgcgcct catttggttc tgtaatccgt gaggtcgtgc    5580
atgtacttgg cgtattgcat gcagtgaata atttagcttg ggtttgtttg ttgggggcag    5640
tgttggggac ggatttggat tggggtttat gcttggcatc gcgtcgtatc gaaactcagc    5700
tgctgtttcg ctgagtaatg tacatttccc tggtaatggt acttgtggac tctgatgctt    5760
ttatgggaac gagtgcattt tactgccgtg cttggccgtg ctgttgaatt attcccgtag    5820
tgtattaaat attggatgca ccagattgtt tgtcccattt acgcataatt ttcccgtcat    5880
atgttgaatt atttacgaat tataaaatat gtaatttata tttatttta tgaagtatat     5940 aaaattttac ttttttgtta tataattaaa tatttttgt tttgataaaa tggtatgttt     6000
tattttaaat aaaaatctat aaaaaaagat gatatggtgg ctggaaggta acgataaatt    6060
atgtatacta agtattaac gatagtaaat atagttggac gatagatgat gtgacggggt     6120
ttgttctttt gattttaatc tataatgctt gtctatagat tacagccgca tcaatttaaa    6180
tagctgcttt taatctgaag cgaacaaccg ataaaaatag acattaggcc atctccaaca    6240
gttcgaccgt gcaaagtatt attttgctat tgcactattt gaataatgga ttttagaata    6300
gggagtgata aaaagtgaga taaaaagttt aataaaaata gtcttagatc caacaaatat    6360
acgctgccct cccatcagtt gcctggaccc atgccaagaa gtgccagcca tagtcgtatg    6420
aaaaatgatt ctaagggcgt tcgcaatggt tgtcttaaat agttagctat tgtgaagctg    6480
aaactaagag aagaataaaa atataattta tttcacggac cgcgatcgct taattaagct    6540
tgcatgcctg cagtgcagcg tgacccggtc gtgcccctct ctagagataa tgagcattgc    6600
atgtctaagt tataaaaaat taccacatat tttttttgtc acacttgttt gaagtgcagt    6660
ttatctatct ttatacatat atttaaactt tactctacga ataatataat ctatagtact    6720
acaataatat cagtgtttta gagaatcata taaatgaaca gttagacatg gtctaaagga    6780
caattgagta ttttgacaac aggactctac agttttatct ttttagtgtg catgtgttct    6840 ccttttttt tgcaaatagc ttcacctata taatacttca tccatttat tagtacatcc      6900 atttagggtt tagggttaat ggttttata gactaattt tttagtacat ctatttatt      6960 ctattttagc ctctaaatta agaaaactaa aactctattt tagttttttt atttaataat    7020
ttagatataa aatagaataa aataaagtga ctaaaaatta aacaaatacc ctttaagaaa    7080
ttaaaaaaac taaggaaaca ttttttcttgt ttcgagtaga taatgccagc ctgttaaacg    7140
ccgtcgacga gtctaacgga caccaaccag cgaaccagca gcgtcgcgtc gggccaagcg    7200
aagcagacgg cacggcatct ctgtcgctgc ctctggaccc ctctcgagag ttccgctcca    7260
ccgttggact tgctccgctg tcggcatcca gaaattgcgt ggcggagcgg cagacgtgag    7320
ccggcacggc aggcggcctc ctcctcctct cacggcaccg gcagctacgg gggattcctt    7380
tcccaccgct ccttcgcttt ccttcctcg cccgccgtaa taaatagaca ccccctccac      7440
accctctttc cccaacctcg tgttgttcgg agcgcacaca cacacaacca gatctccccc    7500
aaatccaccc gtcggcacct ccgcttcaag gtacgccgct cgtcctcccc cccccccct     7560 ctctaccttc tctagatcgg cgttccggtc catggttagg gcccggtagt tctacttctg    7620
ttcatgtttg tgttagatcc gtgtttgtgt tagatccgtg ctgctagcgt tcgtacacgg    7680
atgcgacctg tacgtcagac acgttctgat tgctaacttg ccagtgtttc tctttgggga    7740
atcctgggat ggctctagcc gttccgcaga cgggatcgat ttcatgattt ttttttgtttc    7800 gttgcatagg gtttggtttg ccctttttcct ttatttcaat atatgccgtg cacttgtttg    7860
```

```
tcgggtcatc ttttcatgct ttttttgtc ttggttgtga tgatgtggtc tggttgggcg    7920
gtcgttctag atcggagtag aattctgttt caaactacct ggtggattta ttaattttgg    7980
atctgtatgt gtgtgccata catattcata gttacgaatt gaagatgatg gatggaaata    8040
tcgatctagg ataggtatac atgttgatgc gggttttact gatgcatata cagagatgct    8100
ttttgttcgc ttggttgtga tgtgtggtg tggttgggcg gtcgttcatt cgttctagat    8160
cggagtagaa tactgtttca aactacctgg tgtatttatt aattttggaa ctgtatgtgt    8220
gtgtcataca tcttcatagt tacgagttta agatggatgg aaatatcgat ctaggatagg    8280
tatacatgtt gatgtgggtt ttactgatgc atatacatga tggcatatgc agcatctatt    8340
catatgctct aaccttgagt acctatctat tataataaac aagtatgttt tataattatt    8400
ttgatcttga tacttggat gatggcata tgcagcagct atatgtggat tttttagcc    8460 ctgccttcat acgctattta tttgcttggt actgtttctt ttgtcgatgc tcaccctgtt    8520
gtttggtgtt acttctgcag ggatccccga tcatgcaaaa actcattaac tcagtgcaaa    8580
actatgcctg gggcagcaaa acggcgttga ctgaactta tggtatggaa atccgtcca    8640 gccagccgat ggccgagctg tggatgggcg cacatccgaa aagcagttca cgagtgcaga    8700
atgccgccgg agatatcgtt tcactgcgtg atgtgattga gagtgataaa tcgactctgc    8760
tcggagaggc cgttgccaaa cgctttggcg aactgccttt cctgttcaaa gtattatgcg    8820
cagcacagcc actctccatt caggttcatc caaacaaaca caattctgaa atcggttttg    8880
ccaaagaaaa tgccgcaggt atcccgatgg atgccgccga cgtaactat aaagatccta    8940 accacaagcc ggagctggtt tttgcgctga cgcctttcct tgcgatgaac gcgtttcgtg    9000
aattttccga gattgtctcc ctactccagc cggtcgcagg tgcacatccg gcgattgctc    9060 acttttaca acagcctgat gccgaacgtt taagcgaact gttcgccagc ctgttgaata    9120
tgcagggtga agaaaaatcc cgcgcgctgg cgatttttaaa atcggccctc gatagccagc    9180
agggtgaacc gtggcaaacg attcgtttaa tttctgaatt ttacccggaa gacagcggtc    9240
tgttctcccc gctattgctg aatgtggtga aattgaaccc tggcgaagcg atgttcctgt    9300
tcgctgaaac accgcacgct tacctgcaag gcgtggcgct ggaagtgatg gcaaactccg    9360
ataacgtgct gcgtgcgggt ctgacgccta aatacattga tattccggaa ctggttgcca    9420
atgtgaaatt cgaagccaaa ccggctaacc agttgttgac ccagccggtg aaacaaggtg    9480
cagaactgga cttcccgatt ccagtggatg atttttgcctt ctcgctgcat gaccttagtg    9540
ataaagaaac caccattagc cagcagagtg ccgccatttt gttctgcgtc gaaggcgatg    9600
caacgttgtg gaaaggttct cagcagttac agcttaaacc gggtgaatca gcgtttattg    9660
ccgccaacga atcaccggtg actgtcaaag gccacgccg tttagcgcgt gtttacaaca    9720
agctgtaaga gcttactgaa aaaattaaca tctcttgcta agctgggagc tcgtcatggg    9780
tcgtttaagc tgccgatgtg cctgcgtcgt ctggtgccct ctctccatat ggaggttgtc    9840
aaagtatctg ctgttcgtgt catgagtcgt gtcagtgttg gtttaataat ggaccggttg    9900
tgttgtgtgt gcgtactacc cagaactatg acaaatcatg ataagtttg atgtttgaaa    9960 ttaaagcctg tgctcattat gttctgtctt tcagttgtct cctaatatt gcctgcaggt    10020 actggctatc taccgtttct tacttaggag gtgtttgaat gcactaaaac taatagttag    10080
tggctaaaat tagttaaaac atccaaacac catagctaat agttgaacta ttagctattt    10140
ttggaaaatt agttaatagt gaggtagtta tttgttagct agctaattca actaacaatt    10200
```

```
tttagccaac taacaattag tttcagtgca ttcaaacacc cccttaatgt taacgtggtt    10260
ctatctaccg tctcctaata tatgttgat tgttcggttt gttgctatgc tattgggttc    10320
tgattgctgc tagttcttgc tgaatccaga agttctcgta gtatagctca gattcatatt   10380
atttatttga gtgataagtg atccaggtta ttactatgtt agctaggttt tttttacaag   10440
gataaattat ctgtgatcat aattcttatg aaagctttat gtttcctgga ggcagtggca   10500
tgcaatgcat gacagcaact tgatcacacc agctgaggta gatacggtaa caaggttctt   10560
aaatctgttc accaaatcat tggagaacac acatacacat tcttgccagt cttggttaga   10620
gaaatttcat gacaaaatgc caaagctgtc ttgactcttc acttttggcc atgagtcgtg   10680
acttagtttg gtttaatgga ccggttctcc tagcttgttc tactcaaaac tgttgttgat   10740
gcgaataagt tgtgatggtt gatctctgga ttttgttttg ctctcaatag tggacgagat   10800
tagatagccc ggaaatttac cggtgcccgg gcggccagca tggccgtatc cgcaatgtgt   10860
tattaagttg tctaagcgtc aatttgttta caccacaata tatcctgcca ccagccagcc   10920
aacagctccc cgaccggcag ctcggcacaa aatcaccact cgatacaggc agcccatcag   10980
aattaattct catgttttgac agcttatcat cgactgcacg gtgcaccaat gcttctggcg   11040
tcaggcagcc atcggaagct gtggtatggc tgtgcaggtc gtaaatcact gcataattcg    11100
tgtcgctcaa ggcgcactcc cgttctggat aatgtttttt gcgccgacat cataacggtt    11160
ctggcaaata ttctgaaatg agctgttgac aattaatcat ccggctcgta taatgtgtgg    11220
aattgtgagc ggataacaat ttcacacagg aaacagacca tgagggaagc gttgatcgcc    11280
gaagtatcga ctcaactatc agaggtagtt ggcgtcatcg agcgccatct cgaaccgacg    11340
ttgctggccg tacatttgta cggctccgca gtggatggcg gcctgaagcc acacagtgat    11400
attgatttgc tggttacggt gaccgtaagg cttgatgaaa caacgcggcg agctttgatc    11460
aacgaccttt tggaaacttc ggcttcccct ggagagagcg agattctccg cgctgtagaa    11520
gtcaccattg ttgtgcacga cgacatcatt ccgtggcgtt atccagctaa gcgcgaactg    11580
caatttggag aatggcagcg caatgacatt cttgcaggta tcttcgagcc agccacgatc    11640
gacattgatc tggctatctt gctgacaaaa gcaagagaac atagcgttgc cttggtaggt    11700
ccagcggcgg aggaactctt tgatccggtt cctgaacagg atctatttga ggcgctaaat    11760
gaaacccttaa cgctatggaa ctcgccgccc gactgggctg gcgatgagcg aaatgtagtg    11820
cttacgttgt cccgcatttg gtacagcgca gtaaccggca aaatcgcgcc gaaggatgtc    11880
gctgccgact gggcaatgga gcgcctgccg gcccagtatc agcccgtcat acttgaagct    11940
aggcaggctt atcttggaca agaagatcgc ttggcctcgc gcgcagatca gttggaagaa    12000
tttgttcact acgtgaaagg cgagatcacc aaagtagtcg gcaaataaag ctctagtgga    12060
tctccgtacc cggggatctg gctcgcggcg gacgcacgac gccggggcga gaccataggc    12120
gatctcctaa atcaatagta gctgtaacct cgaagcgttt cacttgtaac aacgattgag    12180
aatttttgtc ataaaattga aatacttggt tcgcatttt gtcatccgcg gtcagccgca    12240
attctgacga actgcccatt tagctggaga tgattgtaca tccttcacgt gaaaatttct    12300
caagcgctgt gaacaagggt tcagatttta gattgaaagg tgagccgttg aaacacgttc    12360
ttcttgtcga tgacgacgtc gctatgcggc atcttattat tgaataccttt acgatccacg    12420
ccttcaaagt gaccgcggta gccgacagca cccagttcac aagagtactc tcttccgcga    12480
cggtcgatgt cgtggttgtt gatctagatt taggtcgtga agatgggctc gagatcgttc    12540
gtaatctggc ggcaaagtct gatattccaa tcataattat cagtggcgac cgccttgagg    12600
```

```
agacggataa agttgttgca ctcgagctag gagcaagtga tttttatcgct aagccgttca    12660 gtatcagaga gtttctagca cgcattcggg ttgccttgcg cgtgcgcccc aacgttgtcc    12720
gctccaaaga ccgacggtct ttttgtttta ctgactggac acttaatctc aggcaacgtc    12780
gcttgatgtc cgaagctggc ggtgaggtga aacttacggc aggtgagttc aatcttctcc    12840
tcgcgttttt agagaaaccc cgcgacgttc tatcgcgcga gcaacttctc attgccagtc    12900
gagtacgcga cgaggaggtt tatgacagga gtatagatgt tctcattttg aggctgcgcc    12960
gcaaacttga ggcagatccg tcaagccctc aactgataaa aacagcaaga ggtgccggtt    13020
atttctttga cgcggacgtg caggtttcgc acgggggac gatggcagcc tgagccaatt     13080
cccagatccc cgaggaatcg gcgtgagcgg tcgcaaacca tccggcccgg tacaaatcgg    13140
cgcggcgctg ggtgatgacc tggtggagaa gttgaaggcc gcgcaggccg cccagcggca    13200
acgcatcgag gcagaagcac gccccggtga atcgtggcaa gcggccgctg atcgaatccg    13260
caaagaatcc cggcaaccgc cggcagccgg tgcgccgtcg attaggaagc cgcccaaggg    13320
cgacgagcaa ccagattttt tcgttccgat gctctatgac gtgggcaccc gcgatagtcg    13380
cagcatcatg gacgtggccg ttttccgtct gtcgaagcgt gaccgacgag ctggcgaggt    13440
gatccgctac gagcttccag acgggcacgt agaggtttcc gcagggccgg ccggcatggc    13500
cagtgtgtgg gattacgacc tggtactgat ggcggtttcc catctaaccg aatccatgaa    13560
ccgataccgg gaagggaagg gagacaagcc cggccgcgtg ttccgtccac acgttgcgga    13620
cgtactcaag ttctgccggc gagccgatgg cggaaagcag aaagacgacc tggtagaaac    13680
ctgcattcgg ttaaacacca cgcacgttgc catgcagcgt acgaagaagg ccaagaacgg    13740
ccgcctggtg acggtatccg agggtgaagc cttgattagc cgctacaaga tcgtaaagag    13800
cgaaaccggg cggccggagt acatcgagat cgagctagct gattggatgt accgcgagat    13860
cacagaaggc aagaacccgg acgtgctgac ggttcacccc gattactttt tgatcgatcc    13920
cggcatcggc cgttttctct accgcctggc acgccgcgcc gcaggcaagg cagaagccag    13980
atggttgttc aagacgatct acgaacgcag tggcagcgcc ggagagttca agaagttctg    14040
tttcaccgtg cgcaagctga tcgggtcaaa tgacctgccg gagtacgatt tgaaggagga    14100
ggcggggcag gctggcccga tcctagtcat gcgctaccgc aacctgatcg agggcgaagc    14160
atccgccggt tcctaatgta cggagcagat gctagggcaa attgccctag caggggaaaa    14220
aggtcgaaaa ggtctctttc ctgtggatag cacgtacatt gggaacccaa agccgtacat    14280
tgggaaccgg aacccgtaca ttgggaaccc aaagccgtac attgggaacc ggtcacacat    14340
gtaagtgact gatataaaag agaaaaaagg cgattttttcc gcctaaaact cttaaaact    14400 tattaaaact cttaaaaccc gcctggcctg tgcataactg tctggccagc gcacagccga    14460
agagctgcaa aaagcgccta cccttcggtc gctgcgctcc ctacgccccg ccgcttcgcg    14520
tcggcctatc gcggccgctg gccgctcaaa aatggctggc ctacggccag gcaatctacc    14580
agggcgcgga caagccgcgc cgtcgccact cgaccgccgg cgctgaggtc tgcctcgtga    14640
agaaggtgtt gctgactcat accaggcctg aatcgcccca tcatccagcc agaaagtgag    14700
ggagccacgg ttgatgagag ctttgttgta ggtggaccag ttggtgattt tgaactttg     14760 ctttgccacg gaacggtctg cgttgtcggg aagatgcgtg atctgatcct tcaactcagc    14820
aaaagttcga tttattcaac aaagccgccg tcccgtcaag tcagcgtaat gctctgccag    14880
tgttacaacc aattaaccaa ttctgattag aaaaactcat cgagcatcaa atgaaactgc    14940
```

```
aatttattca tatcaggatt atcaatacca tattttttgaa aaagccgttt ctgtaatgaa    15000
ggagaaaact caccgaggca gttccatagg atggcaagat cctggtatcg gtctgcgatt    15060
ccgactcgtc caacatcaat acaacctatt aatttcccct cgtcaaaaat aaggttatca    15120
agtgagaaat caccatgagt gacgactgaa tccggtgaga atggcaaaag ctctgcatta    15180
atgaatcggc caacgcgcgg ggagaggcgg tttgcgtatt gggcgctctt ccgcttcctc    15240
gctcactgac tcgctgcgct cggtcgttcg gctgcggcga cggtatcag ctcactcaaa     15300 ggcggtaata cggttatcca cagaatcagg ggataacgca ggaaagaaca tgtgagcaaa    15360
aggccagcaa aaggccagga accgtaaaaa ggccgcgttg ctggcgtttt tccataggct    15420
ccgcccccct gacgagcatc acaaaaatcg acgctcaagt cagaggtggc gaaacccgac    15480
aggactataa agataccagg cgtttccccc tggaagctcc ctcgtgcgct ctcctgttcc    15540
gaccctgccg cttaccggat acctgtccgc ctttctccct tcgggaagcg tggcgctttc    15600
tcatagctca cgctgtaggt atctcagttc ggtgtaggtc gttcgctcca agctgggctg    15660
tgtgcacgaa ccccccgttc agcccgaccg ctgcgcctta tccggtaact atcgtcttga    15720
gtccaacccg gtaagacacg acttatcgcc actggcagca gccactggta acaggattag    15780
cagagcgagg tatgtaggcg gtgctacaga gttcttgaag tggtggccta actacggcta    15840
cactagaaga acagtatttg gtatctgcgc tctgctgaag ccagttacct tcggaaaaag    15900
agttggtagc tcttgatccg gcaaacaaac caccgctggt agcggtggtt ttttgtttg     15960 caagcagcag attacgcgca gaaaaaaagg atctcaagaa gatcctttga tcttttctac    16020
ggggtctgac gctcagtgga acgaaaactc acgttaaggg attttggtca tgagattatc    16080
aaaaaggatc ttcacctaga tccttttgat ccggaatta                           16119

<210> SEQ ID NO 22
<211> LENGTH: 16210
<212> TYPE: DNA
<213> ORGANISM: Artificial Sequence
<220> FEATURE:
<223> OTHER INFORMATION: Recombinant vector

<400> SEQUENCE: 22
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa tcaattgggc     300
gcgccagctg cttgtgggga ccagacaaaa aaggaatggt gcagaattgt taggcgcacc     360
taccaaaagc atctttgcct ttattgcaaa gataaagcag attcctctag tacaagtggg     420
gaacaaaata acgtggaaaa gagctgtcct gacagcccac tcactaatgc gtatgacgaa     480
cgcagtgacg accacaaaac tcgagacttt tcaacaaagg gtaatatccg gaaacctcct     540
cggattccat tgcccagcta tctgtcactt tattgtgaag atagtggaaa aggaaggtgg     600
ctcctacaaa tgccatcatt gcgataaagg aaaggctatc gttgaagatg cctctgccga     660
cagtggtccc aaagatggac ccccacccac gaggagcatc gtggaaaaag aagacgttcc     720
aaccacgtct tcaaagcaag tggattgatg tgatatctcc actgacgtaa gggatgacga     780
acaatcccac tatccttcgg taccggaccc tctgcctttc tgttcttcaa acgatgtctc     840
atgtctgcgc tggacaactt tcttgttgcc gcctgtcgct tgcgctgtgc tgactggacg     900
```

```
cagctccgga ggtttggttg tgcttggttt tcgtagagaa ctcgccactt gccgcccgca     960
cgttcttggt gtttcctcct ccccgctgtg ttctgcgcac gggcttttc tgagagaccc    1020 atgtttccct tttacttta taaacagtat acatgctatg tttctagaag gaggggaaac    1080 ctaatcccc taatccaatg gcggggagga aatagggtgg ggtggggtgg ggggagggaa    1140
atatctcgct acttttaat ccggacaagc tcatttgcgt ttgcgtctga atgatgatga    1200
ctgcaatgct gatcgcacct cgggtgtcgg atcaccagct tttggctgct ctcaccaaat    1260
cagctgcaag aagattagag cacaaaagaa ttacagaaag agagccttt tcttttcttc    1320 cttgtgggt tcctttcatt tcgtgctctc ctttctctgc cagccagtcc gtccttgcgt    1380
ccactgcacc tgcacacagg tcaccccgac ccgcactgtt ctagactcca ttagaaaaaa    1440
aaaggtctga accttccga aaccagccag ccattggtct ggcaggccag catatgctaa    1500 ttggatttt ttgccgcatc attgagtgcg ccatcaggat ttggaaatcc tggttttgag    1560
taatacagta atttggcatt atccattgcc gaattcccaa gctccgtcag cttgaacgtg    1620 gaccctacc atctgcacca gctcggcacc tcacgctcgc agcgctagga gcctaggagc    1680
agctgcccgt ctatttattg gtccctctcc cgtcccagag aaaccctccc tcctcctcc    1740 attggactgc ttgctccctg ttgaccattg gggtatgctt gctgccttgc tctcctgttc    1800
atctccgtgc taaacctctg tcctctgggt gggttttgc tgggattttg agctaatctg    1860
ctggtcccgg tagaaaaaga tcatgtcccc tgacgtgctc aagcgctcgc cttagccgcg    1920
tccttgcccc ccgccatttt ttgccggtttc ggtgtgttcc cgtgactcgc cgggtgcgtc    1980
atcgcctgaa tcttgtctgg gctctgctga catgttcttg gctagttggg tttatagatt    2040
cctctgatct aaaccgtgcc tgtgctgcgc acagaactct cccctgtcct ttcctggggt    2100
tttggttacg tggtggtagt aagcttggat ttgcacatgg ataaagttgt tctaagctcc    2160
gtgggttgct tgagatcttg ctgttattgc gtgccgtgct cacttttttt gcaatccgag    2220
gaatgaattt gtcgtttact cgttttggtg gattattagc gcgaaaaaaa aactcttttt    2280
tttttgttct tttactacga aaagcatctt cttggatttt gctatcttct tttactacga    2340
aaaactcttg agtctaggaa tttgaatttg tgatgtccat tcttgcagtg cgctgtgctt    2400
tattgggaag ccaaatccta ttatttctg cctctagggt ctgaatggaa tcagtactct    2460
tgagacagaa aatcaatcca atcaagttga tttctttctt taaaaatatt atcacagaac    2520
taagtgcttg tgcggaatca gtactggctt ttgtttggtg gaggatcaat acttgctttt    2580 gtttggggt ggcaactgtt ttgctataag attccatgtg ttcctgttga gatgaatcat    2640
atatagtata gctgcatact acaaatctgt ttttcaaatt taggttgctt tggcatgatc    2700
tatttttttg tcagacagac tttctaagtg gtagctcttg atttcttgtt cttgtacaac    2760
tggtgctgct gaatcttgac cgtatagctc gaattgcagt attctgaacc atcgagccaa    2820
ggctgccaag ctgactcgcc tccacagtct tcgcgaacgc cttggtgcca ccttctcctc    2880
ccatcccaat gaactgatag cactctttc caggtgggct taccaaaatc atataacttg    2940
catttcattc ggtactgaaa gttgttaatt tgttattctc ttcatgcctg tcttaatagc    3000
acacccagat gtaaacacga gattatgcaa cttcttactt ggtttctttt gttggcacca    3060
tcatgcatgc taattgctaa ggatgttacc tattcatcct tgactcatat tatcatatgt    3120
aatgatttta tgatcacgag actattgatt gtgaagcata gtagctgt tcttcagttt    3180 ttgtacccctt ttgttttttt ccttaagcta gaactggtac aatttagttg ataagacagt    3240
```

```
gtagtttgta gtacgtcatt tgacagattg tttgtcttta gctggtaaag tgccatttaa    3300
tatctgtatc cttcagatct aataaaaagg atatgagatg tccatcacaa gaggggaaaa    3360
attacatgat ctgagatgta acatccgttt ttatttgtga ataccactt ctacaggtat    3420
cttcactagg gtaaaccatg acaacaacc ccaacatcaa cgagtgcatc ccctacaact    3480
gcctgagcaa ccccgaggtg gaggtgctgg gcggcgagcg catcgagacc ggctacaccc    3540
ccatcgacat cagcctgagc ctgacccagt tcctgctgag cgagttcgtg cccggcgccg    3600
gcttcgtgct gggcctggtg gacatcatct ggggcatctt cggccccagc cagtgggacg    3660
ccttcctggt gcagatcgag cagctgatca accagcgcat cgaggagttc gcccgcaacc    3720
aggccatcag ccgcctggag ggcctgagca acctgtacca aatctacgcc gagagcttcc    3780
gcgagtggga ggccgacccc accaacccg cctgcgcga ggagatgcgc atccagttca    3840
acgacatgaa cagcgccctg accaccgcca tccccctgtt cgccgtgcag aactaccagg    3900
tgcccctgct gagcgtgtac gtgcaggcgc ccaacctgca cctgagcgtg ctgcgcgacg    3960
tcagcgtgtt cggccagcgc tggggcttcg acgccgccac catcaacagc cgctacaacg    4020
acctgacccg cctgatcggc aactacaccg ccacgccgt cgctggtac aacaccggcc    4080
tggagcgcgt gtggggtcca gacagccgcg actggatcag gtacaaccag ttccgccgcg    4140
agctgaccct gaccgtgctg gacatcgtga gcctgttccc caactacgac agccgcacct    4200
accccatccg caccgtgagc cagctgaccc gcgagattta caccaaccc gtgctggaga    4260
acttcgacgg cagcttccgc ggcagcgccc agggcatcga gggcagcatc gcagcccccc    4320
acctgatgga catcctgaac agcatcacca tctacaccga cgcccaccgc ggcgagtact    4380
actggagcgg ccaccagatc atggccagcc ccgtcggctt cagcggcccc gagttcacct    4440
tccccctgta cggcactatg ggcaacgctg cacctcagca gcgcatcgtg gcacagctgg    4500
gccagggagt gtaccgcacc ctgagcagca ccctgtaccg tcgacctttc aacatcggca    4560
tcaacaacca gcagctgagc gtgctggacg gcaccgagtt cgcctacggc accagcagca    4620
acctgcccag cgccgtgtac cgcaagagcg gcaccgtgga cagcctggac gagatccccc    4680
ctcagaacaa caacgtgcca cctcgacagg gcttcagcca ccgtctgagc cacgtgagca    4740
tgttccgcag tggcttcagc aacagcagcg tgagcatcat ccgtgcacct atgttcagct    4800
ggattcaccg cagtgccgag ttcaacaaca tcatccccag cagccagatc acccagatcc    4860
ccctgaccaa gagcaccaac ctgggcagcg gcaccagcgt ggtgaagggc cccggcttca    4920
ccggcggcga catcctgcgc cgcaccagcc ccggccagat cagcaccctg cgcgtgaaca    4980
tcaccgcccc cctgagccag cgctaccgcg tccgcatccg ctacgccagc accaccaacc    5040
tgcagttcca caccagcatc gacgccgcc ccatcaacca gggcaacttc agcgccacca    5100
tgagcagcgg cagcaacctg cagagcggca gcttccgcac cgtgggcttc accacccct    5160
tcaacttcag caacggcagc agcgtgttca cctgagcgc cacgtgttc aacagcggca    5220
acgaggtgta catcgaccgc atcgagttcg tgccgccga ggtgaccttc gaggccgagt    5280
acgacctgga gagggctcag aaggccgtga acgagctgtt caccagcagc aaccagatcg    5340
gcctgaagac cgacgtgacc gactaccaca tcgatcaggt gtaggagctc tacggggaaa    5400
gaaggagaag aagaagaaga agcccaggcc ggagaaccat cgcctgcatt tcgatctgtt    5460
tcaccgcaat tcgcattgtt agtcgtgtat tggagttatg tgtacttggt ttccaagaac    5520
tttggttcct tctcgttttt ttttccttgc ttgtttgagc gttttgggc agcgctggcc    5580
tggttcctag tatggtggga attggctgca ccttttgctt cgaataaaaa tgcctgctcg    5640
```

```
ttcacctgtc ttccagagtg caatgcgatg ttctgttgcc caggtcgtgt ggttctgact    5700
gatggcgatg ttgtgttctt ctgttaatcg cctgttttaa cgtggtaggc tgatgcttgt    5760
tcttgttgag aaagcttgct gtgccagaca tggctgcttg aatacaagtg aaggaaaaaa    5820
aaagccatgc caagtaaagt tgcacaaaat ttcaactgct cagtggacca ctggaccatg    5880
ttcttggtta ttgcagttgc agggcttcac atggcgtttg gacagcagtc ttggattgat    5940
gcataaagag gtggtggtta atgaggacgc aaggccgttc cctcagagtc agtcacaagg    6000
ttgcagaggt cacggttctc ttcccttccc gcttcctgtc acatcggaat tgttgtttac    6060
gccatctgcc catcacccac caagtctatg tttctgtact ggatctttca atggcggaac    6120
gcgcttagtt cttcgtcaca gtcgaatcac atgatctaat cgatgtcttt aatctcgctg    6180 taaaagggt gggacggtgg gtgcagggta gggaccaggg aaggcctgcc taaacgtatc    6240
cataaacatg cacagcaacc ctaagatatt atactgccta cttcctaaga tatagttatt    6300
tctagtctat ttttttttccg tccacatcca aataagtgat aatatataga catacatata    6360
tatactatat tcatcataga ttaatgaacg aatgtatact tagtttaaac ctaattatat    6420
tttaggaagg atggagtatg aaacatgaca atacaacaaa aaaaaatcat gtaattgcat    6480
atcgtcaaag ttatctgaag taaccaatcc aggggggaaat cccgttagca aacatacaag    6540
agcaccgccc cactacatcc cagaaaataa aacaaaacca gaactcagat ggataaataa    6600
tactaccgga ccgcgatcgc ttaattaagc ttgcatgcct gcagtgcagc gtgacccggt    6660 cgtgccctc tctagagata atgagcattg catgtctaag ttataaaaaa ttaccacata    6720
ttttttttgt cacacttgtt tgaagtgcag tttatctatc tttatacata tatttaaact    6780
ttactctacg aataatataa tctatagtac tacaataata tcagtgtttt agagaatcat    6840
ataaatgaac agttagacat ggtctaaagg acaattgagt attttgacaa caggactcta    6900
cagttttatc ttttttagtgt gcatgtgttc tcctttttttt ttgcaaatag cttcacctat    6960
ataatacttc atccatttta ttagtacatc catttagggt ttagggttaa tggttttttat    7020 agactaattt ttttagtaca tctatttat tctattttag cctctaaatt aagaaaacta    7080
aaactctatt ttagtttttt tatttaataa tttagatata aaatagaata aaataaagtg    7140
actaaaaatt aaacaaatac cctttaagaa attaaaaaaa ctaaggaaac atttttcttg    7200
tttcgagtag ataatgccag cctgttaaac gccgtcgacg agtctaacgg acaccaacca    7260
gcgaaccagc agcgtcgcgt cgggccaagc gaagcagacg gcacggcatc tctgtcgctg    7320
cctctggacc cctctcgaga gttccgctcc accgttggac ttgctccgct gtcggcatcc    7380
agaaattgcg tggcggagcg gcagacgtga gccggcacgg caggcggcct cctcctcctc    7440
tcacggcacc ggcagctacg ggggattcct ttcccaccgc tccttcgctt tcccttcctc    7500
gcccgccgta ataaatagac accccctcca caccctcttt ccccaacctc gtgttgttcg    7560
gagcgcacac acacacaacc agatctcccc caaatccacc cgtcggcacc tccgcttcaa    7620
ggtacgccgc tcgtcctccc cccccccccc tctctacctt ctctagatcg gcgttccggt    7680
ccatggttag ggcccggtag ttctacttct gttcatgttt gtgttagatc cgtgtttgtg    7740
ttagatccgt gctgctagcg ttcgtacacg gatgcgacct gtacgtcaga cacgttctga    7800
ttgctaactt gccagtgttt ctctttgggg aatcctggga tggctctagc cgttccgcag    7860
acgggatcga tttcatgatt ttttttgttt cgttgcatag ggtttggttt gcccttttcc    7920
tttatttcaa tatatgccgt gcacttgttt gtcgggtcat cttttcatgc ttttttttgt    7980
```

```
cttggttgtg atgatgtggt ctggttgggc ggtcgttcta gatcggagta gaattctgtt   8040
tcaaactacc tggtggattt attaattttg gatctgtatg tgtgtgccat acatattcat   8100
agttacgaat tgaagatgat ggatggaaat atcgatctag gataggtata catgttgatg   8160
cgggttttac tgatgcatat acagagatgc tttttgttcg cttggttgtg atgatgtggt   8220
gtggttgggc ggtcgttcat tcgttctaga tcggagtaga atactgtttc aaactacctg   8280
gtgtatttat taattttgga actgtatgtg tgtgtcatac atcttcatag ttacgagttt   8340
aagatggatg gaaatatcga tctaggatag gtatacatgt tgatgtgggt tttactgatg   8400
catatacatg atggcatatg cagcatctat tcatatgctc taaccttgag tacctatcta   8460
ttataataaa caagtatgtt ttataattat tttgatcttg atatacttgg atgatggcat   8520
atgcagcagc tatatgtgga ttttttttagc cctgccttca tacgctattt atttgcttgg   8580
tactgtttct tttgtcgatg ctcaccctgt tgtttggtgt tacttctgca gggatcccg    8640 atcatgcaaa aactcattaa ctcagtgcaa aactatgcct ggggcagcaa aacggcgttg   8700
actgaacttt atggtatgga aaatccgtcc agccagccga tggccgagct gtggatgggc   8760
gcacatccga aaagcagttc acgagtgcag aatgccgccg gagatatcgt ttcactgcgt   8820
gatgtgattg agagtgataa atcgactctg ctcggagagg ccgttgccaa acgctttggc   8880
gaactgcctt tcctgttcaa agtattatgc gcagcacagc cactctccat tcaggttcat   8940
ccaaacaaac acaattctga atcggttttt gccaaagaaa atgccgcagg tatcccgatg   9000
gatgccgccg agcgtaacta taaagatcct aaccacaagc cggagctggt ttttgcgctg   9060 acgccttttcc ttgcgatgaa cgcgtttcgt gaattttccg agattgtctc cctactccag   9120
ccggtcgcag gtgcacatcc ggcgattgct cactttttac aacagcctga tgccgaacgt   9180
ttaagcgaac tgttcgccag cctgttgaat atgcagggtg aagaaaaatc ccgcgcgctg   9240 gcgatttttaa aatcggccct cgatagccag cagggtgaac cgtggcaaac gattcgttta   9300
atttctgaat tttacccgga agacagcggt ctgttctccc cgctattgct gaatgtggtg   9360
aaattgaacc ctggcgaagc gatgttcctg ttcgctgaaa caccgcacgc ttacctgcaa   9420
ggcgtggcgc tggaagtgat ggcaaactcc gataacgtgc tgcgtgcggg tctgacgcct   9480
aaatacattg atattccgga actggttgcc aatgtgaaat tcgaagccaa accggctaac   9540
cagttgttga cccagccggt gaaacaaggt gcagaactgg acttcccgat tccagtggat   9600
gattttgcct tctcgctgca tgaccttagt gataaagaaa ccaccattag ccagcagagt   9660
gccgccattt tgttctgcgt cgaaggcgat gcaacgttgt ggaaaggttc tcagcagtta   9720
cagcttaaac cgggtgaatc agcgtttatt gccgccaacg aatcaccggt gactgtcaaa   9780
ggccacggcc gttagcgcg tgtttacaac aagctgtaag agcttactga aaaaattaac   9840
atctcttgct aagctgggag ctcgtcatgg gtcgtttaag ctgccgatgt gcctgcgtcg   9900
tctggtgccc tctctccata tggaggttgt caaagtatct gctgttcgtg tcatgagtcg   9960
tgtcagtgtt ggtttaataa tggaccggtt gtgttgtgtg tgcgtactac ccagaactat  10020
gacaaatcat gaataagttt gatgtttgaa attaaagcct gtgctcatta tgttctgtct  10080
ttcagttgtc tcctaatatt tgcctgcagg tactggctat ctaccgtttc ttacttagga  10140
ggtgtttgaa tgcactaaaa ctaatagtta gtggctaaaa ttagttaaaa catccaaaca  10200
ccatagctaa tagttgaact attagctatt tttggaaaat tagttaatag tgaggtagtt  10260
atttgttagc tagctaattc aactaacaat ttttagccaa ctaacaatta gtttcagtgc  10320
attcaaacac cccccttaatg ttaacgtggt tctatctacc gtctcctaat atatggttga  10380
```

```
ttgttcggtt tgttgctatg ctattgggtt ctgattgctg ctagttcttg ctgaatccag   10440
aagttctcgt agtatagctc agattcatat tatttatttg agtgataagt gatccaggtt   10500
attactatgt tagctaggtt ttttttacaa ggataaatta tctgtgatca taattcttat   10560
gaaagcttta tgtttcctgg aggcagtggc atgcaatgca tgacagcaac ttgatcacac   10620
cagctgaggt agatacggta acaaggttct taaatctgtt caccaaatca ttggagaaca   10680
cacatacaca ttcttgccag tcttggttag agaaatttca tgacaaaatg ccaaagctgt   10740
cttgactctt cacttttggc catgagtcgt gacttagttt ggtttaatgg accggttctc   10800
ctagcttgtt ctactcaaaa ctgttgttga tgcgaataag ttgtgatggt tgatctctgg   10860
attttgtttt gctctcaata gtggacgaga ttagatagcc cggaaattta ccggtgcccg   10920
ggcggccagc atggccgtat ccgcaatgtg ttattaagtt gtctaagcgt caatttgttt   10980
acaccacaat atatcctgcc accagccagc caacagctcc ccgaccggca gctcggcaca   11040
aaatcaccac tcgatacagg cagcccatca gaattaattc tcatgtttga cagcttatca   11100
tcgactgcac ggtgcaccaa tgcttctggc gtcaggcagc catcggaagc tgtggtatgg   11160
ctgtgcaggt cgtaaatcac tgcataattc gtgtcgctca aggcgcactc ccgttctgga   11220
taatgttttt tgcgccgaca tcataacggt tctggcaaat attctgaaat gagctgttga   11280
caattaatca tccggctcgt ataatgtgtg gaattgtgag cggataacaa tttcacacag   11340
gaaacagacc atgagggaag cgttgatcgc cgaagtatcg actcaactat cagaggtagt   11400
tggcgtcatc gagcgccatc tcgaaccgac gttgctggcc gtacatttgt acggctccgc   11460
agtggatggc ggcctgaagc cacacagtga tattgatttg ctggttacgg tgaccgtaag   11520
gcttgatgaa acaacgcggc gagctttgat caacgacctt ttggaaactt cggcttcccc   11580
tggagagagc gagattctcc gcgctgtaga agtcaccatt gttgtgcacg acgacatcat   11640
tccgtggcgt tatccagcta agcgcgaact gcaatttgga gaatggcagc gcaatgacat   11700
tcttgcaggt atcttcgagc cagccacgat cgacattgat ctggctatct tgctgacaaa   11760
agcaagagaa catagcgttg ccttggtagg tccagcggcg gaggaactct tgatccggt    11820 tcctgaacag gatctatttg aggcgctaaa tgaaacctta acgctatgga actcgccgcc   11880
cgactgggct ggcgatgagc gaaatgtagt gcttacgttg tcccgcattt ggtacagcgc   11940
agtaaccggc aaaatcgcgc cgaaggatgt cgctgccgac tgggcaatgg agcgcctgcc   12000
ggcccagtat cagcccgtca tacttgaagc taggcaggct tatcttggac aagaagatcg   12060
cttggcctcg cgcgcagatc agttggaaga atttgttcac tacgtgaaag gcgagatcac   12120
caaagtagtc ggcaaataaa gctctagtgg atctccgtac ccggggatct ggctcgcggc   12180
ggacgcacga cgccggggcg agaccatagg cgatctccta aatcaatagt agctgtaacc   12240
tcgaagcgtt tcacttgtaa caacgattga gaattttgt cataaaattg aaatacttgg    12300
ttcgcatttt tgtcatccgc ggtcagccgc aattctgacg aactgcccat ttagctggag   12360
atgattgtac atccttcacg tgaaaatttc tcaagcgctg tgaacaaggg ttcagatttt   12420
agattgaaag gtgagccgtt gaaacacgtt cttcttgtcg atgacgacgt cgctatgcgg   12480
catcttatta ttgaataccT tacgatccac gccttcaaag tgaccgcggt agccgacagc   12540
acccagttca caagagtact ctcttccgcg acggtcgatg tcgtggttgt tgatctagat   12600
ttaggtcgtg aagatgggct cgagatcgtt cgtaatctgg cggcaaagtc tgatattcca   12660
atcataatta tcagtggcga ccgccttgag gagacggata aagttgttgc actcgagcta   12720
```

```
ggagcaagtg attttatcgc taagccgttc agtatcagag agtttctagc acgcattcgg   12780
gttgccttgc gcgtgcgccc caacgttgtc cgctccaaag accgacggtc tttttgtttt   12840
actgactgga cacttaatct caggcaacgt cgcttgatgt ccgaagctgg cggtgaggtg   12900
aaacttacgg caggtgagtt caatcttctc ctcgcgtttt tagagaaacc ccgcgacgtt   12960
ctatcgcgcg agcaacttct cattgccagt cgagtacgcg acgaggaggt ttatgacagg   13020
agtatagatg ttctcatttt gaggctgcgc cgcaaacttg aggcagatcc gtcaagccct   13080
caactgataa aaacagcaag aggtgccggt tatttctttg acgcggacgt gcaggtttcg   13140
cacgggggga cgatggcagc ctgagccaat tcccagatcc ccgaggaatc ggcgtgagcg   13200
gtcgcaaacc atccggcccg gtacaaatcg gcgcggcgct gggtgatgac ctggtggaga   13260
agttgaaggc cgcgcaggcc gcccagcggc aacgcatcga ggcagaagca cgccccggtg   13320
aatcgtggca agcggccgct gatcgaatcc gcaaagaatc ccggcaaccg ccggcagccg   13380
gtgcgccgtc gattaggaag ccgcccaagg gcgacgagca accagatttt ttcgttccga   13440
tgctctatga cgtgggcacc cgcgatagtc gcagcatcat ggacgtggcc gttttccgtc   13500
tgtcgaagcg tgaccgacga gctggcgagg tgatccgcta cgagcttcca cgggcacg    13560 tagaggtttc gcagggccg gccggcatgg ccagtgtgtg ggattacgac ctggtactga    13620
tggcggtttc ccatctaacc gaatccatga accgataccg ggaagggaag ggagacaagc   13680
ccggccgcgt gttccgtcca cacgttgcgg acgtactcaa gttctgccgg cgagccgatg   13740
gcggaaagca gaaagacgac ctggtagaaa cctgcattcg gttaaacacc acgcacgttg   13800
ccatgcagcg tacgaagaag gccaagaacg gccgcctggt gacggtatcc gagggtgaag   13860
ccttgattag ccgctacaag atcgtaaaga gcgaaaccgg gcggccggag tacatcgaga   13920
tcgagctagc tgattggatg taccgcgaga tcacagaagg caagaacccg gacgtgctga   13980
cggttcaccc cgattacttt ttgatcgatc ccggcatcgg ccgttttctc taccgcctgg   14040
cacgccgcgc gcaggcaag gcagaagcca gatggttgtt caagacgatc tacgaacgca   14100
gtggcagcgc cggagagttc aagaagttct gtttcaccgt gcgcaagctg atcgggtcaa   14160
atgacctgcc ggagtacgat ttgaaggagg aggcggggca ggctggcccg atcctagtca   14220
tgcgctaccg caacctgatc gagggcgaag catccgccgg ttcctaatgt acggagcaga   14280
tgctagggca aattgcccta gcaggggaaa aaggtcgaaa aggtctcttt cctgtgata    14340 gcacgtacat tgggaaccca aagccgtaca ttgggaaccg gaacccgtac attgggaacc   14400
caaagccgta cattgggaac cggtcacaca tgtaagtgac tgatataaaa gagaaaaaag   14460 gcgattttc cgcctaaaac tctttaaaac ttattaaaac tcttaaaacc cgcctggcct   14520
gtgcataact gtctggccag cgcacagccg aagagctgca aaaagcgcct acccttcggt   14580
cgctgcgctc cctacgcccc gccgcttcgc gtcggcctat cgcggccgct ggccgctcaa   14640
aaatggctgg cctacggcca ggcaatctac cagggcgcgg acaagccgcg ccgtcgccac   14700
tcgaccgccg gcgctgaggt ctgcctcgtg aagaaggtgt tgctgactca taccaggcct   14760
gaatcgcccc atcatccagc cagaaagtga gggagccacg gttgatgaga gctttgttgt   14820
aggtggacca gttggtgatt ttgaactttt gctttgccac ggaacggtct cgttgtcgg    14880 gaagatgcgt gatctgatcc ttcaactcag caaaagttcg atttattcaa caaagccgcc   14940
gtcccgtcaa gtcagcgtaa tgctctgcca gtgttacaac caattaacca attctgatta   15000
gaaaaactca tcgagcatca aatgaaactg caatttattc atatcaggat tatcaatacc   15060 atattttga aaaagccgtt tctgtaatga aggagaaaac tcaccgaggc agttccatag   15120
```

```
gatggcaaga tcctggtatc ggtctgcgat tccgactcgt ccaacatcaa tacaacctat    15180
taatttcccc tcgtcaaaaa taaggttatc aagtgagaaa tcaccatgag tgacgactga    15240
atccggtgag aatggcaaaa gctctgcatt aatgaatcgg ccaacgcgcg gggagaggcg    15300
gtttgcgtat tgggcgctct tccgcttcct cgctcactga ctcgctgcgc tcggtcgttc    15360
ggctgcggcg agcggtatca gctcactcaa aggcggtaat acggttatcc acagaatcag    15420
gggataacgc aggaaagaac atgtgagcaa aaggccagca aaaggccagg aaccgtaaaa    15480
aggccgcgtt gctggcgttt ttccataggc tccgcccccc tgacgagcat cacaaaaatc    15540
gacgctcaag tcagaggtgg cgaaacccga caggactata agataccag gcgtttcccc    15600 ctggaagctc cctcgtgcgc tctcctgttc cgaccctgcc gcttaccgga tacctgtccg    15660
cctttctccc ttcgggaagc gtggcgcttt ctcatagctc acgctgtagg tatctcagtt    15720
cggtgtaggt cgttcgctcc aagctgggct gtgtgcacga accccccgtt cagcccgacc    15780
gctgcgcctt atccggtaac tatcgtcttg agtccaaccc ggtaagacac gacttatcgc    15840
cactggcagc agccactggt aacaggatta gcagagcgag gtatgtaggc ggtgctacag    15900
agttcttgaa gtggtggcct aactacggct acactagaag aacagtattt ggtatctgcg    15960
ctctgctgaa gccagttacc ttcggaaaaa gagttggtag ctcttgatcc ggcaaacaaa    16020
ccaccgctgg tagcggtggt ttttttgttt gcaagcagca gattacgcgc agaaaaaaag    16080
gatctcaaga agatcctttg atcttttcta cggggtctga cgctcagtgg aacgaaaact    16140
cacgttaagg gattttggtc atgagattat caaaaaggat cttcacctag atccttttga    16200
tccggaatta                                                            16210

<210> SEQ ID NO 23
<211> LENGTH: 15881
<212> TYPE: DNA
<213> ORGANISM: Artificial Sequence
<220> FEATURE:
<223> OTHER INFORMATION: Recombinant vector

<400> SEQUENCE: 23
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg     240
aactgacaga accgcaacgc tgcaggaatt ggccgcagcg ccatttaaa tcaattgggc     300 gcgccagctg cttgtgggga ccagacaaaa aaggaatggt gcagaattgt taggcgcacc     360
taccaaaagc atctttgcct ttattgcaaa gataaagcag attcctctag tacaagtggg     420
gaacaaaata acgtggaaaa gagctgtcct gacagcccac tcactaatgc gtatgacgaa     480
cgcagtgacg accacaaaac tcgagacttt tcaacaaagg gtaatatccg gaaacctcct     540
cggattccat tgcccagcta tctgtcactt tattgtgaag atagtggaaa aggaaggtgg     600
ctcctacaaa tgccatcatt gcgataaagg aaaggctatc gttgaagatg cctctgccga     660
cagtggtccc aaagatggac ccccaccac gaggagcatc gtgaaaaag aagacgttcc     720 aaccacgtct tcaaagcaag tggattgatg tgatatctcc actgacgtaa gggatgacga     780
acaatcccac tatccttcgg taccggaccc atgccttacg atcatctgac atcttaaata     840
tttcaaactg cagtatttca aaaactgtgg ttttgtcaaa actttgttc ccaaactgag     900
```

```
actaaaatgt agtgctagat aataaggcct tacccgttgg aatgacaaaa aagaaacaga      960
aaacacctga aaaatagtat tgccttggct ctaaattata aatcgttttg gttttattta     1020
atatctattt tttaagcata ctaaaatcta tgtacctatg aaaaataaaa tatgaactac     1080
aatttaagac tgagtacagt gtacagcgat aagttatatg aaccacaatt gttttgaaa     1140
ggaaaaaaac taaattgaca agagaaacaa tcaactcttt tagaaacttt gtataccaaa    1200
aaacgaaata aagaagaaga aaaaaataca cacgatgagt ttattagccc acaaaacatg    1260
aaaaaaaatg agagttaaag cctaactcag gcccacaaag aatcacaagc gcccatattc    1320
acagccgccg aaaggtttcg gcccccagtt ggatctcaga gcccagtgtg aaataggact    1380
gacttgtctc tgatggttac gttacgtagg gattgaaaca acaggcagt gagccgatgt     1440
ggcagaccgg agcgcagaag cgacgacgac catgaactga aggcgctggc agtgggccat    1500
gcgcccagaa cgctgacgaa ccacgacgac gcggacgttc tacgaggtcg gtggggccgt    1560
cggcagcccg ccggagcata ttcgccgtcg acagaggcag agaaggggaa tgtgtgggag    1620
catattccac ccgtgggaag cctcgagtc ggagatgtgc agatctgccg gacgcacatg     1680
cgcacagctg ccgcaataga aaccagtgtc ttttttatttt attttataag aaaaaactag   1740
aaaagaaaat ccagtcttct atacaggcct gcacagagag agaggaggga aggtcaaatc    1800
gtagaaaaaa aatgcttcct tttattgtta cgacattggc ctgaatatat actcattgtt   1860
tctttcctta acttcaacaa ttattgattt tgacaatcca ttttttattt tagttcgcca   1920
aggttttggt tggagaagaa tttaaaacct agccaagcag tcgagcacga gagccgccgc   1980
cgccgccgcc gccgttggca ggacctgctg acctctgacg accggacacg gacgttttcc   2040
aaagtccaaa ctcggggtag gtaggtcgtg aggctgctgc gttcgccaag ggaagaagca   2100
tctagttgaa gctagaaacg ggcagggggg agggccgac gctatcggaa atctgaagcc    2160
cagcacggac ggacggacgg gcaggggcgg cggcacatcc tcgtctgacc gccgcgccgc   2220
gtccgacatg cgcaagctgc tgctcttccc gcgcccccac ggcggccggg ccggcagagc   2280
acgggacgcg cggggcgggc ctgacgtcgt tttcacgtgg tccgtcaccg ttgcttgcat   2340
agcgtacagg agtatagtcc catttccgaa accaaaaaaa gtaaacaaaa aaatgccgtc   2400
gcattagttg gctggcaagg gaagaccaag atggttttca aatcaaacat gtaaaaaaat   2460
gtttctttct ttttttgaacg aacttaccag ttcgaattct ttaccggcat tattggttta  2520
aattgttccc caagaaagaa agaaaagaaa agcgggggga aatatgcctt ccttccttct   2580
tgcgtcacag accacgcgcg gatacaccgc acaacagcca ggcagcaagc agagcaccca   2640
ccgccggaag cggccgtcgg acagaacgac acgtggggca cggcacagtc cgggcccgca   2700
cgtcatcgaa gacacctgac ctgcccatgc gtcttctaga gaaaggcgga cggacaggtc   2760
acccccgcac ctcattccag gagttgcatt tcgctttctc ctttatttat ttataccaat   2820
aaaaaataaa tccgcctttt ctcctcccta tcgtgtgtct tcctctcgcc ggctttaaaa   2880
acgcacacaa gcgctaaaac cctctccacc gtccacctca gctcccatat ccgctcccct   2940
acctctccag catcctcccg tctccgtcgt ctcgtctccg ctcctcacct gccgctagc    3000
caagggtaac tcctcgctcc cggccggcc ccgcgtcggg gttttccatt tactactact    3060
cgctgctccc tcctgctccg tgctcagact cagatccgac caaagcggtt tcgctgacta   3120
aattctcctt cgttttttt tcttttttctg gacggattcc tggacgcagg caagatcaag   3180
atcggaatca acggtgagtc tgtaccccca acacaaactc gttcttcctg ctcggttcgt   3240
tgggtctgga ctctggagtg atctgagtgg ggtctctgcg cgcctgcgtg ctcaggtttc   3300
```

-continued

```
tgaaggatcg gcagtaaacc atggacaaca accccaacat caacgagtgc atcccctaca    3360
actgcctgag caaccccgag gtggaggtgc tgggcggcga gcgcatcgag accggctaca    3420
cccccatcga catcagcctg agcctgaccc agttcctgct gagcgagttc gtgcccggcg    3480
ccggcttcgt gctgggcctg gtggacatca tctggggcat cttcggcccc agccagtggg    3540
acgccttcct ggtgcagatc gagcagctga tcaaccagcg catcgaggag ttcgcccgca    3600
accaggccat cagccgcctg gagggcctga gcaacctgta ccaaatctac gccgagagct    3660
tccgcgagtg ggaggccgac cccaccaacc ccgccctgcg cgaggagatg cgcatccagt    3720
tcaacgacat gaacagcgcc ctgaccaccg ccatccccct gttcgccgtg cagaactacc    3780
aggtgcccct gctgagcgtg tacgtgcagg ccgccaacct gcacctgagc gtgctgcgcg    3840
acgtcagcgt gttcggccag cgctggggct cgacgccgc caccatcaac agccgctaca    3900
acgacctgac ccgcctgatc ggcaactaca ccgaccacgc cgtgcgctgg tacaacaccg    3960
gcctggagcg cgtgtggggt ccagacagcc gcgactggat caggtacaac cagttccgcc    4020
gcgagctgac cctgaccgtg ctggacatcg tgagcctgtt ccccaactac gacagccgca    4080
cctaccccat ccgcaccgtg agccagctga cccgcgagat ttacaccaac cccgtgctgg    4140
agaacttcga cggcagcttc cgcggcagcg cccagggcat cgagggcagc atccgcagcc    4200
cccacctgat ggacatcctg aacagcatca ccatctacac cgacgcccac cgcggcgagt    4260
actactggag cggccaccag atcatggcca gccccgtcgg cttcagcggc cccgagttca    4320
ccttcccccct gtacggcact atgggcaacg ctgcacctca gcagcgcatc gtggcacagc    4380
tgggccaggg agtgtaccgc accctgagca gcaccctgta ccgtcgacct ttcaacatcg    4440
gcatcaacaa ccagcagctg agcgtgctgg acggcaccga gttcgcctac ggcaccagca    4500
gcaacctgcc cagcgccgtg taccgcaaga gcggcaccgt ggacagcctg gacgagatcc    4560
cccctcagaa caacaacgtg ccacctcgac agggcttcag ccaccgtctg agccacgtga    4620
gcatgttccg cagtggcttc agcaacagca gcgtgagcat catccgtgca cctatgttca    4680
gctggattca ccgcagtgcc gagttcaaca acatcatccc cagcagccag atcacccaga    4740
tcccctgac caagagcacc aacctgggca gcggcaccag cgtggtgaag ggccccggct    4800
tcaccggcgg cgacatcctg cgccgcacca gccccggcca gatcagcacc ctgcgcgtga    4860
acatcaccgc ccccctgagc cagcgctacc gcgtccgcat ccgctacgcc agcaccacca    4920
acctgcagtt ccacaccagc atcgacggcc gccccatcaa ccagggcaac ttcagcgcca    4980
ccatgagcag cggcagcaac ctgcagagcg gcagcttccg caccgtgggc ttcaccaccc    5040
ccttcaactt cagcaacggc agcagcgtgt tcaccctgag cgcccacgtg ttcaacagcg    5100
gcaacgaggt gtacatcgac cgcatcgagt tcgtgcccgc cgaggtgacc ttcgaggccg    5160
agtacgacct ggagagggct cagaaggccg tgaacgagct gttcaccagc agcaaccaga    5220
tcggcctgaa gaccgacgtg accgactacc acatcgatca ggtgtaggag ctcagagaga    5280
tatttctgcc tccctatcgt gggtcgtccc caatggcctt tggtcgcaga ccatctttgc    5340
tgcttgtcta tgctgagaat aaatgtgaac ggtgccctg gacgctggat ccatgctggt    5400
tttggacacg gttgtctttt tgtgtttaac ttatctgcta ccgtcctgta acgaattcac    5460
taagttctag ttcttttgtg ctttgttaag aatataaaca atgaggtttc aattttggtg    5520
gcgccatccg gtctgattgc gtactagtat catgcatatc tgagctggtc tttccggagt    5580
aacagttttt tttgtttcg tgtcaatgat tctcagcctg ttcatttggt cttaatccat    5640
```

```
atcggttact actataatgt tgtcttgtct ctatagattg cagcagtcta acacatgttc   5700
ttggtatcct tttgggtgtg tttaatgcta tttgctctgt gttgtctttt tcgttaatcg   5760
ggacagagtt ttctctctgt tttgacagtt tcggtggttc ttttttgtgt gtggtcagcg   5820
agtcacgaac tgctggttgg ccagcgaaat agcgcagact attatgggtc ttctgctggt   5880
gaatatggaa ggacgaggtt aaattttctg ctttgatgtg tctgccctct gccgctgtgc   5940
tgcatgcatg tgtttgggag cgaagcagcg tgctgtttgg gcgtatggtt ggcatggtgt   6000
taaattattt cgctgattca gctttgggtt atcactggtt ttgatggtca cgctgtgtcg   6060
taagagagat cgtggcagca aaatggagaa aaaggcagtg aaacaaactt tcagggtgtg   6120
gaatgtatgg gattcgtatg gttgaggcca ggatttgtca attggtcaag ttgaaaagta   6180
aaggcgagac agattggcga ggaccgagga gagattgggg ttcagaaact tcggttacac   6240
tttaatcccc tccatctccc tccactcctc ccttctacgg accgcgatcg cttaattaag   6300
cttgcatgcc tgcagtgcag cgtgacccgg tcgtgcccct ctctagagat aatgagcatt   6360
gcatgtctaa gttataaaaa attaccacat atttttttg tcacacttgt ttgaagtgca   6420
gtttatctat ctttatacat atatttaaac tttactctac gaataatata atctatagta   6480
ctacaataat atcagtgttt tagagaatca tataaatgaa cagttagaca tggtctaaag   6540
gacaattgag tattttgaca acaggactct acagttttat cttttagtg tgcatgtgtt   6600 ctccttttt tttgcaaata gcttcaccta tataatactt catccatttt attagtacat   6660
ccatttaggg tttagggtta atggttttta tagactaatt tttttagtac atctatttta   6720
ttctatttta gcctctaaat taagaaaact aaaactctat tttagttttt ttatttaata   6780
atttagatat aaaatagaat aaaataaagt gactaaaaat taaacaaata ccctttaaga   6840
aattaaaaaa actaaggaaa catttttctt gtttcgagta gataatgcca gcctgttaaa   6900
cgccgtcgac gagtctaacg gacaccaacc agcgaaccag cagcgtcgcg tcgggccaag   6960
cgaagcagac ggcacggcat ctctgtcgct gcctctggac ccctctcgag agttccgctc   7020
caccgttgga cttgctccgc tgtcggcatc cagaaattgc gtggcggagc ggcagacgtg   7080
agccggcacg gcaggcggcc tcctcctcct ctcacgcac cggcagctac gggggattcc   7140
tttcccaccg ctccttcgct ttcccttcct cgcccgccgt aataaataga cacccctcc   7200 acaccctctt tccccaacct cgtgttgttc ggagcgcaca cacacacaac cagatctccc   7260
ccaaatccac ccgtcggcac ctccgcttca aggtacgccg ctcgtcctcc cccccccc   7320 ctctctacct tctctagatc ggcgttccgg tccatggtta gggcccggta gttctacttc   7380
tgttcatgtt tgtgttagat ccgtgtttgt gttagatccg tgctgctagc gttcgtacac   7440
ggatgcgacc tgtacgtcag acacgttctg attgctaact tgccagtgtt tctctttggg   7500
gaatcctggg atggctctag ccgttccgca gacgggatcg atttcatgat tttttttgtt   7560
tcgttgcata gggtttggtt tgccccttttc ctttatttca atatatgccg tgcacttgtt   7620
tgtcgggtca tcttttcatg ctttttttg tcttggttgt gatgatgtgg tctggttggg   7680
cggtcgttct agatcggagt agaattctgt ttcaaactac ctggtggatt tattaatttt   7740
ggatctgtat gtgtgtgcca tacatattca tagttacgaa ttgaagatga tggatggaaa   7800
tatcgatcta ggataggtat acatgttgat gcgggtttta ctgatgcata tacagagatg   7860 cttttttgttc gcttggttgt gatgatgtgg tgtggttggg cggtcgttca ttcgttctag   7920
atcggagtag aatactgttt caaactacct ggtgtattta ttaattttgg aactgtatgt   7980
gtgtgtcata catcttcata gttacgagtt taagatggat ggaaatatcg atctaggata   8040
```

```
ggtatacatg ttgatgtggg ttttactgat gcatatacat gatggcatat gcagcatcta   8100
ttcatatgct ctaaccttga gtacctatct attataataa acaagtatgt tttataatta   8160
ttttgatctt gatatacttg gatgatggca tatgcagcag ctatatgtgg attttttag    8220 ccctgccttc atacgctatt tatttgcttg gtactgtttc ttttgtcgat gctcaccctg   8280
ttgtttggtg ttacttctgc agggatcccc gatcatgcaa aaactcatta actcagtgca   8340
aaactatgcc tggggcagca aaacggcgtt gactgaactt tatggtatgg aaaatccgtc   8400
cagccagccg atggccgagc tgtggatggg cgcacatccg aaaagcagtt cacgagtgca   8460
gaatgccgcc ggagatatcg tttcactgcg tgatgtgatt gagagtgata aatcgactct   8520
gctcggagag gccgttgcca aacgctttgg cgaactgcct ttcctgttca agtattatg    8580 cgcagcacag ccactctcca ttcaggttca tccaaacaaa cacaattctg aaatcggttt   8640
tgccaaagaa aatgccgcag gtatcccgat ggatgccgcc gagcgtaact ataaagatcc   8700
taaccacaag ccggagctgg tttttgcgct gacgcctttc cttgcgatga acgcgtttcg   8760
tgaattttcc gagattgtct ccctactcca gccggtcgca ggtgcacatc cggcgattgc   8820
tcacttttta caacagcctg atgccgaacg tttaagcgaa ctgttcgcca gcctgttgaa   8880
tatgcagggt gaagaaaaat cccgcgcgct ggcgatttta aaatcggccc tcgatagcca   8940
gcagggtgaa ccgtggcaaa cgattcgttt aatttctgaa ttttacccgg aagacagcgg   9000
tctgttctcc ccgctattgc tgaatgtggt gaaattgaac cctggcgaag cgatgttcct   9060
gttcgctgaa acaccgcacg cttacctgca aggcgtggcg ctggaagtga tggcaaactc   9120
cgataacgtg ctgcgtgcgg gtctgacgcc taaatacatt gatattccgg aactggttgc   9180
caatgtgaaa ttcgaagcca aaccggctaa ccagttgttg acccagccgg tgaaacaagg   9240
tgcagaactg gacttcccga ttccagtgga tgattttgcc ttctcgctgc atgaccttag   9300
tgataaagaa accaccatta gccagcagag tgccgccatt ttgttctgcg tcgaaggcga   9360
tgcaacgttg tggaaaggtt ctcagcagtt acagcttaaa ccgggtgaat cagcgtttat   9420
tgccgccaac gaataccggg tgactgtcaa aggccacggc cgtttagcgc gtgtttacaa   9480
caagctgtaa gagcttactg aaaaaattaa catctcttgc taagctggga gctcgtcatg   9540
ggtcgtttaa gctgccgatg tgcctgcgtc gtctggtgcc ctctctccat atggaggttg   9600
tcaaagtatc tgctgttcgt gtcatgagtc gtgtcagtgt tggtttaata atggaccggt   9660
tgtgttgtgt gtgcgtacta cccagaacta tgacaaatca tgaataagtt tgatgtttga   9720
aattaaagcc tgtgctcatt atgttctgtc tttcagttgt ctcctaatat ttgcctgcag   9780
gtactggcta tctaccgttt cttacttagg aggtgtttga atgcactaaa actaatagtt   9840
agtggctaaa attagttaaa acatccaaac accatagcta atagttgaac tattagctat   9900
ttttggaaaa ttagttaata gtgaggtagt tatttgttag ctagctaatt caactaacaa   9960
tttttagcca actaacaatt agtttcagtg cattcaaaca cccccttaat gttaacgtgg  10020
ttctatctac cgtctcctaa tatatggttg attgttcggt ttgttgctat gctattgggt  10080
tctgattgct gctagttctt gctgaatcca gaagttctcg tagtatagct cagattcata  10140
ttatttattt gagtgataag tgatccaggt tattactatg ttagctaggt ttttttaca   10200 aggataaatt atctgtgatc ataattctta tgaaagcttt atgtttcctg gaggcagtgg  10260
catgcaatgc atgacagcaa cttgatcaca ccagctgagg tagatacggt aacaaggttc  10320
ttaaatctgt tcaccaaatc attggagaac acacatacac attcttgcca gtcttggtta  10380
```

```
gagaaatttc atgacaaaat gccaaagctg tcttgactct tcactttttgg ccatgagtcg   10440 tgacttagtt tggttttaatg gaccggttct cctagcttgt tctactcaaa actgttgttg   10500
atgcgaataa gttgtgatgg ttgatctctg gattttgttt tgctctcaat agtggacgag   10560
attagatagc ccgaaatttt accggtgccc gggcggccag catggccgta tccgcaatgt   10620
gttattaagt tgtctaagcg tcaatttgtt tacaccacaa tatatcctgc caccagccag   10680
ccaacagctc cccgaccggc agctcggcac aaaatcacca ctcgatacag gcagcccatc   10740
agaattaatt ctcatgtttg acagcttatc atcgactgca cggtgcacca atgcttctgg   10800
cgtcaggcag ccatcggaag ctgtggtatg gctgtgcagg tcgtaaatca ctgcataatt   10860
cgtgtcgctc aaggcgcact cccgttctgg ataatgtttt ttgcgccgac atcataacgg   10920
ttctggcaaa tattctgaaa tgagctgttg acaattaatc atccggctcg tataatgtgt   10980
ggaattgtga gcggataaca atttcacaca ggaaacagac catgagggaa gcgttgatcg   11040
ccgaagtatc gactcaacta tcagaggtag ttggcgtcat cgagcgccat ctcgaaccga   11100
cgttgctggc cgtacatttg tacggctccg cagtggatgg cggcctgaag ccacacagtg   11160
atattgattt gctggttacg gtgaccgtaa ggcttgatga acaacgcgg cgagctttga   11220 tcaacgacct tttggaaact tcggcttccc ctggagagag cgagattctc cgcgctgtag   11280
aagtcaccat tgttgtgcac gacgacatca ttccgtggcg ttatccagct aagcgcgaac   11340
tgcaatttgg agaatggcag cgcaatgaca ttcttgcagg tatcttcgag ccagccacga   11400
tcgacattga tctggctatc ttgctgacaa aagcaagaga acatagcgtt gccttggtag   11460
gtccagcggc ggaggaactc tttgatccgg ttcctgaaca ggatctattt gaggcgctaa   11520
atgaaacctt aacgctatgg aactcgccgc ccgactgggc tggcgatgag cgaaatgtag   11580
tgcttacgtt gtcccgcatt tggtacagcg cagtaaccgg caaaatcgcg ccgaaggatg   11640
tcgctgccga ctgggcaatg gagcgcctgc cggcccagta tcagcccgtc atacttgaag   11700
ctaggcaggc ttatcttgga caagaagatc gcttggcctc gcgcgcagat cagttggaag   11760
aatttgttca ctacgtgaaa ggcgagatca ccaaagtagt cggcaaataa agctctagtg   11820
gatctccgta cccggggatc tggctcgcgg cggacgcacg acgccggggc gagaccatag   11880
gcgatctcct aaatcaatag tagctgtaac ctcgaagcgt ttcacttgta caacgattg    11940 agaattttttg tcataaaatt gaaatacttg gttcgcattt ttgtcatccg cggtcagccg   12000
caattctgac gaactgccca tttagctgga gatgattgta catccttcac gtgaaaattt   12060
ctcaagcgct gtgaacaagg gttcagattt tagattgaaa ggtgagccgt tgaaacacgt   12120
tcttcttgtc gatgacgacg tcgctatgcg gcatcttatt attgaatacc ttacgatcca   12180
cgccttcaaa gtgaccgcgg tagccgacag cacccagttc acaagagtac tctcttccgc   12240
gacggtcgat gtcgtggttg ttgatctaga tttaggtcgt gaagatgggc tcgagatcgt   12300
tcgtaatctg gcggcaaagt ctgatattcc aatcataatt atcagtggcg accgccttga   12360
ggagacggat aaagttgttg cactcgagct aggagcaagt gatttttatcg ctaagccgtt   12420 cagtatcaga gagtttctag cacgcattcg ggttgccttg cgcgtgcgcc caacgttgt    12480 ccgctccaaa gaccgacggt ctttttgttt tactgactgg acacttaatc tcaggcaacg   12540
tcgcttgatg tccgaagctg gcggtgaggt gaaacttacg gcaggtgagt tcaatcttct   12600
cctcgcgttt ttagagaaac cccgcgacgt tctatcgcgc gagcaacttc tcattgccag   12660
tcgagtacgc gacgaggagg tttatgacag gagtatagat gttctcattt tgaggctgcg   12720
ccgcaaactt gaggcagatc cgtcaagccc tcaactgata aaaacagcaa gaggtgccgg   12780
```

```
ttatttctttt gacgcggacg tgcaggtttc gcacgggggg acgatggcag cctgagccaa    12840
ttcccagatc cccgaggaat cggcgtgagc ggtcgcaaac catccggccc ggtacaaatc    12900
ggcgcggcgc tgggtgatga cctggtggag aagttgaagg ccgcgcaggc cgcccagcgg    12960
caacgcatcg aggcagaagc acgccccggt gaatcgtggc aagcggccgc tgatcgaatc    13020
cgcaaagaat cccggcaacc gccggcagcc ggtgcgccgt cgattaggaa gccgcccaag    13080
ggcgacgagc aaccagattt tttcgttccg atgctctatg acgtgggcac ccgcgatagt    13140
cgcagcatca tggacgtggc cgttttccgt ctgtcgaagc gtgaccgacg agctggcgag    13200
gtgatccgct acgagcttcc agacgggcac gtagaggttt ccgcagggcc ggccggcatg    13260
gccagtgtgt gggattacga cctggtactg atggcggttt cccatctaac cgaatccatg    13320
aaccgatacc gggaagggaa gggagacaag cccggccgcg tgttccgtcc acacgttgcg    13380
gacgtactca agttctgccg gcgagccgat ggcggaaagc agaaagacga cctggtagaa    13440
acctgcattc ggttaaacac cacgcacgtt gccatgcagc gtacgaagaa ggccaagaac    13500
ggccgcctgg tgacggtatc cgagggtgaa gccttgatta gccgctacaa gatcgtaaag    13560
agcgaaaccg ggcggccgga gtacatcgag atcgagctag ctgattggat gtaccgcgag    13620
atcacagaag gcaagaaccc ggacgtgctg acggttcacc ccgattactt tttgatcgat    13680
cccggcatcg gccgttttct ctaccgcctg gcacgccgcg ccgcaggcaa ggcagaagcc    13740
agatggttgt tcaagacgat ctacgaacgc agtggcagcg ccggagagtt caagaagttc    13800
tgtttcaccg tgcgcaagct gatcgggtca aatgacctgc cggagtacga tttgaaggag    13860
gaggcggggc aggctggccc gatcctagtc atgcgctacc gcaacctgat cgagggcgaa    13920
gcatccgccg gttcctaatg tacggagcag atgctagggc aaattgccct agcaggggaa    13980
aaaggtcgaa aagtctcttt tcctgtggat agcacgtaca ttgggaaccc aaagccgtac    14040
attgggaacc ggaaccccgta cattgggaac ccaaagccgt acattgggaa ccggtcacac    14100
atgtaagtga ctgatataaa agagaaaaaa ggcgattttt ccgcctaaaa ctctttaaaa    14160
cttattaaaa ctcttaaaac ccgcctggcc tgtgcataac tgtctggcca gcgcacagcc    14220
gaagagctgc aaaaagcgcc taccttcgg tcgctgcgct ccctacgccc cgccgcttcg    14280
cgtcggccta tcgcggccgc tggccgctca aaaatggctg gcctacggcc aggcaatcta    14340
ccagggcgcg gacaagccgc gccgtcgcca ctcgaccgcc ggcgctgagg tctgcctcgt    14400
gaagaaggtg ttgctgactc ataccaggcc tgaatcgccc catcatccag ccagaaagtg    14460
agggagccac ggttgatgag agctttgttg taggtggacc agttggtgat tttgaacttt    14520
tgctttgcca cggaacggtc tgcgttgtcg ggaagatgcg tgatctgatc cttcaactca    14580 gcaaagttc gatttattca acaaagccgc cgtcccgtca agtcagcgta atgctctgcc    14640
agtgttacaa ccaattaacc aattctgatt agaaaaactc atcgagcatc aaatgaaact    14700
gcaatttatt catatcagga ttatcaatac catattttttg aaaagccgt ttctgtaatg    14760 aaggagaaaa ctcaccgagg cagttccata ggatggcaag atcctggtat cggtctgcga    14820
ttccgactcg tccaacatca atacaaccta ttaatttccc ctcgtcaaaa ataaggttat    14880
caagtgagaa atcaccatga gtgacgactg aatccggtga agatgcaaa agctctgcat    14940 taatgaatcg gccaacgcgc ggggagaggc ggtttgcgta ttgggcgctc ttccgcttcc    15000
tcgctcactg actcgctgcg ctcggtcgtt cggctgcggc gagcggtatc agctcactca    15060
aaggcggtaa tacggttatc cacagaatca ggggataacg caggaaagaa catgtgagca    15120
```

| | |
|---|---|
| aaaggccagc aaaaggccag gaaccgtaaa aaggccgcgt tgctggcgtt tttccatagg | 15180 |
| ctccgccccc ctgacgagca tcacaaaaat cgacgctcaa gtcagaggtg gcgaaacccg | 15240 |
| acaggactat aaagatacca ggcgtttccc cctggaagct ccctcgtgcg ctctcctgtt | 15300 |
| ccgaccctgc cgcttaccgg atacctgtcc gcctttctcc cttcgggaag cgtggcgctt | 15360 |
| tctcatagct cacgctgtag gtatctcagt tcggtgtagg tcgttcgctc caagctgggc | 15420 |
| tgtgtgcacg aaccccccgt tcagcccgac cgctgcgcct tatccggtaa ctatcgtctt | 15480 |
| gagtccaacc cggtaagaca cgacttatcg ccactggcag cagccactgg taacaggatt | 15540 |
| agcagagcga gtatgtagg cggtgctaca gagttcttga agtggtggcc taactacggc | 15600 |
| tacactagaa gaacagtatt tggtatctgc gctctgctga agccagttac cttcggaaaa | 15660 |
| agagttggta gctcttgatc cggcaaacaa accaccgctg gtagcggtgg tttttttgtt | 15720 |
| tgcaagcagc agattacgcg cagaaaaaaa ggatctcaag aagatccttt gatcttttct | 15780 |
| acggggtctg acgctcagtg gaacgaaaac tcacgttaag ggattttggt catgagatta | 15840 |
| tcaaaaagga tcttcaccta gatccttttg atccggaatt a | 15881 |

<210> SEQ ID NO 24
<211> LENGTH: 15436
<212> TYPE: DNA
<213> ORGANISM: Artificial Sequence
<220> FEATURE:
<223> OTHER INFORMATION: Recombinant vector

<400> SEQUENCE: 24

| | |
|---|---|
| attcctgtgg ttggcatgca catacaaatg gacgaacgga taaaccttt cacgcccttt | 60 |
| taaatatccg attattctaa taaacgctct tttctcttag gtttaccccgc caatatatcc | 120 |
| tgtcaaacac tgatagttta aactgaaggc gggaaacgac aatctgatca tgagcggaga | 180 |
| attaagggag tcacgttatg accccgccg atgacgcggg acaagccgtt ttacgtttgg | 240 |
| aactgacaga accgcaacgc tgcaggaatt ggccgcagcg gccatttaaa tcaattgggc | 300 |
| gcgccagctg cttgtgggga ccagacaaaa aaggaatggt gcagaattgt taggcgcacc | 360 |
| taccaaaagc atctttgcct ttattgcaaa gataaagcag attcctctag tacaagtggg | 420 |
| gaacaaaata acgtggaaaa gagctgtcct gacagcccac tcactaatgc gtatgacgaa | 480 |
| cgcagtgacg accacaaaac tcgagacttt tcaacaaagg gtaatatccg gaaacctcct | 540 |
| cggattccat tgcccagcta tctgtcactt tattgtgaag atagtggaaa aggaaggtgg | 600 |
| ctcctacaaa tgccatcatt gcgataaagg aaaggctatc gttgaagatg cctctgccga | 660 |
| cagtggtccc aaagatggac ccccacccac gaggagcatc gtggaaaaag aagacgttcc | 720 |
| aaccacgtct tcaaagcaag tggattgatg tgatatctcc actgacgtaa gggatgacga | 780 |
| acaatcccac tatccttcgg taccggaccc aaatgaatta atatattatc taaattcaga | 840 |
| cgggaaaaag agagaaggaa tcaggaaggc tgagtgcaat attagttttt cattgagcac | 900 |
| aatcttatta tgtttgatga acatcttgaa caaagtatga gtggaaaaca acacttatgt | 960 |
| tatatctgca gcacagattg ttagaagtga aggctacctt gagatggtga taggtctctg | 1020 |
| aacccatctg cattgcttct tcgaagttca tagcaccaac aagaagaatc ataatttcct | 1080 |
| acaaataaga aatgtttata gttactccaa aactacagtt aaacatattg atatggttga | 1140 |
| tatacatgaa caactaactg tcttaatatg tttctgttta ggcaaagat gacacaagtg | 1200 |
| gacaaagtaa gggaataatg cattcaactt ctcagactct aaaggtttgg atgaatactt | 1260 |
| gaatgggaag accatttcca gcatgctttc caccattaat gactgtattt gcagggacag | 1320 |

```
gaagagttgt agcgcttttg ccaacaagat ccgctatatg cttgtagagt ggaacctgca    1380
cagcaacaag catccaatga tctgagaata agaattatgt gcggtggcat gacacattta    1440
ccaaattatg atgattttag cagaagagca gcacctcttt ttcagcagca ccagctttgc    1500
aagctgcaat tgacactgcc agcatagtat ttgctccaag ctcagcctgc atttcgcaca    1560
atatcatatc tatttccatt tggataaaat ctatttgcca gaaatatggg aacggaatca    1620
agatacagaa aaaagttgag gctgtagtgg taagtgggaa cacaagtaca gtgaaaagat    1680
agcattattt tccgaacagt caaattaacc gaaataagta gtatcacata ctgaccctaa    1740
attgactaca cccaatgtaa agaattgctt gtgcatattg agccatcagt tgtttgtttg    1800
tgtaatggat ttgacaatgc agaattcagg agcaaaaaaa accgcaaagg agagagaggg    1860
aaaggatctc cgagtatccc acctgtggcg cgccttgtca agtccatgat ggcctggtcg    1920
atctgcgcct gctgctgcgg atccatccca acgagtgcct ccgacacctt gtcgttgatc    1980
acccgcaccg cgtaggcgac cccctggcg aggaacttcc gcctctcgga ggccccggcc    2040
gcgtcggcgg cggcgcccac gagcgcgccc acgctagccg tagatgctcg gtgcacggcc    2100
ttgttggtgt gcaactcgac ctcaacggcc ggtgcgctac gcccgtcaag gatctggcgc    2160
gcccgcaccc tcgtgatcac ggtgggcgcc tcccgcctca tgtggccgac gatgaaaagc    2220
gccgggtcag gggccttggc gcggagcgcc gtattcaggg cctcctcgct cttgcgcgag    2280
agcaggtgct tccccaggta ctcctgcact gacatggctg ccacagcggt ggaattttct    2340
tgtcctcacg acttcgccac gtcgtcctca cctccctggc ttcccacgac tccgccgtat    2400
cgaggtgctc ggtgggtcgc cttaatccga agtccgaact aggaagacga gacagagagg    2460
tctgaggaat gggcctcgtt tgatgttgag ctgaattatt tttccagcat aagcccaggt    2520
cttggtccat gaacaaaatt actagaaacc cagcccagta ctacgatcta aagagggac    2580 tgccactgga tagctctctc tagcattctc cacgctccaa tacagcggcg tagggtctat    2640
ccgggtctat ccgcgaacac gtgagaactc tccagaaact gctttctcct ccacttcatc    2700
tctctcgctt tccctctata aaagacccc ttctaggaat tgagggagac agcaagcagc    2760
gatccgaagc tcaatcaatt cactcaaacc tcttccccaa atcttcgatt agattctcgt    2820
tgacaagaag actataaccg aacctgaccg taaaccatgg acaacaaccc caacatcaac    2880
gagtgcatcc cctacaactg cctgagcaac cccgaggtgg aggtgctggg cggcgagcgc    2940
atcgagaccg gctacacccc catcgacatc agcctgagcc tgacccagtt cctgctgagc    3000
gagttcgtgc ccggcgccgg cttcgtgctg ggcctggtgg acatcatctg gggcatcttc    3060
ggccccagcc agtgggacgc cttcctggtg cagatcgagc agctgatcaa ccagcgcatc    3120
gaggagttcg cccgcaacca ggccatcagc cgcctggagg gcctgagcaa cctgtaccaa    3180
atctacgccg agagcttccg cgagtgggag gccgacccca ccaacccgc cctgcgcgag    3240 gagatgcgca tccagttcaa cgacatgaac agcgccctga ccaccgccat ccccctgttc    3300
gccgtgcaga actaccaggt gcccctgctg agcgtgtacg tgcaggccgc caacctgcac    3360
ctgagcgtgc tgcgcgacgt cagcgtgttc ggccagcgct ggggcttcga cgccgccacc    3420
atcaacagcc gctacaacga cctgacccgc ctgatcggca actacaccga ccacgccgtg    3480
cgctggtaca acaccggcct ggagcgcgtg tggggtccag acagccgcga ctggatcagg    3540
tacaaccagt tccgccgcga gctgaccctg accgtgctgg acatcgtgag cctgttcccc    3600
aactacgaca gccgcaccta ccccatccgc accgtgagcc agctgacccg cgagatttac    3660
```

```
accaaccccg tgctggagaa cttcgacggc agcttccgcg gcagcgccca gggcatcgag    3720
ggcagcatcc gcagccccca cctgatggac atcctgaaca gcatcaccat ctacaccgac    3780
gcccaccgcg gcgagtacta ctggagcggc caccagatca tggccagccc cgtcggcttc    3840
agcggccccg agttcacctt ccccctgtac ggcactatgg gcaacgctgc acctcagcag    3900
cgcatcgtgg cacagctggg ccagggagtg taccgcaccc tgagcagcac cctgtaccgt    3960
cgacctttca acatcggcat caacaaccag cagctgagcg tgctggacgg caccgagttc    4020
gcctacggca ccagcagcaa cctgcccagc gccgtgtacc gcaagagcgg caccgtggac    4080
agcctggacg agatccccc tcagaacaac aacgtgccac ctcgacaggg cttcagccac    4140
cgtctgagcc acgtgagcat gttccgcagt ggcttcagca acagcagcgt gagcatcatc    4200
cgtgcaccta tgttcagctg gattcaccgc agtgccgagt tcaacaacat catccccagc    4260
agccagatca cccagatccc cctgaccaag agcaccaacc tgggcagcgg caccagcgtg    4320
gtgaagggcc ccggcttcac cggcggcgac atcctgcgcc gcaccagccc cggccagatc    4380
agcaccctgc gcgtgaacat caccgccccc ctgagccagc gctaccgcgt ccgcatccgc    4440
tacgccagca ccaccaacct gcagttccac accagcatcg acggccgccc catcaaccag    4500
ggcaacttca gcgccaccat gagcagcggc agcaacctgc agagcggcag cttccgcacc    4560
gtgggcttca ccacccccctt caacttcagc aacggcagca gcgtgttcac cctgagcgcc    4620
cacgtgttca cagcggcaa cgaggtgtac atcgaccgca tcgagttcgt gcccgccgag    4680
gtgaccttcg aggccgagta cgacctggag agggctcaga aggccgtgaa cgagctgttc    4740
accagcagca accagatcgg cctgaagacc gacgtgaccg actaccacat cgatcaggtg    4800
taggagctca cctcggtctg cggtcgtcgt acctgcgtgg tttgaggaac ggcagttcgc    4860
ctcggtcgtt ctgtgaaata aaattgggtt acaagaatta tggcgtttgt caatatggtc    4920
gtaatgtcgt aggatggtgg aatgtggtca caaactttgc gtatgttggg tctactggtg    4980
gtgtctgaat ctatgtatgg atgtcatgag tttgtctact agagttctag ttcctgtggt    5040
gttcgtatga tgtatatcat gagttaactc tatctaaaat ttcttcatta tggtattttt    5100
aagaaataaa ttctttatta tggttttttt aaagggacta tgtccatcct aacaagagca    5160
acgtccaata attctctaaa acttaaatt aagaaccgaa taaaaatga gtagttttta    5220
aatactttct atctaacctt atttactctt ctccatattt tagtagtttt ttaaatagac    5280
ttactaaatt tagttactct atattttggt aactcgacag aatacaatct gtgattaatt    5340
tttctcacat gtggtagcta gatacgacac ttttttttt acttttttagc acatgcacaa    5400
tggagtagtt agattcaaca cttatgacac aagttttttc ttcaccgttg gactattatt    5460
gtcgcatatg ttgccaccgc gaaccaccgc tcctctatag gttatgtcaa tcgacctttc    5520
ctcttttgtc ttcgacatca tccaagacta acaaagttag attcaaatca actagatgt    5580
ccagactggc aaagttagat ttaaaatcaa actactatct acatataagc aactattagg    5640
gactaagtta tttttctact tcaatagttg ttgctagcaa cttgctaaac ataatttag    5700
aaaactttt tagagaacta ttagagttgc tctaaaaggt tttgtagtcc catttactgt    5760
tttgtgacta ttattaggtg gagtttgggc agtaaaaagg ccaaatagaa aatgggttg    5820
agattgggaa aacggaccgc gatcgcttaa ttaagcttgc atgcctgcag tgcagcgtga    5880
cccggtcgtg cccctctcta gagataatga gcattgcatg tctaagttat aaaaaattac    5940
cacatatttt ttttgtcaca cttgtttgaa gtgcagttta tctatcttta tacatatatt    6000
taaactttac tctacgaata atataatcta tagtactaca ataatatcag tgttttagag    6060
```

```
aatcatataa atgaacagtt agacatggtc taaaggacaa ttgagtattt tgacaacagg    6120
actctacagt tttatctttt tagtgtgcat gtgttctcct ttttttttgc aaatagcttc    6180
acctatataa tacttcatcc attttattag tacatccatt tagggtttag ggttaatggt    6240
ttttatagac taatttttt agtacatcta ttttattcta ttttagcctc taaattaaga    6300
aaactaaaac tctattttag tttttttatt taataattta gatataaaat agaataaaat    6360
aaagtgacta aaaattaaac aaatacccct taagaaatta aaaaaactaa ggaaacattt    6420
ttcttgtttc gagtagataa tgccagcctg ttaaacgccg tcgacgagtc taacggacac    6480
caaccagcga accagcagcg tcgcgtcggg ccaagcgaag cagacggcac ggcatctctg    6540
tcgctgcctc tggacccctc tcgagagttc cgctccaccg ttggacttgc tccgctgtcg    6600
gcatccagaa attgcgtggc ggagcggcag acgtgagccg gcacggcagg cggcctcctc    6660
ctcctctcac ggcaccggca gctacggggg attccttttcc caccgctcct tcgctttccc    6720
ttcctcgccc gccgtaataa atagacaccc cctccacacc ctctttcccc aacctcgtgt    6780
tgttcggagc gcacacacac acaaccagat ctcccccaaa tccacccgtc ggcacctccg    6840
cttcaaggta cgccgctcgt cctccccccc ccccctctc taccttctct agatcggcgt    6900
tccggtccat ggttagggcc cggtagttct acttctgttc atgtttgtgt tagatccgtg    6960
tttgtgttag atccgtgctg ctagcgttcg tacacggatg cgacctgtac gtcagacacg    7020
ttctgattgc taacttgcca gtgttctctc ttggggaatc ctgggatggc tctagccgtt    7080
ccgcagacgg gatcgatttc atgatttttt ttgtttcgtt gcatagggtt tggtttgccc    7140
ttttccttta tttcaatata tgccgtgcac ttgtttgtcg ggtcatcttt tcatgctttt    7200
ttttgtcttg gttgtgatga tgtggtctgg ttgggcggtc gttctagatc ggagtagaat    7260
tctgtttcaa actacctggt ggatttatta attttggatc tgtatgtgtg tgccatacat    7320
attcatagtt acgaattgaa gatgatggat ggaaatatcg atctaggata ggtatacatg    7380
ttgatgcggg ttttactgat gcatatacag agatgctttt tgttcgcttg gttgtgatga    7440
tgtggtgtgg ttgggcggtc gttcattcgt tctagatcgg agtagaatac tgtttcaaac    7500
tacctggtgt atttattaat tttggaactg tatgtgtgtg tcatacatct tcatagttac    7560
gagtttaaga tggatggaaa tatcgatcta ggataggtat acatgttgat gtgggttta    7620
ctgatgcata tacatgatgg catatgcagc atcattcat atgctctaac cttgagtacc    7680
tatctattat aataaacaag tatgttttat aattattttg atcttgatat acttggatga    7740
tggcatatgc agcagctata tgtggatttt tttagccctg ccttcatacg ctatttattt    7800
gcttggtact gtttcttttg tcgatgctca ccctgttgtt tggtgttact tctgcaggga    7860
tcccccgatca tgcaaaaact cattaactca gtgcaaaact atgcctgggg cagcaaaacg    7920
gcgttgactg aactttatgg tatggaaaat ccgtccagcc agccgatggc cgagctgtgg    7980
atgggcgcac atccgaaaag cagttcacga gtgcagaatg ccgccggaga tatcgtttca    8040
ctgcgtgatg tgattgagag tgataaatcg actctgctcg gagaggccgt tgccaaacgc    8100
tttggcgaac tgcctttcct gttcaaagta ttatgcgcag cacagccact ctccattcag    8160
gttcatccaa acaaacacaa ttctgaaatc ggttttgcca agaaaatgc cgcaggtatc    8220
ccgatggatg ccgccgagcg taactataaa gatcctaacc acaagccgga gctggttttt    8280
gcgctgacgc ctttccttgc gatgaacgcg tttcgtgaat tttccgagat tgtctcccta    8340
ctccagccgg tcgcaggtgc acatccggcg attgctcact ttttacaaca gcctgatgcc    8400
```

```
gaacgtttaa gcgaactgtt cgccagcctg ttgaatatgc agggtgaaga aaaatcccgc    8460
gcgctggcga ttttaaaatc ggccctcgat agccagcagg gtgaaccgtg gcaaacgatt    8520
cgtttaattt ctgaatttta cccggaagac agcggtctgt tctccccgct attgctgaat    8580
gtggtgaaat tgaaccctgg cgaagcgatg ttcctgttcg ctgaaacacc gcacgcttac    8640
ctgcaaggcg tggcgctgga agtgatggca aactccgata acgtgctgcg tgcgggtctg    8700
acgcctaaat acattgatat tccggaactg gttgccaatg tgaaattcga agccaaaccg    8760
gctaaccagt tgttgaccca gccggtgaaa caaggtgcag aactggactt cccgattcca    8820
gtggatgatt ttgccttctc gctgcatgac cttagtgata agaaaccac cattagccag    8880
cagagtgccg ccattttgtt ctgcgtcgaa ggcgatgcaa cgttgtggaa aggttctcag    8940
cagttacagc ttaaaccggg tgaatcagcg tttattgccg ccaacgaatc accggtgact    9000
gtcaaaggcc acggccgttt agcgcgtgtt acaacaagc tgtaagagct tactgaaaaa    9060
attaacatct cttgctaagc tgggagctcg tcatgggtcg tttaagctgc cgatgtgcct    9120
gcgtcgtctg gtgccctctc tccatatgga ggttgtcaaa gtatctgctg ttcgtgtcat    9180
gagtcgtgtc agtgttggtt taataatgga ccggttgtgt tgtgtgtgcg tactacccag    9240
aactatgaca aatcatgaat aagtttgatg tttgaaatta aagcctgtgc tcattatgtt    9300
ctgtctttca gttgtctcct aatatttgcc tgcaggtact ggctatctac cgtttcttac    9360
ttaggaggtg tttgaatgca ctaaaactaa tagttagtgg ctaaaattag ttaaaacatc    9420
caaacaccat agctaatagt tgaactatta gctattttg gaaaattagt taatagtgag    9480
gtagttattt gttagctagc taattcaact aacaattttt agccaactaa caattagttt    9540
cagtgcattc aaacacccc ttaatgttaa cgtggttcta tctaccgtct cctaatatat    9600
ggttgattgt tcggtttgtt gctatgctat tgggttctga ttgctgctag ttcttgctga    9660
atccagaagt tctcgtagta tagctcagat tcatattatt tatttgagtg ataagtgatc    9720
caggttatta ctatgttagc taggtttttt ttacaaggat aaattatctg tgatcataat    9780
tcttatgaaa gctttatgtt tcctggaggc agtggcatgc aatgcatgac agcaacttga    9840
tcacaccagc tgaggtagat acggtaacaa ggttcttaaa tctgttcacc aaatcattgg    9900
agaacacaca tacacattct tgccagtctt ggttagagaa atttcatgac aaaatgccaa    9960
agctgtcttg actcttcact tttggccatg agtcgtgact tagtttggtt taatggaccg   10020
gttctcctag cttgttctac tcaaaactgt tgttgatgcg aataagttgt gatggttgat   10080
ctctggattt tgttttgctc tcaatagtgg acgagattag atagcccgga aatttaccgg   10140
tgcccgggcg gccagcatgg ccgtatccgc aatgtgttat taagttgtct aagcgtcaat   10200
ttgtttacac cacaatatat cctgccacca gccagccaac agctccccga ccggcagctc   10260
ggcacaaaat caccactcga tacaggcagc ccatcagaat taattctcat gtttgacagc   10320
ttatcatcga ctgcacggtg caccaatgct tctggcgtca ggcagccatc ggaagctgtg   10380
gtatggctgt gcaggtcgta aatcactgca taattcgtgt cgctcaaggc gcactcccgt   10440
tctggataat gttttttgcg ccgacatcat aacggttctg gcaaatattc tgaaatgagc   10500
tgttgacaat taatcatccg gctcgtataa tgtgtggaat tgtgagcgga taacaatttc   10560
acacaggaaa cagaccatga gggaagcgtt gatcgccgaa gtatcgactc aactatcaga   10620
ggtagttggc gtcatcgagc gccatctcga accgacgttg ctggccgtac atttgtacgg   10680
ctccgcagtg gatggcggcc tgaagccaca cagtgatatt gatttgctgg ttacggtgac   10740
cgtaaggctt gatgaaacaa cgcggcgagc tttgatcaac gaccttttgg aaacttcggc   10800
```

```
ttcccctgga gagagcgaga ttctccgcgc tgtagaagtc accattgttg tgcacgacga   10860
catcattccg tggcgttatc cagctaagcg cgaactgcaa tttggagaat ggcagcgcaa   10920
tgacattctt gcaggtatct tcgagccagc cacgatcgac attgatctgg ctatcttgct   10980
gacaaaagca agagaacata gcgttgcctt ggtaggtcca gcggcggagg aactctttga   11040
tccggttcct gaacaggatc tatttgaggc gctaaatgaa accttaacgc tatggaactc   11100
gccgcccgac tgggctggcg atgagcgaaa tgtagtgctt acgttgtccc gcatttggta   11160
cagcgcagta accggcaaaa tcgcgccgaa ggatgtcgct gccgactggg caatggagcg   11220
cctgccggcc cagtatcagc ccgtcatact tgaagctagg caggcttatc ttggacaaga   11280
agatcgcttg gcctcgcgcg cagatcagtt ggaagaattt gttcactacg tgaaaggcga   11340
gatcaccaaa gtagtcggca aataaagctc tagtggatct ccgtacccgg ggatctggct   11400
cgcggcggac gcacgacgcc ggggcgagac cataggcgat ctcctaaatc aatagtagct   11460
gtaacctcga agcgtttcac ttgtaacaac gattgagaat ttttgtcata aaattgaaat   11520
acttggttcg catttttgtc atccgcggtc agccgcaatt ctgacgaact gcccatttag   11580
ctggagatga ttgtacatcc ttcacgtgaa aatttctcaa gcgctgtgaa caagggttca   11640
gattttagat tgaaaggtga gccgttgaaa cacgttcttc ttgtcgatga cgacgtcgct   11700
atgcggcatc ttattattga ataccttacg atccacgcct tcaaagtgac cgcggtagcc   11760
gacagcaccc agttcacaag agtactctct tccgcgacgg tcgatgtcgt ggttgttgat   11820
ctagatttag gtcgtgaaga tgggctcgag atcgttcgta atctggcggc aaagtctgat   11880
attccaatca taattatcag tggcgaccgc cttgaggaga cggataaagt tgttgcactc   11940
gagctaggag caagtgattt tatcgctaag ccgttcagta tcagagagtt tctagcacgc   12000
attcgggttg ccttgcgcgt gcgccccaac gttgtccgct ccaaagaccg acggtctttt   12060
tgttttactg actggacact taatctcagg caacgtcgct tgatgtccga agctggcggt   12120
gaggtgaaac ttacggcagg tgagttcaat cttctcctcg cgttttttaga gaaacccgc    12180 gacgttctat cgcgcgagca acttctcatt gccagtcgag tacgcgacga ggaggtttat   12240
gacaggagta tagatgttct cattttgagg ctgcgccgca aacttgaggc agatccgtca   12300
agccctcaac tgataaaaac agcaagaggt gccggttatt tctttgacgc ggacgtgcag   12360
gtttcgcacg gggggacgat ggcagcctga gccaattccc agatccccga ggaatcggcg   12420
tgagcggtcg caaaccatcc ggcccggtac aaatcggcgc ggcgctgggt gatgacctgg   12480
tggagaagtt gaaggccgcg caggccgccc agcggcaacg catcgaggca gaagcacgcc   12540
ccggtgaatc gtggcaagcg gccgctgatc gaatccgcaa agaatcccgg caaccgccgg   12600 cagcggtgc gccgtcgatt aggaagccgc ccaaggcga cgagcaacca gatttttcg     12660 ttccgatgct ctatgacgtg gcacccgcg atagtcgcag catcatggac gtggccgttt    12720
tccgtctgtc gaagcgtgac cgacgagctg gcgaggtgat ccgctacgag cttccagacg   12780
ggcacgtaga ggtttccgca gggccggccg gcatggccag tgtgtgggat tacgacctgg   12840
tactgatggc ggtttcccat ctaaccgaat ccatgaaccg ataccgggaa gggaagggag   12900
acaagcccgg ccgcgtgttc cgtccacacg ttgcggacgt actcaagttc tgccggcgag   12960
ccgatggcgg aaagcagaaa gacgacctgg tagaaacctg cattcggtta aacaccacgc   13020
acgttgccat gcacgctacg aagaaggcca agaacggccg cctggtgacg gtatccgagg   13080
gtgaagcctt gattagccgc tacaagatcg taaagagcga aaccgggcgg ccggagtaca   13140
```

```
tcgagatcga gctagctgat tggatgtacc gcgagatcac agaaggcaag aacccggacg    13200
tgctgacggt tcaccccgat tactttttga tcgatcccgg catcggccgt tttctctacc    13260
gcctggcacg ccgcgccgca ggcaaggcag aagccagatg gttgttcaag acgatctacg    13320
aacgcagtgg cagcgccgga gagttcaaga agttctgttt caccgtgcgc aagctgatcg    13380
ggtcaaatga cctgccggag tacgatttga aggaggaggc ggggcaggct ggcccgatcc    13440
tagtcatgcg ctaccgcaac ctgatcgagg gcgaagcatc cgccggttcc taatgtacgg    13500
agcagatgct agggcaaatt gccctagcag gggaaaaagg tcgaaaaggt ctctttcctg    13560
tggatagcac gtacattggg aacccaaagc cgtacattgg gaaccggaac ccgtacattg    13620
ggaacccaaa gccgtacatt gggaaccggt cacacatgta agtgactgat ataaaagaga    13680
aaaaaggcga ttttccgcc taaaactctt taaaacttat taaaactctt aaaacccgcc    13740
tggcctgtgc ataactgtct ggccagcgca cagccgaaga gctgcaaaaa gcgcctaccc    13800
ttcggtcgct gcgctcccta cgccccgccg cttcgcgtcg gcctatcgcg gccgctggcc    13860
gctcaaaaat ggctggccta cggccaggca atctaccagg gcgcggacaa gccgcgccgt    13920
cgccactcga ccgccggcgc tgaggtctgc ctcgtgaaga aggtgttgct gactcatacc    13980
aggcctgaat cgccccatca tccagccaga aagtgaggga gccacggttg atgagagctt    14040
tgttgtaggt ggaccagttg gtgattttga acttttgctt tgccacggaa cggtctgcgt    14100
tgtcgggaag atgcgtgatc tgatccttca actcagcaaa agttcgattt attcaacaaa    14160
gccgccgtcc cgtcaagtca gcgtaatgct ctgccagtgt tacaaccaat taaccaattc    14220
tgattagaaa aactcatcga gcatcaaatg aaactgcaat ttattcatat caggattatc    14280
aataccatat ttttgaaaaa gccgtttctg taatgaagga gaaaactcac cgaggcagtt    14340
ccataggatg gcaagatcct ggtatcggtc tgcgattccg actcgtccaa catcaataca    14400
acctattaat ttcccctcgt caaaaataag gttatcaagt gagaaatcac catgagtgac    14460
gactgaatcc ggtgagaatg gcaaaagctc tgcattaatg aatcggccaa cgcgcgggga    14520
gaggcggttt gcgtattggg cgctcttccg cttcctcgct cactgactcg ctgcgctcgg    14580
tcgttcggct gcggcgagcg gtatcagctc actcaaaggc ggtaatacgg ttatccacag    14640
aatcagggga taacgcagga aagaacatgt gagcaaaagg ccagcaaaag gccaggaacc    14700
gtaaaaaggc cgcgttgctg gcgtttttcc ataggctccg ccccctgac gagcatcaca    14760
aaaatcgacg ctcaagtcag aggtggcgaa acccgacagg actataaaga taccaggcgt    14820
ttccccctgg aagctccctc gtgcgctctc ctgttccgac cctgccgctt accggatacc    14880
tgtccgcctt tctcccttcg ggaagcgtgg cgctttctca tagctcacgc tgtaggtatc    14940
tcagttcggt gtaggtcgtt cgctccaagc tgggctgtgt gcacgaaccc cccgttcagc    15000
ccgaccgctg cgccttatcc ggtaactatc gtcttgagtc aacccggta agacacgact    15060
tatcgccact ggcagcagcc actggtaaca ggattagcag agcgaggtat gtaggcggtg    15120
ctacagagtt cttgaagtgg tggcctaact acggctacac tagaagaaca gtatttggta    15180
tctgcgctct gctgaagcca gttaccttcg gaaaaagagt tggtagctct tgatccggca    15240
aacaaaccac cgctggtagc ggtggttttt tgtttgcaa gcagcagatt acgcgcagaa    15300
aaaaaggatc tcaagaagat cctttgatct tttctacggg gtctgacgct cagtggaacg    15360
aaaactcacg ttaagggatt ttggtcatga gattatcaaa aaggatcttc acctagatcc    15420
ttttgatccg gaatta                                                    15436
```

```
<210> SEQ ID NO 25
<211> LENGTH: 15884
<212> TYPE: DNA
<213> ORGANISM: Artificial Sequence
<220> FEATURE:
<223> OTHER INFORMATION: Recombinant vector

<400> SEQUENCE: 25
```

| | | | | | |
|---|---|---|---|---|---|
| attcctgtgg | ttggcatgca | catacaaatg | gacgaacgga | taaaccttt | cacgcccttt | 60 |
| taaatatccg | attattctaa | taaacgctct | tttctcttag | gtttaccgc | caatatatcc | 120 |
| tgtcaaacac | tgatagttta | aactgaaggc | gggaaacgac | aatctgatca | tgagcggaga | 180 |
| attaagggag | tcacgttatg | accccgccg | atgacgcggg | acaagccgtt | ttacgtttgg | 240 |
| aactgacaga | accgcaacgc | tgcaggaatt | ggccgcagcg | gccattaaa | tcaattgggc | 300 |
| gcgccagctg | cttgtgggga | ccagacaaaa | aggaatggt | gcagaattgt | taggcgcacc | 360 |
| taccaaaagc | atctttgcct | ttattgcaaa | gataaagcag | attcctctag | tacaagtggg | 420 |
| gaacaaaata | acgtggaaaa | gagctgtcct | gacagcccac | tcactaatgc | gtatgacgaa | 480 |
| cgcagtgacg | accacaaaac | tcgagacttt | tcaacaaagg | gtaatatccg | gaaacctcct | 540 |
| cggattccat | tgcccagcta | tctgtcactt | tattgtgaag | atagtggaaa | aggaaggtgg | 600 |
| ctcctacaaa | tgccatcatt | gcgataaagg | aaaggctatc | gttgaagatg | cctctgccga | 660 |
| cagtggtccc | aaagatggac | ccccacccac | gaggagcatc | gtggaaaaag | aagacgttcc | 720 |
| aaccacgtct | tcaaagcaag | tggattgatg | tgatatctcc | actgacgtaa | gggatgacga | 780 |
| acaatcccac | tatccttcgg | taccggaccc | tagtcaccac | accatgatca | tcttgtttgt | 840 |
| tgtagaatac | ccacttgtta | cctacaacaa | tttggtttgg | acgtggaact | aaatgcaaga | 900 |
| ccttattcct | cgtgaagttg | ttgagcacct | cttgcattgc | caccacccag | tctggatctc | 960 |
| taagtgcatc | ctctatcatg | tatggctcaa | tagaagacac | acaagagtaa | tgttcacaaa | 1020 |
| aatgagcaac | ttgagagcga | gtgattaacc | cctttttgaat | gtcaccaagg | atggagttga | 1080 |
| cggggtgata | tcgctgaatt | gcttggtgaa | ctcttgagtg | aggtggtctt | tgatcttgaa | 1140 |
| tctcttggtc | atcctccttt | tcttgaacaa | cttcatctcc | cccttgattg | attcgttctt | 1200 |
| cttgaggtgg | ctcattgtct | tgaacttgat | cttcttcttc | ttcttgagct | ggttcctcat | 1260 |
| cttaagttgg | tggagatgtt | tgtatggaat | atgatagttg | atcatgtgct | tgtgaaggct | 1320 |
| cttcgggttt | ttgtggacac | atgtctccaa | tggacatgtt | tcttagcgcg | atgcatggag | 1380 |
| cctctttatc | atctaaatca | tcaagatcaa | cttgctctag | ttgagagcct | ctagtggaca | 1440 |
| cacatcttcg | ggttaaatgg | ttttatgaa | tatttttct | tcacagatac | aaatagtatc | 1500 |
| gaatatttca | gatatttcat | ggttttgtcg | aatacaaata | taaatcgga | tagagaaaac | 1560 |
| taaatttaat | tatatccatt | tccatccata | ttaaaattga | atacggatat | agatatccat | 1620 |
| attagcattt | tatttgaata | cgaatatata | taatttggat | gtctagacat | tcgaatccat | 1680 |
| ctctaattag | tgtgggaatg | agggacactg | aaaaacaatg | acgtgcatgg | tgacatcata | 1740 |
| caatagtaca | attctgacga | cgatgaagga | atttacgtgc | ggatcagcga | caccacctgg | 1800 |
| tttggtggtt | cctgtcgccg | gaggcgcaag | aaataaagag | ggcacataac | tacgtgaaat | 1860 |
| caagcccaat | tagtctgcct | tggctcccctt | atgctgtttt | aaaaagttta | gggttaagtc | 1920 |
| attagtagac | tgttgcgggt | ttagaaattt | ttagagaatt | ttgttacaa | cagcccctaa | 1980 |
| actaaagttt | ttgggaacaa | attttagtag | tcttttaagt | tgctctaaga | ctatattttt | 2040 |
| ttagttgagg | aggacagtga | caattttgga | gttgctctaa | aaccatgttt | tttagtcgag | 2100 |

```
tgggacagtg gcaattactt aactacaatg cacaacacca ggaatccagg atgaaaaatt   2160
actacaccga gggctagttt gggaacctca ttttcccaag agattttcat ttcccaaag    2220 aaaattagtt tatttttcct tgggaaaata gaaatccttt ggaaaattgg agtttccaaa   2280
ctagccttga ttttttttcc taagatatgt gcagatcttt ctttgagagg acacaaaaaa   2340
aatggattgg gattgggctc atcgaaggcc gaatattcct atccatcgtt cgtgccggat   2400
taggcccaga accagaaaag agctaggccg ggctgcagta gcactatcct ctgtttcaca   2460
atattatgca cttttgatca ctttatttat gtcaaaaata cttgatacat cacgttttat   2520
tttcactttc gcctctataa aagtattaag ggatttctag acaattcaaa atgtaatttt   2580
ataagactat gtttgtcatt ttataaaaaa aaatagtttg attattttgg tgaacgtgcc   2640
ttggtcaaaa tttgtgggaa cggaggatgc tatcaaattc gtctgcgcag atgtacgccc   2700
agtaacgaag tatcgtcaat cgactgatga ccccgtcacc gtcagcaaga cagcaactca   2760
acattcaaat tcgaccgtaa taacatccac atacatacac ggagtatcaa tctagactag   2820
aggagacggg tgaacgtggt gagcctccgc ccataatgca accctactag tgctagcttt   2880
cggccgcgaa aaacgtccc cacccccacg tctcaacttt atagccgccc cctccccacc    2940
gccgcggccg ccacgcgcag cagcaacccg gtagcaggag cgcagccagc aagctcaggc   3000
ccccagccct actgccaccg cgccgaacga caaggccgag ccggcggagc accgtccagc   3060
tgaggaggag gaggccgcgg cggccggcga ggatgaggac accggcgccc aggtcgcgcc   3120
catcgtgaag ctggaggagg tcgccgttac cactggagag gaggacgagg acgcgctcct   3180
ggacttgtga ggcatccgcg gccgcttcga ttccccccc tccccgatcc gatttgccca    3240
tgtcttgttg atctgatgtg cggcggctgt gcaggaaggc gaagctctac cggtaaacca   3300
tggacaacaa ccccaacatc aacgagtgca tcccctacaa ctgcctgagc aaccccgagg   3360
tggaggtgct gggcggcgag cgcatcgaga ccggctacac ccccatcgac atcagcctga   3420
gcctgaccca gttcctgctg agcgagttcg tgcccggcgc cggcttcgtg ctgggcctgg   3480
tggacatcat ctggggcatc ttcggcccca gccagtggga cgccttcctg gtgcagatcg   3540
agcagctgat caaccagcgc atcgaggagt tcgcccgcaa ccaggccatc agccgcctgg   3600
agggcctgag caacctgtac caaatctacg ccgagagctt ccgcgagtgg gaggccgacc   3660
ccaccaaccc cgccctgcgc gaggagatgc gcatccagtt caacgacatg aacagcgccc   3720
tgaccaccgc catccccctg ttcgccgtgc agaactacca ggtgcccctg ctgagcgtgt   3780
acgtgcaggc cgccaacctg cacctgagcg tgctgcgcga cgtcagcgtg ttcggccagc   3840
gctggggctt cgacgccgcc accatcaaca gccgctacaa cgacctgacc cgcctgatcg   3900
gcaactacac cgaccacgcc gtgcgctggt acaacaccgg cctggagcgc gtgtgggtc    3960 cagacagccg cgactggatc aggtacaacc agttccgccg cgagctgacc ctgaccgtgc   4020
tggacatcgt gagcctgttc cccaactacg acagccgcac ctaccccatc cgcaccgtga   4080
gccagctgac ccgcgagatt tacaccaacc ccgtgctgga aacttcgac ggcagcttcc    4140 gcggcagcgc ccagggcatc gagggcagca tccgcagccc ccacctgatg acatcctga    4200 acagcatcac catctacacc gacgccacc gcggcgagta ctactggagc ggccaccaga   4260
tcatggccag ccccgtcggc ttcagcggcc ccgagttcac cttcccctg tacggcacta    4320 tgggcaacgc tgcacctcag cagcgcatcg tggcacagct gggccaggga gtgtaccgca   4380
ccctgagcag caccctgtac cgtcgacctt tcaacatcgg catcaacaac cagcagctga   4440
gcgtgctgga cggcaccgag ttcgcctacg gcaccagcag caacctgccc agcgccgtgt   4500
```

```
accgcaagag cggcaccgtg gacagcctgg acgagatccc ccctcagaac aacaacgtgc   4560
cacctcgaca gggcttcagc caccgtctga gccacgtgag catgttccgc agtggcttca   4620
gcaacagcag cgtgagcatc atccgtgcac ctatgttcag ctggattcac cgcagtgccg   4680
agttcaacaa catcatcccc agcagccaga tcacccagat cccctgacc aagagcacca    4740 acctgggcag cggcaccagc gtggtgaagg gccccggctt caccggcggc gacatcctgc   4800
gccgcaccag ccccggccag atcagcaccc tgcgcgtgaa catcaccgcc ccctgagcc    4860 agcgctaccg cgtccgcatc cgctacgcca gcaccaccaa cctgcagttc cacaccagca   4920
tcgacggccg ccccatcaac cagggcaact tcagcgccac catgagcagc ggcagcaacc   4980
tgcagagcgg cagcttccgc accgtgggct tcaccacccc cttcaacttc agcaacggca   5040
gcagcgtgtt caccctgagc gcccacgtgt caacagcgg caacgaggtg tacatcgacc    5100
gcatcgagtt cgtgcccgcc gaggtgacct tcgaggccga gtacgacctg gagagggctc   5160
agaaggccgt gaacgagctg ttcaccagca gcaaccagat cggcctgaag accgacgtga   5220
ccgactacca catcgatcag gtgtaggagc tcaggttgaa ggcaaacaag ggtcaaatgg   5280
atgccattcc attcatttcg tttccaaggt tcagcttccc cgcaaatttt cattgtgttt   5340
tctccgagat gaatgtttgt gttcggtgaa atcagagtcg tcagtcatct acatagcttt   5400
tcttggttga tagactgtta ttttaagtcg catgtttatc tgggatggct ggggtcagca   5460
tgtttgtaca attatttgga gttgcttttg gaatggtcgc ggtttgatga gttgcctaca   5520
gccatgagat gtcttttcgc tccactttta tggttcattc gttctcaata atatgggatg   5580
ctatacttgt gttgatccat tatcttgatg catcgttgtc tgtgcactgc aacaacaata   5640
cccatctgaa cacccctatc aataaaatac cattttttt ctttccatcc cactaatcta    5700
ggcccacttt ctcactcttt tcttatccac tatattgtca atatagaatc tggggagaga   5760
gagagagaga gagagattga gagagagaga gagagagaga tttaggctcc ctcccttcct   5820
atattcaaaa taggtatcgc ctttgggtca cctgttggaa tgatttattt tagtatcgtc   5880
catatttaat ttaaacaaat gttgaatttt acatgcatat tgatttaaag tttgttagtt   5940
tatgagcatc accaactaag atctctaatg ccaaagagca tctccactag ttccaaaaaa   6000
ctctctaaat ttaatttagg atgttagtaa ccagaaatta tgctccaaca gtttcctaaa   6060
tgagttcctt aaatatacca acttttaaa tatctctatt tagtcaaact tgagaaattg    6120
tttcacactc ccaatagttg tcatcaatca catcgtaaaa tcatttgagt tcgcacccgt   6180
gtacaagtgg tgcactttaa ataaattaaa ttacgaaaat gataaattta ctatcgagtt   6240
agcataattt aaaaatatat aacaacataa gaactgggaa cggaccgcga tcgcttaatt   6300
aagcttgcat gcctgcagtg cagcgtgacc cggtcgtgcc cctctctaga gataatgagc   6360
attgcatgtc taagttataa aaaattacca catattttt ttgtcacact tgtttgaagt    6420
gcagtttatc tatctttata catatattta aactttactc tacgaataat ataatctata   6480
gtactacaat aatatcagtg ttttagagaa tcatataaat gaacagttag acatggtcta   6540
aaggacaatt gagtattttg acaacaggac tctacagttt tatcttttta gtgtgcatgt   6600
gttctccttt ttttttgcaa atagcttcac ctatataata cttcatccat tttattagta   6660
catccattta gggtttaggg ttaatggttt ttatagacta attttttag tacatctatt    6720 ttattctatt ttagcctcta aattaagaaa actaaaactc tattttagtt tttttattta   6780
ataatttaga tataaaatag aataaaataa agtgactaaa aattaaacaa atacccttta   6840
```

```
agaaattaaa aaaactaagg aaacattttt cttgtttcga gtagataatg ccagcctgtt    6900
aaacgccgtc gacgagtcta acggacacca accagcgaac cagcagcgtc gcgtcgggcc    6960
aagcgaagca gacggcacgg catctctgtc gctgcctctg gaccctctc gagagttccg     7020 ctccaccgtt ggacttgctc cgctgtcggc atccagaaat tgcgtggcgg agcggcagac    7080
gtgagccggc acggcaggcg gcctcctcct cctctcacgg caccggcagc tacgggggat    7140 tccttccca ccgctccttc gctttccctt cctcgcccgc cgtaataaat agacacccc     7200 tccacaccct cttccccaa cctcgtgttg ttcggagcgc acacacacac aaccagatct     7260
cccccaaatc cacccgtcgg cacctccgct tcaaggtacg ccgctcgtcc tccccccccc    7320
cccctctcta ccttctctag atcggcgttc cggtccatgg ttagggcccg gtagttctac    7380
ttctgttcat gtttgtgtta gatccgtgtt tgtgttagat ccgtgctgct agcgttcgta    7440
cacggatgcg acctgtacgt cagacacgtt ctgattgcta acttgccagt gtttctcttt    7500
ggggaatcct gggatggctc tagccgttcc gcagacggga tcgatttcat gatttttttt    7560
gtttcgttgc atagggtttg gtttgccctt ttcctttatt tcaatatatg ccgtgcactt    7620
gtttgtcggg tcatctttc atgcttttt ttgtcttggt tgtgatgatg tggtctggtt      7680
gggcggtcgt tctagatcgg agtagaattc tgtttcaaac tacctggtgg atttattaat    7740
tttggatctg tatgtgtgtg ccatacatat tcatagttac gaattgaaga tgatggatgg    7800
aaatatcgat ctaggatagg tatacatgtt gatgcgggtt ttactgatgc atatacagag    7860 atgcttttttg ttcgcttggt tgtgatgatg tggtgtggtt gggcggtcgt tcattcgttc    7920
tagatcggag tagaatactg tttcaaacta cctggtgtat ttattaattt tggaactgta    7980
tgtgtgtgtc atacatcttc atagttacga gtttaagatg gatggaaata tcgatctagg    8040
ataggtatac atgttgatgt gggttttact gatgcatata catgatggca tatgcagcat    8100
ctattcatat gctctaacct tgagtaccta tctattataa taaacaagta tgtttttataa    8160 ttattttgat cttgatatac ttggatgatg gcatatgcag cagctatatg tggatttttt    8220
tagccctgcc ttcatacgct atttatttgc ttggtactgt ttcttttgtc gatgctcacc    8280
ctgttgtttg gtgttacttc tgcagggatc cccgatcatg caaaaactca ttaactcagt    8340
gcaaaactat gcctggggca gcaaaacggc gttgactgaa ctttatggta tggaaaatcc    8400
gtccagccag ccgatggccg agctgtggat gggcgcacat ccgaaaagca gttcacgagt    8460
gcagaatgcc gccggagata tcgtttcact gcgtgatgtg attgagagtg ataaatcgac    8520
tctgctcgga gaggccgttg ccaaacgctt ggcgaactg ccttcctgt tcaaagtatt      8580 atgcgcagca cagccactct ccattcaggt tcatccaaac aaacacaatt ctgaaatcgg    8640
ttttgccaaa gaaatgccg caggtatccc gatggatgcc gccgagcgta actataaaga     8700
tcctaaccac aagccggagc tggttttgc gctgacgcct ttccttgcga tgaacgcgtt     8760
tcgtgaattt tccgagattg tctccctact ccagccggtc gcaggtgcac atccggcgat    8820
tgctcacttt ttacaacagc ctgatgccga acgtttaagc gaactgttcg ccagcctgtt    8880
gaatatgcag ggtgaagaaa atcccgcgc gctggcgatt taaaatcgg ccctcgatag      8940 ccagcagggt gaaccgtggc aaacgattcg tttaatttct gaattttacc cggaagacag    9000
cggtctgttc tccccgctat tgctgaatgt ggtgaaattg aaccctggcg aagcgatgtt    9060
cctgttcgct gaaacaccgc acgcttacct gcaaggcgtg gcgctggaag tgatggcaaa    9120
ctccgataac gtgctgcgtg cgggtctgac gcctaaatac attgatattc cggaactggt    9180
tgccaatgtg aaattcgaag ccaaaccggc taaccagttg ttgacccagc cggtgaaaca    9240
```

```
aggtgcagaa ctggacttcc cgattccagt ggatgatttt gccttctcgc tgcatgacct   9300
tagtgataaa gaaaccacca ttagccagca gagtgccgcc attttgttct gcgtcgaagg   9360
cgatgcaacg ttgtggaaag gttctcagca gttacagctt aaaccgggtg aatcagcgtt   9420
tattgccgcc aacgaatcac cggtgactgt caaaggccac ggccgtttag cgcgtgttta   9480
caacaagctg taagagctta ctgaaaaaat taacatctct tgctaagctg ggagctcgtc   9540
atgggtcgtt taagctgccg atgtgcctgc gtcgtctggt gccctctctc catatggagg   9600
ttgtcaaagt atctgctgtt cgtgtcatga gtcgtgtcag tgttggttta ataatggacc   9660
ggttgtgttg tgtgtgcgta ctcccagaa ctatgacaaa tcatgaataa gtttgatgtt   9720
```
(Note: line 9720 in source appears as "ggttgtgttg tgtgtgcgta ctcccagaa ctatgacaaa tcatgaataa gtttgatgtt" — preserved as visible)

```
tgaaattaaa gcctgtgctc attatgttct gtctttcagt tgtctcctaa tatttgcctg   9780
caggtactgg ctatctaccg tttcttactt aggaggtgtt tgaatgcact aaaactaata   9840
gttagtggct aaaattagtt aaaacatcca aacaccatag ctaatagttg aactattagc   9900
tatttttgga aaattagtta atagtgaggt agttatttgt tagctagcta attcaactaa   9960 caattttag ccaactaaca attagtttca gtgcattcaa acacccctt aatgttaacg   10020 tggttctatc taccgtctcc taatatatgg ttgattgttc ggtttgttgc tatgctattg   10080
ggttctgatt gctgctagtt cttgctgaat ccagaagttc tcgtagtata gctcagattc   10140
atattattta tttgagtgat aagtgatcca ggttattact atgttagcta ggttttttt   10200 acaaggataa attatctgtg atcataattc ttatgaaagc tttatgtttc ctggaggcag   10260
tggcatgcaa tgcatgacag caacttgatc acaccagctg aggtagatac ggtaacaagg   10320
ttcttaaatc tgttcaccaa atcattggag aacacacata cacattcttg ccagtcttgg   10380
ttagagaaat ttcatgacaa aatgccaaag ctgtcttgac tcttcacttt tggccatgag   10440
tcgtgactta gtttggttta atggaccggt tctcctagct tgttctactc aaaactgttg   10500
ttgatgcgaa taagttgtga tggttgatct ctggatttg ttttgctctc aatagtggac   10560
gagattagat agcccggaaa tttaccggtg cccgggcggc cagcatggcc gtatccgcaa   10620
tgtgttatta agttgtctaa gcgtcaattt gtttacacca caatatatcc tgccaccagc   10680
cagccaacag ctccccgacc ggcagctcgg cacaaaatca ccactcgata caggcagccc   10740
atcagaatta attctcatgt ttgacagctt atcatcgact gcacggtgca ccaatgcttc   10800
tggcgtcagg cagccatcgg aagctgtggt atggctgtgc aggtcgtaaa tcactgcata   10860
attcgtgtcg ctcaaggcgc actcccgttc tggataatgt tttttgcgcc gacatcataa   10920
cggttctggc aaatattctg aaatgagctg ttgacaatta atcatccggc tcgtataatg   10980
tgtggaattg tgagcggata acaatttcac acaggaaaca gaccatgagg gaagcgttga   11040
tcgccgaagt atcgactcaa ctatcagagg tagttggcgt catcgagcgc catctcgaac   11100
cgacgttgct ggccgtacat ttgtacggct ccgcagtgga tggcggcctg aagccacaca   11160
gtgatattga tttgctggtt acggtgaccg taaggcttga tgaaacaacg cggcgagctt   11220
tgatcaacga cctttggaa acttcggctt ccctggaga gagcgagatt ctccgcgctg   11280
tagaagtcac cattgttgtg cacgacgaca tcattccgtg gcgttatcca gctaagcgcg   11340
aactgcaatt tggagaatgg cagcgcaatg acattcttgc aggtatcttc gagccagcca   11400
cgatcgacat tgatctggct atcttgctga caaaagcaag agaacatagc gttgccttgg   11460
taggtccagc ggcggaggaa ctctttgatc cggttcctga acaggatcta tttgaggcgc   11520
taaatgaaac cttaacgcta tggaactcgc cgcccgactg ggctggcgat gagcgaaatg   11580
```

```
tagtgcttac gttgtcccgc atttggtaca gcgcagtaac cggcaaaatc gcgccgaagg    11640
atgtcgctgc cgactgggca atggagcgcc tgccggccca gtatcagccc gtcatacttg    11700
aagctaggca ggcttatctt ggacaagaag atcgcttggc ctcgcgcgca gatcagttgg    11760
aagaatttgt tcactacgtg aaaggcgaga tcaccaaagt agtcggcaaa taaagctcta    11820
gtggatctcc gtacccgggg atctggctcg cggcggacgc acgacgccgg ggcgagacca    11880
taggcgatct cctaaatcaa tagtagctgt aacctcgaag cgtttcactt gtaacaacga    11940
ttgagaattt ttgtcataaa attgaaatac ttggttcgca tttttgtcat ccgcggtcag    12000
ccgcaattct gacgaactgc ccatttagct ggagatgatt gtacatcctt cacgtgaaaa    12060
tttctcaagc gctgtgaaca agggttcaga ttttagattg aaaggtgagc cgttgaaaca    12120
cgttcttctt gtcgatgacg acgtcgctat gcggcatctt attattgaat accttacgat    12180
ccacgccttc aaagtgaccg cggtagccga cagcacccag ttcacaagag tactctcttc    12240
cgcgacggtc gatgtcgtgg ttgttgatct agatttaggt cgtgaagatg ggctcgagat    12300
cgttcgtaat ctggcggcaa agtctgatat tccaatcata attatcagtg cgaccgcct    12360 tgaggagacg gataaagttg ttgcactcga gctaggagca agtgatttta tcgctaagcc    12420
gttcagtatc agagagtttc tagcacgcat tcgggttgcc ttgcgcgtgc gccccaacgt    12480
tgtccgctcc aaagaccgac ggtctttttg ttttactgac tggacactta atctcaggca    12540
acgtcgcttg atgtccgaag ctggcggtga ggtgaaactt acggcaggtg agttcaatct    12600
tctcctcgcg ttttttagaga aaccccgcga cgttctatcg cgcgagcaac ttctcattgc    12660
cagtcgagta cgcgacgagg aggtttatga caggagtata gatgttctca ttttgaggct    12720
gcgccgcaaa cttgaggcag atccgtcaag ccctcaactg ataaaaacag caagaggtgc    12780
cggttatttc tttgacgcgg acgtgcaggt ttcgcacggg gggacgatgg cagcctgagc    12840
caattcccag atccccgagg aatcggcgtg agcggtcgca aaccatccgg cccggtacaa    12900
atcggcgcgg cgctgggtga tgacctggtg gagaagttga aggccgcgca ggccgcccag    12960
cggcaacgca tcgaggcaga agcacgcccc ggtgaatcgt ggcaagcggc cgctgatcga    13020
atccgcaaag aatcccggca accgccggca gccggtgcgc cgtcgattag gaagccgccc    13080
aagggcgacg agcaaccaga ttttttcgtt ccgatgctct atgacgtggg cacccgcgat    13140
agtcgcagca tcatgacgt ggccgttttc cgtctgtcga agcgtgaccg acgagctggc    13200
gaggtgatcc gctacgagct tccagacggg cacgtagagg tttccgcagg gccggccggc    13260
atggccagtg tgtgggatta cgacctggta ctgatggcgg tttcccatct aaccgaatcc    13320
atgaaccgat accgggaagg gaaggagac aagcccggcc gcgtgttccg tccacacgtt    13380
gcggacgtac tcaagttctg ccggcgagcc gatggcggaa agcagaaaga cgacctggta    13440
gaaacctgca ttcggttaaa caccacgcac gttgccatgc agcgtacgaa gaaggccaag    13500 aacgccgcc tggtgacggt atccgagggt gaagccttga ttagccgcta caagatcgta    13560
aagagcgaaa ccgggcggcc ggagtacatc gagatcgagc tagctgattg gatgtaccgc    13620
gagatcacag aaggcaagaa cccggacgtg ctgacggttc accccgatta cttttttgatc    13680 gatcccggca tcgccgtttt tctctaccgc ctggcacgcc gcgccgcagg caaggcgaaa    13740
gccagatggt tgttcaagac gatctacgaa cgcagtggca gcgccggaga gttcaagaag    13800
ttctgtttca ccgtgcgcaa gctgatcggg tcaaatgacc tgccggagta cgatttgaag    13860
gaggaggcgg ggcaggctgg cccgatccta gtcatgcgct accgcaacct gatcgagggc    13920
gaagcatccg ccggttccta atgtacggag cagatgctag ggcaaattgc cctagcaggg    13980
```

```
gaaaaaggtc gaaaaggtct ctttcctgtg gatagcacgt acattgggaa cccaaagccg   14040
tacattggga accggaaccc gtacattggg aacccaaagc cgtacattgg gaaccggtca   14100
cacatgtaag tgactgatat aaaagagaaa aaggcgatt tttccgccta aaactcttta    14160
aaacttatta aaactcttaa acccgcctg gcctgtgcat aactgtctgg ccagcgcaca    14220
gccgaagagc tgcaaaaagc gcctaccctt cggtcgctgc gctccctacg ccccgccgct   14280
tcgcgtcggc ctatcgcggc cgctggccgc tcaaaaatgg ctggcctacg ccaggcaat    14340 ctaccagggc gcggacaagc cgcgccgtcg ccactcgacc gccggcgctg aggtctgcct   14400
cgtgaagaag gtgttgctga ctcataccag gcctgaatcg ccccatcatc cagccagaaa   14460
gtgagggagc cacggttgat gagagctttg ttgtaggtgg accagttggt gattttgaac   14520
ttttgctttg ccacggaacg gtctgcgttg tcgggaagat gcgtgatctg atccttcaac   14580
tcagcaaaag ttcgatttat tcaacaaagc cgccgtcccg tcaagtcagc gtaatgctct   14640
gccagtgtta caaccaatta accaattctg attagaaaaa ctcatcgagc atcaaatgaa   14700
actgcaattt attcatatca ggattatcaa taccatattt ttgaaaaagc cgtttctgta   14760
atgaaggaga aaactcaccg aggcagttcc ataggatggc aagatcctgg tatcggtctg   14820
cgattccgac tcgtccaaca tcaatacaac ctattaattt ccccctcgtca aaataaggt   14880 tatcaagtga gaaatcacca tgagtgacga ctgaatccgg tgagaatggc aaaagctctg   14940
cattaatgaa tcggccaacg cgcggggaga ggcggtttgc gtattgggcg ctcttccgct   15000
tcctcgctca ctgactcgct gcgctcggtc gttcggctgc ggcgagcggt atcagctcac   15060
tcaaaggcgg taatacggtt atccacagaa tcaggggata acgcaggaaa gaacatgtga   15120
gcaaaaggcc agcaaaaggc caggaaccgt aaaaaggccg cgttgctggc gtttttccat   15180
aggctccgcc cccctgacga gcatcacaaa aatcgacgct caagtcagag gtggcgaaac   15240
ccgacaggac tataaagata ccaggcgttt ccccctggaa gctccctcgt gcgctctcct   15300
gttccgaccc tgccgcttac cggatacctg tccgcctttc tcccttcggg aagcgtggcg   15360
ctttctcata gctcacgctg taggtatctc agttcggtgt aggtcgttcg ctccaagctg   15420
ggctgtgtgc acgaaccccc cgttcagccc gaccgctgcg ccttatccgg taactatcgt   15480
cttgagtcca acccggtaag acacgactta tcgccactgg cagcagccac tggtaacagg   15540
attagcagag cgaggtatgt aggcggtgct acagagttct tgaagtggtg gcctaactac   15600
ggctacacta gaagaacagt atttggtatc tgcgctctgc tgaagccagt taccttcgga   15660
aaaagagttg gtagctcttg atccggcaaa caaaccaccg ctggtagcgg tggtttttt    15720 gtttgcaagc agcagattac gcgcagaaaa aaggatctc aagaagatcc tttgatcttt    15780
tctacggggt ctgacgctca gtggaacgaa aactcacgtt aagggatttt ggtcatgaga   15840
ttatcaaaaa ggatcttcac ctagatcctt ttgatccgga atta                    15884
```

<210> SEQ ID NO 26
<211> LENGTH: 15689
<212> TYPE: DNA
<213> ORGANISM: Artificial Sequence
<220> FEATURE:
<223> OTHER INFORMATION: Recombinant vector

<400> SEQUENCE: 26

```
attcctgtgg ttggcatgca catacaaatg gacgaacgga taaaccttt cacgcccttt      60 taaatatccg attattctaa taaacgctct tttctcttag gttacccgc caatatatcc     120
```

```
tgtcaaacac tgatagttta aactgaaggc gggaaacgac aatctgatca tgagcggaga    180
attaagggag tcacgttatg accccgccg atgacgcggg acaagccgtt ttacgtttgg    240
aactgacaga accgcaacgc tgcaggaatt ggccgcagcg gccatttaaa tcaattgggc    300
gcgccagctg cttgtgggga ccagacaaaa aaggaatggt gcagaattgt taggcgcacc    360
taccaaaagc atctttgcct ttattgcaaa gataaagcag attcctctag tacaagtggg    420
gaacaaaata acgtggaaaa gagctgtcct gacagcccac tcactaatgc gtatgacgaa    480
cgcagtgacg accacaaaac tcgagacttt tcaacaaagg gtaatatccg gaaacctcct    540
cggattccat tgcccagcta tctgtcactt tattgtgaag atagtggaaa aggaaggtgg    600
ctcctacaaa tgccatcatt gcgataaagg aaaggctatc gttgaagatg cctctgccga    660
cagtggtccc aaagatggac ccccacccac gaggagcatc gtggaaaaag aagacgttcc    720
aaccacgtct tcaaagcaag tggattgatg tgatatctcc actgacgtaa gggatgacga    780
acaatcccac tatccttcgg taccggaccc tttgtattgt tgtatgtaat gaataatctt    840
tatatatata tatatatata tatatatata tatatatata tatatatata tatatatgtg    900
tgtgtgtggg ggggtgtggg ggtgtgtgta ttgatgtctc ttggacaaca agattacaca    960
aaacacaatt agaataaaaa aatatcctcg tgtatataaa cttgtccgta taccatatta   1020
gaacacataa attttaggca acatttttt c catcaacatt cttcaatcat caaccaaaat   1080
ttacggatac acaagataag aggggtatg taaggttgta cgtaatgggc tacatgataa   1140
catcaaagat tatgcaagca aatctcaatc caccaggcga tcataaacat catagttcac   1200
atgcttcagt ttt aaagcca tcgtagttcc cgtgcaaaga caaaaacatt agaattattc   1260
aatacaagtt gcacaagata gttcaataaa atttaaacca caatagtatt atccaacaaa   1320
gctagttcat accattatag tttctagtaa acaagaatag agaacatata ttaagcaaac   1380
agaccacata ggataaggct aaggatgtat ttttgtctat tgttttctgt gacatcgatc   1440
tcgtttgcac gagtaaaact aaaacatgag aaaattccga taaaaatag gaatctagaa   1500 atacgaacgg aaaacactaa accatttta ttcctgtttc taaaatatat catctcgttt   1560 ctgttttct ctgtaaatat gaaaacgatc agatcatagt taaaacgaa tacagtaccg   1620 gacgaaacaa tatttctctc tcgtttcccc cttatagcat ctccaaaagc tccccagaag   1680 tctccctaa atctatttt ttggaaaaac acaaaaacat gtctccaaca gttcctctaa   1740
agcgccccca acttttttcat agcccttaaa actccctcat ttgtagctac aaatgagggg   1800 tttttgggc tccccagaaa caaactgctg ctttaagatg tttggttgag gagccaagta   1860
gaatggagtc gtttcatccc tgattctagg aacggagccg ttctgttctg tgtttggtaa   1920
tctggaacgg agcggctctg ttttttgttt ggttgcagag tgaacggaac ggagcgtgac   1980
tgtgagagcg ggatgagaac ggagcggctc cgttcggttg attttttgga gcggaatggt   2040
tccggatttg aggagaatat tccataattg gagtcattcc gttctagttc ctttataacc   2100
aaacagcaac aaaactggga tagaatggtt ccgttctact tggctcttca accaaacact   2160
aactaaggga cctgttggag aaatgattaa aatttaccct cacttattat ttagatattc   2220
cttaaaacta attttgagaa gtcgttttat ggagtgctct tggagatgct cttagttcgt   2280
agatctgatt gtgtgtatgt atgtaagcat atgcgtctgt actacgatcc acggtaaaaa   2340
agtcacaaac atataataat agcgtcattc aataaattga taacgtaaag tataaatgaa   2400
cttttaactc tgtttgagta aacaactcgt gcagagactg caatgaaatc tattattttt   2460
tctaaaataa ttatacaagt tgaggaaatg ctatttgttc cactaagcga cgatgtattt   2520
```

```
tgttttttaa aaaaatcgac gaggtactgc tcggttatta ttttcacatg caccgcgcgt    2580
tgttttgggg ccggcccatt tgtattgcga atttgcggag acgaatatga ccgaatggag    2640
tttagaaagc ccagctcact taggattgtc tattttctca agaaaagaga gaatgggccc    2700
aaaggcctaa acaccaaaac ccgatccgct tatgggatgt catggacatg gagtctggga    2760
ccgtccggca gatgagacga cagccgtcgg atcagaaacc ctagcgcggg aggctctccc    2820
tattaatacc caccctgcac cccgcgggag gagtctttcc tagggtttcg tagcttctag    2880
ccgccgccgc gtccgcctcg ccaagcgcag cagccgccgc agcacatcgc tctctcgatc    2940
tcagccatag cggaggtgga gcagcaacag gacacgccga agctcttcaa ccgctggacc    3000
ttcgatgatg tccaggtacg cgaacgagtc ttcgcatctc tgcatgcttc gattctttag    3060
ccttgccgct actagcagtg gatggaaccg acgatgaaat ctgcaggtga acgacatctc    3120
gctgtaaacc atggacaaca accccaacat caacgagtgc atcccctaca actgcctgag    3180
caaccccgag gtggaggtgc tgggcggcga gcgcatcgag accggctaca cccccatcga    3240
catcagcctg agcctgaccc agttcctgct gagcgagttc gtgcccggcg ccggcttcgt    3300
gctgggcctg gtggacatca tctggggcat cttcggcccc agccagtggg acgccttcct    3360
ggtgcagatc gagcagctga tcaaccagcg catcgaggag ttcgcccgca accaggccat    3420
cagccgcctg gagggcctga gcaacctgta ccaaatctac gccgagagct tccgcgagtg    3480
ggaggccgac cccaccaacc ccgccctgcg cgaggagatg cgcatccagt tcaacgacat    3540
gaacagcgcc ctgaccaccg ccatccccct gttcgccgtg cagaactacc aggtgcccct    3600
gctgagcgtg tacgtgcagg ccgccaacct gcacctgagc gtgctgcgcg acgtcagcgt    3660
gttcggccag cgctgggggct tcgacgccgc caccatcaac agccgctaca acgacctgac    3720
ccgcctgatc ggcaactaca ccgaccacgc cgtgcgctgg tacaacaccg gcctggagcg    3780
cgtgtggggt ccagacagcc gcgactggat caggtacaac cagttccgcc gcagctgac    3840 cctgaccgtg ctggacatcg tgagcctgtt ccccaactac gacagccgca cctacccccat    3900 ccgcaccgtg agccagctga cccgcgagat ttacaccaac cccgtgctgg agaacttcga    3960
cggcagcttc cgcggcagcg cccagggcat cgagggcagc atccgcagcc cccacctgat    4020
ggacatcctg aacagcatca ccatctacac cgacgcccac cgcggcgagt actactggag    4080
cggccaccag atcatggcca gccccgtcgg cttcagcggc cccgagttca ccttcccccct    4140 gtacggcact atgggcaacg ctgcacctca gcagcgcatc gtggcacagc tgggccaggg    4200
agtgtaccgc accctgagca gcaccctgta ccgtcgacct ttcaacatcg gcatcaacaa    4260
ccagcagctg agcgtgctgg acggcaccga gttcgcctac ggcaccagca gcaacctgcc    4320
cagcgccgtg taccgcaaga gcggcaccgt ggacagcctg gacgagatcc cccctcagaa    4380
caacaacgtg ccacctcgac agggcttcag ccaccgtctg agccacgtga gcatgttccg    4440
cagtggcttc agcaacagca gcgtgagcat catccgtgca cctatgttca gctggattca    4500
ccgcagtgcc gagttcaaca acatcatccc cagcagccag atcacccaga tcccctgac    4560 caagagcacc aacctgggca gcggcaccag cgtggtgaag ggccccggct tcaccggcgg    4620
cgacatcctg cgccgcacca gccccggcca gatcagcacc ctgcgcgtga acatcaccgc    4680
ccccctgagc cagcgctacc gcgtccgcat ccgctacgcc agcaccacca acctgcagtt    4740
ccacaccagc atcgacggcc gccccatcaa ccagggcaac ttcagcgcca ccatgagcag    4800
cggcagcaac ctgcagagcg gcagcttccg caccgtgggc ttcaccaccc ccttcaactt    4860
```

```
cagcaacggc agcagcgtgt tcaccctgag cgcccacgtg ttcaacagcg gcaacgaggt   4920
gtacatcgac cgcatcgagt tcgtgcccgc cgaggtgacc ttcgaggccg agtacgacct   4980
ggagagggct cagaaggccg tgaacgagct gttcaccagc agcaaccaga tcggcctgaa   5040
gaccgacgtg accgactacc acatcgatca ggtgtaggag ctcactgagc ttgtatcctg   5100
gtgcactctg cgctggaaac ttttatgtcg ctggcagtcg tatcggttct tgttttacca   5160
atgtttagag ttttttgaga cctatatgcg gttttggttt tcagtgcaca attaaaatta   5220
ctgagtaatg tagttgattg ggaacagaaa tgtttggtgc ctggtttacc gaactccagt   5280
tctcttgtca ttttttcttta ttctatagtc tgtattatgt atgcgtatga gtattgagat   5340
gattctgcat ttgaattgtc tgctttgttg ctgtcgctgt atgcgtacca atggtaacag   5400
ggtagttgtg ggaagtagac acggccggtt ctatgttttc gtgcttccgc ggttcaggct   5460
ggttaagcct atggagcgta cgcacgctcc tcccgtctct ccgtgtcctg catgctggca   5520
acaggagtgc ggcccagcgc acgccctaat cgacggcggt atatttgtct gtccctccat   5580
tttgtggtga ggctattcgc aaccgttatc cttaaatttt ttctcctata tcactattcc   5640
cctatttttc cttatatttt ttcatcttca gcagcggttc tcctaaatac tccctctata   5700
cccactacaa ctataaatat tattttccat atctattcat catttattac cacttttttt   5760
caactaaaaa atactcgcat gcatggattt tacggaaggg gggctgtcac agtatcccct   5820
tgatctgctg tgagagaaaa gggggacact aggtagggtg caaggtaggg agcagcggtg   5880
cgggtggtag cgtggttact gcagccgcta cgacgtgagc agtgttaggg gagaggatgg   5940
aagggtggtg cgctgctgca gataacccga gcgccaaaca ctcatgggtg ataattaggt   6000
ataagaaaag atattttatg gttaggagag tatagagaga atttagtggt aacttctatg   6060
gaagatggaa aaatagggggt gaaatcggac cgcgatcgct taattaagct tgcatgcctg   6120
cagtgcagcg tgacccggtc gtgcccctct ctagagataa tgagcattgc atgtctaagt   6180
tataaaaaat taccacatat ttttttttgtc acacttgttt gaagtgcagt ttatctatct   6240
ttatacatat atttaaactt tactctacga ataatataat ctatagtact acaataatat   6300
cagtgtttta gagaatcata taaatgaaca gttagacatg gtctaaagga caattgagta   6360
ttttgacaac aggactctac agttttatct ttttagtgtg catgtgttct ccttttttttt   6420 tgcaaatagc ttcacctata taatacttca tccattttat tagtacatcc atttagggtt   6480
tagggttaat ggttttttata gactaatttt tttagtacat ctattttatt ctattttagc   6540
ctctaaatta agaaaactaa aactctattt tagttttttt atttaataat ttagatataa   6600
aatagaataa aataaagtga ctaaaaatta aacaaatacc ctttaagaaa ttaaaaaaac   6660
taaggaaaca ttttttcttgt ttcgagtaga taatgccagc ctgttaaacg ccgtcgacga   6720
gtctaacgga caccaaccag cgaaccagca gcgtcgcgtc gggccaagcg aagcagacgg   6780
cacggcatct ctgtcgctgc ctctggaccc ctctcgagag ttccgctcca ccgttggact   6840
tgctccgctg tcggcatcca gaaattgcgt ggcggagcgg cagacgtgag ccggcacggc   6900
aggcggcctc ctcctcctct cacggcaccg gcagctacgg gggattcctt tcccaccgct   6960
ccttcgcttt cccttcctcg cccgccgtaa taaatagaca cccccctccac accctctttc   7020 cccaacctcg tgttgttcgg agcgcacaca cacacaacca gatctccccc aaatccaccc   7080
gtcggcacct ccgcttcaag gtacgccgct cgtcctcccc ccccccccct ctctaccttc   7140
tctagatcgg cgttccggtc catggttagg gcccggtagt tctacttctg ttcatgtttg   7200
tgttagatcc gtgtttgtgt tagatccgtg ctgctagcgt tcgtacacgg atgcgacctg   7260
```

```
tacgtcagac acgttctgat tgctaacttg ccagtgtttc tctttgggga atcctgggat    7320
ggctctagcc gttccgcaga cgggatcgat ttcatgattt tttttgtttc gttgcatagg    7380
gtttggtttg ccctttttcct ttatttcaat atatgccgtg cacttgtttg tcgggtcatc    7440
ttttcatgct ttttttttgtc ttggttgtga tgatgtggtc tggttgggcg gtcgttctag    7500
atcggagtag aattctgttt caaactacct ggtggattta ttaattttgg atctgtatgt    7560
gtgtgccata catattcata gttacgaatt gaagatgatg gatggaaata tcgatctagg    7620
ataggtatac atgttgatgc gggttttact gatgcatata cagagatgct ttttgttcgc    7680
ttggttgtga tgatgtggtg tggttgggcg gtcgttcatt cgttctagat cggagtagaa    7740
tactgtttca aactacctgg tgtatttatt aattttggaa ctgtatgtgt gtgtcataca    7800
tcttcatagt tacgagttta agatggatgg aaatatcgat ctaggatagg tatacatgtt    7860
gatgtgggtt ttactgatgc atatacatga tggcatatgc agcatctatt catatgctct    7920
aaccttgagt acctatctat tataataaac aagtatgttt tataattatt ttgatcttga    7980
tatacttgga tgatggcata tgcagcagct atatgtggat ttttttagcc ctgccttcat    8040
acgctattta tttgcttggt actgtttctt ttgtcgatgc tcaccctgtt gtttggtgtt    8100
acttctgcag ggatccccga tcatgcaaaa actcattaac tcagtgcaaa actatgcctg    8160
gggcagcaaa acgcgttga ctgaacttta tggtatggaa aatccgtcca gccagccgat    8220
ggccgagctg tggatgggcg cacatccgaa aagcagttca cgagtgcaga atgccgccgg    8280
agatatcgtt tcactgcgtg atgtgattga gagtgataaa tcgactctgc tcggagaggc    8340
cgttgccaaa cgctttggcg aactgccttt cctgttcaaa gtattatgcg cagcacagcc    8400
actctccatt caggttcatc caaacaaaca caattctgaa atcggttttg ccaaagaaaa    8460
tgccgcaggt atcccgatgg atgccgccga gcgtaactat aaagatccta accacaagcc    8520
ggagctggtt tttgcgctga cgcctttcct tgcgatgaac gcgtttcgtg aattttccga    8580
gattgtctcc ctactccagc cggtcgcagg tgcacatccg gcgattgctc acttttttaca    8640 acagcctgat gccgaacgtt taagcgaact gttcgccagc ctgttgaata tgcagggtga    8700
agaaaaatcc cgcgcgctgg cgattttaaa atcggccctc gatagccagc agggtgaacc    8760
gtggcaaacg attcgtttaa tttctgaatt ttacccggaa gacagcggtc tgttctcccc    8820
gctattgcta aatgtggtga aattgaaccc tggcgaagcg atgttcctgt tcgctgaaac    8880
accgcacgct tacctgcaag gcgtggcgct ggaagtgatg gcaaactccg ataacgtgct    8940
gcgtgcgggt ctgacgccta aatacattga tattccggaa ctggttgcca atgtgaaatt    9000
cgaagccaaa ccggctaacc agttgttgac ccagccggtg aaacaaggtg cagaactgga    9060
cttcccgatt ccagtggatg attttgcctt ctcgctgcat gaccttagtg ataaagaaac    9120
caccattagc cagcagagtg ccgccatttt gttctgcgtc gaaggcgatg caacgttgtg    9180
gaaaggttct cagcagttac agcttaaacc gggtgaatca gcgttattg ccgccaacga    9240 atcaccggtg actgtcaaag gccacggccg tttagcgcgt gtttacaaca agctgtaaga    9300
gcttactgaa aaaattaaca tctcttgcta agctgggagc tcgtcatggg tcgtttaagc    9360
tgccgatgtg cctgcgtcgt ctggtgccct ctctccatat ggaggttgtc aaagtatctg    9420
ctgttcgtgt catgagtcgt gtcagtgttg gtttaataat ggaccggttg tgttgtgtgt    9480
gcgtactacc cagaactatg acaaatcatg aataagtttg atgtttgaaa ttaaagcctg    9540
tgctcattat gttctgtctt tcagttgtct cctaatattt gcctgcaggt actggctatc    9600
```

```
taccgtttct tacttaggag gtgtttgaat gcactaaaac taatagttag tggctaaaat    9660
tagttaaaac atccaaacac catagctaat agttgaacta ttagctattt ttggaaaatt    9720
agttaatagt gaggtagtta tttgttagct agctaattca actaacaatt tttagccaac    9780
taacaattag tttcagtgca ttcaaacacc cccttaatgt taacgtggtt ctatctaccg    9840
tctcctaata tatggttgat tgttcggttt gttgctatgc tattgggttc tgattgctgc    9900
tagttcttgc tgaatccaga agttctcgta gtatagctca gattcatatt atttatttga    9960
gtgataagtg atccaggtta ttactatgtt agctaggttt tttttacaag gataaattat   10020
ctgtgatcat aattcttatg aaagctttat gtttcctgga ggcagtggca tgcaatgcat   10080
gacagcaact tgatcacacc agctgaggta gatacggtaa caaggttctt aaatctgttc   10140
accaaatcat tggagaacac acatacacat tcttgccagt cttggttaga gaaatttcat   10200
gacaaaatgc caaagctgtc ttgactcttc acttttggcc atgagtcgtg acttagtttg   10260
gtttaatgga ccggttctcc tagcttgttc tactcaaaac tgttgttgat gcgaataagt   10320
tgtgatggtt gatctctgga ttttgttttg ctctcaatag tggacgagat tagatagccc   10380
ggaaatttac cggtgcccgg gcggccagca tggccgtatc cgcaatgtgt tattaagttg   10440
tctaagcgtc aatttgttta caccacaata tatcctgcca ccagccagcc aacagctccc   10500
cgaccggcag ctcggcacaa aatcaccact cgatacaggc agcccatcag aattaattct   10560
catgtttgac agcttatcat cgactgcacg gtgcaccaat gcttctggcg tcaggcagcc   10620
atcggaagct gtggtatggc tgtgcaggtc gtaaatcact gcataattcg tgtcgctcaa   10680
ggcgcactcc cgttctggat aatgtttttt gcgccgacat cataacggtt ctggcaaata   10740
ttctgaaatg agctgttgac aattaatcat ccggctcgta taatgtgtgg aattgtgagc   10800
ggataacaat ttcacacagg aaacagacca tgagggaagc gttgatcgcc gaagtatcga   10860
ctcaactatc agaggtagtt ggcgtcatcg agcgccatct cgaaccgacg ttgctggccg   10920
tacatttgta cggctccgca gtggatggcg gcctgaagcc acacagtgat attgatttgc   10980
tggttacggt gaccgtaagg cttgatgaaa caacgcggcg agctttgatc aacgaccttt   11040
tggaaacttc ggcttcccct ggagagagcg agattctccg cgctgtagaa gtcaccattg   11100
ttgtgcacga cgacatcatt ccgtggcgtt atccagctaa gcgcgaactg caatttggag   11160
aatggcagcg caatgacatt cttgcaggta tcttcgagcc agccacgatc gacattgatc   11220
tggctatctt gctgacaaaa gcaagagaac atagcgttgc cttggtaggt ccagcggcgg   11280
aggaactctt tgatccggtt cctgaacagg atctatttga ggcgctaaat gaaaccttaa   11340
cgctatggaa ctcgccgccc gactgggctg gcgatgagcg aaatgtagtg cttacgttgt   11400
cccgcatttg gtacagcgca gtaaccggca aaatcgcgcc gaaggatgtc gctgccgact   11460
gggcaatgga gcgcctgccg gcccagtatc agcccgtcat acttgaagct aggcaggctt   11520
atcttggaca agaagatcgc ttggcctcgc gcgcagatca gttggaagaa tttgttcact   11580
acgtgaaagg cgagatcacc aaagtagtcg gcaaataaag ctctagtgga tctccgtacc   11640
cggggatctg gctcgcggcg gacgcacgac gccgggcga gaccataggc gatctcctaa   11700
atcaatagta gctgtaacct cgaagcgttt cacttgtaac aacgattgag aattttttgtc   11760
ataaaattga aatacttggt tcgcattttt gtcatccgcg gtcagccgca attctgacga   11820
actgcccatt tagctggaga tgattgtaca tccttcacgt gaaaatttct caagcgctgt   11880
gaacaagggt tcagattta gattgaaagg tgagccgttg aaacacgttc ttcttgtcga   11940
tgacgacgtc gctatgcggc atcttattat tgaataacctt acgatccacg ccttcaaagt   12000
```

```
gaccgcggta gccgacagca cccagttcac aagagtactc tcttccgcga cggtcgatgt    12060
cgtggttgtt gatctagatt taggtcgtga agatgggctc gagatcgttc gtaatctggc    12120
ggcaaagtct gatattccaa tcataattat cagtggcgac cgccttgagg agacggataa    12180
agttgttgca ctcgagctag gagcaagtga ttttatcgct aagccgttca gtatcagaga    12240
gtttctagca cgcattcggg ttgccttgcg cgtgcgcccc aacgttgtcc gctccaaaga    12300
ccgacggtct ttttgtttta ctgactggac acttaatctc aggcaacgtc gcttgatgtc    12360
cgaagctggc ggtgaggtga aacttacggc aggtgagttc aatcttctcc tcgcgttttt    12420
agagaaaccc cgcgacgttc tatcgcgcga gcaacttctc attgccagtc gagtacgcga    12480
cgaggaggtt tatgacagga gtatagatgt tctcattttg aggctgcgcc gcaaacttga    12540
ggcagatccg tcaagccctc aactgataaa aacagcaaga ggtgccggtt atttctttga    12600
cgcggacgtg caggtttcgc acgggggggac gatggcagcc tgagccaatt cccagatccc    12660
cgaggaatcg gcgtgagcgg tcgcaaacca tccggcccgg tacaaatcgg cgcggcgctg    12720
ggtgatgacc tggtggagaa gttgaaggcc gcgcaggccg cccagcggca acgcatcgag    12780
gcagaagcac gccccggtga atcgtggcaa gcggccgctg atcgaatccg caaagaatcc    12840
cggcaaccgc cggcagccgg tgcgccgtcg attaggaagc cgcccaaggg cgacgagcaa    12900
ccagattttt tcgttccgat gctctatgac gtgggcaccc gcgatagtcg cagcatcatg    12960
gacgtggccg ttttccgtct gtcgaagcgt gaccgacgag ctggcgaggt gatccgctac    13020
gagcttccag acgggcacgt agaggtttcc gcagggccgg ccggcatggc cagtgtgtgg    13080
gattacgacc tggtactgat ggcggtttcc catctaaccg aatccatgaa ccgataccgg    13140
gaagggaagg gagacaagcc cggccgcgtg ttccgtccac acgttgcgga cgtactcaag    13200
ttctgccggc gagccgatgg cggaaagcag aaagacgacc tggtagaaac ctgcattcgg    13260
ttaaacacca cgcacgttgc catgcagcgt acgaagaagg ccaagaacgg ccgcctggtg    13320
acggtatccg agggtgaagc cttgattagc cgctacaaga tcgtaaagag cgaaaccggg    13380
cggccggagt acatcgagat cgagctagct gattggatgt accgcgagat cacagaaggc    13440
aagaacccgg acgtgctgac ggttcacccc gattactttt tgatcgatcc cggcatcggc    13500
cgttttctct accgcctggc acgccgcgcc gcaggcaagg cagaagccag atggttgttc    13560
aagacgatct acgaacgcag tggcagcgcc ggagagttca agaagttctg tttcaccgtg    13620
cgcaagctga tcgggtcaaa tgacctgccg gagtacgatt tgaaggagga ggcggggcag    13680
gctggcccga tcctagtcat cgcgctaccgc aacctgatcg agggcgaagc atccgccggt    13740
tcctaatgta cggagcagat gctagggcaa attgccctag caggggaaaa aggtcgaaaa    13800
ggtctctttc ctgtggatag cacgtacatt gggaacccaa agccgtacat gggaaccgg    13860 aacccgtaca ttgggaaccc aaagccgtac attgggaacc ggtcacacat gtaagtgact    13920
gatataaaag agaaaaaagg cgattttttcc gcctaaaact cttaaaact tattaaaact    13980 cttaaaaccc gcctggcctg tgcataactg tctggccagc gcacagccga agagctgcaa    14040
aaagcgccta cccttcggtc gctgcgctcc ctacgccccg ccgcttcgcg tcggcctatc    14100
gcggccgctg gccgctcaaa aatggctggc ctacggccag gcaatctacc agggcgcgga    14160
caagccgcgc cgtcgccact cgaccgccgg cgctgaggtc tgcctcgtga agaaggtgtt    14220
gctgactcat accaggcctg aatcgccccca tcatccagcc agaaagtgag ggagccacgg    14280
ttgatgagag ctttgttgta ggtggaccag ttggtgattt tgaacttttg ctttgccacg    14340
```

```
gaacggtctg cgttgtcggg aagatgcgtg atctgatcct tcaactcagc aaaagttcga    14400
tttattcaac aaagccgccg tcccgtcaag tcagcgtaat gctctgccag tgttacaacc    14460
aattaaccaa ttctgattag aaaaactcat cgagcatcaa atgaaactgc aatttattca    14520
tatcaggatt atcaatacca tattttttgaa aaagccgttt ctgtaatgaa ggagaaaact   14580
caccgaggca gttccatagg atggcaagat cctggtatcg gtctgcgatt ccgactcgtc    14640
caacatcaat acaacctatt aatttcccct cgtcaaaaat aaggttatca agtgagaaat    14700
caccatgagt gacgactgaa tccggtgaga atggcaaaag ctctgcatta atgaatcggc    14760
caacgcgcgg ggagaggcgg tttgcgtatt gggcgctctt ccgcttcctc gctcactgac    14820
tcgctgcgct cggtcgttcg gctgcggcga gcggtatcag ctcactcaaa ggcggtaata    14880
cggttatcca cagaatcagg ggataacgca ggaaagaaca tgtgagcaaa aggccagcaa    14940
aaggccagga accgtaaaaa ggccgcgttg ctggcgtttt tccataggct ccgcccccct    15000
gacgagcatc acaaaaatcg acgctcaagt cagaggtggc gaaacccgac aggactataa    15060
agataccagg cgtttccccc tggaagctcc ctcgtgcgct ctcctgttcc gaccctgccg    15120
cttaccggat acctgtccgc ctttctccct tcgggaagcg tggcgctttc tcatagctca    15180
cgctgtaggt atctcagttc ggtgtaggtc gttcgctcca agctgggctg tgtgcacgaa    15240
ccccccgttc agcccgaccg ctgcgcctta tccggtaact atcgtcttga gtccaacccg    15300
gtaagacacg acttatcgcc actggcagca gccactggta acaggattag cagagcgagg    15360
tatgtaggcg gtgctacaga gttcttgaag tggtggccta actacggcta cactagaaga    15420
acagtatttg gtatctgcgc tctgctgaag ccagttacct tcggaaaaag agttggtagc    15480
tcttgatccg gcaaacaaac caccgctggt agcggtggtt ttttttgtttg caagcagcag    15540 attacgcgca gaaaaaaagg atctcaagaa gatcctttga tcttttctac ggggtctgac    15600
gctcagtgga acgaaaactc acgttaaggg attttggtca tgagattatc aaaaaggatc    15660
ttcacctaga tccttttgat ccggaatta                                      15689
```

<210> SEQ ID NO 27
<211> LENGTH: 16054
<212> TYPE: DNA
<213> ORGANISM: Artificial Seuqence
<220> FEATURE:
<223> OTHER INFORMATION: Recombinant vector

<400> SEQUENCE: 27

```
attcctgtgg ttggcatgca catacaaatg gacgaacgga taaaccttt cacgcccttt      60 taaatatccg attattctaa taaacgctct tttctcttag gtttaccgc caatatatcc     120 tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccatttaaa tcaattgggc    300
gcgccagctg cttgtgggga ccagacaaaa aaggaatggt gcagaattgt taggcgcacc    360
taccaaaagc atctttgcct ttattgcaaa gataaagcag attcctctag tacaagtggg    420
gaacaaaata acgtggaaaa gagctgtcct gacagcccac tcactaatgc gtatgacgaa    480
cgcagtgacg accacaaaac tcgagacttt tcaacaaagg gtaatatccg gaaacctcct    540
cggattccat tgcccagcta tctgtcactt tattgtgaag atagtggaaa aggaaggtgg    600
ctcctacaaa tgccatcatt gcgataaagg aaaggctatc gttgaagatg cctctgccga    660
cagtggtccc aaagatggac ccccaccac gaggagcatc gtggaaaaag aagacgttcc    720
```

```
aaccacgtct tcaaagcaag tggattgatg tgatatctcc actgacgtaa gggatgacga    780
acaatcccac tatccttcgg taccggaccc ggatcctgag gtgtggcttg tatgtttcct    840
gaccccctgg tggtgttccc agtttgcaat acatcatttt ctgtagccct tgtacttgct    900
gtgatccctg tttattgttc agggaaaact tagtgcagtg tattagaaat atagaaacct    960
cacatttcga agagcagaat agtgtttgat aacagttttt ttaacgcaac aacgtttgtt   1020
agactgtgtc cagcggccag cgggtagtgt aaaataggtg acgcgaaact atatgtgata   1080
ttgtttgaca ctatttgcag agtatagttt aaaatagggg gtgtgagtaa tctgctgaag   1140
atagccttaa gagttaagat accaaggtat agtttatcat atgcaaaaga aagaaaaaa    1200
aaggaaatac aaaccattgt ttttatgttg gttagagcta ggtaattatc tcttgaccag   1260
tgtatttcca aacctgttct tctcagtttc tgtgctccgt cgatactgaa cattgttgtt   1320
catttctcat tgttgaacg atggtatttc aggagctaga aagaggaga gaggagcttg     1380
agtctctgtt aactgctgac cggatccgct gcgtttgggg gcgcaggat ctccgaccgg    1440
atccgcccgc cgtgcccgcg accggatccg ctgcgtttgg ggggggcag gatctccgac    1500
cggatccgcc cgccgtggcc gcaaccggat ccgctgcgtt tggggcggca ggatctccga   1560
ccggatccgc ccaccgtggc ggcgaccgga tccgctgcgt ttgggggcgg caaggaagcg   1620
ggtgggcctt ctagggttca ggtggcgggc gtcggggtag agagtgcctg cggcgattct   1680
ggcgggcatg cgcagggtgg ggcaggggtg tggtcgagcg ggccatgcac aaccttccat   1740
ccgcgggatt ttgcgggcgt tgctggcgcg acggatttgc aggagttgct ggcgcggagc   1800
tttgagggcg cggccgattt ggggactgcg ggcgttggcg attttgcggg cgttgctggc   1860
gcggcagatt ctgcgggcgt tgctggcgcg gggactgcgg acgcgacagc tgtgctcgcc   1920
tgcggccgcg aggaaggcga cggggactgc gggcgcgggg agggaaatcg cgggcggagc   1980
gcgcgatggc agaacacaca gaactatgga cgcctacact aaggggggtgt ttggtttcta   2040
gggactaatg tttagtccct tcattttatt cctttttagt atataaattg ctaaatatag   2100
aaactaaaat aaagttttag tttctatatt tagcaatttt agaacaaaaa tggaataaaa   2160
tgtagggact aaacattagt ccctaaaaac caaacacccc ttaaatacat aagaagtagt   2220
agagattatt attatttgtg tctattgata tgatcattat gatattatat tttactgttt   2280
taatctaaat atagttatta tattcagata attatttat taaatccaaa aatatttaac    2340
ttctaatgta ataaggagag aatactctaa tatcataata atttcttcta aagtgaccct   2400
cggatttgga gatgactgac agggagggct gtgcacccctt ctttcttttcc ttttcaattg  2460
aagaacttgg gttgtgcttg ctcacacaac cgaatgaccg atgcacaccg acgcgcacgg   2520
agcggaccag cacagcccgg aaactgccct acgccgacac gttttccggt gcggcccagc   2580
agcagcaggg aggaaggttc gctcggtcgc tgggcctggc tccgcgtgcc gtccctccta   2640
taaatgcgag tcctcgccga gtccactggg caccagaagc tcactcactg ctcgttgccg   2700
gctgcccccg cggccccggc cagtccatcc cctcgctcgc tccccaactc cagcaggcag   2760
atcagataca tccatccatt cgcgcaccgg aaggtgagcg ccgtgaacga accatccgcc   2820
ctgctagctg cgatctgtag ccttgcgtcg ctttcgcgcc tagatcgtca cgtcacctat   2880
cacgatccgt gcggttctag atctgtggtt tttccttccc ctggtggtcg aatccttcca   2940
tccaccagac caccacggga cctcgtggat tccttttggt tttcctgtgc cgagagccaa   3000
aatcgagggg gggggcttgt tttttattgg ctcggtctcc cgctgtctcg tgatctgatt   3060
```

```
tgctgtagta atcagcagga aaggaagggt tgaactaaga gcgccgtggc ggtttcgtcg    3120
tcgctgaacc cggacgcgcc gctcttcatc ccggcggcgc tgctgcaggt ggaggacttc    3180
tcgccgcagt ggtgggacct catcaccacc actgcctggt tccgcgacca ctggtcccgc    3240
gagcgcgccc acctggacga gatcgccgag cagatcgacg cggccggcct cctccccgac    3300
gacgaggacc tcttctacga cgaccaggtc gagcagggcc ccgtcgccgc cgcccttaag    3360
ataggtactg atgtctctct ctctctctct ctcttactct cccctcgatt ttagatctgc    3420
ctgaaggacg aatcatagtg acctcacgtt ggtgcgtttt tctccaccag attcggtgct    3480
caaggcgctg taaaccatgg acaacaaccc caacatcaac gagtgcatcc cctacaactg    3540
cctgagcaac cccgaggtgg aggtgctggg cggcgagcgc atcgagaccg gctacacccc    3600
catcgacatc agcctgagcc tgacccagtt cctgctgagc gagttcgtgc ccggcgccgg    3660
cttcgtgctg ggcctggtgg acatcatctg gggcatcttc ggccccagcc agtgggacgc    3720
cttcctggtg cagatcgagc agctgatcaa ccagcgcatc gaggagttcg cccgcaacca    3780
ggccatcagc cgcctggagg gcctgagcaa cctgtaccaa atctacgccg agagcttccg    3840
cgagtgggag gccgaccccca ccaacccccgc cctgcgcgag gagatgcgca tccagttcaa    3900
cgacatgaac agcgccctga ccaccgccat ccccctgttc gccgtgcaga actaccaggt    3960
gccccctgctg agcgtgtacg tgcaggccgc caacctgcac ctgagcgtgc tgcgcgacgt    4020
cagcgtgttc ggccagcgct ggggcttcga cgccgccacc atcaacagcc gctacaacga    4080
cctgacccgc ctgatcggca actacaccga ccacgccgtg cgctggtaca acaccggcct    4140
ggagcgcgtg tggggtccag acagccgcga ctggatcagg tacaaccagt tccgccgcga    4200
gctgaccctg accgtgctgg acatcgtgag cctgttcccc aactacgaca gccgcaccta    4260
cccccatccgc accgtgagcc agctgacccg cgagatttac accaaccccg tgctggagaa    4320
cttcgacggc agcttccgcg gcagcgccca gggcatcgag ggcagcatcc gcagccccca    4380
cctgatggac atcctgaaca gcatcaccat ctacaccgac gccccaccgcg gcgagtacta    4440
ctggagcggc caccagatca tggccagccc cgtcggcttc agcggccccg agttcacctt    4500
cccccctgtac ggcactatgg gcaacgctgc acctcagcag cgcatcgtgg cacagctggg    4560
ccagggagtg taccgcaccc tgagcagcac cctgtaccgt cgaccttttca acatcggcat    4620
caacaaccag cagctgagcg tgctggacgg caccgagttc gcctacggca ccagcagcaa    4680
cctgccagc gccgtgtacc gcaagagcgg caccgtggac agcctggacg agatcccccc    4740
tcagaacaac aacgtgccac ctcgacaggg cttcagccac cgtctgagcc acgtgagcat    4800
gttccgcagt ggcttcagca acagcagcgt gagcatcatc cgtgcaccta tgttcagctg    4860
gattcaccgc agtgccgagt tcaacaacat catccccagc agccagatca cccagatccc    4920
cctgaccaag agcaccaacc tgggcagcgg caccagcgtg gtgaagggcc ccggcttcac    4980
cggcggcgac atcctgcgcc gcaccagccc cggccagatc agcaccctgc gcgtgaacat    5040
caccgcccc ctgagccagc gctaccgcgt ccgcatccgc tacgccagca ccaccaacct    5100
gcagttccac accagcatcg acggccgccc catcaaccag gcaacttca gcgccaccat    5160
gagcagcggc agcaacctgc agagcggcag cttccgcacc gtgggcttca ccacccccctt    5220
caacttcagc aacggcagca gcgtgttcac cctgagcgcc cacgtgttca acagcggcaa    5280
cgaggtgtac atcgaccgca tcgagttcgt gcccgccgag gtgaccttcg aggccgagta    5340
cgacctggag agggctcaga aggccgtgaa cgagctgttc accagcagca accagatcgg    5400
cctgaagacc gacgtgaccg actaccacat cgatcaggtg taggagctcg ttcgctgggg    5460
```

```
gaactcatca ggaaggctgc tgccctctct gcagccttgc tcctggctgc cgccgctgtc    5520
gtggtctgct ctttcaagtc gaagtaacgg tggttcgagc tagtggatag tgtggctcaa    5580
ctgtagaagt tccttttgta tagcaagcaa gtaaaaaaaa aaaatgacca aaaaatataa    5640
caaaatgcag ctgtaagttt actgctgctc tctaagtcgt gttcagtcat ccagtgtgtc    5700
tagtctaggg aaaccccata aaaatggtga aggtggaatc ccatcccagt gtcataatta    5760
aggatgcact tcttctgtaa gcaaatgtat gatgtacaat ggccggccgg cagtctaaat    5820
gttacaacta gctcttcttg gtgaattcac cggtccacac tgatgtgctg ctatgtatca    5880
ttactatcca gttagggctt gttcggttat tcctacgcca tatggattgg acgggattgg    5940
aaaattttag tagacatttt gacttctatg gatttaaacc cacccaatcc cctccaatcc    6000
acatggattg agatgaaacc gaacaagccc ttagttggat ggatggatga tctcacgcgc    6060
ttgagtttat ctagttgctg atatgggaga gcccctcaac acctcaaata ttgtggataa    6120
gtttaatcct acactgtcag tcttcagtta taaggcacgc actcttcgac gttgggcgct    6180
gtcttttgtt tcaaaggttg aggcaacctc aacctcgttt aaaacagaga gcaaagctaa    6240
tttccaaact gatgtaagtc atgtgtcctt aattaccaaa gtagcaatga tgacattgtt    6300
atgttgtgtg ctaatgagcc attacgtgaa catcagttcc tgccttgccg cttcgttcag    6360
ccgggccggg gtatattttg agtcactaaa aggacacgtc ggatgaatgg aaaattgcct    6420 cttgtctttta ccaagagtgt cgcccgcgag cggaccgcga tcgcttaatt aagcttgcat    6480
gcctgcagtg cagcgtgacc cggtcgtgcc cctctctaga gataatgagc attgcatgtc    6540
taagttataa aaaattacca catattttttt ttgtcacact tgtttgaagt gcagtttatc    6600
tatctttata catatattta aactttactc tacgaataat ataatctata gtactacaat    6660
aatatcagtg ttttagagaa tcatataaat gaacagttag acatggtcta aaggacaatt    6720
gagtattttg acaacaggac tctacagttt tatctttttta gtgtgcatgt gttctccttt    6780
ttttttgcaa atagcttcac ctatataata cttcatccat tttattagta catccattta    6840
gggtttaggg ttaatggttt ttatagacta atttttttag tacatctatt ttattctatt    6900
ttagcctcta aattaagaaa actaaaactc tattttagtt ttttttattta ataatttaga    6960 tataaaatag aataaaataa agtgactaaa aattaaacaa atacccttta agaaattaaa    7020
aaaactaagg aaacattttt cttgtttcga gtagataatg ccagcctgtt aaacgccgtc    7080
gacgagtcta acggacacca accagcgaac cagcagcgtc gcgtcgggcc aagcgaagca    7140
gacggcacgg catctctgtc gctgcctctg gaccctctc gagagttccg ctccaccgtt    7200
ggacttgctc cgctgtcggc atccagaaat tgcgtggcgg agcggcagac gtgagccggc    7260
acggcaggcg gcctcctcct cctctcacgg caccggcagc tacggggat tccttttccca    7320 ccgctccttc gctttccctt cctcgcccgc cgtaataaat agacacccc tccacaccct    7380 ctttccccaa cctcgtgttg ttcggagcgc acacacacac aaccagatct cccccaaatc    7440
cacccgtcgg cacctccgct tcaaggtacg ccgctcgtcc tccccccccc cccctctcta    7500
ccttctctag atcggcgttc cggtccatgg ttagggcccg gtagttctac ttctgttcat    7560
gtttgtgtta gatccgtgtt tgtgttagat ccgtgctgct agcgttcgta cacgatgcg    7620 acctgtacgt cagacacgtt ctgattgcta acttgccagt gtttctcttt ggggaatcct    7680
gggatggctc tagccgttcc gcagacggga tcgattcat gatttttttt gtttcgttgc    7740
atagggtttg gtttgcccctt tcctttatt tcaatatatg ccgtgcactt gtttgtcggg    7800
```

```
tcatcttttc atgctttttt ttgtcttggt tgtgatgatg tggtctggtt gggcggtcgt    7860
tctagatcgg agtagaattc tgtttcaaac tacctggtgg atttattaat tttggatctg    7920
tatgtgtgtg ccatacatat tcatagttac gaattgaaga tgatggatgg aaatatcgat    7980
ctaggatagg tatacatgtt gatgcgggtt ttactgatgc atatacagag atgcttttg     8040 ttcgcttggt tgtgatgatg tggtgtggtt gggcggtcgt tcattcgttc tagatcggag    8100
tagaatactg tttcaaacta cctggtgtat ttattaattt tggaactgta tgtgtgtgtc    8160
atacatcttc atagttacga gtttaagatg gatggaaata tcgatctagg ataggtatac    8220
atgttgatgt gggttttact gatgcatata catgatggca tatgcagcat ctattcatat    8280
gctctaacct tgagtaccta tctattataa taaacaagta tgttttataa ttattttgat    8340
cttgatatac ttggatgatg gcatatgcag cagctatatg tggattttt  tagccctgcc    8400 ttcatacgct atttatttgc ttggtactgt ttcttttgtc gatgctcacc ctgttgtttg    8460
gtgttacttc tgcagggatc cccgatcatg caaaaactca ttaactcagt gcaaaactat    8520
gcctggggca gcaaaacggc gttgactgaa ctttatggta tggaaaatcc gtccagccag    8580
ccgatggccg agctgtggat gggcgcacat ccgaaaagca gttcacgagt gcagaatgcc    8640
gccggagata tcgtttcact gcgtgatgtg attgagagta taaatcgac  tctgctcgga    8700 gaggccgttg ccaaacgctt tggcgaactg cctttcctgt tcaaagtatt atgcgcagca    8760
cagccactct ccattcaggt tcatccaaac aaacacaatt ctgaaatcgg ttttgccaaa    8820
gaaaatgccg caggtatccc gatggatgcc gccgagcgta actataaaga tcctaaccac    8880
aagccggagc tggttttgc  gctgacgcct ttccttgcga tgaacgcgtt tcgtgaattt    8940
tccgagattg tctccctact ccagccggtc gcaggtgcac atccggcgat tgctcacttt    9000
ttacaacagc ctgatgccga acgtttaagc gaactgttcg ccagcctgtt gaatatgcag    9060
ggtgaagaaa atcccgcgc  gctggcgatt ttaaaatcgg ccctcgatag ccagcagggt    9120
gaaccgtggc aaacgattcg tttaatttct gaattttacc cggaagacag cggtctgttc    9180
tccccgctat tgctgaatgt ggtgaaattg aaccctggcg aagcgatgtt cctgttcgct    9240
gaaacaccgc acgcttacct gcaaggcgtg gcgctggaag tgatggcaaa ctccgataac    9300
gtgctgcgtg cgggtctgac gcctaaatac attgatattc cggaactggt tgccaatgtg    9360
aaattcgaag ccaaaccggc taaccagttg ttgacccagc cggtgaaaca aggtgcagaa    9420
ctggacttcc cgattccagt ggatgatttt gccttctcgc tgcatgacct tagtgataaa    9480
gaaaccacca ttagccagca gagtgccgcc atttttgttct gcgtcgaagg cgatgcaacg    9540
ttgtggaaag gttctcagca gttacagctt aaaccgggtg aatcagcgtt tattgccgcc    9600
aacgaatcac cggtgactgt caaaggccac ggccgtttag cgcgtgttta caacaagctg    9660
taagagctta ctgaaaaaat taacatctct tgctaagctg ggagctcgtc atgggtcgtt    9720
taagctgccg atgtgcctgc gtcgtctggt gccctctctc catatggagg ttgtcaaagt    9780
atctgctgtt cgtgtcatga gtcgtgtcag tgttggttta ataatggacc ggttgtgttg    9840
tgtgtgcgta ctacccagaa ctatgacaaa tcatgaataa gtttgatgtt tgaaattaaa    9900
gcctgtgctc attatgttct gtctttcagt tgtctcctaa tatttgcctg caggtactgg    9960
ctatctaccg tttcttactt aggaggtgtt tgaatgcact aaaactaata gttagtggct    10020
aaaattagtt aaaacatcca aacaccatag ctaatagttg aactattagc tattttggga   10080
aaattagtta atagtgaggt agttatttgt tagctagcta attcaactaa caattttag    10140 ccaactaaca attagtttca gtgcattcaa acacccccctt aatgttaacg tggttctatc   10200
```

```
taccgtctcc taatatatgg ttgattgttc ggtttgttgc tatgctattg ggttctgatt   10260
gctgctagtt cttgctgaat ccagaagttc tcgtagtata gctcagattc atattattta   10320
tttgagtgat aagtgatcca ggttattact atgttagcta ggttttttt acaaggataa    10380 attatctgtg atcataattc ttatgaaagc tttatgtttc ctggaggcag tggcatgcaa   10440
tgcatgacag caacttgatc acaccagctg aggtagatac ggtaacaagg ttcttaaatc   10500
tgttcaccaa atcattggag aacacacata cacattcttg ccagtcttgg ttagagaaat   10560
ttcatgacaa aatgccaaag ctgtcttgac tcttcacttt tggccatgag tcgtgactta   10620
gtttggttta atggaccggt tctcctagct tgttctactc aaaactgttg ttgatgcgaa   10680
taagttgtga tggttgatct ctggattttg ttttgctctc aatagtggac gagattagat   10740
agcccggaaa tttaccggtg cccgggcggc cagcatggcc gtatccgcaa tgtgttatta   10800
agttgtctaa gcgtcaattt gtttacacca caatatatcc tgccaccagc cagccaacag   10860
ctccccgacc ggcagctcgg cacaaaatca ccactcgata caggcagccc atcagaatta   10920
attctcatgt ttgacagctt atcatcgact gcacggtgca ccaatgcttc tggcgtcagg   10980
cagccatcgg aagctgtggt atggctgtgc aggtcgtaaa tcactgcata attcgtgtcg   11040
ctcaaggcgc actcccgttc tggataatgt ttttgcgcc gacatcataa cggttctggc    11100
aaatattctg aaatgagctg ttgacaatta atcatccggc tcgtataatg tgtggaattg   11160
tgagcggata acaatttcac acaggaaaca gaccatgagg aagcgttga tcgccgaagt    11220 atcgactcaa ctatcagagg tagttggcgt catcgagcgc catctcgaac cgacgttgct   11280
ggccgtacat ttgtacggct ccgcagtgga tggcggcctg aagccacaca gtgatattga   11340
tttgctggtt acggtgaccg taaggcttga tgaaacaacg cggcgagctt tgatcaacga   11400 cctttggaa acttcggctt cccctggaga gagcgagatt ctccgcgctg tagaagtcac    11460
cattgttgtg cacgacgaca tcattccgtg gcgttatcca gctaagcgcg aactgcaatt   11520
tggagaatgg cagcgcaatg acattcttgc aggtatcttc gagccagcca cgatcgacat   11580
tgatctggct atcttgctga caaaagcaag agaacatagc gttgccttgg taggtccagc   11640
ggcggaggaa ctctttgatc cggttcctga acaggatcta tttgaggcgc taaatgaaac   11700
cttaacgcta tggaactcgc cgcccgactg ggctggcgat gagcgaaatg tagtgcttac   11760
gttgtcccgc atttggtaca gcgcagtaac cggcaaaatc gcgccgaagg atgtcgctgc   11820
cgactgggca atggagcgcc tgccggccca gtatcagccc gtcatacttg aagctaggca   11880
ggcttatctt ggacaagaag atcgcttggc ctcgcgcgca gatcagttgg aagaatttgt   11940
tcactacgtg aaaggcgaga tcaccaaagt agtcggcaaa taaagctcta gtggatctcc   12000
gtacccgggg atctggctcg cggcggacg acgacgccgg ggcgagacca taggcgatct    12060
cctaaatcaa tagtagctgt aacctcgaag cgtttcactt gtaacaacga ttgagaattt   12120
ttgtcataaa attgaaatac ttggttcgca tttttgtcat ccgcggtcag ccgcaattct   12180
gacgaactgc ccatttagct ggagatgatt gtacatcctt cacgtgaaaa tttctcaagc   12240
gctgtgaaca agggttcaga ttttagattg aaaggtgagc cgttgaaaca cgttcttctt   12300
gtcgatgacg acgtcgctat gcggcatctt attattgaat accttacgat ccacgccttc   12360
aaagtgaccg cggtagccga cagcacccag ttcacaagag tactctcttc cgcgacggtc   12420
gatgtcgtgg ttgttgatct agatttaggt cgtgaagatg ggctcgagat cgttcgtaat   12480
ctggcggcaa agtctgatat tccaatcata attatcagtg gcgaccgcct tgaggagacg   12540
```

```
gataaagttg ttgcactcga gctaggagca agtgatttta tcgctaagcc gttcagtatc   12600
agagagtttc tagcacgcat tcggttgcc ttgcgcgtgc gccccaacgt tgtccgctcc    12660
aaagaccgac ggtcttttg ttttactgac tggacactta atctcaggca acgtcgcttg    12720
atgtccgaag ctggcggtga ggtgaaactt acggcaggtg agttcaatct tctcctcgcg   12780
tttttagaga aaccccgcga cgttctatcg cgcgagcaac ttctcattgc cagtcgagta   12840
cgcgacgagg aggtttatga caggagtata gatgttctca ttttgaggct gcgccgcaaa   12900
cttgaggcag atccgtcaag ccctcaactg ataaaaacag caagaggtgc cggttatttc   12960
tttgacgcgg acgtgcaggt ttcgcacggg gggacgatgg cagcctgagc caattcccag   13020
atccccgagg aatcggcgtg agcggtcgca aaccatccgg cccggtacaa atcggcgcgg   13080
cgctgggtga tgacctggtg gagaagttga aggccgcgca ggccgcccag cggcaacgca   13140
tcgaggcaga agcacgcccc ggtgaatcgt ggcaagcggc cgctgatcga atccgcaaag   13200
aatcccggca accgccggca gccggtgcgc cgtcgattag gaagccgccc aagggcgacg   13260
agcaaccaga tttttcgtt ccgatgctct atgacgtggg caccgcgat agtcgcagca     13320 tcatggacgt ggccgttttc cgtctgtcga agcgtgaccg acgagctggc gaggtgatcc   13380
gctacgagct tccagacggg cacgtagagg tttccgcagg gccggccggc atggccagtg   13440
tgtgggatta cgacctggta ctgatggcgg tttcccatct aaccgaatcc atgaaccgat   13500
accgggaagg gaagggagac aagcccggcc gcgtgttccg tccacacgtt gcggacgtac   13560
tcaagttctg ccggcgagcc gatggcggaa agcagaaaga cgacctggta gaaacctgca   13620
ttcggttaaa caccacgcac gttgccatgc agcgtacgaa gaaggccaag aacgccgcc    13680 tggtgacggt atccgagggt gaagccttga ttagccgcta caagatcgta aagagcgaaa   13740
ccgggcggcc ggagtacatc gagatcgagc tagctgattg gatgtaccgc gagatcacag   13800
aaggcaagaa cccggacgtg ctgacggttc accccgatta cttttttgatc gatcccggca   13860 tcggccgttt tctctaccgc ctggcacgcc gcgccgcagg caaggcagaa gccagatggt   13920
tgttcaagac gatctacgaa cgcagtggca gcgccggaga gttcaagaag ttctgtttca   13980
ccgtgcgcaa gctgatcggg tcaaatgacc tgccggagta cgatttgaag gaggaggcgg   14040
ggcaggctgg cccgatccta gtcatgcgct accgcaacct gatcgagggc gaagcatccg   14100
ccggttccta atgtacggag cagatgctag ggcaaattgc cctagcaggg gaaaaaggtc   14160
gaaaaggtct ctttcctgtg gatagcacgt acattgggaa cccaaagccg tacattggga   14220
accggaaccc gtacattggg aacccaaagc cgtacattgg gaaccggtca cacatgtaag   14280
tgactgatat aaaagagaaa aaaggcgatt tttccgccta aaactcttta aaacttatta   14340
aaactcttaa aacccgcctg gcctgtgcat aactgtctgg ccagcgcaca gccgaagagc   14400
tgcaaaaagc gcctacccctt cggtcgctgc gctccctacg ccccgccgct tcgcgtcggc   14460
ctatcgcggc cgctggccgc tcaaaaatgg ctggcctacg gccaggcaat ctaccagggc   14520
gcggacaagc cgcgccgtcg ccactcgacc gccggcgctg aggtctgcct cgtgaagaag   14580
gtgttgctga ctcataccag gcctgaatcg ccccatcatc cagccagaaa gtgagggagc   14640
cacggttgat gagagctttg ttgtaggtgg accagttggt gattttgaac ttttgctttg    14700
ccacggaacg gtctgcgttg tcgggaagat gcgtgatctg atccttcaac tcagcaaaag   14760
ttcgatttat tcaacaaagc cgccgtcccg tcaagtcagc gtaatgctct gccagtgtta   14820
caaccaatta accaattctg attagaaaaa ctcatcgagc atcaaatgaa actgcaattt   14880
attcatatca ggattatcaa taccatattt ttgaaaaagc cgtttctgta atgaaggaga   14940
```

```
aaactcaccg aggcagttcc ataggatggc aagatcctgg tatcggtctg cgattccgac   15000
tcgtccaaca tcaatacaac ctattaattt cccctcgtca aaataaggt tatcaagtga    15060 gaaatcacca tgagtgacga ctgaatccgg tgagaatggc aaaagctctg cattaatgaa   15120
tcggccaacg cgcggggaga ggcggtttgc gtattgggcg ctcttccgct tcctcgctca   15180
ctgactcgct gcgctcggtc gttcggctgc ggcgagcggt atcagctcac tcaaaggcgg   15240
taatacggtt atccacagaa tcaggggata acgcaggaaa gaacatgtga gcaaaaggcc   15300
agcaaaaggc caggaaccgt aaaaaggccg cgttgctggc gtttttccat aggctccgcc   15360
cccctgacga gcatcacaaa aatcgacgct caagtcagag gtggcgaaac ccgacaggac   15420
tataaagata ccaggcgttt ccccctggaa gctccctcgt gcgctctcct gttccgaccc   15480
tgccgcttac cggatacctg tccgcctttc tcccttcggg aagcgtggcg ctttctcata   15540
gctcacgctg taggtatctc agttcggtgt aggtcgttcg ctccaagctg ggctgtgtgc   15600
acgaaccccc cgttcagccc gaccgctgcg ccttatccgg taactatcgt cttgagtcca   15660
acccggtaag acacgactta tcgccactgg cagcagccac tggtaacagg attagcagag   15720
cgaggtatgt aggcggtgct acagagttct tgaagtggtg gcctaactac ggctacacta   15780
gaagaacagt atttggtatc tgcgctctgc tgaagccagt taccttcgga aaaagagttg   15840
gtagctcttg atccggcaaa caaaccaccg ctggtagcgg tggttttttt gtttgcaagc   15900
agcagattac gcgcagaaaa aaggatctc aagaagatcc tttgatcttt tctacggggt    15960
ctgacgctca gtggaacgaa aactcacgtt aagggatttt ggtcatgaga ttatcaaaaa   16020
ggatcttcac ctagatcctt ttgatccgga atta                                16054
```

<210> SEQ ID NO 28
<211> LENGTH: 22075
<212> TYPE: DNA
<213> ORGANISM: Artificial Sequence
<220> FEATURE:
<223> OTHER INFORMATION: Recombinant vector

<400> SEQUENCE: 28

```
attcctgtgg ttggcatgca catacaaatg gacgaacgga taaaccttt cacgcccttt      60 taaatatccg attattctaa taaacgctct tttctcttag gtttacccgc caatatatcc    120
tgtcaaacac tgatagttta aactgaaggc gggaaacgac aatctgatca tgagcggaga   180
attaagggag tcacgttatg acccccgccg atgacgcggg acaagccgtt ttacgtttgg    240
aactgacaga accgcaacgc tgcaggaatt ggccgcagcg gccatttaaa tcaattgggc    300
gcgccagctg cttgtgggga ccagacaaaa aaggaatggt gcagaattgt taggcgcacc    360
taccaaaagc atctttgcct ttattgcaaa gataaagcag attcctctag tacaagtggg    420
gaacaaaata acgtggaaaa gagctgtcct gacagcccac tcactaatgc gtatgacgaa    480
cgcagtgacg accacaaaac tcgagacttt tcaacaaagg gtaatatccg gaaacctcct    540
cggattccat tgcccagcta tctgtcactt tattgtgaag atagtggaaa aggaaggtgg    600
ctcctacaaa tgccatcatt gcgataaagg aaaggctatc gttgaagatg cctctgccga    660
cagtggtccc aaagatggac ccccacccac gaggagcatc gtggaaaaag aagacgttcc    720
aaccacgtct tcaaagcaag tggattgatg tgatatctcc actgacgtaa gggatgacga    780
acaatcccac tatccttcgg taccggaccc tatagaatag ctcactatcc tatttattat    840
agtttaagta tatagccaat attttaaatt tactatttat taaattctag ggaagatagt    900
```

| | |
|---|---|
| ctcaattcat aactttatta taatacgttt gaaattttaa atctttagga aattttctta | 960 |
| attcacctag atacgattct ggagtgttac aagctgcgaa tatactgtg ccattgagta | 1020 |
| tacataaatg gatttaggtg gtgctcaata ggtgaaaatg agatactaat cacttaaatt | 1080 |
| tcaaaatttc tatggtgcca ctgtactcgg ataggtctat ctagggctgg acaaaatgct | 1140 |
| cgtggctcgc tggctcgctc gtttcgtggt cagctcggct cggctcggat cggctcattt | 1200 |
| gaattttgtc acgagctgag ctgacattct agctcggttc gttaacgagc cagctcgcga | 1260 |
| gctaaacgag ctaccatatt ctagtaaaac gaaattatat tcatatcatt tatagaataa | 1320 |
| ttgatgaaca tgttatatat atgtgagatg tctatggcct atgaattaaa ctaatgatta | 1380 |
| atgaactatg cctatgtgtt aatttggtct atgcaaatat aattatgggt taaactgatg | 1440 |
| aacatgcatg tgaattgtga attaatgagt gatgaattgt gctaatttgg tgttatattg | 1500 |
| acatggtttg tgaaactatg agtataatta ctattttcta ttgttaaatt agtttgaaat | 1560 |
| taactaaaaa ataattatta tatacatttt attttttttc tgctctggct cgcgagctaa | 1620 |
| acgagccagc tcgacctcgt aaacgagccg agccgagctg actctgtggc tcgttacctt | 1680 |
| aacgagccga gccgagctgg ctcgttagct taacgagcca gctcgaactc ggacgagccg | 1740 |
| agccgagctg gctcgttatc caccccctagg tctatctagc ttctgatgtt tgcaaacctt | 1800 |
| agagttggag tgttcagcca gctactcctt tgctttgctg aataaccata ccaaacacgc | 1860 |
| ccatattaat acccgctcgg cggtggttct gcaatcaaac gcaggccgca gtcgcgtgcg | 1920 |
| gaactagagg tccttcagag aagtgccgtg ccagtgccac cgccggccgc atcatcgttc | 1980 |
| cgccccctg gtacgagcac ttcgcagagc tgcaacctac atccctttta cataaatcta | 2040 |
| ttgtctcgta ttgccgttga cgccggaata gtcttcgcat ccctttaca taaatccgat | 2100 |
| gttttctttc tccgattcct ttgaggaatc atcacgggtc agggcaggtg ttctgccgtt | 2160 |
| tgccctttc tttatattct ccttagaaga aatatttagt tggaggctgg acatagccgg | 2220 |
| aggagctaac taatcgagcg gtgtactggc aaaacaaaag gagcggagca agaaagggga | 2280 |
| gaaaaaacta gccactgccg gagcgctatt ggccgtgttg ggcctggaag cttgcatcaa | 2340 |
| tacttccctc gccccgattt ggttccaaaa tcatacaagt cccaaagttg tcaagatatt | 2400 |
| ggaggtatgc aagcgacttg gatctcaaaa tagaagaaat ttcggatctg agcacaaatc | 2460 |
| tgagttgaaa aaactgcaac tcaaaatcat caaaaaaaga agaagaaaga aacgaatata | 2520 |
| ttcgctcctc ttctcagccg aacccaaagg aattgaatcc aaaccctggg taggcagaca | 2580 |
| gtgagatatg gaggagagca ggaggcgaac aagagaggct gcggccacga atatctcacg | 2640 |
| aacaagcaca tcatgggtcc acggagcggg cagggtgacg ggctcccgac ggcgagctac | 2700 |
| atctcggaag agcaccaggg cagcatgtcg tgttgggcag gttggccgtc tggcggacgg | 2760 |
| cggacggtga ctcgtggtca gggtgcacct gctcgattaa ggcgcctgac tactcatgtc | 2820 |
| ttggtctctt tgcttgtgtt tgctatatgc tgctcgtacc tcatgagcat actaagttga | 2880 |
| ctgctcagtc tgctgagtct gttttttctag ggtatagtgc tgagcacaag ggatatcatt | 2940 |
| gttgggatat gattgctcgt tggatgaggg tctcttggga tgttgtcttt gatgaggctc | 3000 |
| attctttta ttcttgtcct tctttcgatg ctttgtcaac atcctggtt gatcccatct | 3060 |
| cttttctata ttttctagat gcccgtgtta ctattggacc tgcctcacgc ttggtgcgcc | 3120 |
| cacgatagta gccttagctc cttctgacat gttcatctct ctttcggtgc cttcctttgt | 3180 |
| ggtgccttct atagtgtttt ctttggagcc tgctgcttta gccctgact acgctatgaa | 3240 |
| cacttgtcta cacccgccgg gtcatcaatt cttttggtac accatcatcc tctcatgcgt | 3300 |

```
tgccctctta tgatgtgcgc tcttctgcaa ctcattcatt ttcttgcgat ttacctttga    3360
ctgatgctcc ctattcatct ctggatccag cttcctcagt tgactctttg ctggagccac    3420
ctcttagacg gagtcatcgt tttcgtcagc cacctaatgg gtactctcct tcaggtttag    3480
tcgctaccgt tctttctgag ctgacttctt atcatgatgc tattcttcat ctgtaacgac    3540
aacatgcgat ttctgaggag attgctactc ttgagcgcac tagcacgttg gaacttgttc    3600
cttgtccatc acgtgtttgt cctatcacca gtatgtgggt ctataaggtc aagacccgtt    3660
ctgatggttc tcttgatcgc tataaatctc gtctagttgc ccaaggcttc cagtaggaac    3720
atggttgtgg ctatgatgag attttttgcac ctgttgctca tatgaccact gttcgcactc    3780
ttcttgctat ggcctctgtt cgtgcgtggt ccatctctca tcttgatgtc aagaatacct    3840
ttcttgatgg taagctactt gagttctata tgtagccatc gcctaggtat tctatttctg    3900
cttgtatggt ttgttgtctt cgccgttccc cttatggcct caagcaggct ccacattctt    3960
ggtttcagct ctttgcttct atgataactg ttgttggttt ttctaccagt aatcatggtc    4020
ctgcactctt tgtgtactac ctcctctcgg ggtcggactc ttctttatgt tgatgatata    4080
attatcactg gagataacct tgagtatgtt gactttgtta aggcacgtct tagttatcat    4140
tttctcatgt ctgatcttgg tcctctgtgt tactttcttg ggacaaaggt ttcttctttg    4200
tctcagggcc tttatctatc tcaagaggag tacattcaag attttcttca tcgggcttct    4260
cttaccgatc actagattgt tgagactccc aagcagctca atcttcacct tagtgccgat    4320
gatggcgagt cttttcccga ccatactcgt tatcgtcaac atactgtagg aagttttgtt    4380
tatctctgtg tcactcgtct tgacatttca tatgttgtgt gtatcctgag ttagtttgct    4440
tcagatccca tccaggtaca ctatagtcac ttgctttgtg tcctacaata tctttgtgga    4500
accatatcta gatgtatgtt cttccacat tctagctcgt tgcaactgca atcttgttct    4560
gatgctactt gggctagtga ttttttcgat agttggtctc tttctcaata ttgtgttttt    4620
cttggtggtt ctctcattgc tcggaagact aagtagcagg tagcagtttc tcgtttgagt    4680
accgaggctg agttgcgtgc tatggcccctt gtgactgcag aggttacttg gttacgatag    4740
ttgcttgagg attttcatgt ttctgtttcc atgacgactc cttttgtctg acagtacagg    4800
tgttatcagt attgctcgtg atgcggtgaa gcatgaggtc accaagcata ttggagttga    4860
tgtttcgtat acacgagctg aagtctagga tgatgttatc ttgatttggt atgtgccttt    4920
agagcttcag ttggctaatt tcttcacgag ggcacaggct cgcgctgagc ataaattttt    4980
cctctcaaaa ctcagtgtta tagatccacc ttgagtttga gggagtatta gatagatatg    5040
ggtttatttg tattttttcca ttttataagg gtattagata gataggcaac gactgctatg    5100
caagtagtca ttctgtgcaa gcgtgcaagc aaaccatctg atccattata tcgtgatcca    5160
accgtgggtc acatttaaca cttaaaccct tccaccacca actcaataat ctttataaaa    5220 aaaccccctaa caaacaatgg ttatatctgt ggttggatcg taatctaata gatcagatgg    5280
tttgcttgta cgcttgcaca gaatgactgc ttgcatagca gttgttgcct agatagatat    5340
gggtttattt gtattttttct cttaagggtt tttgtgtata tttgtactca tgtacctata    5400
tatttgtgct agttgacccc ataatgaata gacctgctat tcataatatt tgcaaaccat    5460
gaaaatttga ttattacgaa ctatccaaat actcgaacac atgggcatta tagctcacaa    5520
aaatggaagg ttgagctgct gcttgaagaa cctcaacatc tttgaacaac aacctcaacg    5580
aaacttgtat atgaaccaac ttccaaacaa tcccttgtgg aaggatagta atgacttcag    5640
```

-continued

```
ggcattgatc acacatatcc gacggtggaa ctactgtaac aaccctcttt tctgtggaat    5700
atagttgaaa ctctacaact tgaccaaaac caagatgacg acatatggtg aactaacaa     5760 aacaagagga ctacactacc tcattagctt attaagcaca atctcttggc accacaacaa    5820
cgaacaacaa aaccatcatt tggatgctct gtgggcgact aaatgcaaat tctttgcatg    5880
gttgatcatc ccaaattggt ggcacttagc tataggctag cagtgagagg atggccgaac    5940
aacatgcatt gtccactatg ttggtgtagc catgagacca accaccacat aaatgccaaa    6000
cgttcattca ccaaaaaaat ctaggcaaca atggcttgga tttcttacct gcagctccac    6060
caagctaact ggagttcaat taggtcaacg tatgggtggt ggtcgagtat agcagtcaca    6120
aatgatgttc taaagatggg gttgtgttaa cacatcttgc ttgtagcacg agaacactgg    6180
aaggagtgaa accaaagaat ctttcaacac aaggacctat caacgctatc catgattggg    6240
aaattcaagg acgaaactag aatttgggtg aacacatgca caaggcacct aggagagcct    6300
ttcttttgta ctgttaatcc cttttaaac tctctctgtc cttaggagtt cgtttcttcc      6360
gctctattca atgaagttag gcacaatctt gtgtgatttc attagaaaaa cacaagtaaa    6420
ttgcatggtc agtacttgaa gtattacagg aatctcgtct gccccaaac tattaaacct      6480 tatatttggc tccctaatgt acttaactga tctcattctg gtcaaactaa acatggtgat    6540
ggcaaggagc cgatatggtc gcccatgtgg atgtgattta agcaaaaat ctcatggtcc      6600 atagctgtgt caacaagcca acatgccatc gcttccttat gccgagactg cccatgtcgc    6660
tcgcttttac tgtcatcatc atcaaactgc ctgtcatgtc tacggatgcc atgaccgctg    6720
tcacacatga tgtggagatg aacctgtcca tcaacttcca cgtgctgcca ctatcgctag    6780
ctgacaccgt cttggtcatt gctgtgtagg gctaggctaa gagtcgctga atgatccttt    6840
cgctctcctt tacaggaaca tgctgtttac tttgtgtcgc caaggcgtgc tagagtacct    6900
cttctacacc tccagcacca gtagccttat tgttagcttg cacatcccac ataagcaggc    6960
cgatgtgaat gataacttca gggacgtcga cggcatgtca ctgccaagag tcatttggtg    7020
ggaagcgttg tcatgccatc tgtcgtgcca ttttgtcctc agttcgaccg ccattaccgt    7080
gagcacaacc tttgcgcatg gttggccgct tccatcaccc ttattccgtt tcctcgtgtt    7140
ggtcttgccc caaggctatg gttagcagac cgtgcatatg gccggcaaaa gactattttg    7200
cactgtagat tgcactcttt atatagtgaa gtttaaaata ggagatgaga tgaataaggc    7260
tgctggagat agcctaaacc cttgcagctc gtgcttgcat cggggagcc aaaaggcgtc     7320 cacctccacc atcgccgaag cactgagcac tactctggct tgtgtttcag caccacaccg    7380
cagagtgctt agggccacca acctcctctt gcctctgtgc ccagagcacc atcagctctg    7440
ctgcctccct ctgttccttg tgcttgctag gcaggcaatt ccgagctggg gcccaacttg    7500
taacgctgat ttcaccatct tgccactgcc gggcaccaag tggacacatt tgacttggcc    7560
tagtgggttt tctgcataaa tcacatacat gtggatgcca tatcaggctc tttggtgttg    7620
tcgtgtctac tttcgacaag gatgagatca cttaaacata ttagggagcc aagtatgtaa    7680
tttcatagtt tagggaccta cacaaaaatc gtataatact ttagaacagc cgtgcagttt    7740
actcaatcaa cacatacaaa gtcagatctt aagctctgat acttcaaagg aatggttgag    7800
cccagttgac aaacaatctt gcttcattca ttgaattgtt tataggagtg ctatgtaac     7860 tactgggtgg ttttgtttga cctgtcatcc aaattgtgta gtcaaccata acatacacg     7920 tcacacaata catttggat gtgacagata ggatttaggc gagagaatgt acaatgtcac     7980
tgaaaaatta ccactgtatg gaaggacaa tctaagtgaa aagagaacca gggcctaatg     8040
```

```
gtttcaggac ttcaaactcc ggccaaatga atttacagtg cttaaattaa ctcatgttaa    8100
tcatgatagc caaagcatgg gcaaaagaga aactatgaat aaatcgacaa tgtattctat    8160
atagcagtaa tataccatgt cacgagcttt tacactaatg gctgtatttt ttctgcagtt    8220
attttaactg gcaatattct atgtcacagt aatatttgtt aaattttttc cagaatagca    8280
actgaactag aagtctagta tttcttaatt ggataacaaa aggaattagt gtgcatttgg    8340
cttacgaaca atcagtcacc caacattgaa tttgaagttc tgtttcctct ttgttcagac    8400
gacactctcc aaatgaatgc cttatatttt gtgttgctcc tcttttctgc agagtgttca    8460
gtaacttctt ccgatgtaaa ccatggacaa caacccccaac atcaacgagt gcatcccta    8520 caactgcctg agcaaccccg aggtggaggt gctgggcggc gagcgcatcg agaccggcta    8580
cacccccatc gacatcagcc tgagcctgac ccagttcctg ctgagcgagt tcgtgcccgg    8640
cgccggcttc gtgctgggcc tggtggacat catctggggc atcttcggcc ccagccagtg    8700
ggacgccttc ctggtgcaga tcgagcagct gatcaaccag cgcatcgagg agttcgcccg    8760
caaccaggcc atcagccgcc tggagggcct gagcaacctg taccaaatct acgccgagag    8820
cttccgcgag tgggaggccg accccaccaa ccccgccctg cgcgaggaga tgcgcatcca    8880
gttcaacgac atgaacagcg ccctgaccac cgccatcccc ctgttcgccg tgcagaacta    8940
ccaggtgccc ctgctgagcg tgtacgtgca ggccgccaac ctgcacctga gcgtgctgcg    9000
cgacgtcagc gtgttcggcc agcgctgggg cttcgacgcc gccaccatca acagccgcta    9060
caacgacctg acccgcctga tcggcaacta caccgaccac gccgtgcgct ggtacaacac    9120
cggcctggag cgcgtgtggg gtccagacag ccgcgactgg atcaggtaca accagttccg    9180
ccgcgagctg accctgaccg tgctggacat cgtgagcctg ttccccaact acgacagccg    9240
cacctacccc atccgcaccg tgagccagct gacccgcgag atttacacca ccccgtgct    9300 ggagaacttc gacggcagct tccgcggcag cgccccaggg catcgagggca gcatccgcag    9360 ccccccacctg atggacatcc tgaacagcat caccatctac accgacgccc ccgcggcga    9420 gtactactgg agcggccacc agatcatggc cagcccgtcg ggcttcagcg gccccgagtt    9480
cacccttccc ctgtacggca ctatgggcaa cgctgcacct cagcagcgca tcgtggcaca    9540
gctgggccag ggagtgtacc gcaccctgag cagcaccctg taccgtcgac ctttcaacat    9600
cggcatcaac aaccagcagc tgagcgtgct ggacggcacc gagttcgcct acggcaccag    9660
cagcaacctg cccagcgccg tgtaccgcaa gagcggcacc gtggacagcc tggacgagat    9720
cccccctcag aacaacaacg tgccaccctcg acagggcttc agccaccgtc tgagccacgt    9780
gagcatgttc cgcagtggct tcagcaacag cagcgtgagc atcatccgtg cacctatgtt    9840
cagctggatt caccgcagtg ccgagttcaa caacatcatc cccagcagcc agatcaccca    9900 gatcccccctg accaagagca ccaacctggg cagcggcacc agcgtggtga agggccccgg    9960
cttcaccggc ggcgacatcc tgcgccgcac cagccccggc cagatcagca ccctgcgcgt    10020
gaacatcacc gccccccctga ccagcgcta ccgcgtccgc atccgctacg ccagcaccac    10080
caacctgcag ttccacacca gcatcgacgg ccgccccatc aaccaggggca acttcagcgc    10140 caccatgagc agcggcagca acctgcagag cggcagcttc cgcaccgtgg gcttcaccac    10200
ccccttcaac ttcagcaacg gcagcagcgt gttcaccctg agcgccacg tgttcaacag    10260 cggcaacgag gtgtacatcg accgcatcga gttcgtgccc gccgaggtga ccttcgaggc    10320
cgagtacgac ctggagaggg ctcagaaggc cgtgaacgag ctgttcacca gcagcaacca    10380
```

```
gatcggcctg aagaccgacg tgaccgacta ccacatcgat caggtgtagg agctcgacgt   10440
acaaatctca tctgtgcctt gctctagttt cccaaatgga attaactatg catgatttgt   10500
ttggaaactc ttattgcatc catccagata atgcatccac cataaggtaa tatcttgatg   10560
acatctgtgc ctgatggtgt accaaatgtc tctatctctg cattgagcca cgagtaggag   10620
gatagcctag gggtgccttg actccaaagt tgtattgaaa aagatggatg aagcaggcaa   10680
atgctgcctg aatccatgac tcagggcaca gattttccac tcaaaggaag ataagattgc   10740
attacttcat gatcttttga actgcctctg caagacggga ctcggatagt ggatgcaaag   10800
atctaatact ggcctcaggc aacgagttgt ttcactcgaa agtctagaaa tgaccgggct   10860
caaattttgc accccaagga aagtgagttt gcattacttc atgacctttt gaactgcctc   10920
tgcaagactg gactcagatt acgcttgatt ggttgccggc ctcaccttcg cctggcttgc   10980
gcgagcctgc gtctatagaa atgcgccgga ctcacgtctc cgtcgatgca ggcattcgac   11040
tgaaaaaaca tttaaactgc acccatgcgt gcgggctgag cttatgtcat acaagtaacc   11100
aatcacaggc ttaagttcag tcaacgcatg cgctaagctt ggatgtggct gaccgggcaa   11160
ccaatcacac agatagtgga tgcacggatc taatattggc taatttggtt aaacttgtct   11220
aaccttagac gtggcaagtg agtcagcgga tcaaatctgc tctaaaattg tctgcctcct   11280
agatgtcctt ggtgttccaa gatttaatca tcactgcact atttctttgc gttgcttcgc   11340
tgcagcttcg cgttacttgc attcgcttaa tcaggattac tttgatcaac taggtttcta   11400
acttctacta ccttcacttg cacagggtgc ccgtcctgct agccggtgtg cttgctgtgc   11460
gatcgtttgg catgtgcttg ttgagggggtt gctaggggat tggagaggat tgaagggatt   11520
aaatctcctc ctattcaatt ttgaatagga ggggatttaa tccccttcaa tcccccctcaa   11580 accactagta accgaacgtg gcctgagggg gcgggcgagt ctttatattg aatgaaacta   11640
cataaaatag catgccgtct ctgtcactgg caatggacgg tggtgcctag cgcaactcag   11700
cgcacaactg tgtgtcttga ttttctttct gtttatcacg gcattagtgc catgccgttt   11760
tatgttacag tgttgtgtgc tcgcaagcat ccgaaaatat gcgtctgagt ttagggttgg   11820
gtcaaacttg tcgaatttgg ggttctgtta taatatgttg agcatgaata aagatggatg   11880
ctggtgactc tgtcgccatc gccgtccatc atgagtgtcc tgtaattcaa cttatatcta   11940
tcatgtatgt atgtatgtat gtatgtatgt atgtatatgc tgtctactat gcttctttgt   12000
tttaactgaa atgtgtgtta cagtgttact tctctggggt ccatttaaaa cggcatttcg   12060
tttacgatag gaaccagcca ttataatctt taaccaataa tttcgctaac caatttcaac   12120
tattgcaatg cgaacttaat attatcagat ttataaccga atgcgctatc aaataatcat   12180
aaggttgtaa tcataataat ataatataaa ataaatgagt gctcgaagtg aaatttttaga   12240 gagcgttata agaaaaattg atgtgatctc caagaataat agcccctccc ggctcccggt   12300
acaaacatag ggcttcttta gaatgcagga ttgtgagaac ataggaatag gaaaaatata   12360
ggaattctat aggaatgtat atggaaaaca gaggattgaa aaacacagaa aaaatgtgaa   12420
agcaagtctt tggatgaagc gtaggaaact tataggaata ggaattcata acggaccgcg   12480
atcgcttaat taagcttgca tgcctgcagt gcagcgtgac ccggtcgtgc ccctctctag   12540
agataatgag cattgcatgt ctaagttata aaaaattacc acatattttt tttgtcacac   12600
ttgtttgaag tgcagtttat ctatcttttat acatatattt aaactttact ctacgaataa   12660
tataatctat agtactacaa taatatcagt gttttagaga atcatataaa tgaacagtta   12720
gacatggtct aaaggacaat tgagtatttt gacaacagga ctctacagtt ttatcttttt   12780
```

```
agtgtgcatg tgttctcctt ttttttttgca aatagcttca cctatataat acttcatcca   12840
ttttattagt acatccattt agggtttagg gttaatggtt tttatagact aattttttta   12900
gtacatctat tttattctat tttagcctct aaattaagaa aactaaaact ctattttagt   12960
ttttttattt aataatttag atataaaata gaataaaata aagtgactaa aaattaaaca   13020
aatacccttt aagaaattaa aaaaactaag gaaacatttt tcttgtttcg agtagataat   13080
gccagcctgt taaacgccgt cgacgagtct aacggacacc aaccagcgaa ccagcagcgt   13140
cgcgtcgggc caagcgaagc agacggcacg gcatctctgt cgctgcctct ggacccctct   13200
cgagagttcc gctccaccgt tggacttgct ccgctgtcgg catccagaaa ttgcgtggcg   13260
gagcggcaga cgtgagccgg cacggcaggc ggcctcctcc tcctctcacg gcaccggcag   13320
ctacggggga ttcctttccc accgctcctt cgctttccct tcctcgcccg ccgtaataaa   13380
tagacacccc ctccacaccc tctttcccca acctcgtgtt gttcggagcg cacacacaca   13440
caaccagatc tcccccaaat ccacccgtcg gcacctccgc ttcaaggtac gccgctcgtc   13500
ctccccccccc cccccctctct accttctcta gatcggcgtt ccggtccatg gttagggccc   13560
ggtagttcta cttctgttca tgtttgtgtt agatccgtgt ttgtgttaga tccgtgctgc   13620
tagcgttcgt acacggatgc gacctgtacg tcagacacgt tctgattgct aacttgccag   13680
tgtttctctt tggggaatcc tgggatggct ctagccgttc cgcagacggg atcgatttca   13740
tgattttttt tgtttcgttg catagggttt ggtttgccct tttcctttat ttcaatatat   13800
gccgtgcact tgtttgtcgg gtcatctttt catgcttttt tttgtcttgg ttgtgatgat   13860
gtggtctggt tgggcggtcg ttctagatcg gagtagaatt ctgtttcaaa ctacctggtg   13920
gatttattaa ttttggatct gtatgtgtgt gccatacata ttcatagtta cgaattgaag   13980
atgatggatg gaaatatcga tctaggatag gtatacatgt tgatgcgggt tttactgatg   14040
catatacaga gatgcttttt gttcgcttgg ttgtgatgat gtggtgtggt tgggcggtcg   14100
ttcattcgtt ctagatcgga gtagaatact gtttcaaact acctggtgta tttattaatt   14160
ttggaactgt atgtgtgtgt catacatctt catagttacg agtttaagat ggatggaaat   14220
atcgatctag gataggtata catgttgatg tgggttttac tgatgcatat acatgatggc   14280
atatgcagca tctattcata tgctctaacc ttgagtacct atctattata ataaacaagt   14340
atgttttata attattttga tcttgatata cttggatgat ggcatatgca gcagctatat   14400
gtggatttttt ttagccctgc cttcatacgc tatttatttg cttggtactg tttcttttgt   14460
cgatgctcac cctgttgttt ggtgttactt ctgcagggat ccccgatcat gcaaaaactc   14520
attaactcag tgcaaaacta tgcctggggc agcaaacgg cgttgactga actttatggt   14580
atggaaaatc cgtccagcca gccgatggcc gagctgtgga tgggcgcaca tccgaaaagc   14640
agttcacgag tgcagaatgc cgccggagat atcgtttcac tgcgtgatgt gattgagagt   14700
gataaatcga ctctgctcgg agaggccgtt gccaaacgct ttggcgaact gccttttcctg   14760
ttcaaagtat tatgcgcagc acagccactc tccattcagg ttcatccaaa caaacacaat   14820
tctgaaatcg gttttgccaa agaaaatgcc gcaggtatcc cgatggatgc cgccgagcgt   14880
aactataaag atcctaacca caagccggag ctggttttttg cgctgacgcc tttccttgcg   14940
atgaacgcgt ttcgtgaatt ttccgagatt gtctccctac tccagccggt cgcaggtgca   15000
catccggcga ttgctcactt tttacaacag cctgatgccg aacgtttaag cgaactgttc   15060
gccagcctgt tgaatatgca gggtgaagaa aaatcccgcg cgctggcgat tttaaaatcg   15120
```

```
gccctcgata gccagcaggg tgaaccgtgg caaacgattc gtttaatttc tgaattttac    15180
ccggaagaca gcggtctgtt ctccccgcta ttgctgaatg tggtgaaatt gaaccctggc    15240
gaagcgatgt tcctgttcgc tgaaacaccg cacgcttacc tgcaaggcgt ggcgctggaa    15300
gtgatggcaa actccgataa cgtgctgcgt gcgggtctga cgcctaaata cattgatatt    15360
ccggaactgg ttgccaatgt gaaattcgaa gccaaaccgg ctaaccagtt gttgacccag    15420
ccggtgaaac aaggtgcaga actggacttc ccgattccag tggatgattt tgccttctcg    15480
ctgcatgacc ttagtgataa agaaaccacc attagccagc agagtgccgc cattttgttc    15540
tgcgtcgaag gcgatgcaac gttgtggaaa ggttctcagc agttacagct taaaccgggt    15600
gaatcagcgt ttattgccgc caacgaatca ccggtgactg tcaaaggcca cggccgttta    15660
gcgcgtgttt acaacaagct gtaagagctt actgaaaaaa ttaacatctc ttgctaagct    15720
gggagctcgt catgggtcgt ttaagctgcc gatgtgcctg cgtcgtctgg tgccctctct    15780
ccatatggag gttgtcaaag tatctgctgt tcgtgtcatg agtcgtgtca gtgttggttt    15840
aataatggac cggttgtgtt gtgtgtgcgt actacccaga actatgacaa atcatgaata    15900
agtttgatgt ttgaaattaa agcctgtgct cattatgttc tgtcttttcag ttgtctccta    15960 atatttgcct gcaggtactg gctatctacc gtttcttact taggaggtgt ttgaatgcac    16020
taaaactaat agttagtggc taaaattagt taaaacatcc aaacaccata gctaatagtt    16080
gaactattag ctattttttgg aaaattagtt aatagtgagg tagttatttg ttagctagct    16140
aattcaacta acaattttta gccaactaac aattagtttc agtgcattca acaccccct    16200 taatgttaac gtggttctat ctaccgtctc ctaatatatg gttgattgtt cggtttgttg    16260
ctatgctatt gggttctgat tgctgctagt tcttgctgaa tccagaagtt ctcgtagtat    16320
agctcagatt catattattt atttgagtga taagtgatcc aggttattac tatgttagct    16380
aggttttttt tacaaggata aattatctgt gatcataatt cttatgaaag ctttatgttt    16440
cctggaggca gtggcatgca atgcatgaca gcaacttgat cacaccagct gaggtagata    16500
cggtaacaag gttcttaaat ctgttcacca aatcattgga gaacacacat acacattctt    16560
gccagtcttg gttagagaaa tttcatgaca aaatgccaaa gctgtcttga ctcttcactt    16620
ttggccatga gtcgtgactt agtttggttt aatggaccgg ttctcctagc ttgttctact    16680
caaaactgtt gttgatgcga ataagttgtg atggttgatc tctggatttt gttttgctct    16740
caatagtgga cgagattaga tagcccggaa atttaccggt gcccgggcgg ccagcatggc    16800
cgtatccgca atgtgttatt aagttgtcta agcgtcaatt tgtttacacc acaatatatc    16860
ctgccaccag ccagccaaca gctccccgac cggcagctcg gcacaaaatc accactcgat    16920
acaggcagcc catcagaatt aattctcatg tttgacagct tatcatcgac tgcacggtgc    16980
accaatgctt ctggcgtcag gcagccatcg gaagctgtgg tatggctgtg caggtcgtaa    17040
atcactgcat aattcgtgtc gctcaaggcg cactcccgtt ctggataatg ttttttgcgc    17100
cgacatcata acggttctgg caaatattct gaaatgagct gttgacaatt aatcatccgg    17160
ctcgtataat gtgtggaatt gtgagcggat aacaatttca cacaggaaac agaccatgag    17220
ggaagcgttg atcgccgaag tatcgactca actatcagag gtagttggcg tcatcgagcg    17280
ccatctcgaa ccgacgttgc tggccgtaca tttgtacggc tccgcagtgg atggcggcct    17340
gaagccacac agtgatattg atttgctggt tacggtgacc gtaaggcttg atgaaacaac    17400
gcggcgagct ttgatcaacg acctttggga aacttcggct tccccggag agagcgagat    17460 tctccgcgct gtagaagtca ccattgttgt gcacgacgac atcattccgt ggcgttatcc    17520
```

```
agctaagcgc gaactgcaat ttggagaatg gcagcgcaat gacattcttg caggtatctt    17580
cgagccagcc acgatcgaca ttgatctggc tatcttgctg acaaaagcaa gagaacatag    17640
cgttgccttg gtaggtccag cggcggagga actctttgat ccggttcctg aacaggatct    17700
atttgaggcg ctaaatgaaa ccttaacgct atggaactcg ccgcccgact gggctggcga    17760
tgagcgaaat gtagtgctta cgttgtcccg catttggtac agcgcagtaa ccggcaaaat    17820
cgcgccgaag gatgtcgctg ccgactgggc aatggagcgc ctgccggccc agtatcagcc    17880
cgtcatactt gaagctaggc aggcttatct tggacaagaa gatcgcttgg cctcgcgcgc    17940
agatcagttg gaagaatttg ttcactacgt gaaaggcgag atcaccaaag tagtcggcaa    18000
ataaagctct agtggatctc cgtacccggg gatctggctc gcggcggacg cacgacgccg    18060
gggcgagacc ataggcgatc tcctaaatca atagtagctg taacctcgaa gcgtttcact    18120
tgtaacaacg attgagaatt tttgtcataa aattgaaata cttggttcgc attttttgtca    18180 tccgcggtca gccgcaattc tgacgaactg cccatttagc tggagatgat tgtacatcct    18240
tcacgtgaaa atttctcaag cgctgtgaac aagggttcag attttagatt gaaaggtgag    18300
ccgttgaaac acgttcttct tgtcgatgac gacgtcgcta tgcggcatct tattattgaa    18360
taccttacga tccacgcctt caaagtgacc gcggtagccg acagcaccca gttcacaaga    18420
gtactctctt ccgcgacggt cgatgtcgtg gttgttgatc tagatttagg tcgtgaagat    18480
gggctcgaga tcgttcgtaa tctggcggca aagtctgata ttccaatcat aattatcagt    18540
ggcgaccgcc ttgaggagac ggataaagtt gttgcactcg agctaggagc aagtgatttt    18600
atcgctaagc cgttcagtat cagagagttt ctagcacgca ttcgggttgc cttgcgcgtg    18660
cgccccaacg ttgtccgctc caaagaccga cggtcttttt gttttactga ctggacactt    18720
aatctcaggc aacgtcgctt gatgtccgaa gctggcggtg aggtgaaact tacggcaggt    18780
gagttcaatc ttctcctcgc gttttttagag aaacccgcg acgttctatc gcgcgagcaa    18840
cttctcattg ccagtcgagt acgcgacgag gaggtttatg acaggagtat agatgttctc    18900
attttgaggc tgcgccgcaa acttgaggca gatccgtcaa gccctcaact gataaaaaca    18960
gcaagaggtg ccggttattt ctttgacgcg gacgtgcagg tttcgcacgg ggggacgatg    19020
gcagcctgag ccaattccca gatccccgag gaatcggcgt gagcggtcgc aaaccatccg    19080
gcccggtaca aatcggcgcg gcgctgggtg atgacctggt ggagaagttg aaggccgcgc    19140
aggccgccca gcggcaacgc atcgaggcag aagcacgccc cggtgaatcg tggcaagcgg    19200
ccgctgatcg aatccgcaaa gaatcccggc aaccgccggc agccggtgcg ccgtcgatta    19260
ggaagccgcc caagggcgac gagcaaccag atttttttcgt tccgatgctc tatgacgtgg    19320
gcacccgcga tagtcgcagc atcatggacg tggccgtttt ccgtctgtcg aagcgtgacc    19380
gacgagctgg cgaggtgatc cgctacgagc ttccagacgg gcacgtagag gtttccgcag    19440
ggccggccgg catggccagt gtgtgggatt acgacctggt actgatggcg gtttcccatc    19500
taaccgaatc catgaaccga taccgggaag ggaagggaga caagcccggc cgcgtgttcc    19560
gtccacacgt tgcggacgta ctcaagttct gccggcgagc cgatggcgga aagcagaaag    19620
acgacctggt agaaacctgc attcggttaa acaccacgca cgttgccatg cagcgtacga    19680
agaaggccaa gaacggccgc ctggtgacgg tatccgaggg tgaagccttg attagccgct    19740
acaagatcgt aaagagcgaa accggcggcg cggagtacat cgagatcgag ctagctgatt    19800
ggatgtaccg cgagatcaca gaaggcaaga acccggacgt gctgacggtt caccccgatt    19860
```

```
acttttttgat cgatcccggc atcggccgtt ttctctaccg cctggcacgc cgcgccgcag    19920
gcaaggcaga agccagatgg ttgttcaaga cgatctacga acgcagtggc agcgccgag     19980
agttcaagaa gttctgtttc accgtgcgca agctgatcgg gtcaaatgac ctgccggagt    20040
acgatttgaa ggaggaggcg gggcaggctg gcccgatcct agtcatgcgc taccgcaacc    20100
tgatcgaggg cgaagcatcc gccggttcct aatgtacgga gcagatgcta gggcaaattg    20160
ccctagcagg ggaaaaaggt cgaaaaggtc tctttcctgt ggatagcacg tacattggga    20220
acccaaagcc gtacattggg aaccggaacc cgtacattgg gaacccaaag ccgtacattg    20280
ggaaccggtc acacatgtaa gtgactgata taaaagagaa aaaaggcgat ttttccgcct    20340
aaaactcttt aaaacttatt aaaactctta aaacccgcct ggcctgtgca taactgtctg    20400
gccagcgcac agccgaagag ctgcaaaaag cgcctaccct tcggtcgctg cgctccctac    20460
gccccgccgc ttcgcgtcgg cctatcgcgg ccgctggccg ctcaaaaatg gctggcctac    20520
ggccaggcaa tctaccaggg cgcggacaag ccgcgccgtc gccactcgac cgccggcgct    20580
gaggtctgcc tcgtgaagaa ggtgttgctg actcatacca ggcctgaatc gccccatcat    20640
ccagccagaa agtgagggag ccacggttga tgagagcttt gttgtaggtg gaccagttgg    20700
tgattttgaa cttttgcttt gccacggaac ggtctgcgtt gtcgggaaga tgcgtgatct    20760
gatccttcaa ctcagcaaaa gttcgattta ttcaacaaag ccgccgtccc gtcaagtcag    20820
cgtaatgctc tgccagtgtt acaaccaatt aaccaattct gattagaaaa actcatcgag    20880
catcaaatga aactgcaatt tattcatatc aggattatca ataccatatt tttgaaaaag    20940
ccgtttctgt aatgaaggag aaaactcacc gaggcagttc cataggatgg caagatcctg    21000
gtatcggtct gcgattccga ctcgtccaac atcaatacaa cctattaatt tcccctcgtc    21060
aaaaataagg ttatcaagtg agaaatcacc atgagtgacg actgaatccg gtgagaatgg    21120
caaaagctct gcattaatga atcggccaac gcgcggggag aggcggtttg cgtattgggc    21180
gctcttccgc ttcctcgctc actgactcgc tgcgctcggt cgttcggctg cggcgagcgg    21240
tatcagctca ctcaaaggcg gtaatacggt tatccacaga atcaggggat aacgcaggaa    21300
agaacatgtg agcaaaaggc cagcaaaagg ccaggaaccg taaaaaggcc gcgttgctgg    21360
cgttttttcca taggctccgc cccctgacg agcatcacaa aaatcgacgc tcaagtcaga    21420
ggtggcgaaa cccgacagga ctataaagat accaggcgtt tccccctgga agctccctcg    21480
tgcgctctcc tgttccgacc ctgccgctta ccggatacct gtccgccttt ctcccttcgg    21540
gaagcgtggc gctttctcat agctcacgct gtaggtatct cagttcggtg taggtcgttc    21600
gctccaagct gggctgtgtg cacgaacccc ccgttcagcc cgaccgctgc gccttatccg    21660
gtaactatcg tcttgagtcc aacccggtaa gacacgactt atcgccactg gcagcagcca    21720
ctggtaacag gattagcaga gcgaggtatg taggcggtgc tacagagttc ttgaagtggt    21780
ggcctaacta cggctacact agaagaacag tatttggtat ctgcgctctg ctgaagccag    21840
ttaccttcgg aaaaagagtt ggtagctctt gatccggcaa acaaaccacc gctggtagcg    21900
gtggtttttt tgtttgcaag cagcagatta cgcgcagaaa aaaggatct caagaagatc    21960
ctttgatctt ttctacgggg tctgacgctc agtggaacga aaactcacgt taagggattt    22020
tggtcatgag attatcaaaa aggatcttca cctagatcct tttgatccgg aatta         22075
```

<210> SEQ ID NO 29
<211> LENGTH: 7910
<212> TYPE: DNA
<213> ORGANISM: Artificial Sequence
<220> FEATURE:
<223> OTHER INFORMATION: Cry1Ai expression cassette

<400> SEQUENCE: 29

```
agctgcttgt ggggaccaga caaaaaagga atggtgcaga attgttaggc gcacctacca      60
aaagcaactt tgcctttatt gcaaagataa agcagattcc tctagtacaa gtggggaaca     120
aaataacgtg gaaagagct gtcctgacag cccactcact attgcgtttg acgaacgcag      180
tgacgaccac aaaactcgag acttttcaac aaagggtatt atccggaaac ctcctcggat     240
tccattgccc agctatctgt cactttattg tgaagatagt ggaaaaggaa ggtggctcct     300
acaaatgcca tcattgcgat aaaggaaagg ctatcgttga agatgcctct gccgacagtg     360
gtcccaaaga tggaccccca cccacgagga gcatcgtgga aaagaagac gttccaacca      420
cgtcttcaaa gcaagtggat tgatgtgata tctccactga cgtaagggtt gacgaacaat     480
cccactatcc ttctgcctaa ttagctaacg acccctctgc ctttctgttc ttcaaacgat     540
gtcacatgtc tgcgctggac aactttcttg ttgccgcctg tcgcttgcgc tgtgctgact     600
ggacgcagct ccggaggttt ggttgtgctt ggttttcgta gagaactcgc cacttgccgc     660
ccgcacgttc ttggtgtttc ctcctcccg ctgtgttctg cgcacgggct tttctgaga     720
gacccatgtt tcccttttac ttttataaac agtatacatg ctatgtttct agaaggaggg     780
gaaacctaat cccctaatc caatggcggg gaggaaatag ggtggggtgg ggtgggggga     840
gggaaatatc tcgctacttt ttaatccgga caagctcatt tgcgtttgcg tctgaatgat     900
gatgactgca atgctgatcg cacctcgggt gtcggatcac cagcttttgg ctgctctcac     960
caaatcagct gcaagaagat tagagcacaa aagaattaca gaaagagagc ctttttcttt    1020
tcttccttgt ggggttcctt tcatttcgtg ctctcctttc tctgccagcc agtccgtcct    1080
tgcgtccact gcacctgcac acaggtcacc ccgacccgca ctgttctaga ctccattaga    1140
aaaaaaaagg tctgaacctt tccgaaacca gccagccatt ggtctggcag gccagcatat    1200
gctaattgga tttttttgcc gcatcattga gtgcgccatc aggatttgga atcctggtt     1260
ttgagtaata cagtaatttg gcattatcca ttgccgaatt cccaagctcc gtcagcttga    1320
acgtggaccc ctaccatctg caccagctcg gcacctcacg ctcgcagcgc taggagccta    1380
ggagcagctg cccgtctatt tattggtccc tctcccgtcc cagagaaacc ctccctccct    1440
cctccattgg actgcttgct ccctgttgac cattggggta tgcttgctgc cttgctctcc    1500
tgttcatctc cgtgctaaac ctctgtcctc tgggtgggtt tttgctggga ttttgagcta    1560
atctgctggt cccggtagaa aaagatcatg tcccctgacg tgctcaagcg ctcgccttag    1620
ccgcgtcctt gccccccgcc attttttgcg gtttcggtgt gttcccgtga ctcgccgggt    1680
gcgtcatcgc ctgaatcttg tctgggctct gctgacatgt tcttggctag ttgggtttat    1740
agattcctct gatctaaacc gtgcctgtgc tgcgcacaga actctcccct gtcctttcct    1800
ggggttttgg ttacgtggtg gtagtaagct tggatttgca catggataaa gttgttctaa    1860
gctccgtggg ttgcttgaga tcttgctgtt attgcgtgcc gtgctcactt tttttgcaat    1920
ccgaggaatg aatttgtcgt ttactcgttt tggtggatta ttagcgcgaa aaaaaaactc    1980
ttttttttt gttcttttac tacgaaaagc atcttcttgg attttgctat cttcttttac    2040
tacgaaaaac tcttgagtct aggaatttga atttgtgatg tccattcttg cagtgcgctg    2100
tgctttattg ggaagccaaa tcctattatt ttctgcctct agggtctgaa tggaatcagt    2160
actcttgaga cagaaaatca atccaatcaa gttgatttct ttctttaaaa atattatcac    2220
```

```
agaactaagt gcttgtgcgg aatcagtact ggcttttgtt tggtggagga tcaatacttg    2280
cttttgtttg ggggtggcaa ctgttttgct ataagattcc atgtgttcct gttgagatga    2340
atcatatata gtatagctgc atactacaaa tctgttttc aaatttaggt tgctttggca    2400
tgatctattt ttttgtcaga cagactttct aagtggtagc tcttgattc ttgttcttgt     2460 acaactggtg ctgctgaatc ttgaccgtat agctcgaatt gcagtattct gaaccatcga    2520
gccaaggctg ccaagctgac tcgcctccac agtcttcgcg aacgccttgg tgccaccttc    2580
tcctcccatc ccaatgaact gatagcactc ttttccaggt gggcttacca aaatcatata    2640
acttgcattt cattcggtac tgaaagttgt taatttgtta ttctcttcat gcctgtctta    2700
atagcacacc cagatgtaaa cacgagatta tgcaacttct tacttggttt cttttgttgg    2760
caccatcatg catgctaatt gctaaggatg ttacctattc atccttgact catattatca    2820
tatgtaatga ttttatgatc acgagactat tgattgtgaa gcatagtata gctgttcttc    2880 agttttgta ccctttttgtt ttttccctta agctagaact ggtacaattt agttgataag    2940
acagtgtagt ttgtagtacg tcatttgaca gattgtttgt ctttagctgg taaagtgcca    3000
tttaatatct gtatccttca gatctaataa aaaggatatg agatgtccat cacaagaggg    3060
gaaaaattac atgatctgag atgtaacatc cgttttttatt tgtgaaatac cacttctaca    3120
ggtatcttca ctagggtaaa ccatggacaa taatcctaat attaacgagt gcattccata    3180
caactgcctg agcaatcctg aggtggaggt tctcggcggg gagaggattg agacgggcta    3240
cacgccgatc gacatctccc tgagcctcac ccagttcctc ctgtccgagt tcgtgccggg    3300
cgccggcttc gtgctgggcc tcgtcgacat catctgggggc atcttcggcc ccagccagtg    3360
ggacgccttc ctggtccaga tcgagcagct catcaaccag aggatcgagg agttcgcgcg    3420
caaccaggcc atctccaggc tggagggcct cagcaacctg taccagatct acgccgagtc    3480
cttccgcgag tgggaggcgg acccgaccaa cccggctctg agggaggaga tgcgcatcca    3540
gttcaacgac atgaactcgg ccctgaccac cgctatcccc ctcttcgccg tgcagaacta    3600
ccaggtgccg ctcctgtcgg tctacgtgca ggctgccaac ctgcacctct cggtgctgag    3660
ggacgtgagc gtcttcggcc agcgctgggg cttcgacgcg ccacgatca actcccgcta    3720 caacgacctc acgaggctga tcggcaacta caccgactac gccgtccgct ggtacaacac    3780
cggcctcgag agggtgtggg gcccggacag caggactgg gtcaggtaca accagttccg    3840
cagggagctg accctcacgg tgctggacat cgtcgccctc ttctccaact acgactcgag    3900
gaggtacccc atcaggaccg tgtcccagct gacgagggag atctacacca cccccgtcct    3960
cgagaacttc gacggcagct ccgcggcat ggcccagagg atcgagcaga acatccgcca    4020
gccgcacctg atggacatcc tcaactccat caccatctac acggacgtgc acagggctt    4080 caactactgg tcgggccacc agatcacggc ttccccagtg ggcttcagcg gcccggagtt    4140
cgccttccca ctgttcggca acgcgggcaa cgcggccccg ccagtgctcg tctccctcac    4200
cggcctcggc atcttccgca ccctgtccag cccgctctac aggaggatca tcctcggcag    4260
cggccccaat aatcaggagc tgttcgtgct cgacggcacg gagttctcct cgcgagcct    4320 gaccacgaac ctcccgtcca cgatctacag gcagaggggc acggtggact ccctggacgt    4380
catcccgccc caggacaact cggtcccgcc ccgcgccggc ttctcccaca ggctgagcca    4440
cgtgaccatg ctcagccagg cggccggcgc cgtctacacc ctcagggccc cgaccttctc    4500
ctggcagcac aggagcgcgg agttcaacaa catcatcgcc tccgcacagca tcacgcgat   4560 cccggcggtg aagggcaact tcctcttcaa cggctccgtc atcagcggcc ccggcttcac    4620
```

```
cggcggcgac ctggtgcgcc tcaactccag cggcaacaac atccagaaca ggggctacat   4680
cgaggtcccg atccacttcc cgtccaccag caccaggtac agggtgcgcg tcaggtacgc   4740
ttcggtgacc ccgatccacc tgaacgtcaa ctggggcaac tccagcatct tctccaacac   4800
ggtgccggct acgccaccca gcctggacaa cctccagtcc agcgacttcg gctacttcga   4860
gtccgccaac gcgttcacgt ccagcctcgg caacatcgtg ggcgtccgca acttctcggg   4920
gacggctggc gtgatcatcg acaggttcga gttcatcccc gtcacggcca ccctggaggc   4980
tgagtacaac ctcgagcgcg cccagaaggc cgtgaacgcc ctgttcacct ccacgaacca   5040
gctgggcctc aagaccaacg tcacggacta ccacatcgac caggtgtcca acctggtcac   5100
ctgcctcagc gacgagttct gcctggacga gaagagggag ctgagcgaga aggtgaagca   5160
cgccaagcgc ctctccgacg agaggaacct cctgcaggac agcaacttca aggacattaa   5220
taggcagccc gagaggggct ggggcggctc cacgggcatc accatccagg cggcgacga   5280 cgtcttcaag gagaactacg tcaccctgag cggcacgttc gacgagtgct accccacgta   5340
cctctaccag aagatcgacg agtccaagct gaaggcgttc acccgctacc agctcagggg   5400
ctacatcgag gacagccagg acctggaggt gtacctcatc cgctacaacg ccaagcacga   5460
gacgctgaac gtgcccggca cgggctccct gtggcccctc gcggtcaaga gccccatcgg   5520
caggtgcggc gagcccaaca ggtgcgcccc caggatcgag tggaagccgg acgtggactg   5580
cagctgcagg gacggcgaga gtgcgctca ccactcccac cacttcagcc tcgacatcga   5640
cgtcggctgc acggacctga cgaggacctc cggcgtgtgg gtcatcttca agattaaaac   5700
ccaggacggc cacgcgaaga tcggcaacct ggagttcctc gaggagaagc tgctgctggg   5760
cgaggctctg gccagggtga agaaggccga gaagaagtgg cgcgacaaga gggagaagct   5820
cgagtgggag acgaacatcg tctacaagga ggcgaaggag tccgtggacg ccctgttcgt   5880
cgacagccag tacaaccgcc tccagaccga cacgaacatc gcgatgatcc acgccgcgga   5940
caagagggtg caccgcatca gggaggccta cctgcccgag ctgagcgtga tcccgggcgt   6000
caacgctgcg atcttcgagg agctggaggg cctcatcttc accgcgttct ccctgtacga   6060
cgcccgcaac gtgatcaaga acggcgactt caactacggc ctcagctgct ggaacgtcaa   6120
gggccacgtg gacgtcgagg agcagaacaa ccacaggtcg gtgctggtca tccccgagtg   6180
ggaggccgag gtgagccagg aggtgcgcgt ctgcccgggc aggggctaca tcctccgcgt   6240
caccgcctac aaggagggct acggcgaggg ctgcgtcacg atccacgaga tcgaggacaa   6300
caccgacgag ctgaagttct ccaactgcgt ggaggaggag gtctacccga ataataccgt   6360
gacgtgcaac gactacaccg ccacgcagga ggagtacgag ggcacctaca cctcgaggaa   6420
caggggctac gacggcgcct acgagtccaa cagctcggtc ccgcggact acgctagcgc   6480 gtacgaggag aaggcctaca ccgacggcag gagggacaac ccgtgcgagt ccaaccgcgg   6540
ctaccgggac tacacgccgc tgccggcggg ctacgtgacc aaggagctgg agtacttccc   6600
ggagacggac aaggtctgga tcgagctggg ggagaccgag gggactttcc tggttgattc   6660
agtggagctg ctgctgatgg aggagtgaga gctctacggg gaaagaagga gaagaagaag   6720
aagaagccca ggccggagaa ccatcgcctg catttcgatc tgtttcaccg caattcgcat   6780
tgttagtcgt gtattggagt tatgtgtact tggtttccaa gaactttggt tccttctcgt   6840
ttttttttcc ttgcttgttt gagcgttttt gggcagcgct ggcctggttc ctagtatggt   6900
gggaattggc tgcaccttt gcttcgaata aaaatgcctg ctcgttcacc tgtcttccag   6960
```

```
agtgcaatgc gatgttctgt tgcccaggtc gtgtggttct gactgatggc gatgttgtgt   7020
tcttctgtta atcgcctgtt ttaacgtggt aggctgttgc ttgttcttgt tgagaaagct   7080
tgctgtgcca gacatggctg cttgaataca agtgaaggaa aaaaaaagcc atgccaagta   7140
aagttgcaca aaatttcaac tgctcagtgg accactggac catgttcttg gttattgcag   7200
ttgcagggct tcacatggcg tttggacagc agtcttggat tgatccataa agaggtggtg   7260
gttaatgagg acgcaaggcc gttccctcag agtcagtcac aaggttgcag aggtcacggt   7320
tctcttccct ttccgcttcc tgtcacatcg gaattgttgt ttacgccatc tgcccatcac   7380
ccaccaagtc tatgtttctg tactggatct ttcaatggcg gaacgcgctt agttcttcgt   7440
cacagtcgaa tcacatgatc taatcgatgt ctttaatctc gctgtaaaaa gggtgggacg   7500
gtgggtgcag ggtagggacc agggaaggcc tgcctaaacg tatccataaa catgcacagc   7560
aaccctaaga tattatactg cctacttcct aagatatagt tatttctagt ctatttttt   7620 tccgtccaca tccaaataag tgataatata tagacataca tatatatact atattcatca   7680
tagattaatg aacgaatgta tacttagttt aaacctaatt atattttagg aaggatggag   7740
tatgaaacat gacaatacaa caaaaaaaaa tcatgtaatt gcatatcgtc aaagttatct   7800
gaagtaacca atccaggggg aaatcccgtt agcaaacata caagagcacc gccccactac   7860
atcccagaaa ataaaacaaa accagaactc agatggataa ataatactac              7910
```

PROMOTERS FOR REGULATION OF GENE EXPRESSION IN PLANTS

RELATED APPLICATION INFORMATION

This application is a 371 of International Application No. PCT/US2020/47899, filed Aug. 26, 2020, which claims priority to U.S. Provisional Application No. 62/896,735, filed Sep. 6, 2019, the contents of both of which are incorporated herein by reference herein.

SEQUENCE LISTING

A Sequence Listing in ASCII text format, submitted under 37 C.F.R. § 1.821, entitled "81937-US-REG-ORG-P-1 Seqs.txt", 238 kilobytes in size, generated on Mar. 3, 2022, and filed via EFS-Web is provided in lieu of a paper copy. This Sequence Listing is hereby incorporated by reference into the specification for its disclosures.

FIELD OF THE INVENTION

The present invention relates generally to the field of plant molecular biology and the regulation of gene expression in plants. Also disclosed are transgenic eukaryotes, including transgenic plant cells, plants, and seeds, whose genome includes molecular constructs for controlling heterologous gene expression.

BACKGROUND

Transgenic crops consist of increasingly complex genetic modifications including multiple transgenes that confer different traits, also called "gene stacks" or "trait stacks." For example, many transgenic corn products currently on the market contain within the same plant multiple genes encoding insecticidal proteins for controlling a broad spectrum of insect pests, multiple genes encoding proteins that confer on the plant tolerance to a wide spectrum of chemical herbicides and multiple genes encoding proteins that are used as selectable markers during the plant transformation process. Many of the transgenic proteins used to control insect pests, for example the crystal endotoxins from *Bacillus thuringiensis* (called Cry proteins) are active against lepidopteran or coleopteran insect pests. Examples of lepidopteran-active Cry proteins include Cry1A, Cry1B, Cry1C, Cry1D, Cry1E, Cry1F and Cry9. Examples of coleopteran-active Cry proteins include, Cry3A, Cry3B, Cry3C, Cry8, the binary Cry23-Cry37 and the binary Cry34-Cry35. Most individual Cry proteins are biologically active against a narrow spectrum of insect species within a given insect order. Even with this narrow spectrum of activity, certain Cry proteins may have low to moderate activity against certain non-pest species in the same order of insects as the target pest insects. For example, Hellmich et al. (2001) Proc. Natl. Aca. Sci. 98:11925-11930, found that certain purified Cry proteins that are active against a lepidopteran pest, e.g. European corn borer (*Ostrinia nubilalis*), also have some activity against the first instar of the non-pest lepidopteran insect, monarch butterfly (*Danaus plexippus*). However, later larval instars *D. plexippus* were far less susceptible.

Currently, expression of most transgenes encoding insecticidal proteins in commercial transgenic crops is driven by constitutive promoters, i.e. promoters that are functional throughout the plant in all or a majority of tissue types, including pollen, throughout the entire growth cycle of the plant. Since plant pollen may be a food source for some non-pest insect species or it is hypothesized that plant pollen may be carried by wind to deposit on non-pest insect host plants, there is some concern within regulatory agencies that regulate transgenic crop commercialization that high levels of expression of certain insecticidal proteins, e.g. certain Cry proteins, in pollen may have adverse effects on localized populations of non-pest insects. In addition, it has been observed that expression of certain insecticidal proteins in pollen has adverse effects on the transgenic plant's male fertility. For example, high levels of a Vip3 insecticidal protein expressed in corn pollen may cause a decrease in male fertility or complete sterility in certain inbred genetic backgrounds (U.S. Pat. No. 10,214,784; herein incorporated by reference). Therefore, it would be beneficial to modulate the expression of insecticidal proteins in transgenic plants, for example, to have high levels of expression in vegetative tissues, e.g. leaf tissue, where a majority of pest insects initially feed, but have reduced expression in pollen, a plant tissue that some non-pest insects may feed upon.

It is, therefore, desirable to provide plants, particularly corn plants that exclude expression of a transgene in the tissues of the reproductive structures of the plant such as pollen and/or the tassel. This could be achieved within the scope of the present invention by providing a regulatory nucleotide sequence, at least part of which has a transcription initiation function directing expression of an operably linked polynucleotide encoding a protein of interest to basically all plant tissues, but essentially excluding expression in the tissues of the male reproductive structures of the plant, particularly in pollen and/or tassel tissues so that little or no expression product is present in those tissues. The regulatory nucleotide sequence can then be used to develop expression systems that enable effective accumulation of the protein of interest such as, for example, an insecticidal protein, in tissues that target pests normally feed on, and eliminate or reduce accumulation of the insecticidal protein in non-target tissues or organs and/or in those tissues that may be compromised by the protein of interest.

SUMMARY

The present invention provides compositions and methods for selectively directing transgene expression in transgenic plant tissues. In particular, novel promoter polynucleotides capable of initiating and/or modulating transcription of a DNA polynucleotide to which they are operably linked are provided. The promoters of the invention are characterized by their ability to selectively modulate expression of any operably linked DNA polynucleotide, such as a polynucleotide encoding an insecticidal protein, preferentially in multiple plant tissues such as leaves, stems, roots, and the like, but not in male reproductive tissues such as pollen.

In some aspects, a promoter polynucleotide of the invention comprises any of SEQ ID NOS:1-11 or their complements, or a fragment, region, cis element, or polynucleotides related to any of SEQ ID NOS:1-11, that function as promoters in plants. The promoters of the invention direct functional transcription in any plant tissue other than a male reproductive tissue, e.g. pollen, in which transcription is eliminated or significantly reduced compared to other non-male reproductive tissues of the plant.

The invention is further drawn to chimeric constructs, expression cassettes and vectors comprising a promoter of the invention operably linked to a heterologous DNA polynucleotide which encodes a protein which is desired to be expressed in plant tissues other than pollen. For example, a recombinant DNA molecule of the invention may comprise, in a 5' to 3' direction, a promoter of the invention operably linked to a DNA sequence which encodes an insecticidal protein that is active against insect pests that feed on plant tissues and a terminator sequence operably linked to the 3' end of the gene of interest. In some aspects, the terminator sequence of the invention comprises any of SEQ ID NOS: 12-20 or their complements, or a fragment, region, or nucleotide sequences related to any of SEQ ID NOS:12-20. In other aspects, a vector of the invention is a binary vector useful for plant transformation. In other aspects, the binary vector comprises any of SEQ ID NOS:21-28 or sequences related to any of SEQ ID NOS:21-28.

In other aspects, the regulatory sequences of the invention are operably linked to a nucleotide sequence that encodes an insecticidal protein. Therefore, upon insertion of the expression cassette comprising a promoter of the invention operably linked to the insecticidal protein coding sequence into a genome of a plant, the resulting transgenic plant will be protected from attack by pest insects which feed on non-pollen tissues, such as leaves and stems, but will not impact beneficial insects that feed on pollen.

The invention is still further drawn to transgenic plants, such as transgenic maize plants, comprising a promoter, a chimeric construct, an expression cassette or a vector of the invention.

The invention also provides methods for specifically expressing a heterologous coding sequence in transgenic plant tissues excluding certain male reproductive tissues, for example pollen, by incorporating into the plant's genome a recombinant DNA molecule containing a promoter of the invention operably linked to a DNA polynucleotide that encodes a protein of interest, such as an insecticidal protein.

The invention further provides a method of mitigating male sterility in a transgenic plant, for example an inbred corn plant, by incorporating into the plant's genome a recombinant DNA molecule containing a promoter of the invention operably linked to a DNA polynucleotide that encodes a protein that causes male sterility when expressed in a male reproductive tissue such as pollen. In some aspects, the protein is a Vip3 insecticidal protein and the transgenic plant is an inbred corn plant.

The foregoing and other aspects of the invention will be apparent from the following detailed description, accompanying drawings and sequence listings.

BRIEF DESCRIPTION OF THE SEQUENCES IN THE SEQUENCE LISTING

SEQ ID NO:1 is a nucleotide sequence of a PMP370-3 promoter.
SEQ ID NO:2 is a nucleotide sequence of a PMP393-1 promoter.
SEQ ID NO:3 is a nucleotide sequence of a PMP393-2 promoter.
SEQ ID NO:4 is a nucleotide sequence of a PMP393-3 promoter.
SEQ ID NO:5 is a nucleotide sequence of a PMP393-4 promoter.
SEQ ID NO:6 is a nucleotide sequence of a PMP855-1 promoter.
SEQ ID NO:7 is a nucleotide sequence of a PMP747-1 promoter.
SEQ ID NO:8 is a nucleotide sequence of a PMP004-1 promoter.
SEQ ID NO:9 is a nucleotide sequence of a PMP335-1 promoter.
SEQ ID NO:10 is a nucleotide sequence of a PMP722-1 promoter.
SEQ ID NO:11 is a nucleotide sequence of a PMP948-2 promoter.
SEQ ID NO:12 is a nucleotide sequence of a t370-2 terminator.
SEQ ID NO:13 is a nucleotide sequence of a t393-1 terminator.
SEQ ID NO:14 is a nucleotide sequence of a t393-2 terminator.
SEQ ID NO:15 is a nucleotide sequence of a t855-1 terminator.
SEQ ID NO:16 is a nucleotide sequence of a t747-1 terminator.
SEQ ID NO:17 is a nucleotide sequence of a t004-1 terminator.
SEQ ID NO:18 is a nucleotide sequence of a t335-1 terminator.
SEQ ID NO:19 is a nucleotide sequence of a t722-1 terminator.
SEQ ID NO:20 is a nucleotide sequence of a t948-2 terminator.
SEQ ID NO:21 is a nucleotide sequence of pSYN18499 binary vector.
SEQ ID NO:22 is a nucleotide sequence of pSYN18500 binary vector.
SEQ ID NO:23 is a nucleotide sequence of pSYN18501 binary vector.
SEQ ID NO:24 is a nucleotide sequence of pSYN18498 binary vector.
SEQ ID NO:25 is a nucleotide sequence of pSYN18617 binary vector.
SEQ ID NO:26 is a nucleotide sequence of pSYN18618 binary vector.
SEQ ID NO:27 is a nucleotide sequence of pSYN18619 binary vector.
SEQ ID NO:28 is a nucleotide sequence of pSYN18705 binary vector.
SEQ ID NO:29 is a nucleotide sequence of a PMP393-4: Cry1Ai expression cassette.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

For clarity, certain terms used in the specification are defined and presented as follows:

As used herein and in the appended claims, the singular forms "a," "an," and "the" include plural reference unless the context clearly dictates otherwise. Thus, for example, reference to "a plant" is a reference to one or more plants and includes equivalents thereof known to those skilled in the art, and so forth.

As used herein, the term "and/or" refers to and encompasses any and all possible combinations of one or more of the associated listed items, as well as the lack of combinations when interpreted in the alternative, "or."

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

As used herein, the term "amplified" means the construction of multiple copies of a nucleic acid molecule or multiple copies complementary to the nucleic acid molecule using at least one of the nucleic acid molecules as a template.

Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

"Activity" of an insecticidal protein is meant that the insecticidal protein functions as an orally active insect control agent, has a toxic effect, and/or is able to disrupt or deter insect feeding, which may or may not cause death of the insect. When an insecticidal protein is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

As used herein, the terms "backcross" and "backcrossing" refer to the process whereby a progeny plant is crossed back to one of its parents for one or more generations (e.g., 2 or more, 3 or more, 4 or more, 5 or more, 6 or more, or 7 or more times, etc.). In a backcrossing scheme, the "donor" parent refers to the parental plant with the desired gene or DNA construct or locus to be introgressed. The "recipient" parent (used one or more times) or "recurrent" parent (used two or more times) refers to the parental plant into which the gene or DNA construct or locus is being introgressed. For example, see Ragot et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In embodiments, at least one or more generations of progeny are identified and/or selected for the presence of the desired gene or locus (e.g., in a nucleic acid sample from the progeny plant or plant part). In embodiments, two or more generations (or even all generations) of progeny are identified and/or selected for the presence of the desired gene or DNA construct or locus.

The term "chimeric construct" or "chimeric gene" or "chimeric polynucleotide" or "chimeric nucleic acid" or "chimeric protein" (or similar terms) as used herein refers to a construct or nucleic acid molecule or protein comprising two or more polynucleotides or amino acid motifs or domains, respectively, of different origin assembled into a single nucleic acid molecule or protein. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. In some aspects, the RNA is then translated in an organism, such as a corn plant, to produce a protein, e.g. an insecticidal protein of the invention. In other aspects, the RNA is not translated to produce a protein but functions as an RNA molecule to modulate expression of a recombinant insecticidal protein of the invention.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, a DNA sequence of a recombinant DNA construct of the invention includes codons optimized for a cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

As used herein, the term "corn" is synonymous with the term "maize" or "Zea mays."

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Such usage of an expression cassette makes it so it is not naturally occurring in the cell into which it has been introduced. Typically, however, the expression cassette is heterologous with respect to the host, i.e., the particular nucleic acid sequence of the expression cassette does not occur naturally in the host cell and must have been introduced into the host cell or an ancestor of the host cell by a transformation process. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of the invention.

The term "expression" when used with reference to a polynucleotide, such as a gene, open reading frame (ORF) or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In some embodiments of the invention, "expression" refers to the transcription and stable accumulation of sense (mRNA) or functional RNA. In some embodiments of the invention, "expression" refers to the production of protein.

As used herein, the term "functionally transcribed" means that the expression of a regulatory polynucleotide of the invention produces a protein of interest in a quantity that confers upon the tissue in which the protein is produced a phenotype for its intended purpose. For example, without limitation, a polynucleotide encoding an insecticidal protein, that is "functionally transcribed" in leaf tissue of a transgenic plant, for example a transgenic maize plant, produces a quantity of the insecticidal protein that is toxic to an insect pest that feeds on the leaf tissue in which the insecticidal protein is produced. Alternatively, the term "functionally transcribed" means that the quantity of the protein produced in any tissue of a transgenic plant is at least 50 ng/mg total soluble protein (TSP), or at least 100 ng/mg TSP, or at least 500 ng/mg TSP, or at least 800 ng/mg TSP, or at least 1000 ng/mg TSP, or at least 2000 ng/mg TSP or at least 3000 ng/mg TSP. In some embodiments of the invention, a polynucleotide operably linked to a promoter of the invention may be "functionally transcribed" in non-pollen tissues and transcribed at very low levels in pollen tissue of a transgenic plant and therefore produce a very low quantity of protein in the pollen tissue. Such very low quantity of protein may range from about 1 ng/mg TSP to about 15 ng/mg TSP. Such low expression levels does not mean that the polynucleotide is "functionally transcribed" in pollen, particularly compared to other non-pollen tissues in the same transgenic plant. In other embodiments, the level of protein produced in the non-pollen tissue of a transgenic plant, for example a transgenic maize plant, is at least 100-fold higher than in pollen tissue in the same transgenic plant, or at least 200-fold higher, or at least 300-fold higher, or at least 400-fold higher, or at least 500-fold higher, or at least 600-fold higher, or at least 700-fold higher, or at least 800-fold higher, or at least 900-fold higher or at least 1000-fold higher than in pollen tissue of the same transgenic plant.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

The term "identity" or "identical" or "substantially identical," in the context of two nucleic acid or amino acid sequences, refers to two or more sequences or subsequences that have at least 60%, preferably at least 80%, more preferably 90%, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues or bases in length, more preferably over a region of at least about 100 residues or bases, and most preferably the sequences are substantially identical over at least about 150 residues or bases. In an especially preferred embodiment, the sequences are substantially identical over the entire length of the coding regions. Furthermore, substantially identical nucleic acid or amino acid sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, MD 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant. Therefore, a claim to an "isolated" nucleic acid molecule, as enumerated herein, encompasses a nucleic acid molecule that is comprised within a transgenic plant genome.

A "nucleic acid molecule" or "nucleic acid sequence" is a segment of single- or double-stranded DNA or RNA that can be isolated from any source. In the context of the invention, the nucleic acid molecule is typically a segment of DNA. In some embodiments, the nucleic acid molecules of the invention are isolated nucleic acid molecules.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotides in sense or antisense orientation can be operably linked to regulatory polynucleotides.

The terms "protein," "peptide" and "polypeptide" are used interchangeably herein.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue. For example, the "tapetum" is a tissue within the sporangium, especially the anther, of corn plants that provides nutrition for growing spores.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of commercially valuable enzymes or metabolites or altered reproductive capability.

A "promoter" is an untranslated DNA sequence upstream of the coding region that contains the binding site for RNA polymerase and initiates transcription of the DNA. The promoter region may also include other elements that act as regulators of gene expression.

"Preferred expression" is the expression of gene products that are preferably expressed at a higher level in one or a few plant tissues (spatial limitation) and/or to one or a few plant developmental stages (temporal limitation) while in other tissues/developmental stages there is a relatively low level of expression.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized, for example, a polynucleotide synthesize using an assembled nucleotide sequence, and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. Another example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule incorporated into its genome. As a result of such genomic alteration, the recombinant plant is distinctly different from the related wild-type plant.

A "regulatory sequence" or "regulatory element," and the like, is understood herein to refer to a nucleotide sequence that controls the expression of an operably associated coding sequence by providing the recognition for RNA polymerase and other factors required for proper transcription and is typically located upstream (5') to its coding sequence. "Regulatory sequences" include 5' regulatory sequences located proximal and more distal elements upstream of the associated coding region, which influence the transcription, RNA processing or stability, or translation of the associated coding sequence. "Regulatory sequences" may further include 3' sequences, including 3' non-translated and/or 3' non-transcribed sequences, located downstream of the associated coding region, and can include a transcription termination site, i.e. terminators. "Regulatory sequences" may include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Examples of enhancers include, among others, a figwort mosaic virus enhancer (eFMV) and a cauliflower mosaic virus enhancer (e35S). The meaning of the term "regulatory sequences" includes "transcription initiation" or "promoter" sequences and "promoter regulatory sequences." These terms may herein be used interchangeably.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Specific expression" is the expression of gene products that is limited to one or a few plant tissues (spatial limitation) and/or to one or a few plant developmental stages (temporal limitation).

"Tissue-specific promoter" refers to regulated promoters that are not expressed in all plant cells but only in one or more cell types in specific organs (such as leaves, roots or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

A "transcriptional cassette" will comprise in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The "transcription initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

"Transient transformation" in the context of a polynucleotide means that a polynucleotide is introduced into the cell and does not integrate into the genome of the cell. Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

"Transformation" is a process for introducing heterologous nucleic acid into a host cell or organism. In particular embodiments, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

The invention relates generally to regulatory polynucleotides at least part of which have a transcription initiation function directing expression of an operably linked protein encoding polynucleotide to essentially all plant tissues, but essentially excluding expression in male reproductive tissues such as pollen and/or tassel tissue. The regulatory polynucleotides can be used in chimeric constructs, expression cassettes, recombinant vectors and the like to drive expression of a protein of interest, for example an insecticidal protein, in plant tissues that target pests normally feed on, and eliminate or reduce accumulation of the insecticidal protein in tissues not typically feed upon by pest insects or in those tissue that may be compromised by the insecticidal protein, such pollen or tassel.

Promoter sequences are obtained by cloning the genomic sequences that are homologous to the cDNA sequences expressed in tissues other than pollen, i.e. "non-pollen" cDNA sequences. Genomic sequences may be obtained by hybridization methods or by using PCR methods to extend the sequence in either the 5' or 3' direction from the known sequence (sometimes referred to as "genome walking"). For example, to obtain genomic sequences 5' to the known sequence of the cDNA, primers are made to the sequence near the 5' end of the cDNA. A genomic library is constructed with the 5' end of each genomic DNA sequence ligated to a short oligonucleotide adapter. PCR with a primer hybridizing to the adapter sequence and a 5' primer of a non-pollen cDNA sequence allows amplification of a genomic sequence residing 5' to the homologous sequence of the non-pollen sequence. DNA sequences obtained from genome walking are sequenced and if additional 5' regions are desired, the process is repeated with primers now at the 5' end of the longest obtained clone. Genomic sequences homologous to non-pollen cDNA sequences are also obtained by hybridization under high stringency conditions. High stringency conditions select for hybridization of a probe made from a non-pollen cDNA sequence to hybridize to its homologous sequence in the genomic DNA. The genomic DNA is comprised in a genomic DNA library of 5-20 kb maize genomic DNA sequences in a lambda phage vector. Genomic clones that hybridize with the non-pollen cDNA are isolated and sequenced.

The promoters of the invention are located in the 5'-region of a pollen-minus cDNA sequence immediately upstream of the coding sequence. The size of the regulatory region is preferably in a range of between about 2 kb to 8 kb and comprises a 5'-non-transcribed sequence, particularly a 5'-non-transcribed sequence and a 5'-UTR and all or part of a nucleotide sequence representing a first intron. Promoters exemplified herein are set forth in SEQ ID NOS:1-11. The regulatory sequences of the invention may further comprise part of 3'-sequence that begins just past a coding sequence of a pollen-minus cDNA translation stop codon including transcribed but not translated sequence (UTR) and non-transcribed sequence that functions as the transcriptional terminator and a poly-adenylation signal. In particular, the 3'-sequence is in a range of between about 1.0 kb and about 2.5 kb. Terminators exemplified herein are set forth in SEQ ID NOS:12-20.

The genomic clones may include intron sequences, not found in the mRNA or the cDNA clones. The genomic sequences may additionally comprise 5' untranslated sequences, 3' untranslated sequences, and 5' and 3' regulatory sequences. Promoter sequences are found within the genomic sequence 5' to the cDNA sequence. Genomic sequences are cloned which are homologous to the pollen-minus cDNA sequences. Sequences that are 5' to the sequence homologous to the cDNA sequence are herein referred to as the 5' flanking region which comprises the promoter region.

In some embodiments, the invention provides a chimeric DNA construct that comprises an insecticidal protein-coding sequence operably linked to a regulatory sequence, at least part of which has a transcription initiation function directing expression of the encoded insecticidal protein to essentially all tissues of the plant with the exception of male reproductive tissues, such as pollen and/or tassel, such that little or no expression product is present is the pollen and/or tassel tissues to any significant extent. Nucleic acid sequences of the invention can be provided as DNA or as RNA, as specified; disclosure of one necessarily defines the other, as is known to one of ordinary skill in the art. Furthermore, disclosure of a given nucleic acid sequence necessarily defines the exact complement of that sequence, as is known to one of ordinary skill in the art.

In some embodiments, the invention provides an expression cassette comprising a promoter comprising a nucleotide sequence a) having at least 95% identity to at least 99% identity to any of SEQ ID NOS:1-11; or b) of any of SEQ ID NOS:1-11, operably linked to a heterologous polynucleotide of interest, which is operably linked to a 3'-untranslated region including a polyadenylation signal, wherein the heterologous polynucleotide is functionally transcribed in a tissue of a transgenic plant that is not pollen. In other embodiments, the heterologous polynucleotide encodes an insecticidal protein or a double stranded RNA (dsRNA). In other embodiments, the insecticidal protein is a Cry protein or a Vip3 protein.

In still other embodiments, the insecticidal Cry protein is selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5Da, Cry5Ea, Cry6Aa, Cry6Ba, Cry7Aa, Cry7Ab, Cry7Ac, Cry7Ba, Cry7Bb, Cry7Ca, Cry7Cb, Cry7Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8Pa, Cry8Qa, Cry8Ra, Cry8Sa, Cry8Ta, Cry9Aa, Cry9Ba, Cry9Bb, Cry9Ca, Cry9Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32Mb, Cry32Na, Cry32Oa, Cry32Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa, Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa. In still other embodiments, the Cry protein is a Cry1 protein. In other embodiments, the Cry1 protein is a Cry1A protein. In still other embodiments, the Cry1A protein is a Cry1Ab or a Cry1 Ai protein.

In other embodiments, the Vip3 insecticidal protein encoded by a heterologous operably linked to a promoter of the invention is selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3. In still other embodiments, the Vip3 protein is a Vip3A protein. In other embodiments, the Vip3A protein is a Vip3Aa protein. In other embodiments, the Vip3Aa protein is a Vip3Aa19 or a Vip3Aa20 protein.

In some embodiments, the transgenic plant in which the heterologous polynucleotide of the invention is functionally transcribed is a monocot plant. In other embodiments, the monocot plant is maize plant. In other embodiments, the maize plant is an inbred maize plant or a hybrid maize plant. In some embodiments, the tissue of a maize plant in which the heterologous polynucleotide is functionally expressed is leaf, silk or husk.

In some embodiments, the 3'-untranslated region of an expression cassette of the invention comprises a terminator sequence selected from any of SEQ ID NOS:12-20. In still other embodiments, the expression cassette comprises SEQ ID NO:29.

In some embodiments, the invention provides a recombinant vector comprising an expression cassette of the invention. In other embodiments, the recombinant vector is a binary vector capable of functioning in multiple organisms. In other embodiments, the organism is a bacteria or a plant. In other embodiments, the binary vector comprises any of SEQ ID NOS:21-28.

In some embodiments, the invention provides a plant cell transformed with a recombinant vector or an expression cassette of the invention. In other embodiments, the recombinant vector or expression cassette is transiently expressed in the plant cell. In other embodiments, the recombinant vector or expression cassette of the invention is stably integrated into the genome of the plant cell. In other embodiments, the plant cell is a monocot plant cell. In still other embodiments, the monocot plant cell is a maize plant cell. In other embodiments, the expression cassette comprises a sequence of an expression cassette in any of SEQ ID NOS:21-28. In still other embodiments, the expression cassette comprise SEQ ID NO:29.

In some embodiments, the invention provides a transgenic plant comprising an expression cassette or a vector of the invention. In other embodiments, the expression cassette or vector or a portion thereof is stably integrated into the genome of the transgenic plant. In other embodiments, the transgenic plant is a monocot. In still other embodiments, the monocot transgenic plant is a transgenic maize plant. In other embodiments, the transgenic maize plant is an inbred maize plant or a hybrid maize plant. In other embodiments, the transgenic maize plant expresses a protein of interest at functional levels in any tissue that is not pollen. In still other embodiments, the tissue where the protein of interest is expressed at functional levels is leaf, silk or husk.

In other embodiments, the protein of interest that is expressed in a transgenic plant at functional levels in any tissue that is not pollen is a Cry protein or a Vip3 protein. In other embodiments, the Cry protein or the Vip3 protein is selected from a list of Cry and Vip3 proteins described above. In other embodiments, the Cry protein is a Cry1 protein. In other embodiments, the Cry1 protein is a Cry1A protein. In still other embodiments, the Cry1A protein is a Cry1Ab protein or a Cry1Ai protein. In still other embodiments, the Vip3 protein is a Vip3A protein. In other embodiments, the Vip3A protein is a Vip3Aa protein. In still other embodiments, the VIp3Aa protein is a Vip3Aa19 or a Vip3Aa20 protein.

In some embodiments, the invention provides a transgenic seed of any transgenic plant of the invention. In other embodiments, the transgenic seed comprises an expression cassette or a vector, or a portion thereof, of the invention. In other embodiments, the transgenic seed is a maize seed. In other embodiments, the maize seed functions as a maize propagation means. In other embodiments, the transgenic maize seed functions as harvested grain.

In some embodiments, the invention provides an isolated nucleic acid molecule comprising a nucleotide sequence selected from the group consisting of: a) a sequence set forth in any of SEQ ID NOS:1-20; b) a nucleotide sequence that hybridizes under high stringency conditions to a nucleotide sequence of a); and c) a nucleotide sequence comprising a fragment of a nucleotide sequence of a), wherein the fragment maintains the function of the nucleotide sequence of a); wherein the nucleic acid molecule initiates functional transcription or ends functional transcription of an operably linked polynucleotide of interest in a tissue of a transgenic plant that is not pollen.

In some embodiments, the polynucleotide of interest that is operably linked to the isolated nucleic acid molecule of the invention encodes an insecticidal protein or a double stranded RNA (dsRNA),In other embodiments, the insecticidal protein is a Cry protein or a Vip3 protein. In other embodiments, the Cry protein or the Vip3 protein is selected from a list of Cry and Vip3 proteins described above. In other embodiments, the Cry protein is a Cry1 protein. In other embodiments, the Cry1 protein is a Cry1A protein. In other embodiments, the Cry1A protein is a Cry1Ab or a Cry1Ai protein. In still other embodiments, the Vip3 protein is a Vip3A protein. In other embodiment, the Vip3A protein is a Viip3Aa protein. In other embodiments, the Vip3Aa protein is a Vip3Aa19 or Vip3Aa20 protein.

In some embodiments, an isolated nucleic acid molecule of the invention comprises a promoter nucleotide sequence that is set forth in SEQ ID NO:1. In other embodiments, an isolated nucleic acid molecule of the invention comprises a promoter nucleotide sequence that is set forth in SEQ ID NO:1 and a terminator nucleotide sequence that is set forth in SEQ ID NO:12.

In some embodiments, an isolated nucleic acid molecule of the invention comprises a promoter nucleotide sequence that is set forth in SEQ ID NO:2. In other embodiments, an isolated nucleic acid molecule of the invention comprises a promoter nucleotide sequence that is set forth in SEQ ID NO:2 and a terminator nucleotide sequence that is set forth in SEQ ID NO: 13 or SEQ ID NO:14.

In some embodiments, an isolated nucleic acid molecule of the invention comprises a promoter nucleotide sequence that is set forth in SEQ ID NO:3. In other embodiments, an isolated nucleic acid molecule of the invention comprises a promoter nucleotide sequence that is set forth in SEQ ID NO:3 and a terminator nucleotide sequence that is set forth in SEQ ID NO: 13 or SEQ ID NO:14.

In some embodiments, an isolated nucleic acid molecule of the invention comprises a promoter nucleotide sequence that is set forth in SEQ ID NO:4. In other embodiments, an isolated nucleic acid molecule of the invention comprises a promoter nucleotide sequence that is set forth in SEQ ID NO:4 and a terminator nucleotide sequence that is set forth in SEQ ID NO: 13 or SEQ ID NO:14.

In some embodiments, an isolated nucleic acid molecule of the invention comprises a promoter nucleotide sequence that is set forth in SEQ ID NO:5 In other embodiments, an isolated nucleic acid molecule of the invention comprises a promoter nucleotide sequence that is set forth in SEQ ID NO:5 and a terminator nucleotide sequence that is set forth in SEQ ID NO: 13 or SEQ ID NO:14.

In some embodiments, an isolated nucleic acid molecule of the invention comprises a promoter nucleotide sequence that is set forth in SEQ ID NO:6. In other embodiments, an isolated nucleic acid molecule of the invention comprises a promoter nucleotide sequence that is set forth in SEQ ID NO:6 and a terminator nucleotide sequence that is set forth in SEQ ID NO:15.

In some embodiments, an isolated nucleic acid molecule of the invention comprises a promoter nucleotide sequence that is set forth in SEQ ID NO:7. In other embodiments, an isolated nucleic acid molecule of the invention comprises a promoter nucleotide sequence that is set forth in SEQ ID NO:7 and a terminator nucleotide sequence that is set forth in SEQ ID NO:16.

In some embodiments, an isolated nucleic acid molecule of the invention comprises a promoter nucleotide sequence that is set forth in SEQ ID NO:8. In other embodiments, an isolated nucleic acid molecule of the invention comprises a promoter nucleotide sequence that is set forth in SEQ ID NO:8 and a terminator nucleotide sequence that is set forth in SEQ ID NO:17.

In some embodiments, an isolated nucleic acid molecule of the invention comprises a promoter nucleotide sequence that is set forth in SEQ ID NO:9. In other embodiments, an isolated nucleic acid molecule of the invention comprises a promoter nucleotide sequence that is set forth in SEQ ID NO:9 and a terminator nucleotide sequence that is set forth in SEQ ID NO:18.

In some embodiments, an isolated nucleic acid molecule of the invention comprises a promoter nucleotide sequence that is set forth in SEQ ID NO:10. In other embodiments, an isolated nucleic acid molecule of the invention comprises a promoter nucleotide sequence that is set forth in SEQ ID NO:10 and a terminator nucleotide sequence that is set forth in SEQ ID NO:19.

In some embodiments, an isolated nucleic acid molecule of the invention comprises a promoter nucleotide sequence that is set forth in SEQ ID NO:11. In other embodiments, an isolated nucleic acid molecule of the invention comprises a promoter nucleotide sequence that is set forth in SEQ ID NO:11 and a terminator nucleotide sequence that is set forth in SEQ ID NO:20.

In some embodiments, the isolated nucleic acid molecule of the invention initiates functional transcription or ends functional transcription of an operably linked polynucleotide of interest in any non-pollen tissue of a transgenic maize plant.

In some embodiments, the invention provides a method for expressing a protein or polynucleotide of interest in a transgenic plant or a transgenic plant cell comprising introducing into a plant or a plant cell an expression cassette or vector of the invention comprising a promoter operably linked to a heterologous polynucleotide that encodes the protein or polynucleotide of interest, wherein the promoter comprises any of SEQ ID NOS:1-11, and wherein the protein or polynucleotide of interest is functionally expressed in a tissue of the transgenic plant that is not pollen.

In other embodiments, the expression cassette or vector also comprise a terminator sequence operably linked to the heterologous polynucleotide that comprises any of SEQ ID NOS:12-20.

In other embodiments of the method for expressing a protein or polynucleotide of interest in a transgenic plant or a transgenic plant cell, the protein of interest is an insecticidal protein or the polynucleotide of interest is a dsRNA that is insecticidal. In other embodiments, the insecticidal protein is a Cry protein or a Vip3 protein. In other embodiments, the Cry protein or the Vip3 protein is selected from a list of Cry and Vip3 proteins described above. In other embodiments, the Cry protein is a Cry1 protein. In still other embodiments, the Cry1 protein is a Cry1A protein. In other embodiments, the Cry1A protein is a Cry1Ab or a Cry1Ai protein. In still other embodiments, the Vip3 protein is a Vip3A protein. In other embodiment, the Vip3A protein is a Viip3Aa protein. In other embodiments, the Vip3Aa protein is a Vip3Aa19 or a Vip3Aa20 protein.

In other embodiments of the method for expressing a protein or polynucleotide of interest in a transgenic plant or a transgenic plant cell, the transgenic plant is a transgenic maize plant. In other embodiments, the transgenic maize plant is an inbred maize plant or a hybrid maize plant. In still other embodiments, the tissue where the protein of interest is expressed at functional levels in the transgenic maize plant is leaf, silk or husk.

In some embodiments of the invention, to further delineate the sequences required for expression in any tissue that is not pollen as well as those regulatory sequences that influence the overall level of expression, deletions in a pollen-minus promoter region may be made. Deletions are made in the 5' flanking region of each pollen-minus genomic clone. In most promoters 500-1000 base pairs (bp) of 5' flanking sequence are sufficient for promoter activity, including tissue-specific activity. Deletions of the 5' flanking region can result in promoter regions of approximately 50 bp, 100 bp, 250 bp, 500 bp, 750 bp and 1000 bp or more. These promoter deletion sequences serve a two-fold purpose. The deletions allow the further mapping of regulatory sequences within the 5' flanking sequence of each pollen-minus genomic clone. Additionally, the deletions provide a toolbox of promoter and regulatory sequences that vary in their expression levels and expression patterns thus providing additional flexibility in choosing promoter sequences for appropriate gene regulation.

It is also clear to one skilled in the art that mutations, insertions, deletions and/or substitutions of one or more nucleotides can be introduced into the nucleotide sequences of SEQ ID NOS:1-11 using methods known in the art. In addition, shuffling the sequences of the invention can provide new and varied nucleotide sequences. For example, SEQ ID NOS:3-5 are variants of SEQ ID NO:1 that have one or more substitutions, deletions or additions compared to SEQ ID NO:2.

To test for a function of variant DNA sequences according to the invention, such as deletion fragments of SEQ ID NOS:1-11, the sequence of interest is operably linked to a selectable or visible marker gene and expression of the marker gene is tested in transient expression assays with isolated tissues, such as leaf tissue, or cells or by stable transformation into plants. It is known to the skilled artisan that DNA sequences capable of driving expression of an associated coding sequence are built in a modular way. Accordingly, expression levels from shorter DNA fragments may be different than the one from the longest fragment and may be different from each other. For example, deletion of a down-regulating upstream element will lead to an increase in the expression levels of the associated coding sequence while deletion of an up-regulating element will decrease the expression levels of the associated coding sequence. It is also known to the skilled artisan that deletion of development-specific or a tissue-specific elements will lead to a temporally or spatially altered expression profile of the associated coding sequence.

In another embodiment of the invention, DNA and genomic DNA sequences homologous to SEQ ID NOS:1-11 may be isolated from other maize germplasm using either hybridization or PCR techniques well known in the art. The isolated sequences may be identical to SEQ ID NOS:1-11 or they may be substantially identical to SEQ ID NOS:1-11. It is not necessary for the sequences obtained from other maize germplasm to contain identical nucleotide sequences to be functionally identical to the sequences disclosed herein. Some nucleotide deletions, additions, and replacements may have no impact or only a minor impact on gene expression. A preferable isolated nucleic acid molecule, according to the present invention, comprises a nucleotide sequence that has at least 90%, or at least 91%, 92%, 93%, 94%, 95%, 96%, 97%, 98% or at least 99% identity to any one of the nucleotide sequences set forth in SEQ ID NOS:1-11. A more preferable isolated nucleic acid molecule comprises a nucleotide sequence that has at least 90% identity to any one of the nucleotide sequences set forth in SEQ ID NOS:1-11. An even more preferable isolated nucleic acid molecule comprises a nucleotide sequence that has at least 95% identity to any one of the nucleotide sequences set forth in SEQ ID NOS:1-11. An even more preferable isolated nucleic acid molecule comprises a nucleotide sequence that has at least 99% identity to any one of the nucleotide sequences set forth in SEQ ID NOS:1-11. The most preferable isolated nucleic acid molecule comprises any one of the nucleotide sequences set forth is SEQ ID NOS:1-11.

In other embodiments, cDNA and genomic DNA sequences may be cloned from other plants that represent homologues of the pollen-minus maize genes and promoters. These homologues allow one to obtain additional pollen-minus promoters useful for the regulation of multiple genes in plants tissues other than pollen. Hybridization using the maize cDNA and genomic sequences or portions thereof is used to screen for homologous or substantially identical sequences in other plant genomes. These sequences may comprise only a subset of the nucleotides of SEQ ID NOS:1-11. A preferable length of homology is 20 base pairs (bp) in length, more preferably, 50 bp in length, and most preferably at least 100 bp in length. In one embodiment of the present invention, a hybridization probe is prepared from any one SEQ ID NOS:1-11 or portions. Hybridization of such sequences may be carried out under high stringency conditions. Alternatively, low or moderate stringency conditions can be used to allow some mismatching in sequences so that lower degrees of similarity are detected (heterologous probing). Generally, a probe is less than about 1000 nucleotides in length, preferably less than 500 nucleotides in length.

In other embodiments of the invention, cDNA and genomic sequences are isolated by preparing primers comprising sequences within any one of SEQ ID NOS:1-11. The primers may be used in a PCR reaction with cDNA or genomic DNA from a plant to obtain homologous sequences or sequences with substantial identity to any one of SEQ ID NOS:1-11.

Construction of Expression Cassettes

Expression cassettes are constructed comprising the 5' flanking sequences of the pollen-minus genomic clones. In embodiments of the invention, the promoter region utilized in each expression cassette comprises the 5' flanking region up to and including the start of translation. The start of translation is denoted by the first ATG of the open reading frame (ORF) found in the cDNA and the homologous genomic sequence. Thus, the promoter region may include 5' untranslated leader sequence as well as the transcriptional start site, core promoter and additional regulatory elements. In other embodiments of the invention, expression cassettes are constructed comprising the 5' flanking sequence of the pollen-minus genomic clones up to and including the transcriptional initiation site. The transcriptional initiation site may be defined by the first nucleotide of the longest cDNA clone obtained. Additionally, the transcriptional initiation site may be further defined by use of techniques well known in the art including RACE PCR, RNase protection mapping and primer extension analysis.

The expression cassettes may further comprise a transcriptional terminator, downstream (3') to the promoter. A variety of transcriptional terminators are available for use in expression cassettes. The transcriptional terminator is responsible for the termination of transcription beyond the transgene and correct mRNA polyadenylation of the mRNA transcript. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used. For example, the 3' flanking sequence comprising genomic sequence 3' to the region homologous to a pollen-minus cDNA clone may be used. Such terminators exemplified herein include any of SEQ ID NOS:12-20.

In some embodiments of the invention a heterologous coding sequence, for example, an insecticidal coding sequence, a visible marker coding sequence, or a selectable marker coding sequence, is cloned between a promoter of the invention and transcriptional terminator whereby the heterologous coding sequence is operatively linked to the promoter and the transcriptional terminator is operatively linked to the heterologous coding sequence. Examples of visible markers useful for the invention include, but are not limited to, β-glucuronidase (GUS), Chloramphenicol Acetyl Transferase (CAT), Luciferase (LUC) and proteins with fluorescent properties, such as Green Fluorescent Protein (GFP) from *Aequora victoria*. In principle, many more proteins are suitable for this purpose, provided the protein does not interfere with essential plant functions. Further examples of heterologous coding sequences useful for the invention include, but are not limited to, antibiotic resistance, virus resistance, insect resistance, disease resistance, or resistance to other pests, herbicide tolerance, improved nutritional value, improved performance in an industrial process or altered reproductive capability. In other embodiments of the invention, a gene encoding for resistance to insects that feed on the tissues of plants that are not pollen is cloned between a promoter of the invention and a terminator known in the art or of the present invention. In another embodiment of the present invention a sequence encoding a functional RNA such as antisense RNA, a sense RNA for sense-suppression, or a double stranded RNA may also be cloned between the promoter and transcriptional terminator.

Numerous sequences have been found to enhance gene expression from within the transcriptional unit and these sequences can be used in conjunction with the promoters of this invention to increase their expression in transgenic plants. Various intron sequences have been shown to enhance expression, particularly in monocotyledonous cells. For example, a number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711 (1987); Skuzeski et al. *Plant Molec. Biol.* 15: 65-79 (1990)). A pollen-minus promoter of the invention may include, or be modified to include, one or more enhancer elements. In some embodiments, the promoter may include a plurality of enhancer elements. Promoters containing enhancer elements provide for higher levels of transcription in non-pollen tissues as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316) and the FMV enhancer element (Maiti et al. (1997) Transgenic Res. 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Plant Transformation

Procedures for transforming plants are known in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase; PMI), provide resistance to an antibiotic (kanamycin, hygromycin or methotrexate) or a herbicide (glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like Arabidopsis or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Nati. Acad. Sci.* USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) *Proc. Natl. Acad. Sci.* USA 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) *Proc. Natl. Acad. Sci.* USA 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell. As used herein, "selectable marker" means a nucleotide sequence that when expressed imparts a distinct phenotype to the plant, plant part or plant cell expressing the marker and thus allows such transformed plants, plant parts or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci.* USA 75:3737-3741); a nucleotide sequence encoding xylE that encodes a catechol dioxygenase (Zukowsky et al. (1983) *Proc. Natl. Acad. Sci.* USA 80:1101-1105); a nucleotide sequence encoding tyrosinase, an enzyme capable of oxidizing tyrosine to DOPA and dopaquinone, which in turn condenses to form melanin (Katz et al. (1983) *J. Gen.*

Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic plants, plant parts, plant cells or seeds of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into a plant, plant part or plant cell in any number of ways that are known in the art, as described above. Therefore, no particular method for introducing one or more polynucleotides into a plant is relied upon, rather any method that allows the one or more polynucleotides to be transiently expressed in a plant cell or stably integrated into the genome of the plant can be used. Where more than one polynucleotide is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Additional embodiments of the invention include harvested products produced from the transgenic plants or parts thereof of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention, wherein said seed or other plant part comprises a nucleic acid molecule/polynucleotide/nucleotide sequence of this invention.

In other embodiments, the invention provides an extract from a transgenic seed or a transgenic plant of the invention, wherein the extract comprises a nucleic acid molecule, a polynucleotide, a nucleotide sequence or an insecticidal protein of the invention. Extracts from plants or plant parts can be made according to procedures well known in the art (See, de la Torre et al., *Food, Agric. Environ.* 2(1):84-89 (2004); Guidet, *Nucleic Acids Res.* 22(9): 1772-1773 (1994); Lipton et al., *Food Agric. Immun.* 12:153-164 (2000)).

Assessing Promoter Activity

Several methods are available to assess promoter activity. Expression cassettes are constructed with a visible marker, as described above. Transient transformation methods may be used to assess promoter activity. Using transformation methods such as microprojectile bombardment, *Agrobacterium* transformation or protoplast transformation, expression cassettes are delivered to plant cells or tissues. Reporter gene activity, such as β-glucuronidase activity, luciferase activity or GFP fluorescence is monitored after transformation over time, for example 2 hours, 5 hours, 8 hours, 16 hours, 24 hours, 36 hours, 48 hours and 72 hours after DNA delivery using methods known in the art. Reporter gene activity may be monitored by enzymatic activity, by staining cells or tissue with substrate for the enzyme encoded by the reporter gene or by direct visualization under an appropriate wavelength of light. An insecticidal protein, for example Cry1Ab or Vip3 of the invention, may act as a visible marker whereby the transformed plant cells are tested for insecticidal activity. Full-length promoter sequences, deletions and mutations of the promoter sequence may be assayed and their expression levels compared. Additionally, RNA levels may be measured using methods well known in the art such as Northern blotting, competitive reverse transcriptase PCR and RNAse protection assays. These assays measure the level of expression of a promoter by measuring the 'steady state' concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates. The rate of degradation can however be considered to proceed at a fixed rate when the transcribed sequences are identical, and thus this value can serve as a measure of synthesis rates.

Further confirmation of promoter activity is obtained by stable transformation of the promoter in an expression cassette comprising a visible marker or gene of interest into a plant as described above. Using the various methods described above such as enzymatic activity assays, RNA analysis and protein assays as described supra, promoter activity is monitored over development, and additionally by monitoring expression in different tissues in the primary transformants and through subsequent generations of transgenic plants.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual*, 3d Ed., Cold Spring Harbor, NY: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, NY (1984).

Example 1: Identification of Maize Regulatory Elements

Regulatory elements were identified from maize genes on a Syngenta proprietary (Zm80K) Affymetrix chip that are highly expressed in multiple tissue types but not in pollen, i.e. pollen expression was very low or was not detectable. Regulatory elements from eight different maize genes were used to make constructs to drive expression of insect control genes in transgenic corn tissues and plants. A description of the regulatory elements used are shown in Table 1.

TABLE 1

Description of regulatory elements used to make expression constructs.

| Regulatory Element | SEQ ID NO: | Description |
|---|---|---|
| PMP370-3 | 1 | Promoter from the Zm032370 gene (Syngenta chip ID), identified as profilin-like. Includes the 5' UTR. the first exon and intron, and a portion of the second exon. |
| PMP393-1 | 2 | Promoter from the Zm061393 gene (Syngenta chip ID), identified as sucrose synthase. Includes the 5' UTR, the first and second exons, and the first and second introns. Also includes a T to A mutation to remove the start codon. |
| PMP393-2 | 3 | prZm061393 with a TMV enhancer added at the 3' end. |
| PMP393-3 | 4 | prZm061393-02 with a T to A mutation at bp 8 to remove an open reading frame (ORF) |
| PMP393-4 | 5 | prZm041393-01 with a T to A mutation at bp 29 to remove an unintended cross component ORF on the antisense strand. |
| PMP855-1 | 6 | Promoter from the ZmU45855-3 gene (Syngenta chip ID) from Zea mays. Includes the 5' UTR, the first exon, the first intron, and a portion of the second exon. |
| PMP747-1 | 7 | Promoter from the Zm001747 gene (Syngenta chip ID) from Zea mays, identified as encoding a heat shock protein (HSP). Includes the 5' UTR. |
| PMP004-1 | 8 | Promoter from the Zm021004 gene (Syngenta chip ID) from Zea mays, having similarity to genes encoding ran-binding proteins, and includes the 5'-untranslated region, the first exon, the first intron, part of the second exon, and it terminates in a maize optimized Kozak sequence. |
| PMP335-1 | 9 | Promoter from the Zm015335 gene (Syngenta chip ID) from Zea mays similar to genes encoding 40S ribosomal proteins, and includes the 5'-untranslated region, the first exon, the first intron, partial second exon, and it terminates in a maize optimized Kozak sequence. |
| PMP722-1 | 10 | Promoter from the Zm009722 gene from Zea mays, and includes the 5'-untranslated region, the first exon, the first intron and part of the second exon, and it terminates in a maize optimized Kozak sequence. |
| PMP948-2 | 11 | Promoter from the Zm058948 (Syngenta chip ID) gene from Zea mays. Includes the 5'-untranslated region, first exon, first intron, partial second exon, and terminates in a maize optimized Kozak sequence. |

Terminator elements were also identified from the same genes from which the above-identified promoters were cloned. A description of the terminators is in Table 2.

TABLE 2

Description of terminator elements of the invention.

| Terminator Element | SEQ ID NO: | Description |
|---|---|---|
| t370-2 | 12 | 3' regulatory sequence from the AF032370 gene (Syngenta chip ID) from Zea mays. Includes the 3' UTR and downstream non-transcribed region. |
| t393-1 | 13 | 3' regulatory sequence from the Zm061393 gene (Syngenta chip ID) from Zea mays. Includes the 3' UTR and downstream non-transcribed region. |

TABLE 2-continued

Description of terminator elements of the invention.

| Terminator Element | SEQ ID NO: | Description |
| --- | --- | --- |
| t393-2 | 14 | tZm061393-01 with two point mutations to remove unintended ORFS. |
| t855-1 | 15 | 3' regulatory sequence from the ZmU45855-3 gene (Syngenta chip ID) from Zea mays. Includes the 3' UTR and downstream non-transcribed region. |
| t747-1 | 16 | 3' regulatory sequence from the Zm001747 gene (Syngenta chip ID) from Zea mays. Includes the 3' UTR and downstream non-transcribed region. |
| t004-1 | 17 | 3' regulatory sequence from the Zm021004 gene (Syngenta chip ID) from Zea mays. Includes the 3'-UTR and downstream non-transcribed region. |
| t335-1 | 18 | 3' regulatory sequence from the Zm015335 gene (Syngenta chip ID) from Zea mays. Includes the 3' UTR and downstream non-transcribed region. |
| t722-1 | 19 | 3' regulatory sequence from the Zm009722 gene (Syngenta chip ID) from Zea mays. Includes the 3'-UTR and downstream non-transcribed region. |
| t948-2 | 20 | 3' regulatory sequence from the Zm058948 gene (Syngenta chip ID) from Zea mays. Includes the second intron, third exon, 3'-UTR. and downstream non-transcribed region. |

Example 2: Construction of Pollen-Minus Expression Vectors

To test the above-described regulatory elements (promoters and terminators) in transgenic maize plants, eight binary vectors were made. Each binary vector contains two expression cassettes.

The first expression cassette comprises a eFMV/e35S transcriptional enhancer, which is operably linked a promoter of the invention to be tested, which is operably linked to a heterologous coding sequence (cry1Ab) that encodes a Cry1Ab insecticidal protein (U.S. Pat. No. 5,625,136), which is operably linked to the promoter's matching terminator sequence. For example, the expression cassette made to test the prZm061393-01 promoter (SEQ ID NO:2) comprises the tZm061393-01 terminator (SEQ ID NO:13).

The second expression cassette, which was the same for each of the binary vectors, comprises a maize ubiquitin promoter (prUbi1-10) (Christensen et al, 1992 PMB 18: 675) operably linked to a phosphomannose isomerase (PMI; U.S. Pat. No. 5,767,378) coding sequence which is operably linked to a Ubi1 terminator (tUbi1-01). Expression of PMI allows for positive selection of transgenic plants on mannose.

Both expression cassettes were cloned into a suitable vector for Agrobacterium-mediated maize transformation. The binary vectors that were constructed are listed and described in Table 3.

TABLE 3

Binary vectors constructed to test pollen-minus promoters in maize.

| Binary Vector | SEQ ID NO: | Description |
| --- | --- | --- |
| pSYN18499 | 21 | Binary vector with PMI selection containing cCry1Ab under the control of PMP370-3 (PMP370-3:cCry1Ab:t370-2) |
| pSYN18500 | 22 | Binary vector with PMI selection containing cCry1Ab under the control of PMP393-1 and t393-1. |
| pSYN18501 | 23 | Binary vector with PMI selection containing cCry1Ab under the control of PMP855-1 and t855-1. |
| pSYN18498 | 24 | Binary vector with PMI selection containing cCry1Ab under the control PMP747-1. (PMP747:cCry1Ab:t747) |
| pSYN18617 | 25 | Binary vector with PMI selection containing cCry1Ab under the control of PMP004-1. (PMP004-1:cCry1Ab:t004-1). |
| pSYN18618 | 26 | Binary vector with PMI selection containing cCry1Ab under the control of PMP335-1. (prZm015335-01:cCry1Ab:t335-1) |
| pSYN18619 | 27 | Binary vector with PMI selection containing cCry1Ab under the control of PMP722-1 (PMP722-1:cCry1Ab:t722-1). |
| pSYN18705 | 28 | Binary vector with PMI selection containing cCry1Ab under the control of PMP948-2 (PMP948-2:cCry1Ab:t948-2). |

Example 3: Transient Expression of Cry1Ab in Maize Directed by Pollen-Minus Promoters The vectors described above were transferred into Agrobacterium tumefactions strain LBA4404 containing helper plasmid (pSBI) using a freeze-thaw method (An et al., Binary vector. In: Gelvin S B, Schilproot R A (eds), Plant molecular biology manual. Kluwar Academic Publishers, Dordrecht, pp A3 1-19 (1988)). Preparation of Agrobacterium cultures was carried out as described by Azhakanandam et al., Plant Mol. Biol. 63: 393-404 (2007). In brief, the genetically modified agrobacteria were grown overnight in 50 mL of YP medium containing 100 μM acetosyringone and 10 μM MES (pH 5.6), and subsequently were pelleted by centrifugation at 4000×g for 10 min. The pellets were resuspended in the infection medium (Murashige and Skoog salts with vitamins, 2% sucrose, 500 µM MES (pH 5.6), 10 µM MgSO4, and 100 µM acetosyringone) to OD600=0.5 and subsequently held at 28° C. for 2-3 hours.

A maize seedling in planta transient expression assay was performed essentially as described in U.S. Pat. No. 8,642,839, incorporated herein by reference in its entirety. Briefly, maize seeds were germinated under greenhouse conditions in 2.5 inch pots filled with Fafard germination mix. Seedlings were kept under a 14/10 day/night cycle with a day light intensity of 2000 µ-mol-m-2 s-1 maintained with supplemental lighting. The temperature was maintained between 23° C.-26° C. The agroinfiltration experiment performed mostly using primary and secondary leaves of V2 stage (Ritchie S. W., Hanway J. J. Benson G. O. (edts): How a Corn Plant Develops: Iowa State Univ Special Report No. 48, July 2005). To make infiltration easier, the seedlings were watered 1-2 hours prior to agroinfiltration, which keeps the leaf turgid and stomata open. Infiltration of individual leaves was carried out on maize seedlings using a 5 mL syringe body (BD 5 ml syringe with Luer-Lok™. Tip, BD™. Franklin Lakes, N.J. 07427, USA), by pressing the tip of the syringe against the abaxial surface of the leaf. The first and second visible leaves of V2 stage were infiltrated with: 1 ml of *Agrobacterium* suspension/28 seconds/leaf. Infiltrated plants were transferred and maintained under growth chamber conditions set at 25° C. with a 16/8 day/night cycle with a light intensity of 1900 µ-mol-m-2 s-1. Plant tissue was harvested after 4 days post infiltration for subsequent analysis of Cry1Ab protein and PMI protein detection using ELISA. Results demonstrated that both proteins were detected in all eight vector groups, indicating that the promoters of the invention are capable of driving transgene expression in maize cells.

Example 4: Expression of Cry1Ab in Stably Transformed Corn Using Pollen-Minus Promoters

*Agrobacterium* transformation of immature maize embryos was performed essentially as described in Negrotto et al., 2000, Plant Cell Reports 19: 798-803, herein incorporated by reference in its entirety. However, various media constituents known in the art may be substituted. Briefly, *Agrobacterium* strain LBA4404 (pSB1) containing a plant transformation vector described above was grown on YEP (yeast extract (5 g/L), peptone (10 g/L), NaCl (5 g/L), 15 g/l agar, pH 6.8) solid medium for about 2-4 days at about 28° C. Approximately $0.8 \times 10^9$ *Agrobacterium* were suspended in LS-inf media supplemented with 100 µM As (Negrotto et al., supra). Bacteria were pre-induced in this medium for about 30-60 minutes.

Immature embryos from a suitable genotype were excised from about 8-12 day old ears into liquid LS-inf+100 µM As. Embryos were rinsed once with fresh infection medium. *Agrobacterium* solution was then added and embryos were vortexed for about 30 seconds and allowed to settle with the bacteria for about 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

Immature embryos, producing embryogenic callus were transferred to LSD1M0.5S medium. The cultures were selected on this medium for about 6 weeks with a subculture step at about 3 weeks. Surviving calli were transferred to Reg1 medium supplemented with mannose. Following culturing in the light (16 hour light/8 hour dark regiment), green tissues were then transferred to Reg2 medium without growth regulators and incubated for about 1-2 weeks. Plantlets were transferred to Magenta GA-7 boxes (Magenta Corp, Chicago Ill.) containing Reg3 medium and grown in the light. After about 2-3 weeks, plants were tested for the presence of the pmi gene and the cry1Ab-09 coding sequence. Positive plants from the PCR assay are transferred to the greenhouse and tested for expression level of Cry1Ab-09 protein in leaves and pollen and tested for activity against European corn borer (*Ostrinia nubilalis*).

The concentrations of the Cry1Ab protein were determined at the vegetative (V) and reproductive (R) stages of growth of the transgenic maize plants. The "V" stages are designated numerically as V1, V2, V3, etc. by the number of leaves through the VT stage where the last branch of the tassel is visible. The "R" stages are designated R1 to R6 from silking to physiological maturity of the ear, respectively. Cry1Ab was quantified by ELISA in V3-V4 and VT stage leaves as well as silk, husk and pollen from 8-12 events for each promoter tested using ELISA protocols known in the art. Briefly, leaf tissue is lyophilized and then reduced to a fine powder by processing using either a coffee grinder, blender, Grindomix™ grinder (Brinkmann Instruments; Westbury, N.Y., USA), mortar with a pestle or mill, or a combination of these devices. All processing is done in the presence of either dry ice or liquid nitrogen. Samples are mixed well to ensure homogeneity. The percent dry weight of each sample is determined and the processed samples are stored at about -80° C. until lyophilization.

For each sample analyzed, a 1.0 g aliquot of the powdered plant material (other than pollen) is weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl) benzenesulfonyl fluoride HCl, 1 mM leupeptin, pH 10], and extracted using an Autogizer® homogenizer (Tomtek; Hamden, Conn., USA). After centrifugation for 15 min at 10,000×g at 4° C., the supernatant is used for Cry1Ab and PMI analysis by ELISA. After treatment with iodoacetamide as described by Hill and Straka (1988), total protein in the extracts is quantitated using the BCA™ Protein Assay Reagent (Pierce; Rockford, Ill., USA).

Maize pollen extracts are prepared by suspending pollen 1:30 (w/v) in extraction buffer. After about 30 min on ice, the pollen suspensions are disrupted by three passages through a French pressure cell at about 15,000 psi, followed by centrifugation at 14,000×g for about 5 min at 4° C. Cry1Ab and PMI analyses by ELISA were performed on the supernatants as described below. Total protein was quantitated as described above.

The extracts prepared as described above were quantitatively analyzed for Cry1Ab and PMI by ELISA (Tijssen, 1985). Cry1Ab was quantified using immuno-affinity purified monoclonal, anti-Cry1Ab antibody and immuno-affinity purified polyclonal anti-Cry1Ab antibody. The PMI was quantified using Protein A-purified polyclonal rabbit and immunoaffinity-purified polyclonal goat antibodies specific for PMI. The lower limit of quantification of the double-sandwich ELISA for Cry1Ab and PMI was estimated based on the lowest concentration of pure reference protein lying on the linear portion of the standard curve, the maximum volume of a control extract that could be analyzed without background interference, and the corresponding weight of the sample that the aliquot represented.

The Cry1Ab ELISA results are shown in Table 4. The level of detection (LOD) for the Cry1Ab ELISA test was determined to be about 0.37 ng/mg total soluble protein (TSP). Quantifiable levels of Cry1Ab protein were detected in V3-V4 leaves, silks, husks and VT leaves from all events for each of the promoters tested, which were significantly higher than in pollen. Concentrations of Cry1Ab in pollen for each of the promoters was only slightly above the LOD for the ELISA. Five out of the eight promoters tested expressed levels of Cry1Ab in non-pollen tissues that were greater than 1000-fold higher than the LOD. Three of the eight promoters expressed Cry1Ab at levels that were about 500- to about 950-fold higher than the LOD. By comparison, seven of the eight promoters tested expressed Cry1Ab in pollen at levels that were less than 10-fold higher than the LOD, and one promoter, prZmU45855, expressed Cry1Ab in pollen at a concentration that was 15-fold higher than the LOD. However, some plants from each event of each of the vector groups comprising the 001747-01, 061393-01, AF032370-02, 009722-01, 015335-01 or the 058948-02 promoter had no detectable levels of Cry1Ab in pollen. Cry1Ab was expressed at insecticidal levels in all non-pollen tissues tested, whereas Cry1Ab levels in pollen for all of the promoters tested were below the concentration necessary for insecticidal activity.

TABLE 4

Cry1Ab Expression in Tissues of Transgenic Maize Plants.

| | | Mean Cry1Ab Level (ng/mg TSP) | | | | |
|---|---|---|---|---|---|---|
| Vector | Promoter | V3-V4 Leaf | Silk | Husk | VT Leaf | Pollen |
| pSYN18499 | PMP370-2 | 389 | 485 | 290 | 229 | 1.6 |
| pSYN18500 | PMP393-1 | 927 | 359 | 437 | 402 | 2.2 |
| pSYN18501 | PMP855-1 | 910 | 461 | 238 | 693 | 5.7 |
| pSYN18498 | PMP747-1 | 324 | 491 | 505 | 341 | 1.1 |
| pSYN18617 | PMP004-1 | 1037 | 194 | 960 | 462 | 2.7 |
| pSYN18618 | PMP335-1 | 254 | 109 | 243 | 256 | 0.3 |
| pSYN18619 | PMP722-1 | 1132 | 283 | 390 | 476 | 1.3 |
| pSYN18705 | PMP948-2 | 292 | 215 | 409 | 318 | 1.7 |

Example 5: Expression of a Cry1Ai in Stably-Transformed Maize

Maize plants were transformed as described above with an expression cassette comprising a eFMV/e35S transcriptional enhancer operatively linked to the PMP393-4 promoter of the invention (SEQ ID NO:5), operatively linked to a heterologous coding sequence that encodes a full-length Cry1Ai insecticidal protein (US Application publication No. 20190177377), which is operatively linked to the t393-2 terminator of the invention (SEQ ID NO:14). V3-V4 leaf tissue and pollen from 40 events were assayed as described above. The level of detection (LOD) for the Cry1Ai ELISA test was determined to be about 0.75 ng/mg total soluble protein (TSP). Results of the ELISA on the tissues from the 40 transgenic maize events demonstrated that the level of Cry1Ai protein in the V3-V4 leaves ranged from about 10 ng/mg TSP to about 80 ng/mg TSP, whereas no Cri1Ai protein was not detected in pollen, indicating that the level of expression in pollen was below the LOD of the ELISA, i.e. <0.75 ng/mg TSP, in all 40 events.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious to persons skilled in the art that certain changes and modifications may be practiced within the scope of the present invention.

What is claimed is:

1. An expression cassette comprising a promoter comprising the nucleotide sequence of SEQ ID NO: 2 or 5 operably linked to a heterologous polynucleotide of interest, which is operably linked to a 3'-untranslated region including a polyadenylation signal.

2. The expression cassette of claim 1, wherein the heterologous polynucleotide encodes an insecticidal protein or a double stranded RNA (dsRNA).

3. A recombinant vector comprising the expression cassette of claim 1.

4. A plant cell comprising the expression cassette of claim 1.

5. A transgenic plant comprising the expression cassette of claim 1.

6. The transgenic plant of claim 5, wherein said plant is a monocot.

7. The transgenic plant of claim 6, wherein the monocot is maize.

8. A transgenic seed of the plant of claim 5, wherein the seed comprises the expression cassette.

9. The transgenic plant of claim 5, wherein the heterologous polynucleotide encodes an insecticidal protein.

10. A method for expressing a protein or polynucleotide of interest in a plant or a plant cell comprising introducing into the plant or the plant cell an expression cassette comprising a promoter operably linked to a heterologous polynucleotide that encodes the protein or polynucleotide of interest, wherein said promoter comprises the nucleotide sequence of SEQ ID NO: 2 or 5.

11. The method of claim 10, wherein the protein of interest is an insecticidal protein or the polynucleotide of interest is a dsRNA that is insecticidal.

12. The method of claim 10, wherein the plant or plant cell is a maize plant or plant cell.

13. An isolated nucleic acid molecule comprising the nucleotide sequence of SEQ ID NO: 2 or 5.

14. The expression cassette of claim 1, wherein the 3'-untranslated region comprises a terminator sequence comprising the sequence of SEQ ID NO: 12, 13, 14, 15, 16, 17, 18, 19, or 20.

15. The recombinant vector of claim 3, wherein said vector is a binary vector comprising SEQ ID NO: 22.

16. A method of specifically expressing a heterologous coding sequence in a transgenic plant tissue that is not pollen, comprising: a) transforming at least one plant cell with a vector, wherein said vector comprises the expression cassette of claim 1; b) growing the transgenic plant cell comprising said expression cassette; and c) producing at least one transgenic plant from said transformed plant cell, wherein the heterologous coding sequence is specifically expressed in a tissue that is not pollen under control of said nucleotide sequence.

* * * * *